United States Patent
Ribas et al.

(10) Patent No.: US 10,711,312 B2
(45) Date of Patent: Jul. 14, 2020

(54) METHODS FOR IMMUNOTHERAPY-BASED TREATMENT AND ASSESSMENT OF CANCER

(71) Applicant: THE REGENTS OF THE UNIVERSITY OF CALIFORNIA, Oakland, CA (US)

(72) Inventors: Antoni Ribas, Los Angeles, CA (US); Jesse Zaretsky, Santa Monica, CA (US); Daniel Shin, Los Angeles, CA (US); Angel Garcia-Diaz, Los Angeles, CA (US); Blanca Homet Moreno, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/648,423

(22) Filed: Jul. 12, 2017

(65) Prior Publication Data
US 2018/0051347 A1 Feb. 22, 2018

Related U.S. Application Data

(60) Provisional application No. 62/361,474, filed on Jul. 12, 2016.

(51) Int. Cl.
*C12Q 1/6886* (2018.01)
*C07K 16/28* (2006.01)
*A61K 39/00* (2006.01)

(52) U.S. Cl.
CPC ........ *C12Q 1/6886* (2013.01); *C07K 16/2818* (2013.01); *A61K 2039/505* (2013.01); *A61K 2039/55* (2013.01); *C07K 2317/24* (2013.01); *C07K 2317/76* (2013.01); *C12Q 2600/106* (2013.01); *C12Q 2600/156* (2013.01)

(58) Field of Classification Search
None
See application file for complete search history.

(56) References Cited

FOREIGN PATENT DOCUMENTS

| WO | WO-2015184061 A2 * | 12/2015 | ........... C12Q 1/6886 |
| WO | WO-2016100975 A1 * | 6/2016 | ........... C12Q 1/6886 |

OTHER PUBLICATIONS

Shin et al. (J. Immunotherapy of Cancer, Nov. 4, 2015, 3: (Suppl. 2) Ab. No. P311) (Year: 2015).*
Warr et al. (G3 (Bethesda), Jul. 2, 2015 (Year: 2015).*
Fu et al. (Science Translational Med. Apr. 15, 2015 7(283): 1-11), (Year: 2015).*
Ansell, S.M., et al., "PD-1 blockade with nivolumab in relapsed or refractory Hodgkin's lymphoma," N. Engl J Med., 2015, vol. 372, pp. 311-319.
Atefi, M., et al., "Effects of MAPK and PI3K Pathways on PD-L1 expression in mela-noma," Clin Cancer Res., 2014, vol. 20, pp. 3446-3457.
Atkins, M.B., et al., "High-dose recombinant interleukin-2 therapy in patients with metastatic melanoma: long-term survival update," Cancer Journal from Scientific American, 2000, vol. 6 Suppl 1, S11-S14.
Bach, E.A., et al., "The IFN gamma receptor: a paradigm for cytokine receptor signaling," Annu Rev Immunol., 1997, vol. 15, pp. 563-591.
Barretina, J., et al., "The cancer cell line encyclopedia enables predictive mod-elling of anticancer drug sensitivity," Nature, 2012, vol. 483, pp. 603-607.
Beroukhim R., et al., "Assessing the significance of chromosomal aberrations in cancer: methodology and application to glioma," Proc Natl Acad Sci USA, 2007, vol. 104, pp. 20007-20012.
Brinkman, E.K., et al., "Easy quantitative assessment of genome editing by sequence trace decomposition," Nucl. Acids Res., 2014, vol. 42, No. 22, e168, pp. 1-8.
Cerami, E., et al., "The cBio cancer genomics portal: an open platform for exploring multidimensional cancer genomics data," Cancer Discov., 2012, vol. 2, pp. 401-404.
Cibulskis, K., et al., "Sensitive detection of somatic point mutations in impure and heterogeneous cancer samples," Nat Biotechnol., 2013, vol. 31, pp. 213-219.
Corrales, L., et al., "Endogenous and pharmacologic targeting of the STING pathway in cancer immunotherapy," Cytokine, 2016, vol. 77, pp. 245-247.
Dunn, G.P., et al., "Cancer immunoediting: from immunosurveillance to tumor escape," Nat Immunol., 2002, vol. 3, pp. 991-998.
Dunn, G.P., et al., "The three Es of cancer immunoediting," Annual review of immunology, 2004, vol. 22, pp. 329-360.
Dunn, G.P., et al., "IFN unresponsiveness in LNCaP cells due to the lack of JAK1 gene expression," Cancer Res., 2005, vol. 65, pp. 3447-3453.
D'Urso, C.M., et al., "Lack of HLA class I antigen expression by cultured melanoma cells FO-1 due to a defect in B2m gene expression," J Clin Invest., 1991, vol. 87, pp. 284-292.
Eisenhauer, E.A., et al., "New response evaluation criteria in solid tumours: revised RECIST guideline (version 1.1)," Eur J Cancer, 2009, vol. 45, pp. 228-247.
Eroglu, Z., et al., "Long term survival with cytotoxic T lymphocyte-associated antigen 4 blockade using tremelimumab," Eur J Cancer, 2015, vol. 51, pp. 2689-2697.
Escuin-Ordinas, H., et al., "COX-2 inhibition prevents the appearance of cutaneous squamous cell carci¬nomas accelerated by BRAF inhibitors," Mol Oncol., 2014, vol. 8, pp. 250-260.

(Continued)

*Primary Examiner* — Peter J Reddig
(74) *Attorney, Agent, or Firm* — Norton Rose Fulbright US LLP

(57) ABSTRACT

Disclosed herein are methods of treating or assessing cancer in a subject wherein it has been determined whether the cancer comprises a loss of function mutation or disruption in an immune pathway. The loss of function mutation or disruption can be in JAK1 or JAK2. The loss of function mutation or disruption can be in B2M. The methods can include administering an immune checkpoint therapy such as anti-PD1 or anti-PDL1. The methods can include administering an alternative therapy to an immune checkpoint therapy. In some aspects, the method includes determining whether the cancer comprises a loss of function mutation or disruption in an immune pathway.

17 Claims, 65 Drawing Sheets
Specification includes a Sequence Listing.

(56) References Cited

OTHER PUBLICATIONS

Favero, F., et al., "Sequenza: allele-specific copy number and mutation profiles from tumor sequencing data," Ann Oncol., 2015, vol. 26, pp. 64-70.
Finke, J.H., et al., "Loss of T-cell receptor zeta chain p56lck in t-cells infiltrating human renal cell carcinoma," Cancer Research, 1993, vol. 53, pp. 5613-5616.
Fish, E.N., et al., "Interferon receptor signaling in malignancy: a network of cellular pathways defining biological outcomes," Mol Cancer Res., 2014, vol. 12, pp. 1691-1703.
Gao, J., et al., "Integrative analysis of complex cancer genomics and clinical profiles using the cBioPortal," Sci Signal, 2013, vol. 6, Issue 269, pp. 1-19.
Gao, J., et al., "Loss of IFN-gamma pathway genes in tumor cells as a mechanism of resistance to Anti-CTLA-4 Therapy," Cell, 2016, vol. 167, pp. 397-404, e9.
Garcia-Diaz, A., et al., "Interferon Receptor Signaling Pathways Regulating PD-L1 and Pd-L2 Expression," Cell Reports, 2017. vol. 19, pp. 1189-1201.
Garon, E.B., et al., "Pembrolizumab for the treatment of non-small-cell lung cancer," N Engl J Med., 2015, vol. 372, pp. 2018-2028.
Hamid, O., et al., "Safety and tumor responses with lambrolizumab (anti-PD-1) in melanoma," N Engl J Med., 2013, vol. 369, pp. 134-144.
Herbst, R.S., et al., "Predictive correlates of response to the anti-PD-L1 antibody MPDL3280A in cancer patients," Nature, 2014, vol. 515, pp. 563-567.
Huang, A., et al., "T-cell invigoration to tumour burden ratio associated with anti-PD-1 response," Nature, 2017, 18 Pages.
Hugo, W., et al., "Genomic and transcriptomic features of response to Anti-PD-1 therapy in metastatic melanoma," Cell, 2016, vol. 165, pp. 35-44.
Kaplan, D.H., et al., "Demonstration of an interferon gamma-dependent tumor surveillance system in immunocompetent mice," Proc Natl Acad Sci U S A, 1998, vol. 95, pp. 7556-7561.
Kim, D., et al., "TopHat2: accurate alignment of transcriptomes in the presence of insertions, deletions, and gene fusions," Genome Biology, 2013, vol. 14:R36, pp. 1-13.
Koboldt, D.C., et al., "VarScan 2: somatic mutation and copy number alteration discovery in cancer by exome sequencing," Genome research, 2012, vol. 22, pp. 568-576.
Kotecha, N., et al., "Web-based analysis and publication of flow cytometry experiments," Current protocols in cytometry, Jul. 2010, Chapter 10:Unit10.17, pp. 1-40.
Krzywinski, M., et al., "Circos: an information aesthetic for comparative genomics," Genome research, 2009, vol. 19, pp. 1639-1645.
Le, D.T., et al., "PD-1 blockade in tumors with mismatch-repair deficiency," N Engl J Med., 2015, vol. 372, pp. 2509-2520.
Marincola, F.M., et al., "Escape of human solid tumors from T-cell recognition: molecular mechanisms and functional significance," Adv Immunol., 2000, vol. 74, pp. 181-273.
Marvel, D., et al., "Myeloid-derived suppressor cells in the tumor microenvironment: expect the unexpected," J Clin Invest., 2015, vol. 125, pp. 335-6433.
Mazzolini, G., et al., "Pancreatic cancer escape variants that evade immunogene therapy through loss of sensitivity to IFNgamma-induced apoptosis," Gene Ther., 2003, vol. 10, pp. 1067-1078.
McGranahan, N., et al., "Clonal neoantigens elicit T cell immunoreactivity and sensitivity to immune checkpoint blockade," Science, 2016, vol. 351, pp. 1463-1469.
Muller, M., et al., "The protein tyrosine kinase JAK1 complements defects in interferon-alpha/beta and- gamma signal transduction," Nature, 1993, vol. 366, pp. 129-135.
Nazarian, R., et al., "Melanomas acquire resistance to B-RAF(V600E) inhibition by RTK or N-RAS upregulation," Nature, 2010, vol. 468, pp. 973-977.
Nghiem, P.T., et al., "PD-1 blockade with pembrolizumab in advanced merkel-cell carcinoma," N Engl J Med., 2016, vol. 374, pp. 2542-2552.
Pardoll, D.M., "The blockade of immune checkpoints in cancer immunotherapy," Nature reviews Cancer, 2012, vol. 12, pp. 252-264.
Platanias, L.C. Mechanisms of type-I- and type-II-interferon-mediated signaling, Nat Rev Immunol., 2005, vol. 5, pp. 375-386.
Powles, T., et al., "MPDL3280A (anti-PD-L1) treatment leads to clinical activity in meta-static bladder cancer," Nature, 2014, vol. 515, pp. 558-562.
Prieto, P.A., et al., "CTLA-4 blockade with ipilimumab: long-term follow-up of 177 patients with metastatic melanoma," Clinical cancer research: an official journal of the American Association for Cancer Research 2012, vol. 18, pp. 2039-2047.
Ramos, A.H., et al., "Oncotator: cancer variant annotation tool," Human mutation, 2015, vol. 36, pp. E2423-E2429.
Ren, Y., et al., "JAK1 truncating mutations in gynecologic cancer define new role of cancer-associated protein tyrosine kinase aberrations," Scientific reports, 2013, vol. 3, 3042, pp. 1-8.
Restifo, N.P., et al., "Loss of functional beta 2-microglobulin in metastatic melanomas From Five Patients Receiving Immunotherapy," J Natl Cancer Inst., 1996, vol. 88, pp. 100-108.
Ribas, A., et al., "Association of Pembrolizumab With Tumor Response and Survival Among Patients With Advanced Melanoma," JAMA, 2016, vol. 315, pp. 1600-1609.
Ribas, A., "Adaptive Immune Resistance: How Cancer Protects from Immune Attack," Cancer Discov., 2015, vol. 5, pp. 915-919.
Rizvi, N.A., et al., "Cancer immunology. Mutational landscape determines sensitivity to PD-1 blockade in non-small cell lung cancer," Science, 2015, vol. 348, pp. 124-128.
Robbins, P.F., et al., "Tumor regression in patients with metastatic synovial cell sarcoma and melanoma using genetically engineered lymphocytes reactive with NY-ESO-1," Journal of clinical oncology: official journal of the American Society of Clinical Oncology, 2011, vol. 29, pp. 917-924.
Robert, C., et al., "Nivolumab in previously untreated melanoma without BRAF mutation," N Engl J Med., 2015, vol. 372, pp. 320-330.
Robert, C., et al., "Anti-programmed-death-receptor-1 treatment with pembrolizumab in ipilimumab-refractory advanced melanoma: a randomised dose-comparison cohort of a phase 1 trial," Lancet, 2014, vol. 384, pp. 1109-1117.
Robert, C., et al., "Pembrolizumab versus Ipilimumab in Advanced Melanoma," N Engl J Med., 2015, vol. 372, pp. 2521-2532.
Rodig, S.J., et al., "Disruption of the Jak1 gene demonstrates obligatory and non-redundant roles of the Jaks in cytokine-induced biologic responses," Cell, 1998, vol. 93, pp. 373-383.
Rosenberg, J.E., et al., "Atezolizumab in patients with locally advanced and metastatic urothelial carcinoma who have progressed following treatment with platinum-based chemotherapy: a single-arm, multicentre, phase 2 trial," Lancet, 2016, vol. 387, pp. 1909-1920.
Rosenberg, S.A., et al., "Durable complete responses in heavily pretreated patients with metastatic melanoma using T-cell transfer immunotherapy," Clinical cancer research: an official journal of the American Association for Cancer Research, 2011, vol. 17, pp. 4550-4557.
Schadendorf, D., et al., "Pooled Analysis of Long-Term Survival Data From Phase II and Phase III Trials of Ipilimumab in Unresectable or Metastatic Melanoma," J Clin Oncol., 2015, vol. 33, pp. 1889-1894.
Sharma, P., et al., "The future of immune checkpoint therapy," Science, 2015, vol. 348, pp. 56-61.
Sharma, P., et al., "Primary, Adaptive, and Acquired Resistance to Cancer Immunotherapy," Leading Edge Review, Cell, Feb. 9, 2017, vol. 168, pp. 707-723.
Shi, H., et al., "Acquired resistance and clonal evolution in melanoma during BRAF inhibitor therapy," Cancer Discov., 2014, vol. 4, pp. 80-93.

(56) References Cited

OTHER PUBLICATIONS

Shin, D., et al., "Innate resistance of PD-1 blockade through loss of function mutations in JAK resulting in inability to express PD-L1 upon interferon exposure," Journal for ImmunoTherapy of Cancer, 2015, vol. 3, p. 311.

Shin, D., et al., "Primary Resistance to PD-1 Blockade Mediated by JAK1/2 Mutations," Cancer Discovery, Feb. 2017, pp. 189-201, American Association for Cancer Research.

Sondergaard, J.N., et al., "Differential sensitivity of melanoma cell lines with BRAFV600E mutation to the specific raf inhibitor PLX4032," J Transl Med., 2010, vol. 8, No. 39, pp. 1-11.

Spranger, S., et al., "Melanoma-intrinsic beta-catenin signaling prevents anti-tumour immunity," Nature, 2015, vol. 523, pp. 231-235.

Sucker, A., et al., "Genetic evolution of T-cell resistance in the course of melanoma progression," Clin Cancer Res., 2014, vol. 20, pp. 6593-6604.

Sucker, A., et al., "Acquired IFNg resistance impairs anti-tumor immunity and gives rise to T-cell-resistant melanoma lesions," Nature Communications, May 31, 2017, pp. 1-15.

Taube, J.M., et al., "Colocalization of inflammatory response with B7-h1 expression in human melanocytic lesions supports an adaptive resistance mechanism of immune escape," Sci Transl Med., 2012, vol. 4, No. 127ra37, pp. 1-10.

Watling, D., et al., "Complementation by the protein tyrosine kinase JAK2 of a mutant cell line defective in the interferon-gamma signal transduction pathway," Nature, 1993, vol. 366, pp. 166-170.

Wolchok, JD., et al., "Guidelines for the evaluation of immune therapy activity in solid tumors: immune-related response criteria," Clin Cancer Res., 2009, vol. 15, pp. 7412-7420.

Wong, D.J., et al., "Antitumor activity of the ERK inhibitor SCH722984 against BRAF mutant, NRAS mutant and wild-type melanoma," Mol Cancer, 2014, vol. 13, No. 194, pp. 1-15.

Zaretsky, J.M., et al., "Mutations associated with acquired resistance to PD-1 blockade in melanoma," N Engl J Med., 2016, vol. 375, pp. 819-829.

Zaretsky, J.M., et al., "Mutations associated with acquired resistance to PD-1 blockade in melanoma," N Engl J Med., 2016, Supplementary Appendix, 110 Pages.

* cited by examiner

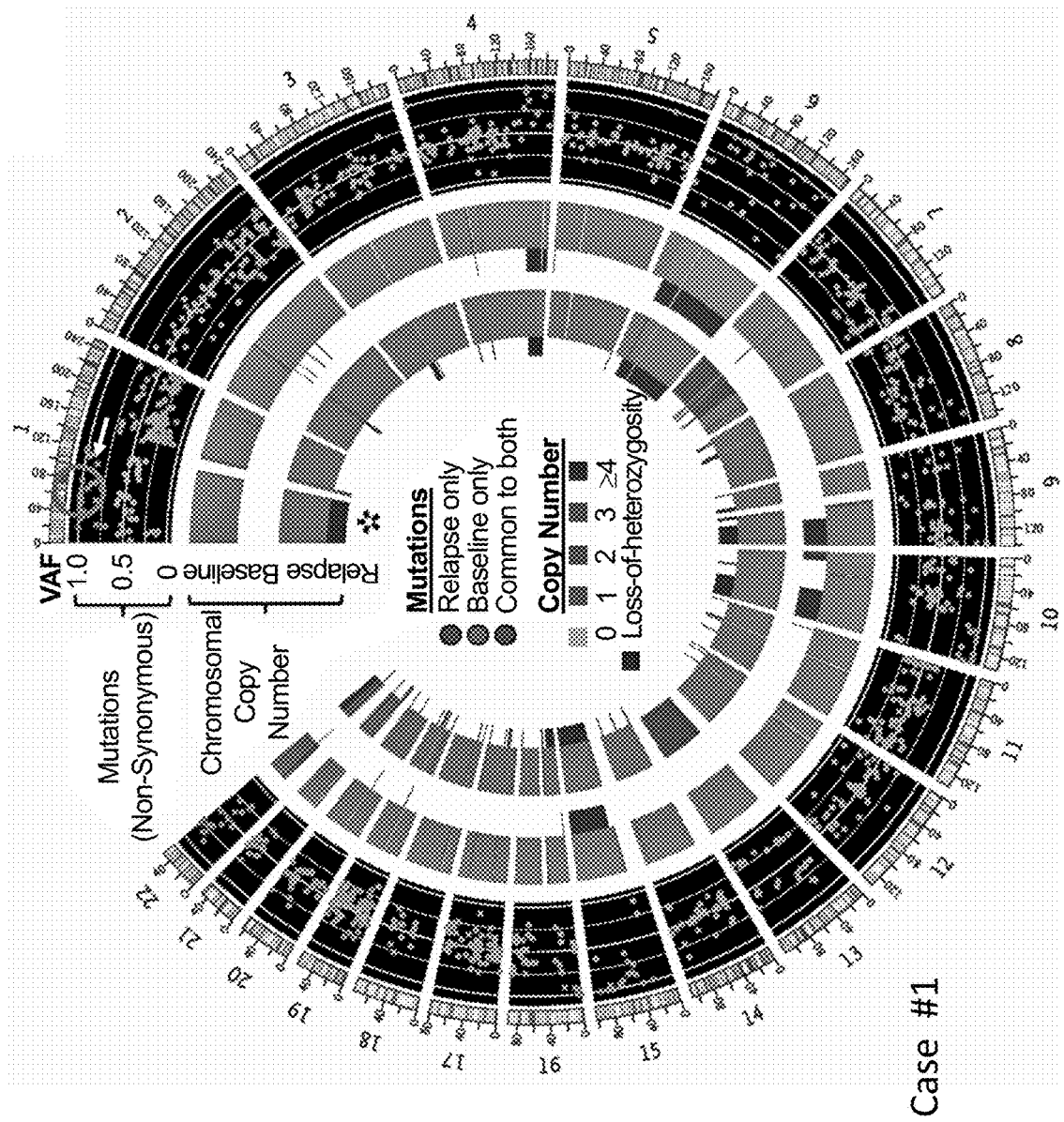
Fig. 2A Case #1

Case #2

METHODS FOR IMMUNOTHERAPY-BASED TREATMENT AND ASSESSMENT OF CANCER

CROSS REFERENCE TO RELATED APPLICATIONS

This application claims the benefit of U.S. Provisional Application No. 62/361,474, filed Jul. 12, 2016, which is hereby incorporated herein in its entirety by reference, for all purposes.

STATEMENT REGARDING FEDERALLY SPONSORED RESEARCH OR DEVELOPMENT

This invention was made with Government support under Grant Numbers CA168585 and CA199205, awarded by the National Institutes of Health. The government has certain rights in the invention.

SEQUENCE LISTING

The instant application contains a Sequence Listing which has been submitted via EFS-Web and is hereby incorporated herein by reference in its entirety. Said ASCII copy, created on Sep. 28, 2017, is named "2017_09_28_33484_37623US_ST25", and is 13,345 bytes in size.

BACKGROUND

Durable responses in metastatic cancers have been obtained with a variety of immunotherapies such as interleukin-2 (IL-2), tumor-infiltrating lymphocyte (TIL) adoptive cell transfer therapy, cytotoxic T lymphocyte antigen-4 (CTLA4) blocking antibodies[1-5] and with programmed death 1 (PD-1) blocking antibodies[6-10]. Approximately 75% of objective responses to anti-programmed death (PD-1) therapy are durable, lasting years but delayed relapses have been noted long after an initial objective tumor regression while on continuous therapy. Approximately 25% of patients with an objective response to PD-1 blockade therapy in melanoma developed progression with a median follow up of 21 months[11]. Mechanisms of immune escape in this setting have remained unknown.

SUMMARY

Disclosed herein is a method of treating a subject having cancer, comprising: administering to the subject an anti-PD-1 therapy, an anti-PD-L1 therapy, an anti-CTLA-4 therapy, or a combination thereof, wherein the cancer has been determined to not comprise a loss of function mutation or disruption in an interferon signaling pathway or a loss of function mutation or disruption in an MHC class I antigen presentation pathway; or administering to the subject an alternative therapy to that in (a) wherein the cancer has been determined to comprise at least one loss of function mutation or disruption in an interferon signaling pathway or at least one loss of function mutation or disruption in an MHC class I antigen presentation pathway.

In some aspects, the loss of function mutation or disruption in an interferon signaling pathway is a mutation or disruption that truncates a Janus kinase 1 (JAK1) or a Janus kinase 2 (JAK2) protein, inactivates a JAK1 or a JAK2 protein, deletes a JAK1 or a JAK2 gene, or alters normal mRNA processing of a JAK1 or a JAK2 gene. In some aspects, the loss of function mutation or disruption in an interferon signaling pathway is a mutation or disruption that truncates a JAK1 protein, inactivates a JAK1 protein, deletes a JAK1 gene, or alters normal mRNA processing of a JAK1 gene. In some aspects, the loss of function mutation or disruption in an interferon signaling pathway is a mutation or disruption that truncates a JAK2 protein, inactivates a JAK2 protein, deletes a JAK2 gene, or alters normal mRNA processing of a JAK2 gene.

In some aspects, the mutation is JAK1 Q503*, JAK1 W690*, JAK1 D775N, JAK1 P429S, JAK1 F111L, JAK2 F547_splice, JAK2 D313_splice, JAK2 T555S, JAK2 N729I, JAK2 R761K, or JAK2 P1023S.

In some aspects, the loss of function mutation or disruption in the interferon signaling pathway is a mutation or disruption that truncates a protein, inactivates a protein, or alters normal mRNA processing of a gene of at least one of: interferon gamma receptor 1 (IFNGR1), interferon gamma receptor 2 (IFNGR2), signal transducer and activator of transcription 1 (STAT1), signal transducer and activator of transcription 3 (STAT3), signal transducer and activator of transcription 5 (STAT5), tyrosine kinase 2 (TYK2), interferon induced proteins with tetratricopeptide repeats (IFIT) genes, or interferon regulatory factor (IRF) genes.

In some aspects, the loss of function mutation or disruption in the MHC class I antigen presentation pathway is a mutation or disruption that truncates a beta-2 microglobulin (B2M) protein, inactivates a B2M protein, deletes a B2M gene, or alters normal mRNA processing of a B2M gene. In some aspects, the mutation is an S14_frame-shift in B2M.

In some aspects, the loss of function mutation or disruption in an interferon signaling pathway is a loss of function mutation. In some aspects, the loss of function mutation or disruption in an MHC class I antigen presentation pathway is a loss of function mutation. In some aspects, the loss of function mutation or disruption in an interferon signaling pathway is a loss of function disruption. In some aspects, the loss of function mutation or disruption in an MHC class I antigen presentation pathway is a loss of function disruption.

In some aspects, the mutation is homozygous. In some aspects, the mutation is present at an allelic frequency different than that of a wild-type allele. In some aspects, no copies of the wild-type allele remain. In some aspects, the disruption is epigenetic silencing.

In some aspects, the method comprises administering to the subject anti-PD-1 therapy, anti-PD-L1 therapy, anti-CTLA-4 therapy, or a combination thereof, wherein the cancer has been determined to not comprise the loss of function mutation or disruption in an interferon signaling pathway or the loss of function mutation or disruption in an MHC class I antigen presentation pathway. In some aspects, the method comprises administering to the subject the alternative therapy wherein the cancer has been determined to comprise the at least one loss of function mutation or disruption in an interferon signaling pathway or the at least one loss of function mutation or disruption in an antigen presentation pathway.

In some aspects, the cancer is PD-L1 positive (+). In some aspects, the cancer is PD-L1+ at least prior to treatment with anti-PD-1 therapy, anti-PD-L1 therapy, or anti-CTLA-4 therapy. In some aspects, the cancer is PD-L1 negative (−). In some aspects, the cancer was previously PD-L1 positive (+). In some aspects, the cancer is melanoma, skin cutaneous melanoma, non-small cell lung cancer, colon cancer, endometrial cancer, kidney cancer, bladder cancer, Merkel cell carcinoma, Hodgkin lymphoma, breast invasive carcinoma, prostate adenocarcinoma, lung adenocarcinoma, or colorectal adenocarcinoma.

In some aspects, the subject has not previously been administered an anti-PD-1 therapy, an anti-PD-L1 therapy, an anti-CTLA-4 therapy, or a combination thereof. In some aspects, the subject has previously been administered an anti-PD-1 therapy, an anti-PD-L1 therapy, an anti-CTLA-4 therapy, or a combination thereof. In some aspects, the cancer is refractory to the anti-PD-1 therapy, the anti-PD-L1 therapy, the anti-CTLA-4 therapy, or the combination thereof. In some aspects, the anti-PD-1 therapy comprises an anti-PD-1 antibody, optionally wherein the antibody comprises nivolumab/BMS-936558/MDX-1106, pembrolizumab/MK-3475, pidilizumab/CT-011, or PDR001. In some aspects, the anti-PD-L1 therapy comprises an anti-PD-L1 antibody, optionally wherein the antibody comprises BMS-936559, MPDL3280A/atezolizumab, MSB00100718C/avelumab, or MEDI4736/durvalumab. In some aspects, the anti-CTLA-4 therapy comprises an anti-CTLA-4 antibody, optionally wherein the antibody comprises ipilimumab or tremelimumab.

In some aspects, the alternative therapy is selected from the group consisting of: a MAPK targeted therapy, optionally at least one of a mutant BRAF inhibitor, Vemurafenib/PLX4032, Dabrafenib, Encorafenib/LGX818, a MEK inhibitor, Trametinib/GSK1120212, Selumetinib/AZD6244, MEK162/Binimetinib, Cobimetinib/GDC0973, PD0325901, an ERK 30 inhibitor, SCH772984, VTX-11e, a Pan RAF inhibitor, Sorafenib, CCT196969, CCT241161, PLX7904, and PLX8394; an anti-angiogenic therapy, optionally at least one of Sorafenib, Sunitinib, Pazopanib, Everolimus, Bevacizumab, Ranibizumab, and PLX3397; an adoptive cell transfer therapy, optionally at least one of a CAR T-cell therapy, a transduced T-cell therapy, and a tumor infiltrating lymphocyte (TIL) therapy; and any combination of the above with or without anti-PD-1 antibody, optionally nivolumab/BMS-936558/MDX-1106, pembrolizumab/MK-3475, pidilizumab, or PDR0001; and/or an anti-PD-L1 antibody, optionally BMS-986559, MPDL3280A/atezolizumab, MSB00100718C/avelumab, or MEDI4736/durvalumab.

In some aspects, the alternative therapy comprises an oncolytic viral therapy when the loss of function mutation or disruption in the interferon signaling pathway is a mutation or disruption that truncates JAK1 or JAK2, inactivates JAK1 or JAK2, deletes JAK1 or JAK2, or alters normal mRNA processing of JAK1 or JAK2.

In some aspects, the alternative therapy comprises a type I interferon therapy or type I interferon-inducing therapy when the loss of function mutation or disruption in the interferon signaling pathway is a mutation or disruption that truncates JAK2, inactivates JAK2, deletes JAK2, or alters normal mRNA processing of JAK2 In some aspects, the type I interferon therapy comprises administering interferon alpha and/or interferon beta. In some aspects, the type I interferon inducing therapy comprises a cyclic GMP-AMP Synthase (cGAS)/Stimulator of Interferon Genes (STING) pathway agonist. In some aspects, the cGAS/STING pathway agonist is 2'3'-cyclic-GMP-AMP (2'3'-cGAMP). In some aspects, the type I interferon inducing therapy comprises a toll-like receptor (TLR) agonist therapy, optionally comprising at least one of a TLR3, a TLR7, a TLR8, and a TLR9 agonist.

In some aspects, the alternative therapy comprises a NK cell activating therapy when the loss of function mutation or disruption in the MHC class I antigen presentation pathway is a mutation or disruption that truncates B2M, inactivates B2M, deletes B2M, or alters normal mRNA processing of B2M.

In some aspects, the method further comprises having determined or determining whether the cancer comprises the loss of function mutation or disruption in an interferon signaling pathway or the loss of function mutation or disruption in an MHC class I antigen presentation pathway. In some aspects, the determining step comprises obtaining a sample from the cancer and processing the sample to experimentally determine its mutation status. In some aspects, the determining step comprises obtaining a dataset from a third party that has processed a sample from the cancer to experimentally determine mutation status. In some aspects, the determining step comprises using a sequencing assay In some aspects, the sequencing assay comprises next generation sequencing (NGS) or Sanger sequencing In some aspects, the sequencing assay further comprises prior target amplification by PCR. In some aspects, NGS comprises whole-exome sequencing, whole-genome sequencing, de novo sequencing, phased sequencing, targeted amplicon sequencing, or shotgun sequencing. In some aspects, the determining step further comprises experimentally determining an RNA profile status of the mutation. In some aspects, the experimentally determining the RNA profile status comprises an RNA-Seq or a qPCR assay.

Also disclosed herein is a method of assessing a subject having cancer, comprising: (a) determining or having determined whether the cancer comprises a loss of function mutation or disruption in an interferon signaling pathway or a loss of function mutation or disruption in an MHC class I antigen presentation pathway; and (b) determining or having determined from the results of (a) that the subject is a candidate for: an anti-PD-1 therapy, an anti-PD-L1 therapy, an anti-CTLA-4 therapy, or a combination thereof when the cancer is negative for a loss of function mutation or disruption in an interferon signaling pathway or a loss of function mutation or disruption in an MHC class I antigen presentation pathway; or an alternative therapy to that of an anti-PD-1 therapy, an anti-PD-L1 therapy, an anti-CTLA-4 therapy, or a combination thereof when the cancer is positive for at least one loss of function mutation or disruption in an interferon signaling pathway or at least one loss of function mutation or disruption in an MHC class I antigen presentation pathway.

In some aspects, step (a) comprises obtaining a sample from the cancer and assaying the sample using NGS, Sanger sequencing, targeted sequencing, whole exome sequencing, and/or whole genome sequencing; and the method further comprises (c) administering a therapy to the subject based on the results of step (b). In some aspects, the determining step comprises obtaining a dataset from a third party that has processed a sample from the cancer to experimentally determine mutation status. In some aspects, the sample is selected from tissue, bodily fluid, blood, tumor biopsy, spinal fluid, and needle aspirate.

In some aspects, the loss of function mutation or disruption in an interferon signaling pathway is a mutation or disruption that truncates a Janus kinase 1 (JAK1) or a Janus kinase 2 (JAK2) protein, inactivates a JAK1 or a JAK2 protein, deletes a JAK1 or a JAK2 gene, or alters normal mRNA processing of a JAK1 or a JAK2 gene. In some aspects, the loss of function mutation or disruption in an interferon signaling pathway is a mutation or disruption that truncates a JAK1 protein, inactivates a JAK1 protein, deletes a JAK1 gene, or alters normal mRNA processing of a JAK1 gene In some aspects, the loss of function mutation or disruption in an interferon signaling pathway is a mutation or disruption that truncates a JAK2 protein, inactivates a JAK2 protein, deletes a JAK2 gene, or alters normal mRNA processing of a JAK2 gene.

In some aspects, the mutation is JAK1 Q503*, JAK1 W690*, JAK1 D775N, JAK1 P429S, JAK1 F111L, JAK2 F547_splice, JAK2 D313_splice, JAK2 T555S, JAK2 N729I, JAK2 R761K, or JAK2 P1023S In some aspects, the loss of function mutation or disruption in the interferon signaling pathway is a mutation or disruption that truncates, inactivates, or alters normal mRNA processing of at least one of: interferon gamma receptor 1 (IFNGR1), interferon gamma receptor 2 (IFNGR2), signal transducer and activator of transcription 1 (STAT1), signal transducer and activator of transcription 3 (STAT3), signal transducer and activator of transcription 5 (STAT5), tyrosine kinase 2 (TYK2), interferon induced proteins with tetratricopeptide repeats (IFIT) genes, or interferon regulatory factor (IRF) genes.

In some aspects, the loss of function mutation or disruption in an interferon signaling pathway is a loss of function mutation In some aspects, the loss of function mutation or disruption in an interferon signaling pathway is a loss of function disruption.

In some aspects, the loss of function mutation or disruption in the MHC class I antigen presentation pathway is a mutation or disruption that truncates a beta-2 microglobulin (B2M) protein, inactivates a B2M protein, deletes a B2M gene, or alters normal mRNA processing of a B2M gene. In some aspects, the mutation is an S14_frame-shift in B2M.

In some aspects, the loss of function mutation or disruption in an MHC class I antigen presentation pathway is a loss of function mutation In some aspects, the loss of function mutation or disruption in an MHC class I antigen presentation pathway is a loss of function disruption.

In some aspects, the mutation is homozygous In some aspects, the mutation is present at an allelic frequency different than that of a wild-type allele In some aspects, no copies of the wild-type allele remain. In some aspects, the disruption is epigenetic silencing.

In some aspects, the method comprises determining or having determined from the results of (a) that the subject is a candidate for: anti-PD-1 therapy, anti-PD-L1 therapy, anti-CTLA-4 therapy, or a combination thereof, wherein the cancer has been determined to not comprise the loss of function mutation or disruption in an interferon signaling pathway or the loss of function mutation or disruption in an MHC class I antigen presentation pathway. In some aspects, the method comprises determining or having determined from the results of (a) that the subject is a candidate for: the alternative therapy wherein the cancer has been determined to comprise the at least one loss of function mutation or disruption in an interferon signaling pathway or the at least one loss of function mutation or disruption in an antigen presentation pathway.

In some aspects, the cancer is PD-L1 positive (+). In some aspects, the cancer is PD-L1+ at least prior to treatment with anti-PD-1 therapy, anti-PD-L1 therapy, or anti-CTLA-4 therapy. In some aspects, the cancer is PD-L1 negative (−). In some aspects, the cancer was previously PD-L1 positive (+). In some aspects, the cancer is melanoma, skin cutaneous melanoma, non-small cell lung cancer, colon cancer, endometrial cancer, kidney cancer, bladder cancer, Merkel cell carcinoma, Hodgkin lymphoma, breast invasive carcinoma, prostate adenocarcinoma, lung adenocarcinoma, or colorectal adenocarcinoma.

In some aspects, the subject has not previously been administered an anti-PD-1 therapy, an anti-PD-L1 therapy, an anti-CTLA-4 therapy, or a combination thereof. In some aspects, the subject has previously been administered an anti-PD-1 therapy, an anti-PD-L1 therapy, an anti-CTLA-4 therapy, or a combination thereof. In some aspects, the cancer is refractory to the anti-PD-1 therapy, the anti-PD-L1 therapy, the anti-CTLA-4 therapy, or the combination thereof. In some aspects, the anti-PD-1 therapy comprises an anti-PD-1 antibody, optionally wherein the antibody comprises nivolumab/BMS-936558/MDX-1106, pembrolizumab/MK-3475, pidilizumab/CT-011, or PDR001. In some aspects, the anti-PD-L1 therapy comprises an anti-PD-L1 antibody, optionally wherein the antibody comprises BMS-936559, MPDL3280A/atezolizumab, MSB00100718C/avelumab, or MEDI4736/durvalumab. In some aspects, the anti-CTLA-4 therapy comprises an anti-CTLA-4 antibody, optionally wherein the antibody comprises ipilimumab or tremelimumab.

In some aspects, the alternative therapy is selected from the group consisting of: a MAPK targeted therapy, optionally at least one of a mutant BRAF inhibitor, Vemurafenib/PLX4032, Dabrafenib, Encorafenib/LGX818, a MEK inhibitor, Trametinib/GSK1120212, Selumetinib/AZD6244, MEK162/Binimetinib, Cobimetinib/GDC0973, PD0325901, an ERK 30 inhibitor, SCH772984, VTX-11e, a Pan RAF inhibitor, Sorafenib, CCT196969, CCT241161, PLX7904, and PLX8394; an anti-angiogenic therapy, optionally at least one of Sorafenib, Sunitinib, Pazopanib, Everolimus, Bevacizumab, Ranibizumab, and PLX3397; an adoptive cell transfer therapy, optionally at least one of a CAR T-cell therapy, a transduced T-cell therapy, and a tumor infiltrating lymphocyte (TIL) therapy; and any combination of the above with or without anti-PD-1 antibody, optionally nivolumab/BMS-936558/MDX-1106, pembrolizumab/MK-3475, pidilizumab, or PDR0001; and/or an anti-PD-L1 antibody, optionally BMS-986559, MPDL3280A/atezolizumab, MSB00100718C/avelumab, or MEDI4736/durvalumab.

In some aspects, the alternative therapy comprises an oncolytic viral therapy when the loss of function mutation or disruption in the interferon signaling pathway is a mutation or disruption that truncates JAK1 or JAK2, inactivates JAK1 or JAK2, deletes JAK1 or JAK2, or alters normal mRNA processing of JAK1 or JAK2.

In some aspects, the alternative therapy comprises a type I interferon therapy or type I interferon-inducing therapy when the loss of function mutation or disruption in the interferon signaling pathway is a mutation or disruption that truncates JAK2, inactivates JAK2, deletes JAK2, or alters normal mRNA processing of JAK2 In some aspects, the type I interferon therapy comprises administering interferon alpha and/or interferon beta. In some aspects, the type I interferon inducing therapy comprises a cyclic GMP-AMP Synthase (cGAS)/Stimulator of Interferon Genes (STING) pathway agonist. In some aspects, the cGAS/STING pathway agonist is 2'3'-cyclic-GMP-AMP (2'3'-cGAMP). In some aspects, the type I interferon inducing therapy comprises a toll-like receptor (TLR) agonist therapy, optionally comprising at least one of a TLR3, a TLR7, a TLR8, and a TLR9 agonist.

In some aspects, the alternative therapy comprises a NK cell activating therapy when the loss of function mutation or disruption in the MHC class I antigen presentation pathway is a mutation or disruption that truncates B2M, inactivates B2M, deletes B2M, or alters normal mRNA processing of B2M.

In some aspects, the determining step (a) comprises using a sequencing assay. In some aspects, the sequencing assay comprises (1) next generation sequencing (NGS); or (2) Sanger sequencing. In some aspects, the sequencing assay further comprises prior target amplification by PCR. In some aspects, NGS comprises whole-exome sequencing, whole-genome sequencing, de novo sequencing, phased sequencing, targeted amplicon sequencing, or shotgun sequencing. In some aspects, the determining step further comprises experimentally determining an RNA profile status of the mutation. In some aspects, the experimentally determining the RNA profile status comprises an RNA-Seq or a qPCR assay.

BRIEF DESCRIPTION OF THE SEVERAL VIEWS OF THE DRAWINGS

These and other features, aspects, and advantages of the present invention will become better understood with regard to the following description, and accompanying drawings, where.

DETAILED DESCRIPTION

Figure 1:
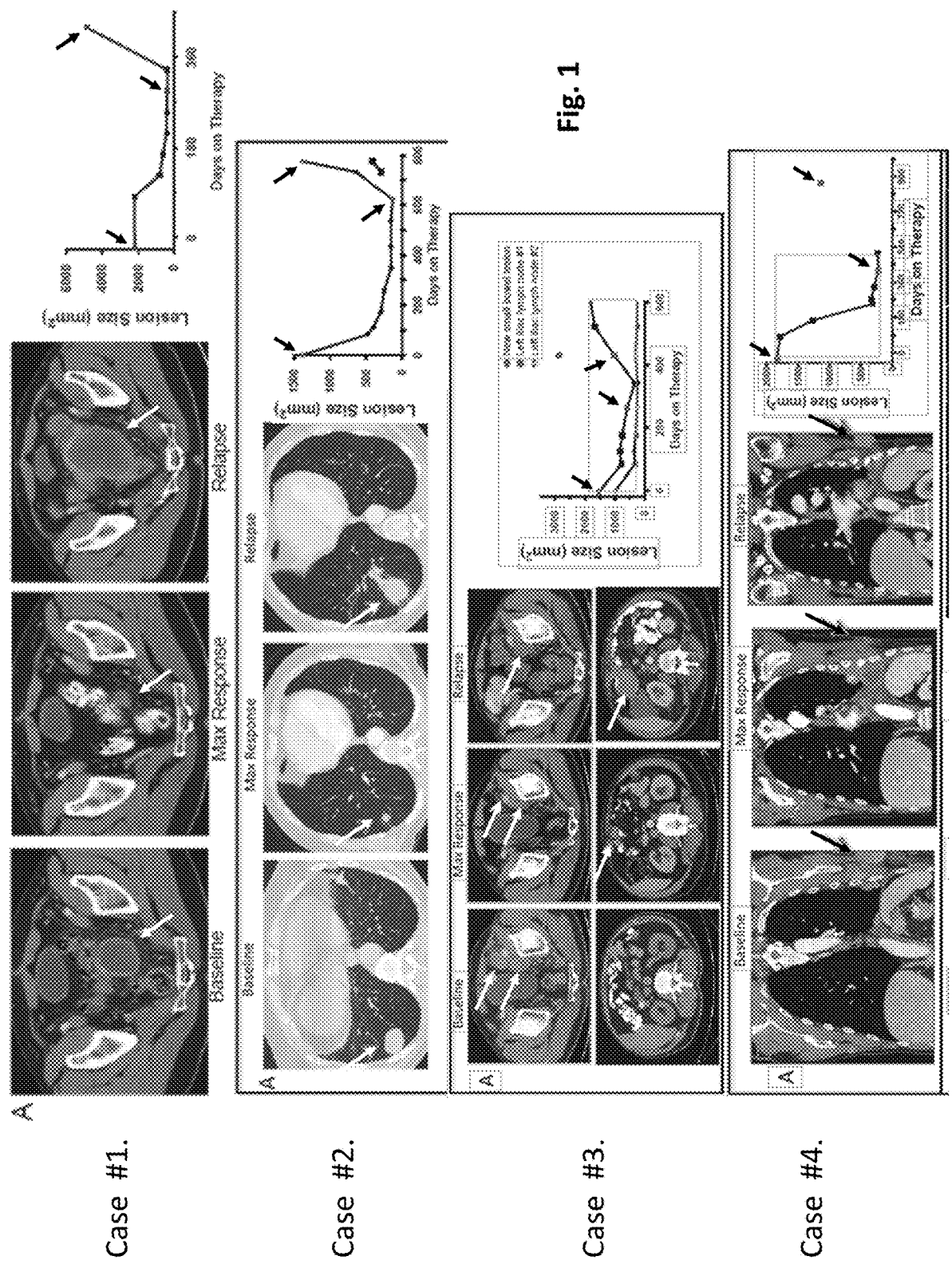
FIG. 1. Clinical pattern of acquired resistance to anti-PD-1 therapy. Case #1, CT images show a melanoma small bowel metastasis at baseline, at the time of maximum response, and with an in-situ relapse after a year of minimal residual disease. Case #2 exhibited a 90% response in a solitary lung metastasis, followed by relapse in-situ after almost two years of minimal residual disease. In case #3, inguinal lesions from baseline showed partial (bottom arrows) or complete (top arrows) regression. The relapse biopsy comes from a small bowel lesion first visualized at 264 days, with clear progression 453 days from therapy start. Case #4 had an initial pseudo-progression followed by a tumor response, as previously described.[40] Arrows in CT images denote lesions. Two-dimensional size of the lesions are indicated on the graph to the right of their respective CT image, and corresponding time-points of images indicated by arrows.

Briefly, and as described in more detail below, described herein is a method for treating a subject with cancer. The present invention relates to the discovery that rarely occurring genetic mutations in the interferon receptor signaling pathway can result in lack of PD-L1 upregulation upon interferon exposure and result in innate resistance to PD-1 blockade immunotherapy. This discovery enables the selection of a more appropriate treatment strategy for a subset of subjects who are unlikely to respond to immunotherapies, including anti-PD-1 therapy, as well as enabling the identification of a subset of subjects who are unlikely to respond to immunotherapies.

Terms used in the claims and specification are defined as set forth below unless otherwise specified.

The term "cancer" refers to all neoplastic cell growth and proliferation, whether malignant or benign, and all precancerous and cancerous cells and tissues. The terms "cancer," "cancerous," "cell proliferative disorder," "proliferative disorder" and "tumor" are not mutually exclusive as referred to herein. The terms "cell proliferative disorder" and "proliferative disorder" refer to disorders that are associated with some degree of abnormal cell proliferation. Types of cancer include, but are not limited to, melanoma, non-small cell lung cancer, colon cancer, endometrial cancer, kidney cancer, bladder cancer, Merkel cell carcinoma, Hodgkin lymphoma, breast invasive carcinoma, or prostate adenocarcinoma.

The term "PD-L1+" refers to a sample, including a cancer tissue sample or biopsy, that is positive for the marker PD-L1. The sample can be determined to be positive for the marker PD-L1 by immunohistochemistry, immunostaining, RT-qPCR, RNA-Seq, or any other method known to those skilled in the art. For example, a cancer or cancer sample can be PD-L1+ or PD-L1−.

The term "administered" refers to treating a subject with a therapeutically effective amount of a pharmaceutical composition. Conventional and pharmaceutically acceptable routes of administration include, but are not limited to, intravenous, intranasal, intramuscular, intra-tracheal, subcutaneous, intradermal, rectal, oral and other parental routes of administration. Routes of administration can be combined, if desired, or adjusted depending upon the disease. The route of administration primarily will depend on the nature of the disease being treated.

The term "pharmaceutical composition" refers to a preparation which is in such form as to permit the biological activity of an active ingredient contained therein to be effective in treating a subject, and which contains no additional components which are unacceptably toxic to the subject in the amounts provided in the pharmaceutical composition.

The term "therapeutically effective amount" is an amount that is effective to ameliorate a symptom of a disease. A therapeutically effective amount can be a "prophylactically effective amount" as prophylaxis can be considered therapy.

The term "treating" (and variations thereof such as "treat" or "treatment") refers to clinical intervention in an attempt to alter the natural course of a disease or condition in a subject in need thereof. Treatment can be performed both for prophylaxis and during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

The term "mutation" refers to an alteration in the nucleotide sequence of a subject's genome. Mutations may affect the coding region of a gene and include, but are not limited to, a missense mutation causing a substitution from one amino acid to another, a nonsense mutation causing a substitution from an amino acid to a stop codon, or a frameshift mutation causing a change in the frame of the protein translated. A mutation may result in the truncation of a protein, wherein the full-length protein is not expressed. A mutation may result in the inactivation of a protein, wherein the protein can no longer perform the full activity of the wild-type protein. A mutation may be in a non-coding region of a gene and include, but are not limited to, mutations in promoter elements, 5' untranslated regions (5'-UTR), 3' untranslated regions (3'-UTR), and introns. A mutation may result in an alteration of the normal RNA processing, such as improper RNA splicing, nonsense mediated decay, nonstop decay, or no-go decay. A mutation may alter the RNA expression level of a gene. A mutation may be a point mutation, wherein there is a single nucleotide difference. A mutation may be an insertion, deletion, or alteration of more than one nucleotide.

The term "loss of function mutation" refers to a mutation that results in a gene product no longer being able to perform its normal function or its normal level of activity, in whole or in part. Loss of function mutations are also referred to as inactivating mutations and typically result in the gene product having less or no function, i.e., being partially or wholly inactivated.

The term "loss of function disruption" refers to an alteration that results in a gene product no longer being able to perform its normal function or its normal level of activity, in whole or in part. Loss of function disruptions include epigenetic silencing. Epigenetic silencing refers to non-mutational gene inactivation that can be propagated from precursor cells to clones of daughter cells. The addition of methyl groups to cytosine residues in CpG dinucleotides in DNA is an exemplary biochemical modification that meets this requirement.

As used herein, the term "sequencing" refers to the process of determining the nucleotide sequence of a polynucleotide, including, but not limited to, RNA, mRNA, DNA, full genomic DNA, or exome DNA. Sequencing can be performed by a number of methods including, but not limited to, Sanger sequencing or next-generation sequencing (Illumina, 454, SOLiD, Ion torrent etc.). Sequencing includes next generation sequencing (NGS).

The term "interferon signaling pathway" refers to any part of either the type-I interferon (interferon α or β) or the type-II interferon (interferon γ) signaling networks, including, but not limited to, receptors, kinases, transcription factors, genes regulated by interferon signaling, positive regulators of interferon signaling, or negative regulators of interferon signaling.

The term "MHC class I antigen presentation pathway" refers to any gene involved in the processing or presenting of antigenic peptides on MHC class I molecules. Genes involved in the pathway include, but are not limited to, components of MHC class I molecules, components of the peptide-loading complex, and components of the immunoproteosome.

The term "refractory" refers to a state of a disease, such as cancer, where the disease is no longer responsive to a given treatment. In some instances, the disease may have previously been responsive to the given treatment but is no longer responsive. In some instances, the disease may be refractory to a given treatment due to mutations.

As used herein the term "exome" is a subset of the genome that encodes for proteins. An exome can be the collective exons of a genome.

The term "immune checkpoint therapy" or "immunotherapy" refers to therapies that stimulate a subject's immune own system to target disease, including cancer. Many immunotherapies work through inhibiting various immune checkpoints that limit activation of the immune system, thus the inhibition of the checkpoints in turn allows activation of the immune system. Illustrative immune checkpoint inhibitors include Tremelimumab (CTLA-4 blocking antibody), anti-OX40, PD-L1 monoclonal antibody (Anti-B7-H1; MEDI4736), ipilimumab, MK-3475 (PD-1 blocker), Nivolumamb (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody) and Yervoy/ipilimumab (anti-CTLA-4 checkpoint inhibitor).

The term "ameliorating" refers to any therapeutically beneficial result in the treatment of a disease state, e.g., a cancerous disease state, including prophylaxis, lessening in the severity or progression, remission, or cure thereof.

The term "in situ" refers to processes that occur in a living cell growing separate from a living organism, e.g., growing in tissue culture.

The term "in vivo" refers to processes that occur in a living organism.

The term "mammal" as used herein includes both humans and non-humans and include but is not limited to humans, non-human primates, canines, felines, murines, bovines, equines, and porcines.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are inputted into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (http://www.ncbi.nlm.nih.gov/).

The term "sufficient amount" means an amount sufficient to produce a desired effect, e.g., an amount sufficient to modulate protein aggregation in a cell.

It must be noted that, as used in the specification and the appended claims, the singular forms "a," "an" and "the" include plural referents unless the context clearly dictates otherwise.

Methods

Methods of treating a subject having cancer are described herein in more detail. Also described herein are methods of assessing a subject having cancer.

I. Cancer Therapy

Described herein is a method of treating a subject having cancer. The method includes administering to the subject a therapy. The choice of therapy provided for by the method is directed by the mutation status of the cancer. In some embodiments, the method includes administering to the subject an immune checkpoint therapy when a cancer has been determined to not comprise a loss of function mutation in pathways involved in immune activation. Alternatively, the method includes administering to the subject an alternative therapy to that of to an immune checkpoint therapy when a cancer has been determined to comprise a loss of function mutation in pathways involved in immune activation. In some embodiments the cancer is melanoma. In some embodiments the melanoma is skin cutaneous melanoma. In some embodiments, melanoma is metastatic. In some embodiments the cancer is non-small cell lung cancer, colon cancer, endometrial cancer, kidney cancer, bladder cancer, Merkel cell carcinoma, Hodgkin lymphoma, breast invasive carcinoma, prostate adenocarcinoma, lung adenocarcinoma, or colorectal adenocarcinoma. In some embodiments, the cancer is PD-L1+.

I.A. Immune Checkpoint Therapy

In some embodiments, the method includes administering an immune checkpoint therapy. Immune checkpoint therapy includes targeting one or more immune checkpoint molecules with a therapeutically effective amount of a pharmaceutical composition in order to block or inhibit the activity of the one or more immune checkpoint molecules. In some embodiments, the immune checkpoint molecules that can be targeted for blocking or inhibition include, but are not limited to, CTLA-4, 4-1BB (CD137), 4-1BBL (CD137L), PDL1, PDL2, PD1, B7-H3, B7-H4, BTLA, HVEM, TIM3, GALS, LAG3, TIM3, B7H3, B7H4, VISTA, KIR, 2B4 (belongs to the CD2 family of molecules and is expressed on all NK, γδ, and memory CD8+ (αβ) T cells), CD160 (also referred to as BY55), and CGEN-15049.

In some embodiments, immune checkpoint therapy includes administration of immune checkpoint inhibitors. In some embodiments, immune checkpoint therapy includes administration of one or more immune checkpoint inhibitors. In some embodiments, the immune checkpoint inhibitors include antibodies that specifically target immune checkpoint molecules. Illustrative immune checkpoint inhibitors include pembrolizumab (MK-3475, PD-1 blocker), Nivolumab (anti-PD1 antibody), pidilizumab (CT-011, anti-PD1 antibody), PDR001, durvalumab (anti-PD-L1 antibody Anti-B7-H1; MEDI4736), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody), anti-OX40, Tremelimumab (anti-CTLA-4 antibody) and Yervoy/ipilimumab (anti-CTLA-4 antibody).

In some embodiments, immune checkpoint therapy can be administered to a subject having cancer, wherein the cancer has been determined to not comprise a loss of function mutation in an immune pathway. In some embodiments, immune checkpoint therapy can be administered to a subject having cancer, wherein the cancer has been determined to not comprise a loss of function mutation in an interferon signaling pathway or a loss of function mutation in an MHC class I antigen presentation pathway. In some embodiments, immune checkpoint therapy can be administered to a subject having cancer, wherein the cancer has been determined to not comprise a loss of function mutation in an interferon signaling pathway.

In some embodiments, the cancer is known to be positive for the marker PD-L1. The cancer can be determined to be positive for the marker PD-L1 by means known to those skilled in the art. An illustrative example is described in detail in Robert et al. [N Engl J Med 2015; 372:320-30, incorporated herein by reference].

In some embodiments, immune checkpoint therapy can be administered to a subject that has not previously received immune checkpoint therapy. In some embodiments, immune checkpoint therapy can be administered to a subject that has previously received immune checkpoint therapy. In some embodiments, immune checkpoint therapy can be administered to a subject that has previously received immune checkpoint therapy but wherein the cancer has relapsed.

In some embodiments, the immune checkpoint therapy can be administered in combination with one or more therapies that are not an immune checkpoint therapy. In some embodiments, the immune checkpoint therapy can be administered in combination with one or more of a MAPK targeted therapy or an anti-angiogenic therapy.

I.B. Alternative Therapies to Immunotherapy

In some embodiments, the method includes administering an alternative therapy to a subject having cancer. In some embodiments, the alternative therapy can be any therapy that is effective in treating the cancer but is not an immune checkpoint therapy. In some embodiments, the method includes administering an alternative therapy to a subject having cancer when the cancer has been determined to comprise at least one loss of function mutation in an interferon signaling pathway or at least one loss of function mutation in an MHC class I antigen presentation pathway.

In some embodiments, the alternative therapy can be an anti-angiogenic therapy. Illustrative examples of anti-angiogenic therapies include, but are not limited to, Sorafenib, Sunitinib, Pazopanib, Everolimus, Bevacizumab, Ranibizumab, and PLX3397.

In some embodiments, the alternative therapy can be a MAPK targeted therapy. Illustrative examples of a MAPK targeted therapies include, but are not limited to, a mutant BRAF inhibitor, Vemurafenib/PLX4032, Dabrafenib, Encorafenib/LGX818, a MEK inhibitor, Trametinib/GSK1120212, Selumetinib/AZD6244, MEK162/Binimetinib, Cobimetinib/GDC0973, PD0325901, an ERK inhibitor, SCH772984, VTX-11e, a Pan RAF inhibitor, Sorafenib, CCT196969, CCT241161, PLX7904, and PLX8394.

In some embodiments, an alternative therapy can be administered in combination with one or more therapies that are not the alternative therapy. In some embodiments, an alternative therapy can be administered in combination with an immune checkpoint therapy.

I.B.1. Interferon Treatment and cGAS/STING Pathway Agonists

In some embodiments, the method includes administering an alternative therapy to a subject having cancer, wherein the alternative therapy includes a type I interferon therapy. In some embodiments, type I interferon therapy includes administering a type I interferon. In some embodiments, type I interferon therapy includes administering interferon alpha or interferon beta.

In some embodiments, the method includes administering an alternative therapy to a subject having cancer, wherein the alternative therapy includes a type I interferon-inducing therapy. In some embodiments, the type I interferon-inducing therapy includes administering a cyclic GMP-AMP Synthase (cGAS)/Stimulator of Interferon Genes (STING) pathway agonist. In some embodiments, the cGAS/STING pathway agonist is 2'3'-cyclic-GMP-AMP (2'3'-cGAMP).

In some embodiments, the type I interferon therapy or type I interferon-inducing therapy is administered to a subject having cancer when the cancer has been determined to comprise at least one loss of function mutation in an interferon signaling pathway. In some embodiments, the at least one loss of function mutation in an interferon signaling pathway is a loss of function is a loss of function of Jak2.

II. Loss of Function Mutations

The method described herein includes administering a therapy to a subject with cancer wherein the cancer has been determined to comprise at least one loss of function mutation. In some embodiments, a mutation can be a point mutation, wherein there is a single nucleotide difference. In some embodiments, a mutation can be an insertion, deletion, or alteration of more than one nucleotide. In some embodiments, the mutations can be homozygous. In some embodiments, the mutations can be heterozygous. In some embodiments, the mutations can be present in greater allelic copy numbers than the wild-type or baseline allele.

In some embodiments, the method includes administering a therapy to a subject with cancer wherein the cancer has been determined to comprise at least one loss of function mutation in an interferon signaling pathway or a loss of function mutation in an MHC class I antigen presentation pathway.

II.A. Mutations in Proteins

In some embodiments, the loss of function mutation can be in the coding region of a gene and include, but are not limited to, a missense mutation causing a substitution from one amino acid to another, a nonsense mutation causing a substitution from an amino acid to a stop codon, or a frameshift mutation causing a change in the frame of the protein translated. In some embodiments, the loss of function mutation includes a mutation that truncates a protein, wherein the full-length protein is no longer expressed. In some embodiments, the loss of function mutation includes a mutation that inactivates a protein, wherein the protein can no longer perform the full activity of the wild-type protein.

II.B. Mutations in mRNA Expression and Processing

In some embodiments, the loss of function mutation can be in a non-coding region of a gene and include, but are not limited to, mutations in promoter elements, 5' untranslated regions (5'-UTR), 3' untranslated regions (3'-UTR), and introns. A mutation in a non-coding region may result in loss of function mutation due to an alteration of normal RNA processing, such as improper RNA splicing, nonsense mediated decay, non-stop decay, or no-go decay. A mutation in a non-coding region may result in loss of function mutation due an alteration in the RNA expression level of a gene.

III. Interferon Signaling Pathways

In some embodiments, the method described herein includes administering a therapy to a subject with cancer wherein the cancer has been determined to comprise at least one loss of function mutation in the interferon signaling pathway. In some embodiments, the at least one loss of function mutation in the interferon signaling pathway renders the cancer refractory to immune checkpoint therapy.

In some embodiments, loss of function mutations include a mutation that truncates or inactivates a protein involved in the interferon signaling pathway. In some embodiments, loss of function mutations include a mutation that alters normal mRNA processing of a gene involved in the interferon signaling pathway.

In some embodiments, the protein or gene involved in the interferon signaling pathway can include any protein or gene in the interferon gamma signaling pathway. In some embodiments, the protein or gene involved in the interferon signaling pathway can include any protein or gene in the type I interferon (interferon alpha or beta) signaling pathway. Illustrative examples of proteins and genes involved in the interferon signaling pathway are described in more detail in Platanias et al. [Nat Rev Immunol 2005; 5:375-86, herein incorporated by reference in its entirety].

In some embodiments, the loss of function mutation in the interferon signaling pathway can be a mutation in an interferon receptor, a kinase, a transcription factor, or a downstream gene regulated by interferon.

In some embodiments, the loss of function mutation in the interferon signaling pathway can be a mutation that truncates or inactivates a JAK1 protein. In some embodiments, the loss of function mutation in the interferon signaling pathway can be a mutation that truncates or inactivates a JAK2 protein. In some embodiments, the loss of function mutation in the interferon signaling pathway can be a mutation that alters normal mRNA processing of a JAK1 gene. In some embodiments, the loss of function mutation in the interferon signaling pathway can be a mutation that alters normal mRNA processing of a JAK2 gene.

In some embodiments, the loss of function mutation in the interferon signaling pathway can be a JAK1 Q503*, JAK1 W690*, JAK1 D775N, JAK1 P429S, JAK1 F111L, JAK2 F547_splice, JAK2 D313_splice, JAK2 T555S, JAK2 N729I, JAK2 R761K, or JAK2 P1023 S mutation.

In some embodiments, the loss of function mutation in the interferon signaling pathway can be is a mutation that truncates, inactivates, or alters normal mRNA processing of at least one of: interferon gamma receptor 1 (IFNGR1), interferon gamma receptor 2 (IFNGR2), signal transducer and activator of transcription 1 (STAT1), signal transducer and activator of transcription 3 (STAT3), signal transducer and activator of transcription 5 (STAT5), tyrosine kinase 2

(TYK2), interferon induced proteins with tetratricopeptide repeats (IFIT) genes, or interferon regulatory factor (IRF) genes.

IV. Antigen Presentation Pathway

In some embodiments, the method described herein includes administering a therapy to a subject with cancer wherein the cancer has been determined to comprise at least one loss of function mutation in the MHC class I antigen presentation pathway. In some embodiments, the at least one loss of function mutation in the MHC class I antigen presentation pathway renders the cancer refractory to immune checkpoint therapy.

In some embodiments, loss of function mutations include a mutation that truncates or inactivates a protein involved in the MHC class I antigen presentation pathway. In some embodiments, loss of function mutations include a mutation that alters normal mRNA processing of a gene involved in the MHC class I antigen presentation pathway. In some embodiments, the loss of function mutation in the MHC class I antigen presentation pathway can be a mutation that truncates or inactivates a B2M protein. In some embodiments, the loss of function mutation in the MHC class I antigen presentation pathway can be a mutation that alters normal processing of a B2M gene. In some embodiments, the loss of function mutation in the MHC class I antigen presentation pathway can be an S14_frame-shift in B2M.

In some embodiments, the loss of function mutation in the MHC class I antigen presentation pathway can be a mutation in a MHC component including, but not limited to, B2M, HLA-A, HLA-B, and HLA-C. In some embodiments, the loss of function mutation in the MHC class I antigen presentation pathway can be a mutation in a peptide loading complex component including, but not limited to, TAP1, TAP2, TAPBP, CALR, CANX, and PDIA3. In some embodiments, the loss of function mutation in the MHC class I antigen presentation pathway can be a mutation in a immuno-proteosome component including, but not limited to, ERAP1, ERAP2, PSMB8, PSMB9, PSMB10, PSMB11, NRD1, THOP1, and TPP2.

V. Next Generation Sequencing

Also described herein is a method to determine the mutation status of a cancer. In some embodiments, the method to determine the mutation status of a cancer can include determining whether the cancer comprises a loss of function mutation. In some embodiments, the method to determine the mutation status of a cancer can include determining whether the loss of function mutation is in an interferon signaling pathway MHC class I antigen presentation pathway.

In some embodiments, the method of determining whether the cancer comprises the loss of function mutation can include the use of an assay. In some embodiments, the assay can include a sequencing step. In some embodiments, the sequencing assay can be a next generation sequencing (NGS) assay. Illustrative examples of NGS assays include, but are not limited to, whole-exome sequencing, whole-genome sequencing, de novo sequencing, phased sequencing, or shotgun sequencing.

In some embodiments, the method of determining whether the cancer comprises the loss of function mutation can be used in combination with other methods to determine the mutation status of the cancer. In some embodiments, the NGS assay used to determine whether the cancer comprises the loss of function mutation can be used in combination with other NGS assays, such as RNA-Seq, to determine the RNA profile of the cancer.

In some embodiments, the sequencing assay can include a targeted sequencing approach using Sanger sequencing. In some embodiments, the targeted sequencing approach can be used in combination with qPCR. In some embodiments, the sequencing assay can include a NGS assay used in combination with a targeted sequencing approach using Sanger sequencing.

In some embodiments, the method to determine the mutation status of a cancer can include determining whether the cancer comprises a loss of heterozygosity. In some embodiments, determining whether the cancer comprises a loss of heterozygosity includes determining whether a loss of function mutation is homozygous. In some embodiments, determining whether the cancer comprises a loss of heterozygosity includes determining whether a loss of function mutation is present in greater allelic copy number than the wild-type or baseline allele.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ Ed. (Plenum Press) Vols A and B(1992).

Example 1: Mutations in the Interferon Gamma Signaling Pathway and Antigen Presentation Pathway Lead to Acquired Resistance to Pd-1 Therapy Methods Patients, Response Assessment and Tumor Biopsies Among 78 patients with metastatic melanoma treated with the anti-PD-1 antibody pembrolizumab at UCLA, 42 had an objective response, and 15 of those went on to progress. Of these, four patients met all three selection criteria for this analysis.

First, they had an objective tumor response while participating in a clinical trial with single agent pembrolizumab[6,7,10,11]. Tumor responses were evaluated at 12 weeks, confirmed 4 weeks later, and imaged every 12 weeks thereafter using both the Response Evaluation Criteria in Solid Tumors (RECIST)[17] and the immune-related response criteria (irRC)[18]. Second, patients had late acquired resistance, defined as in-situ recurrence or new lesion development despite continuous dosing after >6 months of tumor response. Third, patients had adequate biopsy material for whole exome sequencing from both pre-pembrolizumab and post-progression timepoints. Tumor biopsies were processed as described to perform pathology analyses, obtain DNA and RNA and attempt to establish cell lines[19,20].

Immunohistochemistry, Immunofluorescence, Western Blot and Flow Cytometry

Methods for immunohistochemistry[19], and Western blotting and flow cytometry analyses[21] were performed and analyzed as previously described and described in more detail below.

Immunohistochemistry and Immunofluorescence

Slides were stained for immunohistochemistry with S100 (Dako, Carpinteria, Calif.), CD8 (Dako), PD-L1 (all clone SP142, Spring Bio, Pleasanton, Calif., except the PD-L1 in Figs S1B, S2B, and S2C which were previously stained[3] with clone 22C3, Merck). Staining was performed at the UCLA Anatomic Pathology IHC Laboratory. Immunostaining was performed on Leica Bond III autostainers using Leica Bond ancillary reagents and REFINE polymer DAB detection system as previously described[40]. Staining for MHC Class I (clone HC 10, Saphire NA, Ann Arbor, Mich.) and MHC Class II (HLA-DR, sc-53319, Santa Cruz Biotechnology, Santa Cruz, Calif.) was performed by the UCLA Translational Pathology Core Laboratory. Slides were scanned at 40× on an Aperio ScanScope AT (Leica Biosystems, Buffalo Grove, Ill.) and analyzed on the Halo Platform (Indica Labs, Corrales, N. Mex.). Immnofluoresecnce was performed with OPAL-5-plex reagents, imaged at 20× on the Vectra Automated Ouantitative Pathology Imaging System, and analyzed using inForm software (all from Perkin-Elmer, Waltham, Mass.). Staining used the following antibodies: S100 (DAKO), CD8 (DAKO), PD-L1 (all clone SP142, Spring Bio), and Sox10 (Biocare Medical, Concord, Calif.).

Western Blot and Flow Cytometry Analyses

Melanoma cell lines were maintained in 10 cm culture dishes and analyzed when approximately 70% confluent. Western blot and flow cytometry was performed as previously described[48,49] upon exposure to interferon alpha, beta or gamma (BD Bioscience, San Jose, Calif.) for 30 minutes or 18 hours. Experiments were performed at least twice for each cell line. Primary antibodies included JAK1, JAK2, pSTAT1 (Tyr701), pSTAT3 (Tyr705), STAT1 and STAT3 total protein; IRF-1, PD-L1, TAP1 and GAPDH (all from Cell Signaling Technology, Danvers, Mass.) as well as MHC class I heavy chain clones HCA2 for HLA-A and clone HC10 for HLA-B/C (both from Sapphire NA, Ann Arbor, Mich.). Immuno-reactivity was revealed with an ECL-Plus kit (Amersham Biosciences Co, Piscataway, N.J.), using the ChemiDoc MP system (Bio-Rad Laboratories, Hercules, Calif.).

Genetic and Transcriptional Profiling Analyses

Whole exome sequencing was performed at the UCLA Clinical Microarray Core using the Roche Nimblegen SeqCap EZ Human Exome Library v3.0. Mutation calling was performed as previously described[22]. Selected gene expression profiling upon interferon exposure was performed using nCounter (NanoString Technologies, Seattle, Wash.).

JAK Functional Studies with T-Cell Co-Culture and Interferon Treatment

Patient-derived and previously established human melanoma cell lines were used to analyze recognition by T-cell receptor (TCR) transgenic T-cells[23] using in vitro co-culture assays detecting antigen-induced release of interferon gamma assessed by enzyme-linked immunosorbent assay (ELISA). Cell proliferation and growth inhibition assays were performed using an automated live-cell imaging system with or without exposure to interferons.

Parental and M407 JAK2 knock-out cells were co-cultured with human peripheral blood mononuclear cells transduced with an NY-ESO1 specific TCR[51]. Interferon-gamma release was measured in supernatant at 24 hours by ELISA (eBioscience, San Diego, Calif.). Proliferation assays were conducted by real-time live cell imaging in an IncuCyte ZOOM (Essen Biosciences, Ann Arbor, Mich.). Cell lines were stably transfected with a nuclear-localizing RFP (NucLight Red Lentivirus EF1a Reagent, Essen Biosceinces) to facilitate cell counts. Recombinant human interferon gamma (BD Bioscience, San Jose, Calif.), human interferon alpha and beta (EMD Millipore, Temecula, Calif.), and 2'3'-cGAMP (InvivoGen, San Diego, Calif.) were applied once to approximately 5000 cells per well seeded the previous day in a 96-well plate plate. Cells were maintained without media change for the duration of the experiments. 2'3'-cGAMP was complexed with Lipofectamine 2000 (1:500 dilution, Invitrogen, Carlsbad, Calif.) for cytosolic exposure. All experiments were performed with wells in triplicate at in a minimum of three independent runs. Graph production and statistical data were analyzed via Prism software (Graphpad, La Jolla, Calif.).

Study Oversight

Data generated and collected by the study investigators were analyzed by the senior academic investigators, who vouch for the completeness and accuracy of the analyses and reported results. The clinical protocol summaries are available at NEJM.org under references[6,10].

Statistical Analysis

Student's t-test and a two-way analysis of variance were used for cell culture experiments, with Dunnett's correction applied for multiple comparisons to untreated controls.

Tumor Samples and Cell Lines

Patients underwent baseline biopsies before starting on therapy, early on therapy biopsies[38-40] (in some patients), and upon progression. When feasible, biopsy samples were split into three with one aliquot immediately fixed in formalin followed by paraffin embedding for pathological analyses, a second aliquot snap frozen by immediate immersion in liquid nitrogen for genetic analyses, and if there was residual tissue it was sterilely processed in the laboratory to establish a cell line as previously described[41,42] Cell lines were periodically authenticated using GenePrint® 10 System (Promega, Madison, Wis.), and were matched with the earliest passage cell lines. Tumor biopsy and peripheral blood cell collection and analyses were approved by UCLA IRBs 11-001918 and 11-003066. Snap frozen samples were disrupted in lysis buffer by BeadBug microtube homogenizer (Benchmark Scientific, Edison, N.J.) using disposable stainless steel beads. DNA and RNA from snap frozen samples and cell lines were extracted concurrently using the 0iagen All-Prep kit (0iagen, Benelux B.V., Venlo, The Netherlands) and mirVana miRNA isolation kit (ThermoFisher, Canoga Park, Calif.). Ambion RecoverAll kit (also Thermo-Fisher) was used for DNA extraction from FFPE slides.

Genetic Analyses

Exon capture and library preparation were performed at the UCLA Clinical Microarray Core using the Roche Nimblegen SeqCap EZ Human Exome Library v3.0 targeting 64 Mb of genome. 2×100 bp paired-end sequencing was carried out on the HiSeq 2000 platform (Illumina, San Diego, Calif.) and sequences were aligned to the UCSC hg19 reference using BWA-mem (v0.7.9). Sequencing for tumors and matched normal DNA from peripheral blood mononuclear cells was performed to a target depth of 150× (actual: minimum 90×, maximum 348×, median 143×). Pre-processing followed the Genome Analysis Toolkit (GATK) Best Practices Workflow v3, including duplicate removal, indel realignment, and base quality score recalibration.

Somatic mutations were called against a paired normal sample with methods as previously reported[43]. In brief, high-confidence mutations were retained if identified by at least two out of three programs between: MuTect (v1.1.7)[44], Varscan2 Somatic (v2.3.6)[45], and a one-sided Fisher's Exact Test (P value cut-off:5 0.01) for GATK-HaplotypeCaller (HC) calls between tumor/normal pairs for single nucleotide variants. Insertions/deletions were included if called by both Varscan2 and the GATK-HC. Variants were annotated by a stand-alone version of Oncotator[46] using the Dec. 11, 2014, datasource. Non-synonymous mutations were those classified as nonsense, missense, splice site, or nonstop mutations, frameshift, in-frame, or start codon altering insertions/deletions. Purity, ploidy, and allele-specific copy number status was determined by Sequenza[47] with default settings. Adjusted variant allele frequency was calculated according to the following equation to adjust for stromal content and copy number, with tumor/stromal fractions and local copy number from Sequenza output:

$$VAF_{adjusted} = VAF_{observed} \times [1+(2 \times Stromal\ Fraction)/(Tumor\ Fraction \times Local\ Copy\ Number)]$$

Sanger Validation of JAK and B2M Mutations and Targeted Amplicon Re-Sequencing

The following primers pairs were used for PCR amplification of the mutation-containing region of JAK1, JAK2 and B2M from cases #1, #2, and #3 respectively.

```
JAK1 296 bp:
                                (SEQ ID NO: 1)
5' caatgccttctcctggacctt 3'
and (SEQ ID NO: 2)
5' ccgaaccgtgcagactgtag 3'

JAk2 241 bp:
                                (SEQ ID NO: 3)
5' acctcaccaacattacagaggc 3'
and (SEQ ID NO: 4)
5' acatctaacacaaggttggca 3'

B2M 257 bp:
                                (SEQ ID NO: 5)
5' cttgtcctgattggctgggc 3'
and (SEQ ID NO: 6)
5' acttggagaagggaagtcacg 3'
```

PCR was performed with 250 ng input genomic DNA using the AccuPrime Taq DNA Polymerase System (ThermoFisher, Canoga Park, Calif.) and cycling protocol 94° C. 2 min, [94° C. 30 sec, 52° C. 1 min, 68° C. 1 min]×35 cycles, 68° C. 10 min, 4° C. hold.

Products were purified by agarose gel electrophoresis and submitted for either Sanger sequencing (Laragen, Culver City, Calif.) or Illumina deep sequencing with the UCLA Clinical Microarray Core. Library prep of PCR products was performed without fragmentation using the KAPA Hyper Prep kit (Kapa Biosystems, Wilmington, Mass.), and sequenced on an Illumina Miseq 2×150 bp or NextSeq 1×75 bp. All sequencing reactions produced >1 million mapped reads per locus.

Transcriptional Profiling Analysis

Total RNA was extracted from human melanoma cell lines in the absence or presence of interferon-gamma (100 IU/ml) at 3 hours according to the manufacturer's protocol (Oiagen, Benelux B.V., Venlo, The Netherlands). nCounter (NanoString Technologies, Seattle, Wash.) analysis was performed at the Center for Systems Biomedicine, a part of the Integrated Molecular Technologies Core (IMTC) at UCLA using the nCounter PanCancer immune profiling panel, including 769 genes to which we added 21 custom genes to capture the known interferon response genes. Through the use of color-coded probe pairs, mRNA transcripts of specific cellular genes, including housekeeping genes for normalization, were quantified in untreated M420 and M464 cells and after 3 hours of interferon gamma exposure. The list of genes included in the analysis appears in Zaretsky et al. [N Engl J Med. 2016 Sep. 1; 375(9):819-29] Supplementary Table S4, data herein incorporated by reference).

For RNA-seq analysis of JAK2 splicing in M420 and M464, paired-end transcriptome reads were mapped to the UCSC hg19 reference genome using Tophat2[13].

JAK CRISPR/Cas9-Mediated Knockout

M407 with CRISPR/Cas9 mediated JAK1 and JAK2 knock-outs were generated by lentiviral transduction using particles encoding guide RNAs, a fully functional CAS9 cassette, green fluorescent protein, and puromycin as selectable markers (Sigma-Aldrich, St. Louis, Mich.). Two guide sequences were used per gene, targeting exon 4 (ccaagctctg-gtatgctccaaa) (SEQ ID NO: 7) and exon 5 (ccaattggcatg-gaaccaacga) (SEQ ID NO: 8) for JAK1, and exon 1 (cctgc-cttacgatgacagaaat) (SEQ ID NO: 9) and 2 (ccaggcataatgtactctacag) (SEQ ID NO: 10) for JAK2. GFP positive single cell clones were isolated using a FACSARIA sorter (Becton-Dickinson, Franklin Lakes, N.J.). Clones were screened by PCR with the following primers, and reading-frame disruption was confirmed by Sanger sequencing with TIDE analysis (Tracking of Indels by Decomposition, NKI, The Netherlands, https://tide.nki.nl).

```
JAK1 Exon4:
                                (SEQ ID NO: 11)
5' agtcattctcacatcaagca 3'
and (SEQ ID NO: 12)
5' gccaggaatttgtttgcatgt 3'

JAK1 Exon 5:
                                (SEQ ID NO: 13)
5' cagggttgtctgcctgcttc 3'
and (SEQ ID NO: 14)
5' gaagctggagtttgtgggat 3'

JAK2 Exon 1:
                                (SEQ ID NO: 15)
5' acttctgggctcaagctatctg 3'
and (SEQ ID NO: 16)
5' cttgggaaatctgaggcaga 3'
```

-continued

JAK2 Exon2:

5' ggtgctgacagacttactagattc 3' (SEQ ID NO: 17)
and

5' gatattgctggtttgtgcagcg 3' (SEQ ID NO: 18)

Finally, knockout was confirmed by Western blot.

Results

Clinical Course and Immune Infiltrates

Paired tumors were analyzed from four (nonconsecutive) selected patients with metastatic melanoma who relapsed while on PD-1-inhibition therapy with pembrolizumab (Tables 1 and 2). All met objective criteria of partial response[17,18], though with slightly different kinetics (FIG. 1). Mean time to relapse was 623 days (range 419 to 888). The baseline biopsies were taken right before starting on pembrolizumab in cases #2, #3 and #4, while for case #1 the only available baseline biopsy was before an earlier course of therapy with the BRAF inhibitor vemurafenib. The baseline biopsies of cases #1, #2 and #3 displayed pre-existing CD8 T-cell infiltrates at the invasive margin that co-localized with PD-L1 expression on surrounding macrophages and melanoma cells (data not shown, see Zaretsky et al FIG. 1B, and Supplementary Figures S1-3B, herein incorporated by reference). The biopsies at response in cases #2, #3, and #4 showed a marked increase in intratumoral CD8 T-cell infiltrates (percent CD8 infiltration quantified in Table 3 and data not shown, see Zaretsky et al Figs. S1-3C; no on-therapy biopsy was available for case #1, herein incorporated by reference). At relapse, all four biopsies showed CD8 T-cell infiltration and PD-L1 expression concentrated at the tumor margins again (data not shown, see Zaretsky et al FIG. 1C and Supplementary Figures S1-3D, herein incorporated by reference). Multiplex immunofluorescence revealed that melanoma cells at relapse in cases #1 and #2 were PD-L1 negative even when directly adjacent to T cells, while macrophages and stroma cells were PD-L1 positive.

TABLE 1

Demographic and baseline patient clinical characteristics

|  | Case #1 | Case # 2 | Case #3 | Case #4 |
| --- | --- | --- | --- | --- |
| irRECIST | Partial Response | Partial Response | Partial Response | Partial Response |
| Study | Merck MK3475-006 | Merck MK-3475-001 | Merck MK-3475-001 | Merck MK-3475-001 |
| Progression Free Survival (Days) | 419 | 734 | 433 | 888 |
| Overall Survival (Days) | 691 | 945 | 974 | 1262* |
| *ongoing at census |  |  |  |  |
| Age at Tx start | 58 | 60 | 70 | 61 |
| Sex | M | M | M | M |
| ECOG States at Baseline | 0 | 0 | 0 | 0 |
| Disease Status at Baseline | M1c | M1b | M1c | M1c |
| Baseline LDH (ULN 223) | 358 | 83 | 263 | 222 |
| BRAF/NRAS | BRAF V600E | BRAF L597S | NRAS Q61K | BRAF V600E |
| Melanoma Type | Cutaenous | Cutaenous | Cutaenous | Cutaenous |
| # Prior Systemic Therapies | 2 | 0 | 0 | 4 |
| Prior Immunotherapy? | Interferon-alpha | 0 | 0 | IL-2, Ipilimumab. TIL adoptive cell transfer |
| Prior BRAF/MEK inhibitor? | Vemurafenib | 0 | 0 | Vemurafenib |
| Prior Chemotherapy? | 0 | 0 | 0 | 0 |

TABLE 2

Sample list and whole exome sequencing metrics

| Case | Timepoint (Days from C1D1) | Anatomic Location | Clinical Scenario | Sequenced Sample Type | Exome Seq Sample Name |
| --- | --- | --- | --- | --- | --- |
| Case #1 | −233 | Small Bowel | Baseline, pre-response | Bulk tumor - FFPE | Case#1-Baseline |
| Case #1 | 425 | Sigmoid Colon | In-situ Relapse | Bulk tumor - Snap Frozen | Case#1-Relapse |
| Case #1 | NA | Normal (PBMC) | N/A | PBMC | N/A |
| Case #2 | −5 | Lung | Baseline, pre-response | Cell Line (M420) | Case#2-Baseline-M420 |
| Case #2 | 788 | Lung | In-situ Relapse | Bulk tumor - Snap Frozen | Case#2-Relapse-WholeTumor |
| Case #2 | 788 | Lung | In-situ Relapse | Cell Line (M464) | Case#2-Relapse-M464 |
| Case #2 | 788 | Normal (PBMC) | N/A | PBMC | N/A |
| Case #3 | −8 | Inguinal lymph node | Baseline, pre-response | Cell Line (M437) | Case#3-Baseline-M437 |
| Case #3 | 453 | Small Bowel | Relapse; New lesion | Bulk tumor - Snap Frozen | Case#3-Relapse |
| Case #3 | NA | Normal (PBMC) | N/A | PBMC | N/A |
| Case #4 | −28 | Left chestwall | Baseline, pre-response | Bulk tumor - Snap Frozen | Case#4-Baseline |
| Case #4 | 898 | Left chestwall | Relapse; New lesion | Bulk tumor - Snap Frozen | Case#4-Relapse |
| Case #4 | NA | Normal (PBMC) | N/A | PBMC | N/A |

| Case | Non-synonymous Mutation Count | % Tumor Cellularity (Sequenza) | Ploidy (Sequenza) | Total Reads | Mean Coverage | % bases above 15X |
| --- | --- | --- | --- | --- | --- | --- |
| Case #1 | 1173 | 0.79 | 2.2 | 5869797548 | 91.44 | 96.6 |
| Case #1 | 1140 | 0.45 | 2.5 | 8122321016 | 126.53 | 97 |

TABLE 2-continued

Sample list and whole exome sequencing metrics

| Case | | | | | | |
|---|---|---|---|---|---|---|
| Case #1 | | NA | NA | 5810616299 | 90.52 | 96.2 |
| Case #2 | 240 | 0.95 | 3.8 | 9198284962 | 143.3 | 97.1 |
| Case #2 | 305 | 0.56 | 3.3 | 11499597416 | 179.15 | 97.7 |
| Case #2 | 333 | 0.98 | 3.5 | 13430534410 | 209.23 | 97.9 |
| Case #2 | | NA | NA | 9109279242 | 141.91 | 97.3 |
| Case #3 | 453 | 0.95 | 2.9 | 7667504038 | 119.45 | 96.8 |
| Case #3 | 328 | 0.4 | 2.9 | 11983298763 | 186.68 | 97.2 |
| Case #3 | | NA | NA | 9572406229 | 149.12 | 97.5 |
| Case #4 | 347 | 0.89 | 3.4 | 11619208625 | 181.01 | 97.5 |
| Case #4 | 406 | 0.74 | 3.4 | 10358188486 | 161.37 | 97.1 |
| Case #4 | | NA | NA | 7196761543 | 112.12 | 95.9 |

TABLE 3

Quantification of immunohistochemistry for CD8 infiltration and PD-L1 expression

| | | CD8 | | | | | | | |
|---|---|---|---|---|---|---|---|---|---|
| | | Invasive Margin | | | | Intra-tumoral Area | | | |
| Case | Timepoint | % CD8 | Total Nuclei Count | Tissue Area (mm$^2$) | CD8 Density cells/mm$^2$ | % CD8 | Total Nuclei Count | Tissue Area (mm$^2$) | CD8 Density cells/mm$^2$ |
| Case #1 | Baseline | 38 | 242766 | 42 | 2196.5 | 13 | 791627 | 163 | 631.4 |
| Case #1 | Relapse | 16.5 | 35447 | 7.3 | 799.6 | 1.65 | 115919.5 | 26.1 | 73.3 |
| Case #2 | Baseline*+ | NA | NA | NA | NA | 3 | 4309 | 0.663 | 195.1 |
| Case #2 | On-treatment+ | NA | NA | NA | NA | 84 | 604 | 0.059925 | 8466.6 |
| Case #2 | Relapse | 26 | 31086 | 5.3 | 1525.0 | 2.5 | 255321 | 35 | 182.4 |
| Case #3 | Baseline*^ | 58 | 2023 | 0.293 | 4009.4 | 23 | 5653 | 0.921 | 1411.8 |
| Case #3 | On-treatment^+ | NA | NA | NA | NA | 90 | 5557 | 6 | 833.6 |
| Case #3 | Relapse | 18 | 27463 | 4 | 1235.8 | 8.9 | 678132 | 135 | 447.1 |
| Case #4 | Baseline | 24 | 9003 | 1.7 | 1271.0 | 0.3 | 225012 | 41 | 16.5 |
| Case #4 | On-treatment | 62.5 | 90954 | 14.7 | 3867.1 | 39 | 199070 | 36.6 | 2121.2 |
| Case #4 | Relapse | 60 | 53901 | 7.6 | 4255.3 | 15.6 | 322322 | 60 | 838.0 |

| | | PD-L1 | | | | | | | |
|---|---|---|---|---|---|---|---|---|---|
| | | Invasive Margin | | | | Intra-tumoral Area | | | |
| Case | Timepoint | % PD-L1 | Total Nuclei Count | Tissue Area (mm$^2$) | PD-L1 Density cells/mm$^2$ | % PD-L1 | Total Nuclei Count | Tissue Area (mm$^2$) | PD-L1 Density cells/mm$^2$ |
| Case #1 | Baseline | 49 | 206074 | 26 | 3883.7 | 17.5 | 898011 | 162 | 970.1 |
| Case #1 | Relapse | 53.9 | 41978.66667 | 7.03 | 3217.0 | 22.05 | 110552.5 | 24.4 | 999.1 |
| Case #2 | Baseline*+ | NA | NA | NA | NA | 9.4 | 4799 | 0.713 | 632.6 |
| Case #2 | On-treatment+ | NA | NA | NA | NA | 72 | 623 | 0.048498 | 9249.0 |
| Case #2 | Relapse | 38 | 30483 | 4.8 | 2413.2 | 6 | 213040 | 37.7 | 339.1 |
| Case #3 | Baseline*^ | NA | NA | NA | NA | 40 | 3933 | 0.360 | 4374.2 |
| Case #3 | On-treatment^+ | NA | NA | NA | NA | 31 | 50244 | 6 | 2595.9 |
| Case #3 | Relapse | 25 | 28784 | 4.4 | 1635.5 | 20 | 1460378 | 212 | 1377.7 |
| Case #4 | Baseline | 2.9 | 12404 | 1.7 | 211.6 | 0.14 | 194354 | 37.7 | 7.2 |
| Case #4 | On-treatment | 76.6 | 129451 | 14.1 | 7033.1 | 60 | 237179 | 31 | 4590.6 |
| Case #4 | Relapse | 72.5 | 70934 | 7.6 | 6766.7 | 30 | 364649 | 60 | 1823.2 |

*Poor quality tissue/staining
^Lymph node biopsy
+Unable to delineate invasive margin Genetic Changes in Relapse Biopsies The pattern of a strong initial response, long dormancy, and rapid late progression led to the hypothesis that relapse in these cases resulted from immune-mediated clonal selection, and tumor outgrowth[24]. To identify mutations that might confer immune resistance, DNA was extracted from bulk tumor biopsies or early passage primary cell lines and performed whole exome sequencing to compare baseline and matched relapsed tissues. A median coverage of 149× was achieved and tumor compared to stromal content was over 40% in all samples (Table 2). Non-synonymous mutations for all samples were determined (data not shown, see Zaretsky et al. Supplementary Table S4, herein incorporated by reference).

JAK Mutations with Concurrent Loss-of-Heterozygosity at Relapse

Figure 2A:
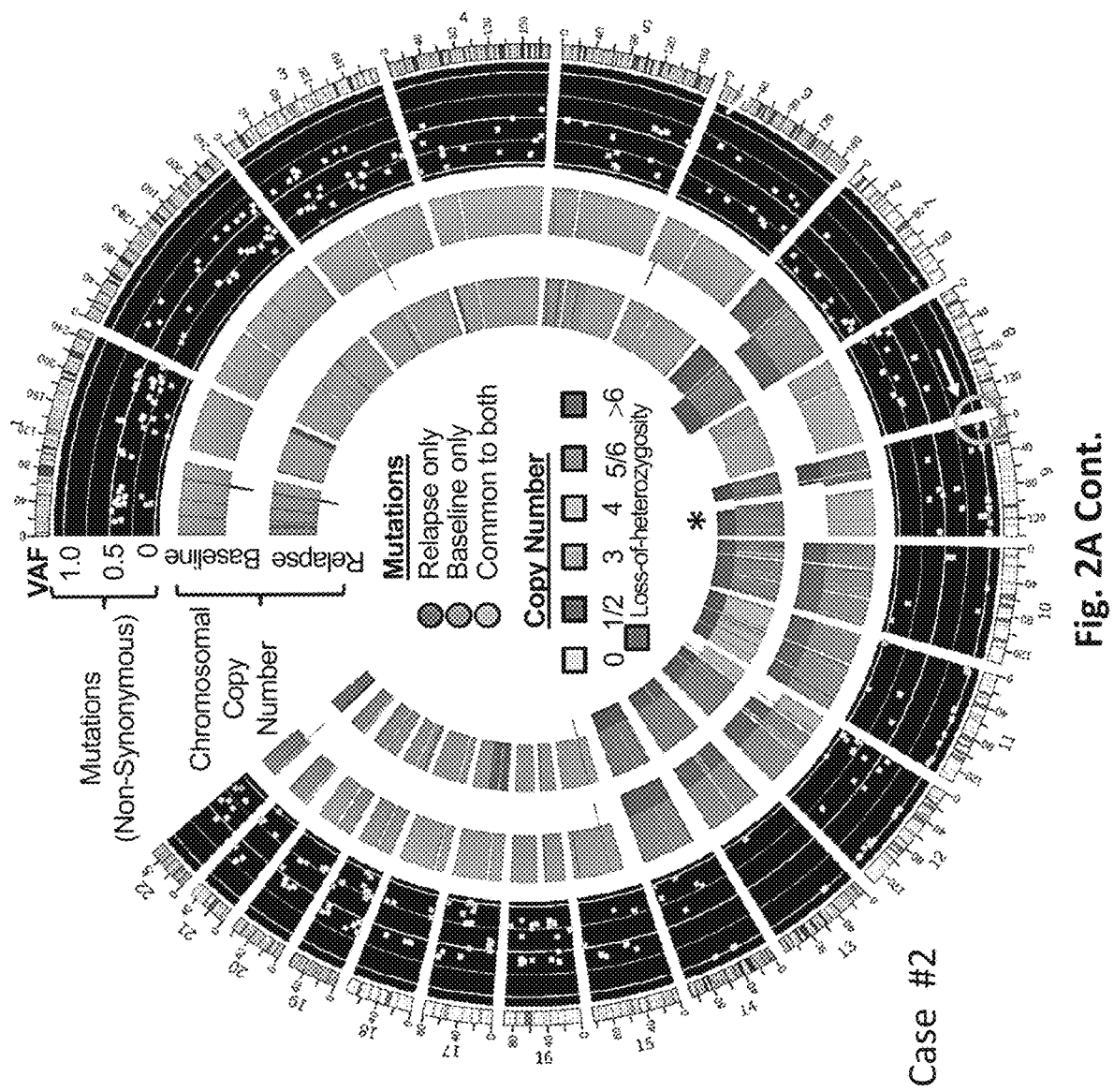
FIG. 2A. Genomic alterations reveal acquired JAK loss of function mutations with accompanying loss-of-heterozygosity. Circos plots[36] from cases #1 and #2 in Panel A show the comparison of whole exome sequencing differences between pre-pembrolizumab and post-relapse biopsies. The arrows highlight a new, high allele-frequency relapse-specific JAK1 mutation (case #1) and JAK2 mutation (case #2) in the setting of chromosomal loss of heterozygosity (asterisks). Each wedge represents a chromosome. In the outer track (black background), each point represents a non-synonymous mutation, with most shared in common between both biopsies (grey) rather than detected at relapse only or baseline only (dark grey). Y-axis position indicates variant allele frequency (VAF) at relapse, unless baseline-specific. The middle and inner tracks show copy number status for the baseline and relapse biopsy, respectively, while the inner subtrack indicates loss-of-heterozygosity.
Figure 2B:
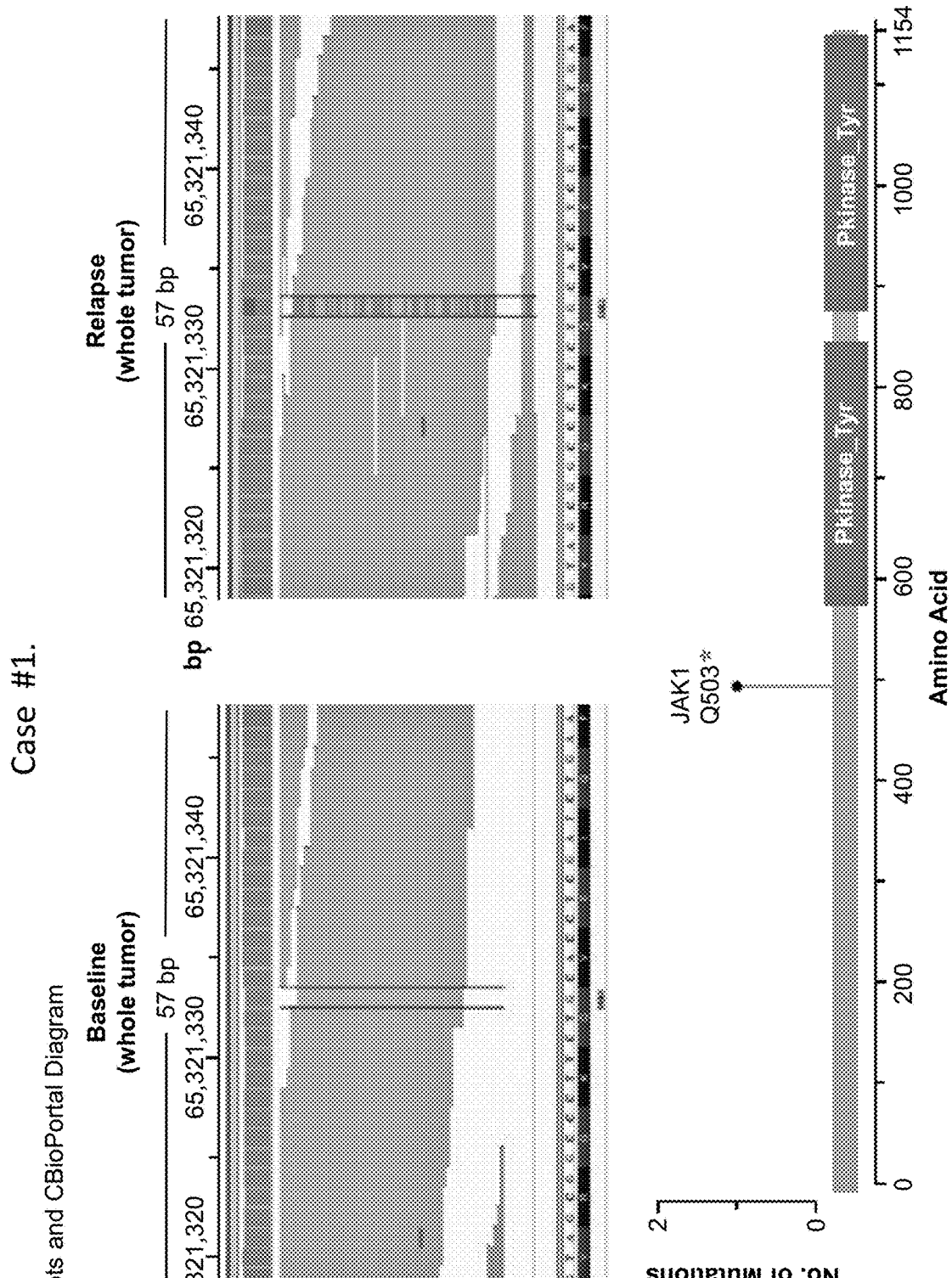
FIG. 2B. (SEQ ID NOs: 21-24) Genomic alterations reveal acquired JAK loss of function mutations with accompanying loss-of-heterozygosity. Case #1, integrated genomics viewer (IGV) plots (top) show the JAK1 0503* nonsense mutation is relapse-specific, while the cBioPortal[37] diagram (bottom) shows the JAK1 mutation is upstream of the kinase domains. Case #2, integrated genomics viewer (IGV) plots (top) show the JAK2 F547 splice-site mutation is relapse-specific, while cBioPortal diagram (bottom) reveals the JAK mutation is upstream of the kinase domains.
Figure 2B:
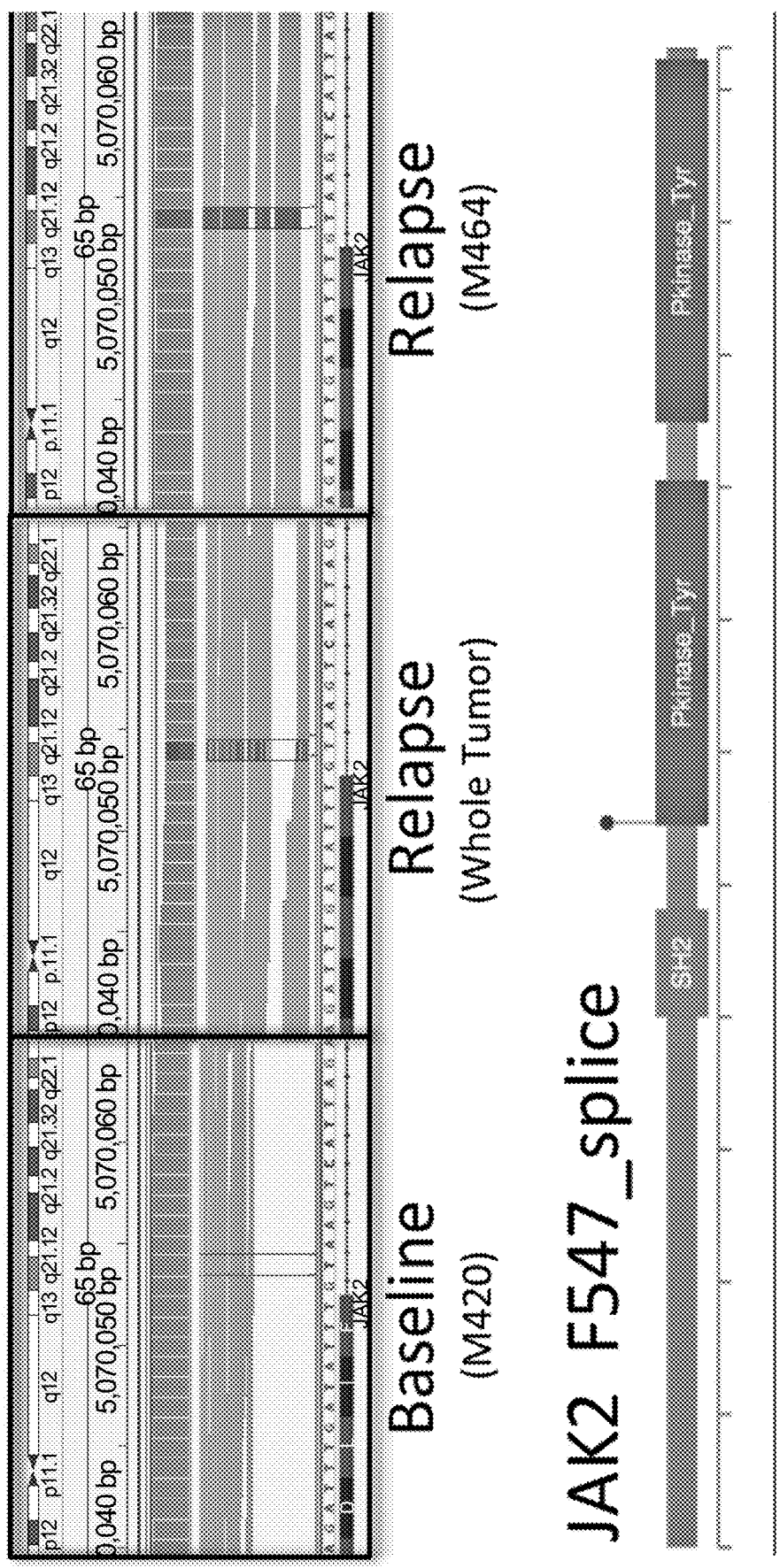

Strong evidence was found that the relapsed tumors were closely genetically related to their baseline counterparts, despite up to two years between biopsies. For cases #1 and #2, out of 1173 and 240 non-synonymous mutations originally identified in the baseline sample, 92.5% and 95.8% were also seen in the resistant tumor, respectively (FIG. 2A).

Figure 3A:
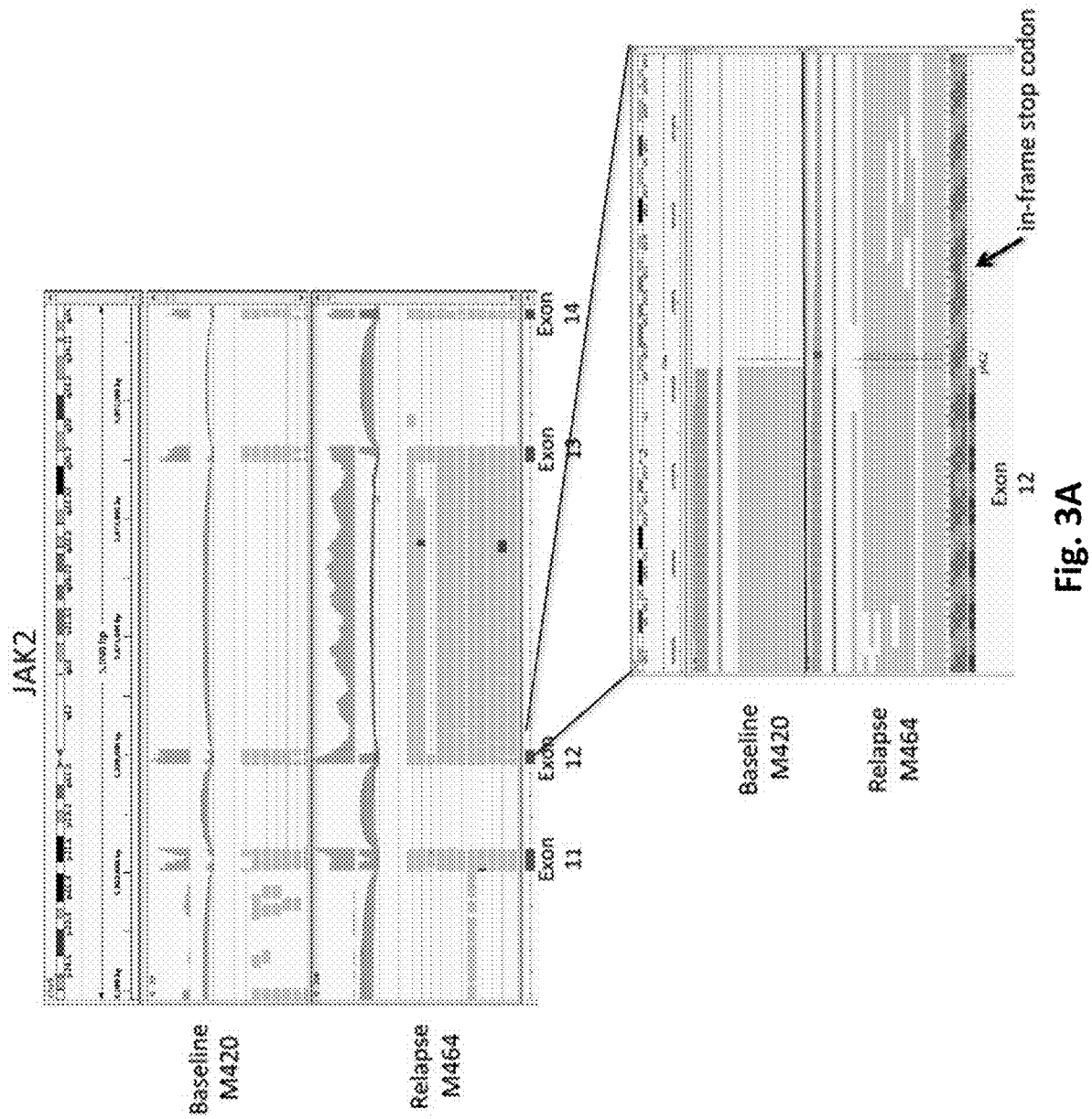
FIG. 3A. Relapse-specific JAK2 splice site mutation causes near universal intron inclusion. IGV plot of RNA-Seq reads for JAK2 exons 11-14 from the baseline and relapse cell lines from case #2. Intron-inclusion is only seen at relapse.
Figure 3B:
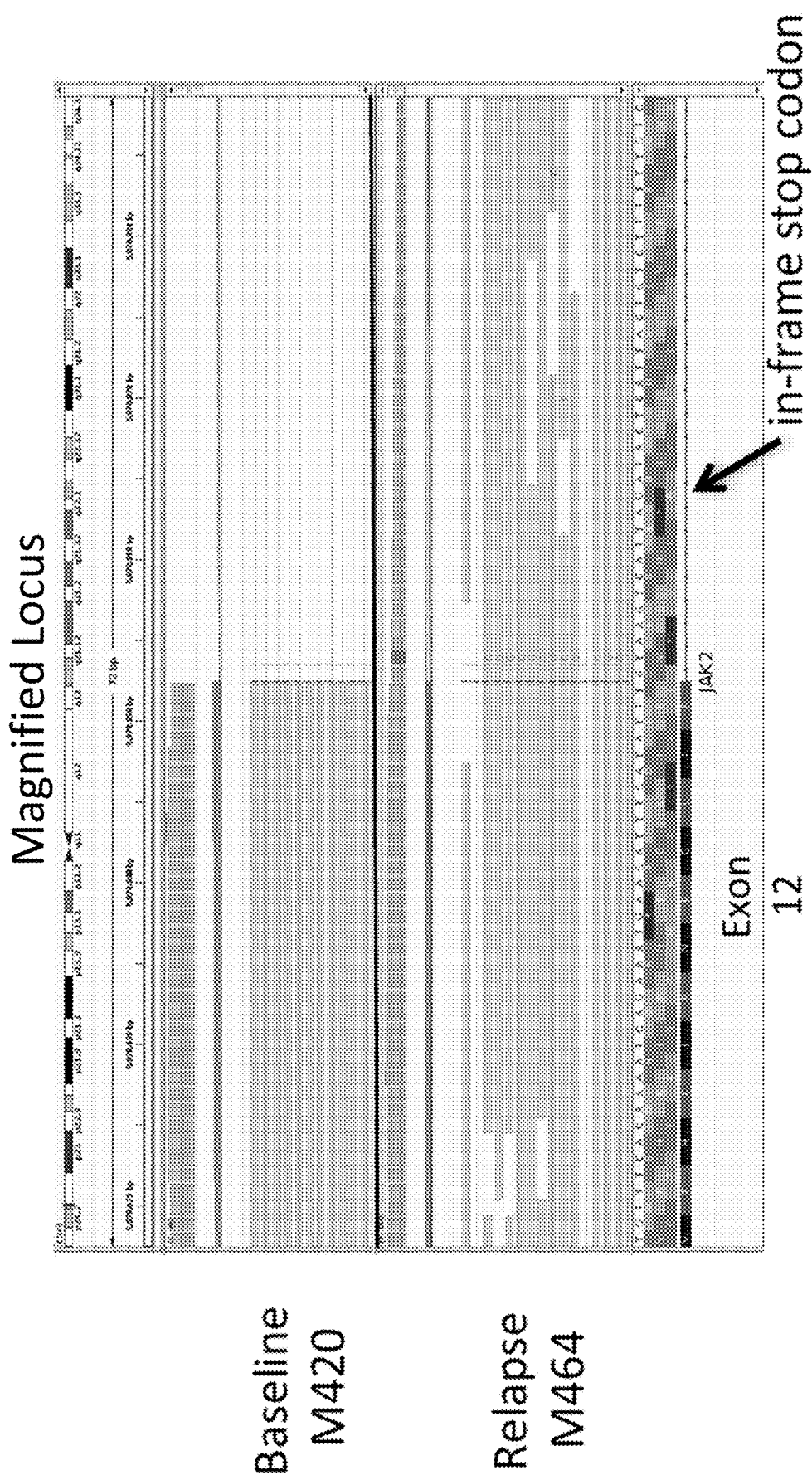
FIG. 3B. (SEQ ID NOs: 25-32) Relapse-specific JAK2 splice site mutation causes near universal intron inclusion. Magnified locus shows RNA reads containing the splice site mutations continuing through the exon 12 exon/intron junction in the relapse cell line, compared to those at baseline that span the exon 12/13 splice junction (Reads with abrupt end at exon 12 with a line indicating continuation of the RNA read at exon 13). Intron inclusion introduces an in-frame stop codon within 10 base pairs of intron (arrow).
Figure 4A:
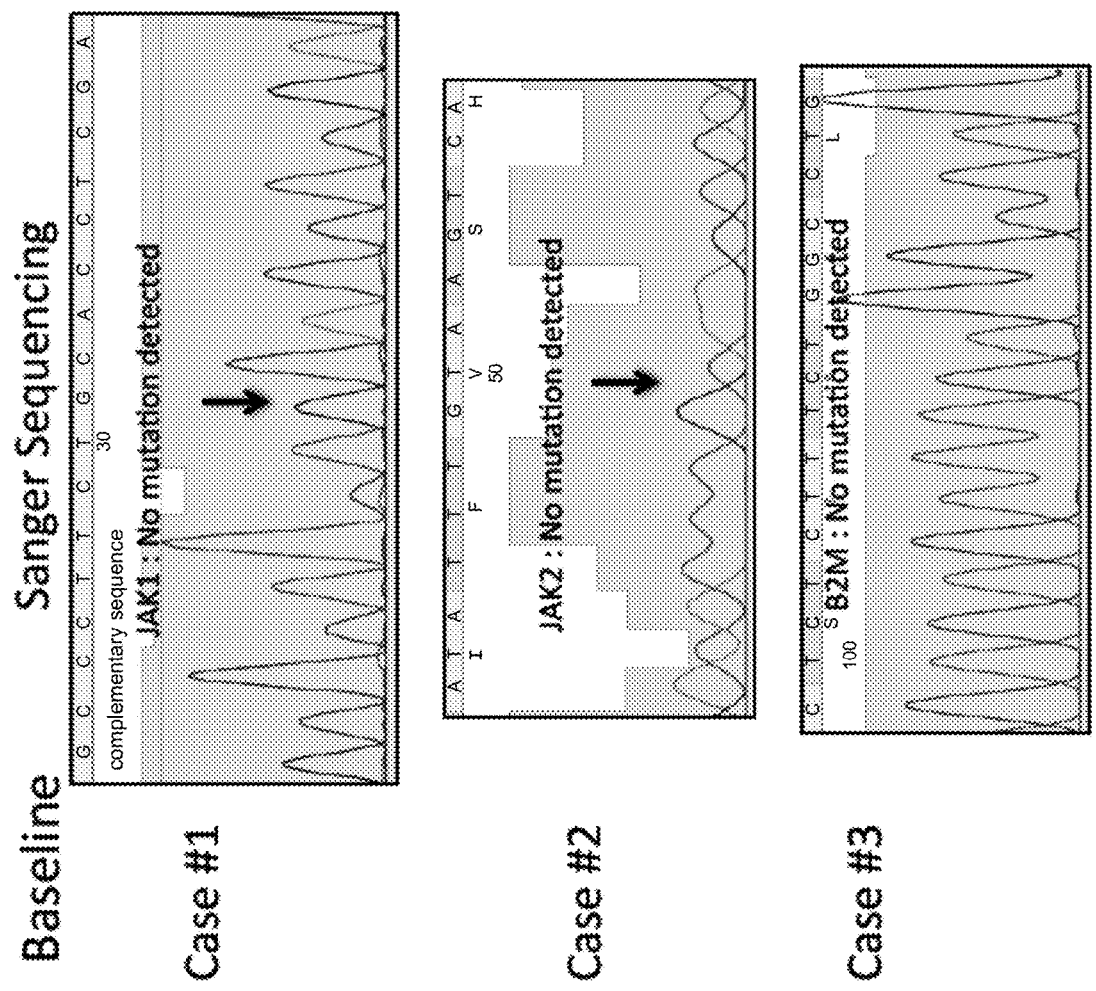
FIG. 4A. (SEQ ID NOs: 33-36, 58, and 59) Relapse-specific JAK1, JAK2, and B2M mutations are not found at baseline by Sanger or Illumina deep amplicon sequencing. Shows the JAK1, JAK2 and 132M mutations identified at relapse were not observed in PCR amplified genomic DNA from the baseline samples for case #1, #2, and #3 respectively, either by Sanger sequencing or Illumina amplicon re-sequencing. For case #1 and #2, graphs show the percentage of each base per position out of 1 million mapped reads. No mutations were observed above the background error rate of –0.25%. The case #3 baseline sample also had 0 detectable reads with the 4 base pair 132M deletion out of 1.6 million mapped reads examined. IGV plot shows representative sampling, with the relapse mutation for reference.
Figure 4A:
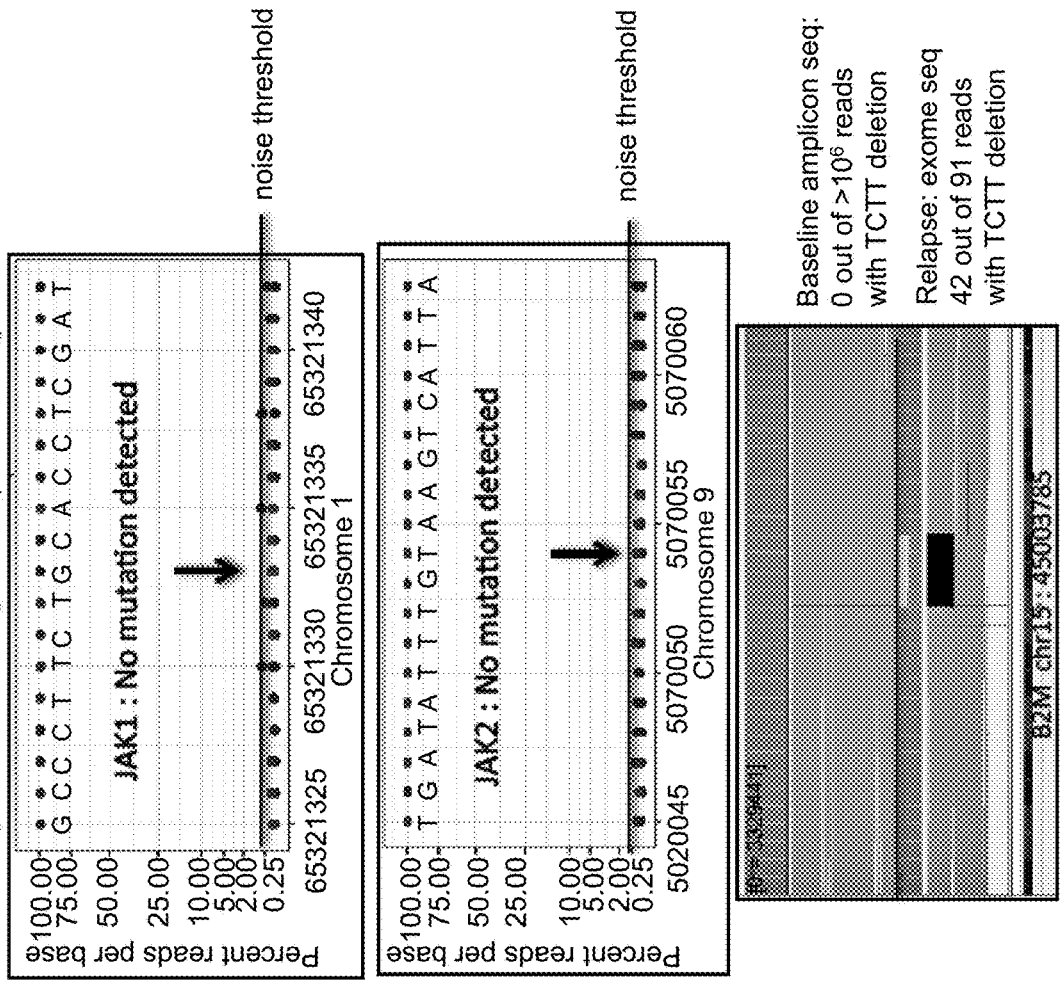
Figure 4B:
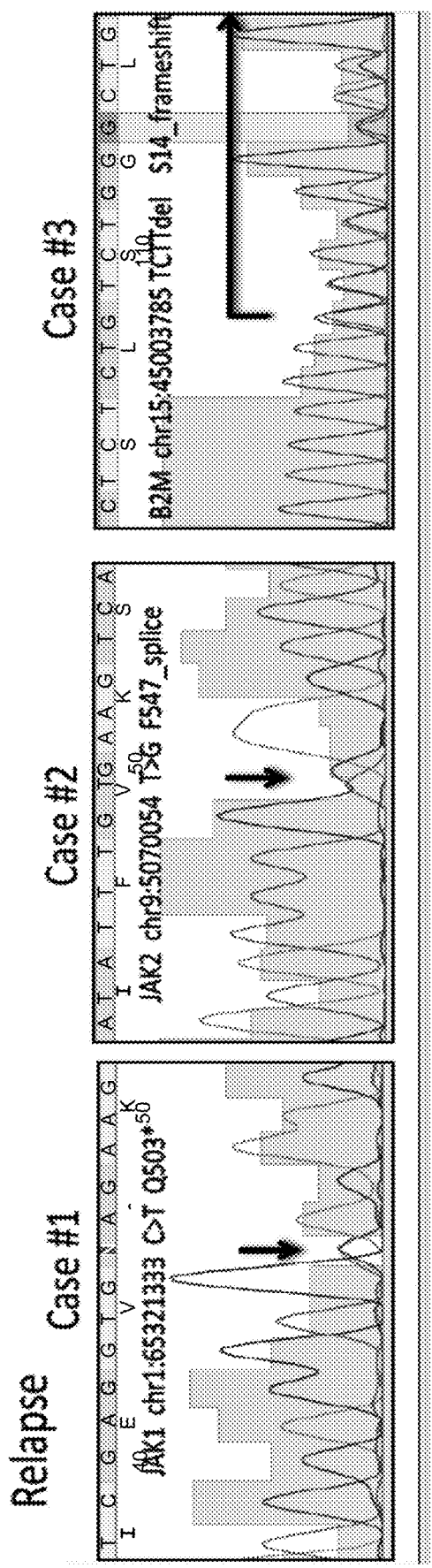
FIG. 4B. (SEQ ID NOs: 60-65) Relapse-specific JAK1, JAK2, and B2M mutations are not found at baseline by Sanger or Illumina deep amplicon sequencing. Sanger sequencing of PCR products from genomic DNA of the relapse biopsies confirms the presence of the indicated mutations.
Figure 5:
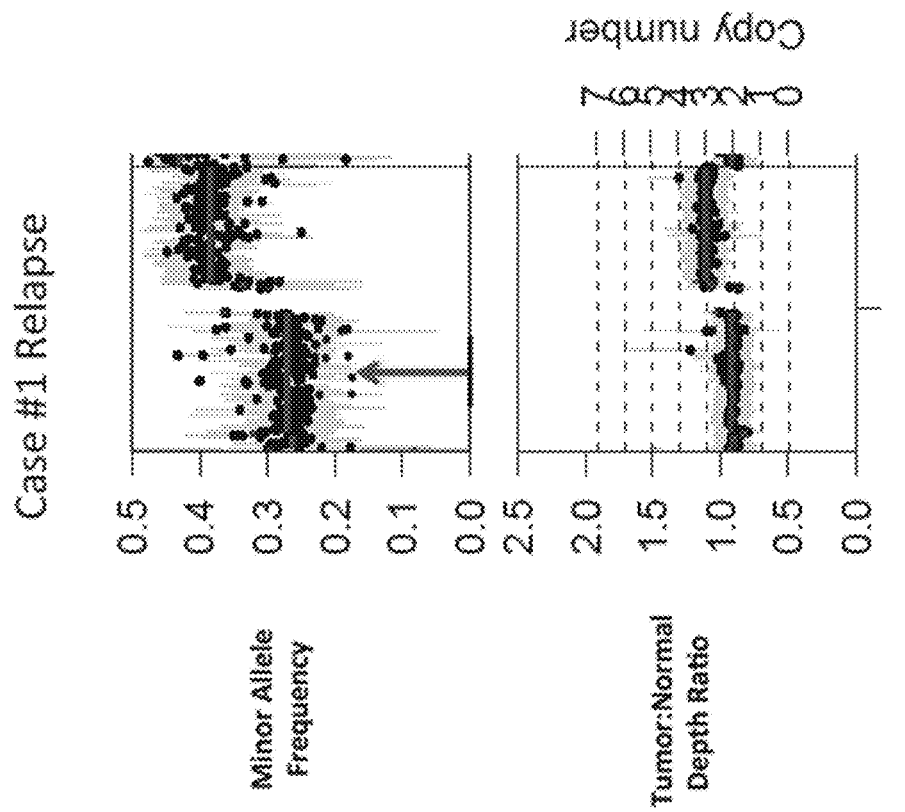
FIG. 5. Changes in germline SNP allele frequency shows loss-of-heterozygosity upon relapse on chromosome 1p. Sequenza output with upper plot showing the minor allele frequencies for germline single nucleotide polymorphisms (SNPs) on chromosome 1, and the lower plot showing the read depth ratio and stroma-adjusted copy number estimate. There is a decrease in SNP frequency for chromosome 1p upon relapse, yet there is no change in relative depth ratio (bottom panel), indicating stable overall copy number. Together, they suggest a copy-number neutral loss of heterozygosity event.
Figure 5:
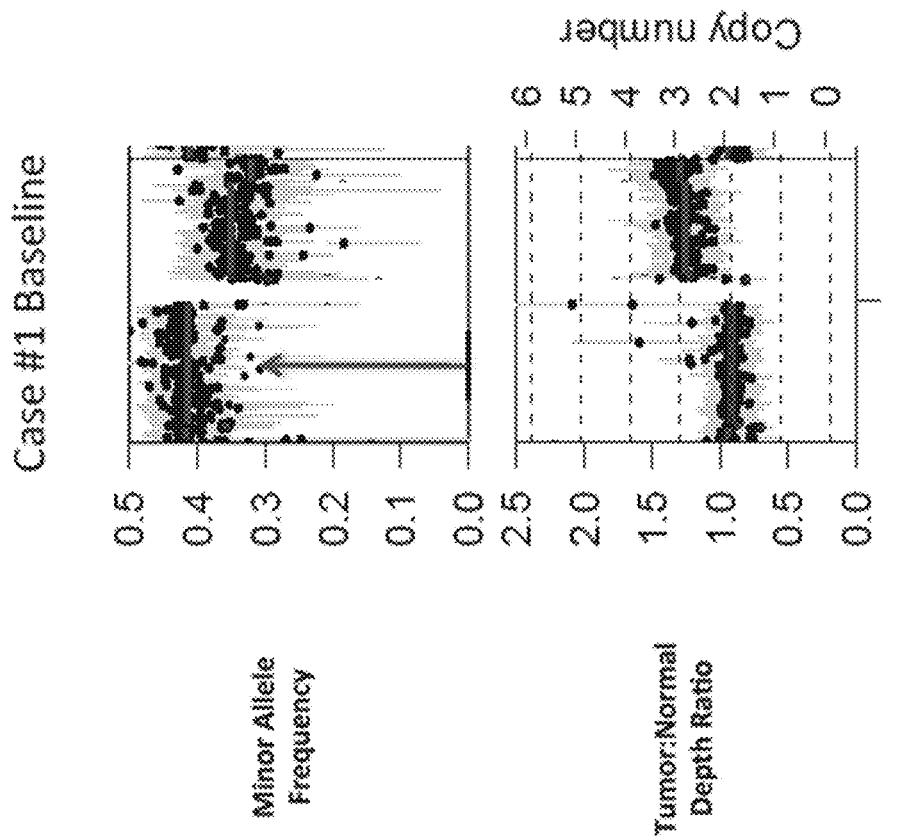
Figure 6:
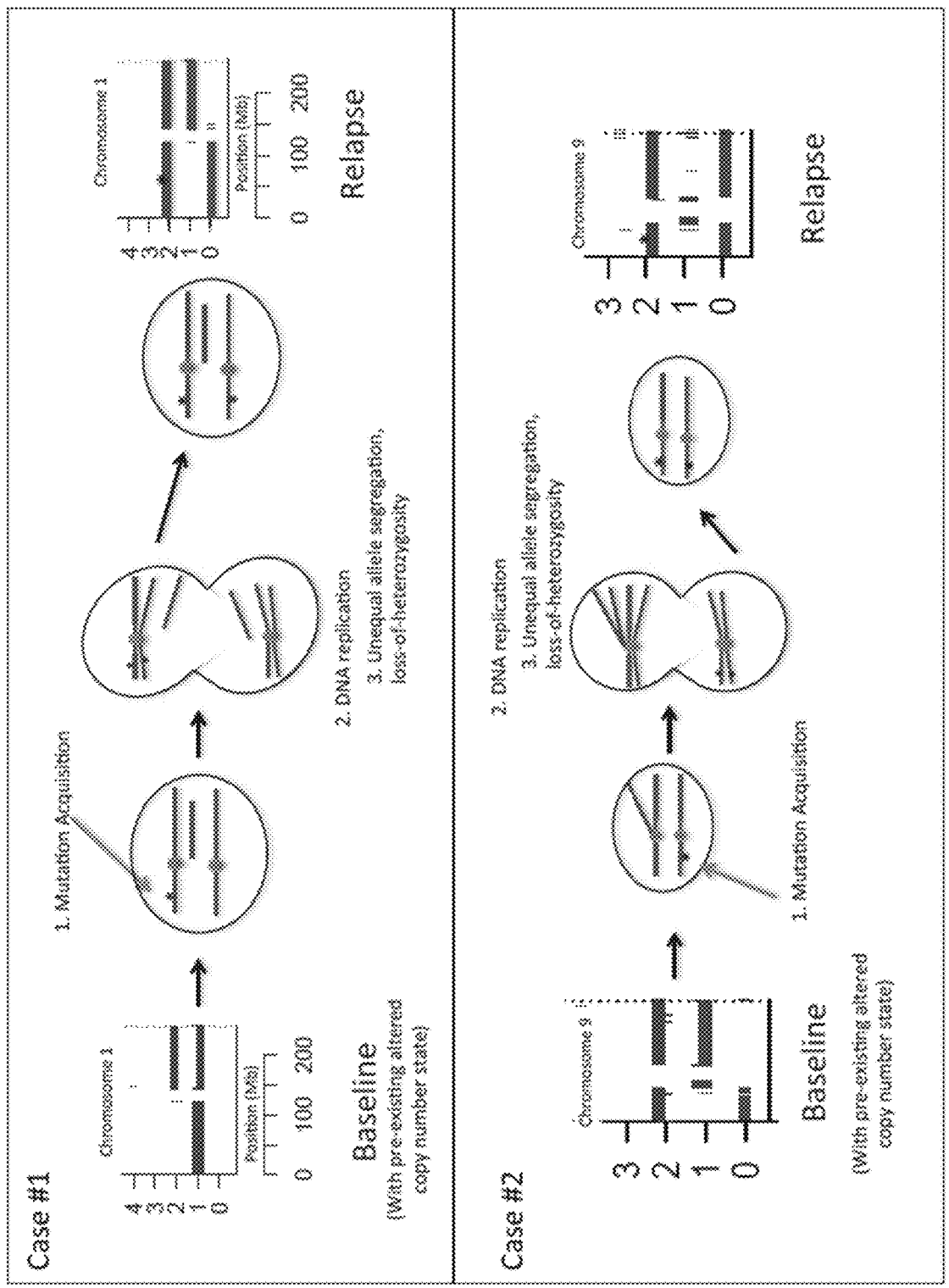
FIG. 6. Model schematic of JAK mutation acquisition in the setting of copy-number neutral loss-of-heterozygosity events. The JAK mutations in case #1 and case #2 were not observed at baseline, but were seen at homozygous allele frequency at relapse. We suggest the mutations were likely first acquired, then later followed by DNA replication and unequal allele segregation, resulting in loss of heterozygosity (and loss of the wild-type allele) without overall copy number change. This is modeled in the top panel for chromosome 1 in case #1, and in the bottom panel for chromosome 9 in case #2. Light grey and dark grey represent the maternal and paternal alleles, with arbitrary shading.

The relapsing tumors also contained the same chromosomal loss-of-heterozygosity (LOH) events as baseline, and all differences were due to further loss in the relapse samples. In the relapse biopsies from both cases, we identified new homozygous loss-of-function mutations in the interferon receptor pathway-associated kinases, with a JAK1 0503* nonsense mutation in case #1 and a JAK2 F547_splice-site mutation in case #2 (FIG. 2A, B). RNA-sequencing showed the JAK2 splice site mutation caused intron inclusion, producing an in-frame stop codon 10 base-pairs after exon 12 (FIG. 3). Therefore, both mutations are upstream of the kinase domains, and likely truncate the protein or cause nonsense-mediated decay. Neither mutation was seen at baseline, either in the exome sequencing reads, by Sanger sequencing or by targeted amplicon re-sequencing (FIG. 4). Significantly, the JAK2 mutation was the only homozygous mutation (adjusted variant allele frequency, VAF>0.85) out of 76 new non-synonymous mutations in case #2, and the JAK1 mutation was one of only three homozygous mutations among 53 new mutations in case #1 (data not shown, see Zaretsky et al Supplementary Table S5, herein incorporated by reference). To become homozygous, both JAK mutations were acquired in the context of a copy-number-neutral non-disjunction event, resulting in loss of the wild-type chromosome and duplication of the mutated allele. This is seen clearly in Case #1, where at relapse chromosome 1p (containing JAK1) showed a decrease in germline SNP minor-allele frequencies relative to baseline (FIG. 5), was missing 36 heterozygous baseline mutations (presumably on the lost allele), and contained 20 mutations (presumably on the amplified allele) that became homozygous (adjusted VAF>0.85, with change >0.35 from baseline). A similar loss-of-heterozygosity event occurred for chromosome 9 in case #2. (FIG. 6 and data not shown, see Zaretsky et al. Supplementary Table S5, herein incorporated by reference). Together, these data suggest that the anti-PD1-resistant tumors are a relatively homogenous population derived directly from the baseline tumor and that acquisition of the JAK mutations was an early founder event before clonal selection and relapse.

Functional Effects of JAK2 Mutation

Figure 7:
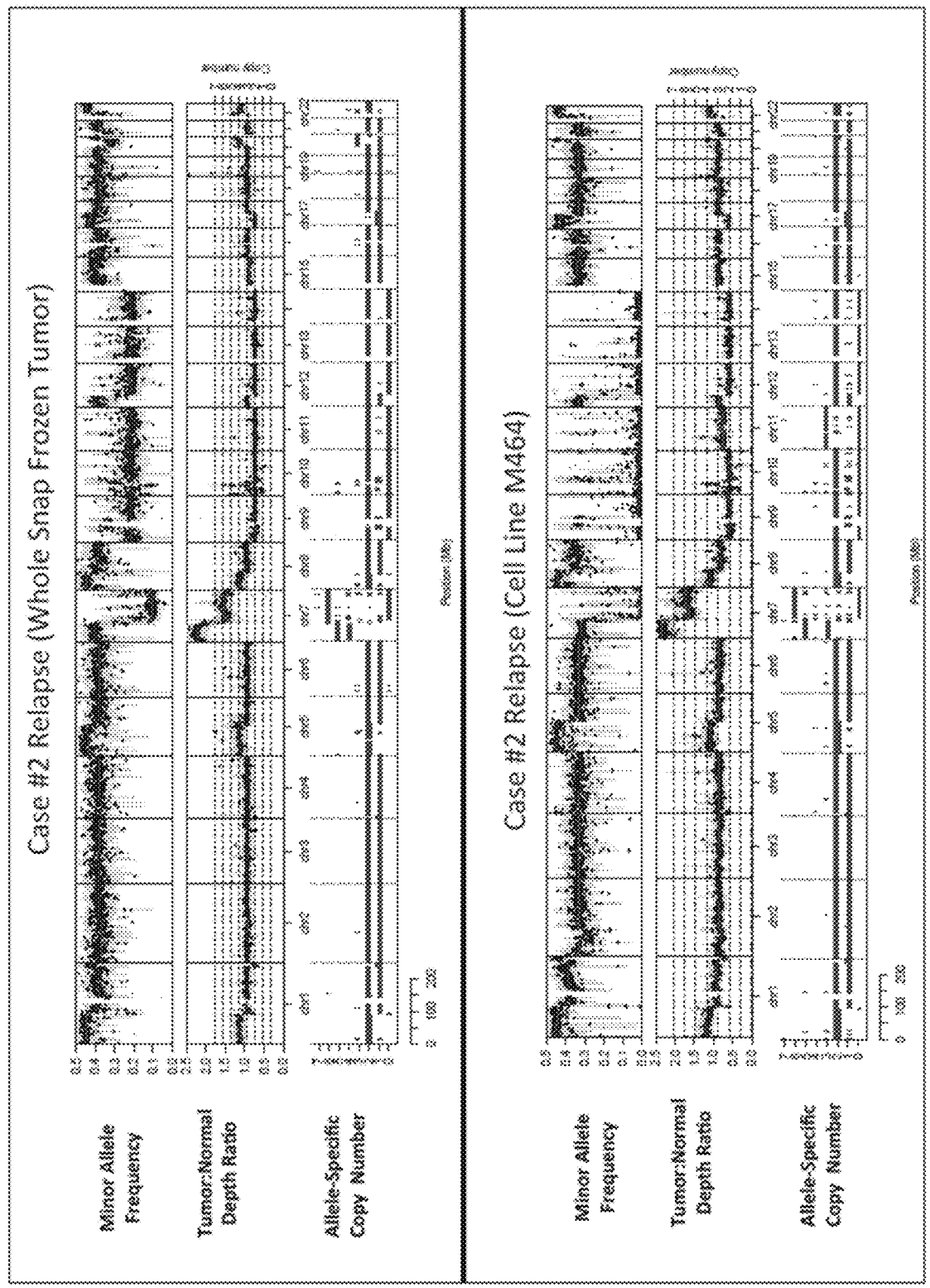
FIG. 7. Cell line M464 derived from case #2 relapse is almost identical to the snap-frozen tumor. Genome-wide Sequenza plots show the minor-allele frequency, depth ratio, and allele-specific copy number from sequencing of both the snap-frozen whole tumor (top) and the cell line (M464, bottom) derived from the relapse biopsy in case #2. After model-fit adjustment for the 44% contaminating normal DNA in the bulk tumor (from lung stroma, immune infiltrates, etc.), the allele-specific copy number estimates (bottom tracks) are nearly identical across most chromosomes between the bulk tumor and cell line.

To assess the functional consequences of the observed JAK mutations, the JAK2 mutation from case #2 using two cell lines established at baseline (M420, JAK2 wild-type) and relapse (M464, JAK2 F547_splice) were analyzed in more detail. Whole-exome sequencing confirmed M464 well represented the original bulk tumor (FIG. 7).

Figure 8:
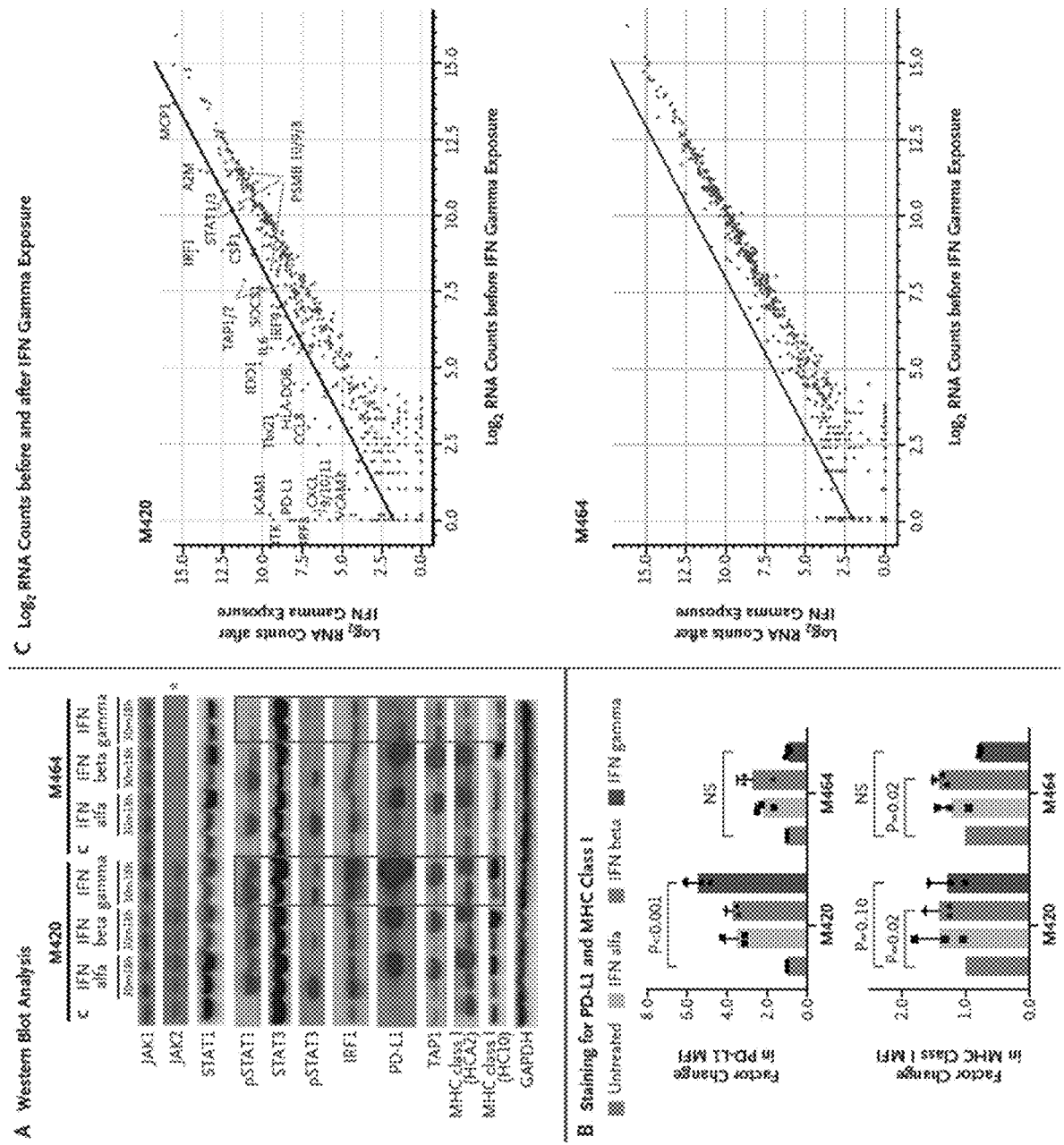
FIG. 8. Acquired JAK2 mutation abolishes interferon-gamma-induced signaling and gene expression changes. Western blot analysis in Panel A of lysates from cell lines M420 (case #2, baseline) and M464 (case #2, relapse) show JAK-STAT signaling events and downstream target induction after either 30 minute or 18-hour exposure to interferon-alpha, beta, or gamma (C indicates untreated control). JAK2 protein expression is absent in the relapse cell line (asterisk), and M464 fails to phosphorylate intermediate signaling components STAT1 and STAT3 or upregulate interferon-response target genes TAP1, PD-L1, and MHC class I following treatment specifically with interferon gamma (boxed lanes, compared to intact signaling in left box for M420). There was no change in response to interferon alpha or beta. Lack of response to interferon gamma exposure was also seen in surface staining of PD-L1 and MHC class I by flow cytometry. Panel C shows $\log_2$ RNA counts of expression for 790 immune-related genes upon exposure to interferon gamma or vehicle control. The baseline cell line M420 (top) shows upregulation of many interferon-stimulated genes (line represents four-fold increase), while the JAK2 mutated progression cell line M464 (bottom) lacks a similar response. In Panel B, MFI=mean fluorescent intensity, each point represents an independent experiment, error bars represent standard deviation and, p=two-way analysis of variance with Dunnett's correction).

Western blot analysis showed that the baseline cell line responded to interferon alpha, beta and gamma with the expected signal transduction, including an increase in signal transducer and activator of transcription 1 (STAT1) and interferon regulatory factor (IRF) expression, and STAT1 phosphorylation (pSTAT1), as well as production of downstream interferon targets such as PD-L1, TAP1, and MHC class I (FIG. 8A). However, the cell line from the progressing lesion showed a total loss of JAK2 protein (FIG. 8A) resulting in a lack of response to interferon gamma, without change in sensitivity to interferon alpha or beta. This was true of the pSTAT1 response (FIG. 8A), and for the expression of PD-L1 and MHC class I molecules (FIGS. 8A, 8B). The progressing cell line also failed to upregulate a wider panel of interferon-induced transcripts involved in antigen presentation and T-cell chemotaxis (FIG. 8C and Table 4). Together, these data indicate a total loss of functional response to interferon gamma, and are consistent with JAK2 being required for signaling through the interferon gamma receptor, as opposed to the interferon alpha/beta receptor which uses TYK2 and JAK1[25-27].

TABLE 4

List of gene transcripts studied in the Nanostring panel

| Number | Gene Name | Accession# | Class name |
|---|---|---|---|
| 1 | A2M | NM_000014.4 | Endogenous |
| 2 | ABCB1 | NM_000927.3 | Endogenous |
| 3 | ABL1 | NM_005157.3 | Endogenous |
| 4 | ADA | NM_000022.2 | Endogenous |
| 5 | ADORA2A | NM_000675.3 | Endogenous |
| 6 | AICDA | NM_020661.1 | Endogenous |
| 7 | AIRE | NM_000383.2 | Endogenous |
| 8 | AKT1* | NM_005163.2 | Endogenous |
| 9 | AKT3 | NM_181690.1 | Endogenous |
| 10 | ALCAM | NM_001627.3 | Endogenous |
| 11 | AMBP | NM_001633.3 | Endogenous |
| 12 | AMICA1 | NM_153206.2 | Endogenous |
| 13 | ANP32B | NM_006401.2 | Endogenous |
| 14 | ANXA1 | NM_000700.1 | Endogenous |
| 15 | APOE | NM_000041.2 | Endogenous |
| 16 | APP | NM_000484.3 | Endogenous |
| 17 | ARG1 | NM_000045.2 | Endogenous |
| 18 | ARG2 | NM_001172.3 | Endogenous |
| 19 | ATF1 | NM_005171.2 | Endogenous |
| 20 | ATF2 | NM_001256090.1 | Endogenous |
| 21 | ATG10 | NM_001131028.1 | Endogenous |
| 22 | ATG12 | NM_004707.2 | Endogenous |
| 23 | ATG16L1 | NM_198890.2 | Endogenous |
| 24 | ATG5 | NM_004849.2 | Endogenous |
| 25 | ATG7 | NM_001136031.2 | Endogenous |
| 26 | ATM | NM_000051.3 | Endogenous |
| 27 | AXL | NM_021913.2 | Endogenous |
| 28 | BAGE | NM_001187.1 | Endogenous |
| 29 | BATF | NM_006399.3 | Endogenous |
| 30 | BAX | NM_138761.3 | Endogenous |
| 31 | BCL10 | NM_003921.2 | Endogenous |
| 32 | BCL2 | NM_000657.2 | Endogenous |
| 33 | BCL2L1 | NM_001191.2 | Endogenous |
| 34 | BCL6 | NM_001706.2 | Endogenous |
| 35 | BID | NM_001196.2 | Endogenous |
| 36 | BIRC5 | NM_001168.2 | Endogenous |
| 37 | BLK | NM_001715.2 | Endogenous |
| 38 | BLNK | NM_013314.2 | Endogenous |
| 39 | BMI1 | NM_005180.5 | Endogenous |
| 40 | BST1 | NM_004334.2 | Endogenous |
| 41 | BST2 | NM_004335.2 | Endogenous |
| 42 | BTK | NM_000061.1 | Endogenous |
| 43 | BTLA | NM_181780.2 | Endogenous |
| 44 | C1QA | NM_015991.2 | Endogenous |
| 45 | C1QB | NM_000491.3 | Endogenous |
| 46 | C1QBP | NM_001212.3 | Endogenous |
| 47 | C1R | NM_001733.4 | Endogenous |
| 48 | C1S | NM_001734.2 | Endogenous |
| 49 | C2 | NM_000063.3 | Endogenous |
| 50 | C3 | NM_000064.2 | Endogenous |
| 51 | C3AR1 | NM_004054.2 | Endogenous |
| 52 | C4B | NM_001002029.3 | Endogenous |
| 53 | C4BPA | NM_000715.3 | Endogenous |
| 54 | C5 | NM_001735.2 | Endogenous |
| 55 | C6 | NM_000065.2 | Endogenous |
| 56 | C7 | NM_000587.2 | Endogenous |
| 57 | C8A | NM_000562.2 | Endogenous |
| 58 | C8B | NM_000066.2 | Endogenous |
| 59 | C8G | NM_000606.2 | Endogenous |
| 60 | C9 | NM_001737.3 | Endogenous |
| 61 | CAMP | NM_004345.3 | Endogenous |
| 62 | CARD11 | NM_032415.2 | Endogenous |
| 63 | CARD9 | NM_052813.4 | Endogenous |
| 64 | CASP1 | NM_001223.3 | Endogenous |
| 65 | CASP10 | NM_032977.3 | Endogenous |
| 66 | CASP3 | NM_032991.2 | Endogenous |
| 67 | CASP8 | NM_001228.4 | Endogenous |
| 68 | CCL1 | NM_002981.1 | Endogenous |
| 69 | CCL11 | NM_002986.2 | Endogenous |
| 70 | CCL13 | NM_005408.2 | Endogenous |
| 71 | CCL14 | NM_032963.3 | Endogenous |
| 72 | CCL15 | NM_032965.3 | Endogenous |

TABLE 4-continued

List of gene transcripts studied in the Nanostring panel

| Number | Gene Name | Accession# | Class name |
|---|---|---|---|
| 73 | CCL16 | NM_004590.2 | Endogenous |
| 74 | CCL17 | NM_002987.2 | Endogenous |
| 75 | CCL18 | NM_002988.2 | Endogenous |
| 76 | CCL19 | NM_006274.2 | Endogenous |
| 77 | CCL2 | NM_002982.3 | Endogenous |
| 78 | CCL20 | NM_004591.1 | Endogenous |
| 79 | CCL21 | NM_002989.2 | Endogenous |
| 80 | CCL22 | NM_002990.3 | Endogenous |
| 81 | CCL23 | NM_145898.1 | Endogenous |
| 82 | CCL24 | NM_002991.2 | Endogenous |
| 83 | CCL25 | NM_005624.2 | Endogenous |
| 84 | CCL26 | NM_006072.4 | Endogenous |
| 85 | CCL27 | NM_006664.2 | Endogenous |
| 86 | CCL28 | NM_148672.2 | Endogenous |
| 87 | CCL3 | NM_002983.2 | Endogenous |
| 88 | CCL3L1 | NM_021006.4 | Endogenous |
| 89 | CCL4 | NM_002984.2 | Endogenous |
| 90 | CCL5 | NM_002985.2 | Endogenous |
| 91 | CCL7 | NM_006273.2 | Endogenous |
| 92 | CCL8 | NM_005623.2 | Endogenous |
| 93 | CCND3 | NM_001760.2 | Endogenous |
| 94 | CCR1 | NM_001295.2 | Endogenous |
| 95 | CCR2 | NM_001123041.2 | Endogenous |
| 96 | CCR3 | NM_001837.2 | Endogenous |
| 97 | CCR4 | NM_005508.4 | Endogenous |
| 98 | CCR5 | NM_000579.1 | Endogenous |
| 99 | CCR6 | NM_031409.2 | Endogenous |
| 100 | CCR7 | NM_001838.2 | Endogenous |
| 101 | CCR9 | NM_031200.1 | Endogenous |
| 102 | CCRL2 | NM_003965.4 | Endogenous |
| 103 | CD14 | NM_000591.2 | Endogenous |
| 104 | CD160 | NM_007053.2 | Endogenous |
| 105 | CD163 | NM_004244.4 | Endogenous |
| 106 | CD164 | NM_006016.4 | Endogenous |
| 107 | CD180 | NM_005582.2 | Endogenous |
| 108 | CD19 | NM_001770.4 | Endogenous |
| 109 | CD1A | NM_001763.2 | Endogenous |
| 110 | CD1B | NM_001764.2 | Endogenous |
| 111 | CD1C | NM_001765.2 | Endogenous |
| 112 | CD1D | NM_001766.3 | Endogenous |
| 113 | CD1E | NM_001042583.1 | Endogenous |
| 114 | CD2 | NM_001767.3 | Endogenous |
| 115 | CD200 | NM_005944.5 | Endogenous |
| 116 | CD207 | NM_015717.2 | Endogenous |
| 117 | CD209 | NM_021155.2 | Endogenous |
| 118 | CD22 | NM_001771.2 | Endogenous |
| 119 | CD24 | NM_013230.2 | Endogenous |
| 120 | CD244 | NM_016382.2 | Endogenous |
| 121 | CD247 | NM_198053.1 | Endogenous |
| 122 | CD27 | NM_001242.4 | Endogenous |
| 123 | CD274 | NM_014143.3 | Endogenous |
| 124 | CD276 | NM_001024736.1 | Endogenous |
| 125 | CD28 | NM_001243078.1 | Endogenous |
| 126 | CD33 | NM_001177608.1 | Endogenous |
| 127 | CD34 | NM_001025109.1 | Endogenous |
| 128 | CD36 | NM_001001548.2 | Endogenous |
| 129 | CD37 | NM_001774.2 | Endogenous |
| 130 | CD38 | NM_001775.2 | Endogenous |
| 131 | CD3D | NM_000732.4 | Endogenous |
| 132 | CD3E | NM_000733.2 | Endogenous |
| 133 | CD3EAP | NM_012099.1 | Endogenous |
| 134 | CD3G | NM_000073.2 | Endogenous |
| 135 | CD4 | NM_000616.4 | Endogenous |
| 136 | CD40 | NM_001250.4 | Endogenous |
| 137 | CD40LG | NM_000074.2 | Endogenous |
| 138 | CD44 | NM_001001392.1 | Endogenous |
| 139 | CD46 | NM_172350.1 | Endogenous |
| 140 | CD47 | NM_001777.3 | Endogenous |
| 141 | CD48 | NM_001778.2 | Endogenous |
| 142 | CD5 | NM_014207.2 | Endogenous |
| 143 | CD53 | NM_001040033.1 | Endogenous |
| 144 | CD55 | NM_000574.3 | Endogenous |
| 145 | CD58 | NM_001779.2 | Endogenous |
| 146 | CD59 | NM_000611.4 | Endogenous |
| 147 | CD6 | NM_006725.3 | Endogenous |
| 148 | CD63 | NM_001780.4 | Endogenous |
| 149 | CD68 | NM_001251.2 | Endogenous |
| 150 | CD7 | NM_006137.6 | Endogenous |
| 151 | CD70 | NM_001252.2 | Endogenous |
| 152 | CD74 | NM_001025159.1 | Endogenous |
| 153 | CD79A | NM_001783.3 | Endogenous |
| 154 | CD79B | NM_021602.2 | Endogenous |
| 155 | CD80 | NM_005191.3 | Endogenous |
| 156 | CD81 | NM_004356.3 | Endogenous |
| 157 | CD83 | NM_004233.3 | Endogenous |
| 158 | CD84 | NM_001184879.1 | Endogenous |
| 159 | CD86 | NM_175862.3 | Endogenous |
| 160 | CD8A | NM_001768.5 | Endogenous |
| 161 | CD8B | NM_004931.3 | Endogenous |
| 162 | CD9 | NM_001769.2 | Endogenous |
| 163 | CD96 | NM_005816.4 | Endogenous |
| 164 | CD97 | NM_078481.2 | Endogenous |
| 165 | CD99 | NM_002414.3 | Endogenous |
| 166 | CDH1 | NM_004360.2 | Endogenous |
| 167 | CDH5 | NM_001795.3 | Endogenous |
| 168 | CDK1 | NM_001786.4 | Endogenous |
| 169 | CDKN1A | NM_000389.2 | Endogenous |
| 170 | CEACAM1 | NM_001712.3 | Endogenous |
| 171 | CEACAM6 | NM_002483.4 | Endogenous |
| 172 | CEACAM8 | NM_001816.3 | Endogenous |
| 173 | CEBPB | NM_005194.2 | Endogenous |
| 174 | CFB | NM_001710.5 | Endogenous |
| 175 | CFD | NM_001928.2 | Endogenous |
| 176 | CFI | NM_000204.3 | Endogenous |
| 177 | CFP | NM_002621.2 | Endogenous |
| 178 | CHIT1 | NM_003465.2 | Endogenous |
| 179 | CHUK | NM_001278.3 | Endogenous |
| 180 | CKLF | NM_181640.2 | Endogenous |
| 181 | CLEC4A | NM_194448.2 | Endogenous |
| 182 | CLEC4C | NM_203503.1 | Endogenous |
| 183 | CLEC5A | NM_013252.2 | Endogenous |
| 184 | CLEC6A | NM_001007033.1 | Endogenous |
| 185 | CLEC7A | NM_197954.2 | Endogenous |
| 186 | CLU | NM_001831.2 | Endogenous |
| 187 | CMA1 | NM_001836.2 | Endogenous |
| 188 | CMKLR1 | NM_004072.1 | Endogenous |
| 189 | COL3A1 | NM_000090.3 | Endogenous |
| 190 | COLEC12 | NM_130386.2 | Endogenous |
| 191 | CR1 | NM_000651.4 | Endogenous |
| 192 | CR2 | NM_001006658.1 | Endogenous |
| 193 | CREB1 | NM_004379.3 | Endogenous |
| 194 | CREB5 | NM_182898.2 | Endogenous |
| 195 | CREBBP | NM_004380.2 | Endogenous |
| 196 | CRK* | NM_016823.2 | Endogenous |
| 197 | CRKL* | NM_005207.3 | Endogenous |
| 198 | CRP | NM_000567.2 | Endogenous |
| 199 | CSF1 | NM_000757.4 | Endogenous |
| 200 | CSF1R | NM_005211.2 | Endogenous |
| 201 | CSF2 | NM_000758.2 | Endogenous |
| 202 | CSF2RB | NM_000395.2 | Endogenous |
| 203 | CSF3 | NM_000759.3 | Endogenous |
| 204 | CSF3R | NM_156038.2 | Endogenous |
| 205 | CT45A1 | NM_001017417.1 | Endogenous |
| 206 | CTAG1B | NM_001327.2 | Endogenous |
| 207 | CTAGE1 | NM_172241.2 | Endogenous |
| 208 | CTCFL | NM_001269042.1 | Endogenous |
| 209 | CTLA4 | NM_005214.3 | Endogenous |
| 210 | CTSG | NM_001911.2 | Endogenous |
| 211 | CTSH | NM_004390.3 | Endogenous |
| 212 | CTSL | NM_001912.4 | Endogenous |
| 213 | CTSS | NM_004079.3 | Endogenous |
| 214 | CTSW | NM_001335.3 | Endogenous |
| 215 | CX3CL1 | NM_002996.3 | Endogenous |
| 216 | CX3CR1 | NM_001337.3 | Endogenous |
| 217 | CXCL1 | NM_001511.1 | Endogenous |
| 218 | CXCL10 | NM_001565.1 | Endogenous |
| 219 | CXCL11 | NM_005409.4 | Endogenous |
| 220 | CXCL12 | NM_000609.5 | Endogenous |
| 221 | CXCL13 | NM_006419.2 | Endogenous |
| 222 | CXCL14 | NM_004887.4 | Endogenous |
| 223 | CXCL16 | NM_001100812.1 | Endogenous |
| 224 | CXCL2 | NM_002089.3 | Endogenous |

TABLE 4-continued

List of gene transcripts studied in the Nanostring panel

| Number | Gene Name | Accession# | Class name |
|---|---|---|---|
| 225 | CXCL3 | NM_002090.2 | Endogenous |
| 226 | CXCL5 | NM_002994.3 | Endogenous |
| 227 | CXCL6 | NM_002993.3 | Endogenous |
| 228 | CXCL9 | NM_002416.1 | Endogenous |
| 229 | CXCR1 | NM_000634.2 | Endogenous |
| 230 | CXCR2 | NM_001557.2 | Endogenous |
| 231 | CXCR3 | NM_001504.1 | Endogenous |
| 232 | CXCR4 | NM_003467.2 | Endogenous |
| 233 | CXCR5 | NM_001716.3 | Endogenous |
| 234 | CXCR6 | NM_006564.1 | Endogenous |
| 235 | CYBB | NM_000397.3 | Endogenous |
| 236 | CYFIP2 | NM_001037332.2 | Endogenous |
| 237 | CYLD | NM_015247.1 | Endogenous |
| 238 | DDX43 | NM_018665.2 | Endogenous |
| 239 | DDX58 | NM_014314.3 | Endogenous |
| 240 | DEFB1 | NM_005218.3 | Endogenous |
| 241 | DMBT1 | NM_007329.2 | Endogenous |
| 242 | DOCK9 | NM_001130048.1 | Endogenous |
| 243 | DPP4 | NM_001935.3 | Endogenous |
| 244 | DUSP4 | NM_057158.2 | Endogenous |
| 245 | DUSP6 | NM_001946.2 | Endogenous |
| 246 | EBI3 | NM_005755.2 | Endogenous |
| 247 | ECSIT | NM_001142464.2 | Endogenous |
| 248 | EGR1 | NM_001964.2 | Endogenous |
| 249 | EGR2 | NM_000399.3 | Endogenous |
| 250 | ELANE | NM_001972.2 | Endogenous |
| 251 | ELK1 | NM_005229.3 | Endogenous |
| 252 | ENG | NM_001114753.1 | Endogenous |
| 253 | ENTPD1 | NM_001098175.1 | Endogenous |
| 254 | EOMES | NM_005442.2 | Endogenous |
| 255 | EP300 | NM_001429.2 | Endogenous |
| 256 | EPCAM | NM_002354.1 | Endogenous |
| 257 | ETS1 | NM_005238.3 | Endogenous |
| 258 | EWSR1 | NM_013986.3 | Endogenous |
| 259 | F12 | NM_000505.3 | Endogenous |
| 260 | F13A1 | NM_000129.3 | Endogenous |
| 261 | F2RL1 | NM_005242.3 | Endogenous |
| 262 | FADD | NM_003824.2 | Endogenous |
| 263 | FAS | NM_000043.3 | Endogenous |
| 264 | FCER1A | NM_002001.2 | Endogenous |
| 265 | FCER1G | NM_004106.1 | Endogenous |
| 266 | FCER2 | NM_002002.4 | Endogenous |
| 267 | FCGR1A | NM_000566.3 | Endogenous |
| 268 | FCGR2A | NM_021642.3 | Endogenous |
| 269 | FCGR2B | NM_001002273.1 | Endogenous |
| 270 | FCGR3A | NM_000569.6 | Endogenous |
| 271 | FEZ1 | NM_005103.4 | Endogenous |
| 272 | FLT3 | NM_004119.1 | Endogenous |
| 273 | FLT3LG | NM_001459.3 | Endogenous |
| 274 | FN1 | NM_212482.1 | Endogenous |
| 275 | FOS | NM_005252.2 | Endogenous |
| 276 | FOXJ1 | NM_001454.3 | Endogenous |
| 277 | FOXP3 | NM_014009.3 | Endogenous |
| 278 | FPR2 | NM_001462.3 | Endogenous |
| 279 | FUT5 | NM_002034.2 | Endogenous |
| 280 | FUT7 | NM_004479.3 | Endogenous |
| 281 | FYN | NM_002037.3 | Endogenous |
| 282 | GAGE1 | NM_001040663.2 | Endogenous |
| 283 | GATA3 | NM_001002295.1 | Endogenous |
| 284 | GNLY | NM_006433.2 | Endogenous |
| 285 | GPI | NM_000175.2 | Endogenous |
| 286 | GTF3C1 | NM_001520.3 | Endogenous |
| 287 | GZMA | NM_006144.2 | Endogenous |
| 288 | GZMB | NM_004131.3 | Endogenous |
| 289 | GZMH | NM_033423.3 | Endogenous |
| 290 | GZMK | NM_002104.2 | Endogenous |
| 291 | GZMM | NM_005317.2 | Endogenous |
| 292 | HAMP | NM_021175.2 | Endogenous |
| 293 | HAVCR2 | NM_032782.3 | Endogenous |
| 294 | HCK | NM_002110.2 | Endogenous |
| 295 | HLA-A | NM_002116.5 | Endogenous |
| 296 | HLA-B | NM_005514.6 | Endogenous |
| 297 | HLA-C | NM_002117.4 | Endogenous |
| 298 | HLA-DMA | NM_006120.3 | Endogenous |
| 299 | HLA-DMB | NM_002118.3 | Endogenous |
| 300 | HLA-DOB | NM_002120.3 | Endogenous |
| 301 | HLA-DPA1 | NM_033554.2 | Endogenous |
| 302 | HLA-DPB1 | NM_002121.4 | Endogenous |
| 303 | HLA-DQA1 | NM_002122.3 | Endogenous |
| 304 | HLA-DQB1 | NM_002123.3 | Endogenous |
| 305 | HLA-DRA | NM_019111.3 | Endogenous |
| 306 | HLA-DRB3 | NM_022555.3 | Endogenous |
| 307 | HLA-DRB4 | NM_021983.4 | Endogenous |
| 308 | HLA-E | NM_005516.4 | Endogenous |
| 309 | HLA-G | NM_002127.4 | Endogenous |
| 310 | HMGB1 | NM_002128.4 | Endogenous |
| 311 | HRAS | NM_005343.2 | Endogenous |
| 312 | HSD11B1 | NM_181755.1 | Endogenous |
| 313 | ICAM1 | NM_000201.2 | Endogenous |
| 314 | ICAM2 | NM_000873.3 | Endogenous |
| 315 | ICAM3 | NM_002162.3 | Endogenous |
| 316 | ICAM4 | NM_001039132.1 | Endogenous |
| 317 | ICOS | NM_012092.2 | Endogenous |
| 318 | ICOSLG | NM_015259.4 | Endogenous |
| 319 | IDO1 | NM_002164.3 | Endogenous |
| 320 | IFI16 | NM_005531.1 | Endogenous |
| 321 | IFI27 | NM_005532.3 | Endogenous |
| 322 | IFI35 | NM_005533.3 | Endogenous |
| 323 | IFIH1 | NM_022168.2 | Endogenous |
| 324 | IFIT1 | NM_001548.3 | Endogenous |
| 325 | IFIT2 | NM_001547.4 | Endogenous |
| 326 | IFITM1 | NM_003641.3 | Endogenous |
| 327 | IFITM2 | NM_006435.2 | Endogenous |
| 328 | IFNA1 | NM_024013.1 | Endogenous |
| 329 | IFNA17 | NM_021268.2 | Endogenous |
| 330 | IFNA2 | NM_000605.3 | Endogenous |
| 331 | IFNA7 | NM_021057.2 | Endogenous |
| 332 | IFNA8 | NM_002170.3 | Endogenous |
| 333 | IFNAR1 | NM_000629.2 | Endogenous |
| 334 | IFNAR2* | NM_000874.3 | Endogenous |
| 335 | IFNB1 | NM_002176.2 | Endogenous |
| 336 | IFNG | NM_000619.2 | Endogenous |
| 337 | IFNGR1 | NM_000416.1 | Endogenous |
| 338 | IFNGR2 | NM_005534.3 | Endogenous |
| 339 | IFNL1 | NM_172140.1 | Endogenous |
| 340 | IFNL2 | NM_172138.1 | Endogenous |
| 341 | IGF1R | NM_000875.2 | Endogenous |
| 342 | IGF2R | NM_000876.1 | Endogenous |
| 343 | IGLL1 | NM_020070.2 | Endogenous |
| 344 | IKBKB | NM_001556.1 | Endogenous |
| 345 | IKBKE | NM_014002.2 | Endogenous |
| 346 | IKBKG | NM_003639.2 | Endogenous |
| 347 | IL10 | NM_000572.2 | Endogenous |
| 348 | IL10RA | NM_001558.2 | Endogenous |
| 349 | IL11 | NM_000641.2 | Endogenous |
| 350 | IL11RA | NM_147162.1 | Endogenous |
| 351 | IL12A | NM_000882.2 | Endogenous |
| 352 | IL12B | NM_002187.2 | Endogenous |
| 353 | IL12RB1 | NM_005535.1 | Endogenous |
| 354 | IL12RB2 | NM_001559.2 | Endogenous |
| 355 | IL13 | NM_002188.2 | Endogenous |
| 356 | IL13RA1 | NM_001560.2 | Endogenous |
| 357 | IL13RA2 | NM_000640.2 | Endogenous |
| 358 | IL15 | NM_172174.1 | Endogenous |
| 359 | IL15RA | NM_002189.2 | Endogenous |
| 360 | IL16 | NM_004513.4 | Endogenous |
| 361 | IL17A | NM_002190.2 | Endogenous |
| 362 | IL17B | NM_014443.2 | Endogenous |
| 363 | IL17F | NM_052872.3 | Endogenous |
| 364 | IL17RA | NM_014339.6 | Endogenous |
| 365 | IL17RB | NM_018725.3 | Endogenous |
| 366 | IL18 | NM_001562.2 | Endogenous |
| 367 | IL18R1 | NM_003855.3 | Endogenous |
| 368 | IL18RAP | NM_003853.2 | Endogenous |
| 369 | IL19 | NM_013371.3 | Endogenous |
| 370 | IL1A | NM_000575.3 | Endogenous |
| 371 | IL1B | NM_000576.2 | Endogenous |
| 372 | IL1R1 | NM_000877.2 | Endogenous |
| 373 | IL1R2 | NM_173343.1 | Endogenous |
| 374 | IL1RAP | NM_002182.2 | Endogenous |
| 375 | IL1RAPL2 | NM_017416.1 | Endogenous |
| 376 | IL1RL1 | NM_016232.4 | Endogenous |

TABLE 4-continued

List of gene transcripts studied in the Nanostring panel

| Number | Gene Name | Accession# | Class name |
|---|---|---|---|
| 377 | IL1RL2 | NM_003854.2 | Endogenous |
| 378 | IL1RN | NM_000577.3 | Endogenous |
| 379 | IL2 | NM_000586.2 | Endogenous |
| 380 | IL21 | NM_021803.2 | Endogenous |
| 381 | IL21R | NM_021798.2 | Endogenous |
| 382 | IL22 | NM_020525.4 | Endogenous |
| 383 | IL22RA1 | NM_021258.2 | Endogenous |
| 384 | IL22RA2 | NM_181310.1 | Endogenous |
| 385 | IL23A | NM_016584.2 | Endogenous |
| 386 | IL23R | NM_144701.2 | Endogenous |
| 387 | IL24 | NM_181339.1 | Endogenous |
| 388 | IL25 | NM_022789.2 | Endogenous |
| 389 | IL26 | NM_018402.1 | Endogenous |
| 390 | IL27 | NM_145659.3 | Endogenous |
| 391 | IL2RA | NM_000417.1 | Endogenous |
| 392 | IL2RB | NM_000878.2 | Endogenous |
| 393 | IL2RG | NM_000206.1 | Endogenous |
| 394 | IL3 | NM_000588.3 | Endogenous |
| 395 | IL32 | NM_001012633.1 | Endogenous |
| 396 | IL34 | NM_152456.1 | Endogenous |
| 397 | IL3RA | NM_002183.2 | Endogenous |
| 398 | IL4 | NM_000589.2 | Endogenous |
| 399 | IL4R | NM_000418.2 | Endogenous |
| 400 | IL5 | NM_000879.2 | Endogenous |
| 401 | IL5RA | NM_000564.3 | Endogenous |
| 402 | IL6 | NM_000600.1 | Endogenous |
| 403 | IL6R | NM_000565.2 | Endogenous |
| 404 | IL6ST | NM_002184.2 | Endogenous |
| 405 | IL7 | NM_000880.2 | Endogenous |
| 406 | IL7R | NM_002185.2 | Endogenous |
| 407 | IL8 | NM_000584.2 | Endogenous |
| 408 | IL9 | NM_000590.1 | Endogenous |
| 409 | ILF3 | NM_001137673.1 | Endogenous |
| 410 | INPP5D | NM_005541.3 | Endogenous |
| 411 | IRAK1 | NM_001569.3 | Endogenous |
| 412 | IRAK2 | NM_001570.3 | Endogenous |
| 413 | IRAK4 | NM_016123.1 | Endogenous |
| 414 | IRF1 | NM_002198.1 | Endogenous |
| 415 | IRF2 | NM_002199.3 | Endogenous |
| 416 | IRF3 | NM_001571.5 | Endogenous |
| 417 | IRF4 | NM_002460.1 | Endogenous |
| 418 | IRF5 | NM_002200.3 | Endogenous |
| 419 | IRF7 | NM_001572.3 | Endogenous |
| 420 | IRF8 | NM_002163.2 | Endogenous |
| 421 | IRF9* | NM_006084.4 | Endogenous |
| 422 | IRGM | NM_001145805.1 | Endogenous |
| 423 | IRS1* | NM_005544.2 | Endogenous |
| 424 | ISG15 | NM_005101.3 | Endogenous |
| 425 | ISG20 | NM_002201.4 | Endogenous |
| 426 | ITCH | NM_001257138.1 | Endogenous |
| 427 | ITGA1 | NM_181501.1 | Endogenous |
| 428 | ITGA2 | NM_002203.2 | Endogenous |
| 429 | ITGA2B | NM_000419.3 | Endogenous |
| 430 | ITGA4 | NM_000885.4 | Endogenous |
| 431 | ITGA5 | NM_002205.2 | Endogenous |
| 432 | ITGA6 | NM_000210.1 | Endogenous |
| 433 | ITGAE | NM_002208.4 | Endogenous |
| 434 | ITGAL | NM_002209.2 | Endogenous |
| 435 | ITGAM | NM_000632.3 | Endogenous |
| 436 | ITGAX | NM_000887.3 | Endogenous |
| 437 | ITGB1 | NM_033666.2 | Endogenous |
| 438 | ITGB2 | NM_000211.2 | Endogenous |
| 439 | ITGB3 | NM_000212.2 | Endogenous |
| 440 | ITGB4 | NM_001005731.1 | Endogenous |
| 441 | ITK | NM_005546.3 | Endogenous |
| 442 | JAK1 | NM_002227.1 | Endogenous |
| 443 | JAK2 | NM_004972.2 | Endogenous |
| 444 | JAK3 | NM_000215.2 | Endogenous |
| 445 | JAM3 | NM_032801.3 | Endogenous |
| 446 | KIR3DL1 | NM_013289.2 | Endogenous |
| 447 | KIR3DL2 | NM_006737.2 | Endogenous |
| 448 | KIR3DL3 | NM_153443.3 | Endogenous |
| 449 | KIR_Activating_Subgroup_1 | NM_001083539.1 | Endogenous |
| 450 | KIR_Activating_Subgroup_2 | NM_014512.1 | Endogenous |
| 451 | KIR_Inhibiting_Subgroup_1 | NM_014218.2 | Endogenous |
| 452 | KIR_Inhibiting_Subgroup_2 | NM_014511.3 | Endogenous |
| 453 | KIT | NM_000222.2 | Endogenous |
| 454 | KLRB1 | NM_002258.2 | Endogenous |
| 455 | KLRC1 | NM_002259.3 | Endogenous |
| 456 | KLRC2 | NM_002260.3 | Endogenous |
| 457 | KLRD1 | NM_002262.3 | Endogenous |
| 458 | KLRF1 | NM_016523.1 | Endogenous |
| 459 | KLRG1 | NM_005810.3 | Endogenous |
| 460 | KLRK1 | NM_007360.3 | Endogenous |
| 461 | LAG3 | NM_002286.5 | Endogenous |
| 462 | LAIR2 | NM_002288.3 | Endogenous |
| 463 | LAMP1 | NM_005561.3 | Endogenous |
| 464 | LAMP2 | NM_001122606.1 | Endogenous |
| 465 | LAMP3 | NM_014398.3 | Endogenous |
| 466 | LBP | NM_004139.2 | Endogenous |
| 467 | LCK | NM_005356.2 | Endogenous |
| 468 | LCN2 | NM_005564.3 | Endogenous |
| 469 | LCP1 | NM_002298.4 | Endogenous |
| 470 | LGALS3 | NM_001177388.1 | Endogenous |
| 471 | LIF | NM_002309.3 | Endogenous |
| 472 | LILRA1 | NM_006863.1 | Endogenous |
| 473 | LILRA4 | NM_012276.3 | Endogenous |
| 474 | LILRA5 | NM_181879.2 | Endogenous |
| 475 | LILRB1 | NM_001081637.1 | Endogenous |
| 476 | LILRB2 | NM_005874.1 | Endogenous |
| 477 | LILRB3 | NM_006864.2 | Endogenous |
| 478 | LRP1 | NM_002332.2 | Endogenous |
| 479 | LRRN3 | NM_001099660.1 | Endogenous |
| 480 | LTA | NM_000595.2 | Endogenous |
| 481 | LTB | NM_002341.1 | Endogenous |
| 482 | LTBR | NM_002342.1 | Endogenous |
| 483 | LTF | NM_002343.2 | Endogenous |
| 484 | LTK | NM_001135685.1 | Endogenous |
| 485 | LY86 | NM_004271.3 | Endogenous |
| 486 | LY9 | NM_001033667.1 | Endogenous |
| 487 | LY96 | NM_015364.2 | Endogenous |
| 488 | LYN | NM_002350.1 | Endogenous |
| 489 | MAF | NM_005360.4 | Endogenous |
| 490 | MAGEA1 | NM_004988.4 | Endogenous |
| 491 | MAGEA12 | NM_001166386.1 | Endogenous |
| 492 | MAGEA3 | NM_005362.3 | Endogenous |
| 493 | MAGEA4 | NM_001011548.1 | Endogenous |
| 494 | MAGEB2 | NM_002364.4 | Endogenous |
| 495 | MAGEC1 | NM_005462.4 | Endogenous |
| 496 | MAGEC2 | NM_016249.3 | Endogenous |
| 497 | MAP2K1 | NM_002755.2 | Endogenous |
| 498 | MAP2K2 | NM_030662.2 | Endogenous |
| 499 | MAP2K4 | NM_003010.2 | Endogenous |
| 500 | MAP3K1 | NM_005921.1 | Endogenous |
| 501 | MAP3K5 | NM_005923.3 | Endogenous |
| 502 | MAP3K7 | NM_145333.1 | Endogenous |
| 503 | MAP4K2 | NM_004579.2 | Endogenous |
| 504 | MAPK1 | NM_138957.2 | Endogenous |
| 505 | MAPK11 | NM_002751.5 | Endogenous |
| 506 | MAPK14 | NM_001315.1 | Endogenous |
| 507 | MAPK3 | NM_001040056.1 | Endogenous |
| 508 | MAPK6* | NM_002748.2 | Endogenous |
| 509 | MAPK8 | NM_002750.2 | Endogenous |
| 510 | MAPKAPK2 | NM_004759.3 | Endogenous |
| 511 | MARCO | NM_006770.3 | Endogenous |
| 512 | MASP1 | NM_139125.3 | Endogenous |
| 513 | MASP2 | NM_139208.1 | Endogenous |
| 514 | MAVS | NM_020746.3 | Endogenous |
| 515 | MBL2 | NM_000242.2 | Endogenous |
| 516 | MCAM | NM_006500.2 | Endogenous |
| 517 | MEF2C | NM_002397.3 | Endogenous |
| 518 | MEFV | NM_000243.2 | Endogenous |
| 519 | MERTK | NM_006343.2 | Endogenous |
| 520 | MFGE8 | NM_001114614.1 | Endogenous |
| 521 | MICA | NM_000247.1 | Endogenous |
| 522 | MICB | NM_005931.3 | Endogenous |
| 523 | MIF | NM_002415.1 | Endogenous |
| 524 | MME | NM_000902.2 | Endogenous |

TABLE 4-continued

List of gene transcripts studied in the Nanostring panel

| Number | Gene Name | Accession# | Class name |
|---|---|---|---|
| 525 | MNX1 | NM_005515.3 | Endogenous |
| 526 | MPPED1 | NM_001044370.1 | Endogenous |
| 527 | MR1 | NM_001531.2 | Endogenous |
| 528 | MRC1 | NM_002438.2 | Endogenous |
| 529 | MS4A1 | NM_152866.2 | Endogenous |
| 530 | MS4A2 | NM_000139.3 | Endogenous |
| 531 | MSR1 | NM_002445.3 | Endogenous |
| 532 | MST1R | NM_002447.1 | Endogenous |
| 533 | MUC1 | NM_001018017.1 | Endogenous |
| 534 | MX1 | NM_002462.2 | Endogenous |
| 535 | MYD88 | NM_002468.3 | Endogenous |
| 536 | NCAM1 | NM_000615.5 | Endogenous |
| 537 | NCF4 | NM_000631.4 | Endogenous |
| 538 | NCR1 | NM_004829.5 | Endogenous |
| 539 | NEFL | NM_006158.3 | Endogenous |
| 540 | NFATC1 | NM_172389.1 | Endogenous |
| 541 | NFATC2 | NM_012340.3 | Endogenous |
| 542 | NFATC3 | NM_004555.2 | Endogenous |
| 543 | NFATC4 | NM_001136022.2 | Endogenous |
| 544 | NFKB1 | NM_003998.2 | Endogenous |
| 545 | NFKB2 | NM_002502.2 | Endogenous |
| 546 | NFKBIA | NM_020529.1 | Endogenous |
| 547 | NLRC5 | NM_032206.4 | Endogenous |
| 548 | NLRP3 | NM_001079821.2 | Endogenous |
| 549 | NOD1 | NM_006092.1 | Endogenous |
| 550 | NOD2 | NM_022162.1 | Endogenous |
| 551 | NOS2A | NM_153292.1 | Endogenous |
| 552 | NOTCH1 | NM_017617.3 | Endogenous |
| 553 | NRP1 | NM_003873.5 | Endogenous |
| 554 | NT5E | NM_002526.2 | Endogenous |
| 555 | NUP107 | NM_020401.2 | Endogenous |
| 556 | OAS3 | NM_006187.2 | Endogenous |
| 557 | OSM | NM_020530.4 | Endogenous |
| 558 | PASD1 | NM_173493.2 | Endogenous |
| 559 | PAX5 | NM_016734.1 | Endogenous |
| 560 | PBK | NM_018492.2 | Endogenous |
| 561 | PDCD1 | NM_005018.1 | Endogenous |
| 562 | PDCD1LG2 | NM_025239.3 | Endogenous |
| 563 | PDGFC | NM_016205.2 | Endogenous |
| 564 | PDGFRB | NM_002609.3 | Endogenous |
| 565 | PECAM1 | NM_000442.3 | Endogenous |
| 566 | PIAS1* | NM_016166.1 | Endogenous |
| 567 | PIK3C2A* | NM_002645.1 | Endogenous |
| 568 | PIK3C2B* | NM_002646.3 | Endogenous |
| 569 | PIK3C2G* | NM_004570.4 | Endogenous |
| 570 | PIK3CA* | NM_006218.2 | Endogenous |
| 571 | PIK3CB* | NM_006219.1 | Endogenous |
| 572 | PIK3CD | NM_005026.3 | Endogenous |
| 573 | PIK3CG | NM_002649.2 | Endogenous |
| 574 | PIK3R1* | NM_181504.2 | Endogenous |
| 575 | PIN1 | NM_006221.2 | Endogenous |
| 576 | PLA2G1B | NM_000928.2 | Endogenous |
| 577 | PLA2G6 | NM_001004426.1 | Endogenous |
| 578 | PLAU | NM_002658.2 | Endogenous |
| 579 | PLAUR | NM_001005376.1 | Endogenous |
| 580 | PMCH | NM_002674.2 | Endogenous |
| 581 | PNMA1 | NM_006029.4 | Endogenous |
| 582 | POU2AF1 | NM_006235.2 | Endogenous |
| 583 | POU2F2 | NM_002698.2 | Endogenous |
| 584 | PPARG | NM_015869.3 | Endogenous |
| 585 | PPBP | NM_002704.2 | Endogenous |
| 586 | PRAME | NM_006115.3 | Endogenous |
| 587 | PRF1 | NM_005041.3 | Endogenous |
| 588 | PRG2 | NM_002728.4 | Endogenous |
| 589 | PRKCD | NM_006254.3 | Endogenous |
| 590 | PRKCE | NM_005400.2 | Endogenous |
| 591 | PRM1 | NM_002761.2 | Endogenous |
| 592 | PSEN1 | NM_000021.2 | Endogenous |
| 593 | PSEN2 | NM_000447.2 | Endogenous |
| 594 | PSMB10 | NM_002801.2 | Endogenous |
| 595 | PSMB7 | NM_002799.2 | Endogenous |
| 596 | PSMB8 | NM_004159.4 | Endogenous |
| 597 | PSMB9 | NM_002800.4 | Endogenous |
| 598 | PSMD7 | NM_002811.3 | Endogenous |
| 599 | PTEN* | NM_000314.4 | Endogenous |
| 600 | PTGDR2 | NM_004778.1 | Endogenous |
| 601 | PTGS2 | NM_000963.1 | Endogenous |
| 602 | PTPRC | NM_080921.3 | Endogenous |
| 603 | PVR | NM_006505.3 | Endogenous |
| 604 | PYCARD | NM_013258.3 | Endogenous |
| 605 | RAC1* | NM_198829.1 | Endogenous |
| 606 | RAG1 | NM_000448.2 | Endogenous |
| 607 | RAPGEF1* | NM_005312.2 | Endogenous |
| 608 | REL | NM_002908.2 | Endogenous |
| 609 | RELA | NM_021975.2 | Endogenous |
| 610 | RELB | NM_006509.2 | Endogenous |
| 611 | REPS1 | NM_001128617.2 | Endogenous |
| 612 | RIPK2 | NM_003821.5 | Endogenous |
| 613 | ROPN1 | NM_017578.2 | Endogenous |
| 614 | RORA | NM_134261.2 | Endogenous |
| 615 | RORC | NM_001001523.1 | Endogenous |
| 616 | RPS6 | NM_001010.2 | Endogenous |
| 617 | RRAD | NM_004165.1 | Endogenous |
| 618 | RUNX1 | NM_001754.4 | Endogenous |
| 619 | RUNX3 | NM_004350.1 | Endogenous |
| 620 | S100A12 | NM_005621.1 | Endogenous |
| 621 | S100A7 | NM_002963.2 | Endogenous |
| 622 | S100A8 | NM_002964.3 | Endogenous |
| 623 | S100B | NM_006272.1 | Endogenous |
| 624 | SAA1 | NM_199161.1 | Endogenous |
| 625 | SBNO2 | NM_014963.2 | Endogenous |
| 626 | SELE | NM_000450.2 | Endogenous |
| 627 | SELL | NR_029467.1 | Endogenous |
| 628 | SELPLG | NM_001206609.1 | Endogenous |
| 629 | SEMG1 | NM_003007.2 | Endogenous |
| 630 | SERPINB2 | NM_002575.1 | Endogenous |
| 631 | SERPING1 | NM_000062.2 | Endogenous |
| 632 | SH2B2 | NM_020979.3 | Endogenous |
| 633 | SH2D1A | NM_001114937.2 | Endogenous |
| 634 | SH2D1B | NM_053282.4 | Endogenous |
| 635 | SIGIRR | NM_021805.2 | Endogenous |
| 636 | SIGLEC1 | NM_023068.3 | Endogenous |
| 637 | SLAMF1 | NM_003037.2 | Endogenous |
| 638 | SLAMF6 | NM_001184714.1 | Endogenous |
| 639 | SLAMF7 | NM_021181.3 | Endogenous |
| 640 | SLC11A1 | NM_000578.2 | Endogenous |
| 641 | SMAD2 | NM_005901.5 | Endogenous |
| 642 | SMAD3 | NM_005902.3 | Endogenous |
| 643 | SMPD3 | NM_018667.3 | Endogenous |
| 644 | SOCS1 | NM_003745.1 | Endogenous |
| 645 | SOCS2* | NM_003877.3 | Endogenous |
| 646 | SPA17 | NM_017425.3 | Endogenous |
| 647 | SPACA3 | NM_173847.3 | Endogenous |
| 648 | SPANXB1 | NM_032461.2 | Endogenous |
| 649 | SPINK5 | NM_006846.3 | Endogenous |
| 650 | SPN | NM_003123.3 | Endogenous |
| 651 | SPO11 | NM_198265.1 | Endogenous |
| 652 | SPP1 | NM_000582.2 | Endogenous |
| 653 | SSX1 | NM_005635.2 | Endogenous |
| 654 | SSX4 | NM_005636.3 | Endogenous |
| 655 | ST6GAL1 | NM_003032.2 | Endogenous |
| 656 | STAT1 | NM_007315.2 | Endogenous |
| 657 | STAT2 | NM_005419.2 | Endogenous |
| 658 | STAT3 | NM_139276.2 | Endogenous |
| 659 | STAT4 | NM_003151.2 | Endogenous |
| 660 | STAT5A* | NM_003152.2 | Endogenous |
| 661 | STAT5B | NM_012448.3 | Endogenous |
| 662 | STAT6 | NM_003153.3 | Endogenous |
| 663 | SYCP1 | NM_003176.2 | Endogenous |
| 664 | SYK | NM_003177.3 | Endogenous |
| 665 | SYT17 | NM_016524.2 | Endogenous |
| 666 | TAB1 | NM_153497.2 | Endogenous |
| 667 | TAL1 | NM_003189.2 | Endogenous |
| 668 | TANK | NM_004180.2 | Endogenous |
| 669 | TAP1 | NM_000593.5 | Endogenous |
| 670 | TAP2 | NM_000544.3 | Endogenous |
| 671 | TAPBP | NM_003190.4 | Endogenous |
| 672 | TARP | NM_001003799.1 | Endogenous |
| 673 | TBK1 | NM_013254.2 | Endogenous |
| 674 | TBX21 | NM_013351.1 | Endogenous |
| 675 | TCF7 | NM_003202.2 | Endogenous |
| 676 | TFE3 | NM_006521.3 | Endogenous |

TABLE 4-continued

List of gene transcripts studied in the Nanostring panel

| Number | Gene Name | Accession# | Class name |
|---|---|---|---|
| 677 | TFEB | NM_007162.2 | Endogenous |
| 678 | TFRC | NM_003234.1 | Endogenous |
| 679 | TGFB1 | NM_000660.3 | Endogenous |
| 680 | TGFB2 | NM_003238.2 | Endogenous |
| 681 | THBD | NM_000361.2 | Endogenous |
| 682 | THBS1 | NM_003246.2 | Endogenous |
| 683 | THY1 | NM_006288.2 | Endogenous |
| 684 | TICAM1 | NM_014261.1 | Endogenous |
| 685 | TICAM2 | NM_021649.4 | Endogenous |
| 686 | TIGIT | NM_173799.2 | Endogenous |
| 687 | TIRAP | NM_148910.2 | Endogenous |
| 688 | TLR1 | NM_003263.3 | Endogenous |
| 689 | TLR10 | NM_030956.2 | Endogenous |
| 690 | TLR2 | NM_003264.3 | Endogenous |
| 691 | TLR3 | NM_003265.2 | Endogenous |
| 692 | TLR4 | NM_138554.2 | Endogenous |
| 693 | TLR5 | NM_003268.3 | Endogenous |
| 694 | TLR6 | NM_006068.2 | Endogenous |
| 695 | TLR7 | NM_016562.3 | Endogenous |
| 696 | TLR8 | NM_016610.2 | Endogenous |
| 697 | TLR9 | NM_017442.2 | Endogenous |
| 698 | TMEFF2 | NM_016192.2 | Endogenous |
| 699 | TNF | NM_000594.2 | Endogenous |
| 700 | TNFAIP3 | NM_006290.2 | Endogenous |
| 701 | TNFRSF10B | NM_003842.3 | Endogenous |
| 702 | TNFRSF10C | NM_003841.3 | Endogenous |
| 703 | TNFRSF11A | NM_003839.2 | Endogenous |
| 704 | TNFRSF11B | NM_002546.2 | Endogenous |
| 705 | TNFRSF12A | NM_016639.1 | Endogenous |
| 706 | TNFRSF13B | NM_012452.2 | Endogenous |
| 707 | TNFRSF13C | NM_052945.3 | Endogenous |
| 708 | TNFRSF14 | NM_003820.2 | Endogenous |
| 709 | TNFRSF17 | NM_001192.2 | Endogenous |
| 710 | TNFRSF18 | NM_004195.2 | Endogenous |
| 711 | TNFRSF1A | NM_001065.2 | Endogenous |
| 712 | TNFRSF1B | NM_001066.2 | Endogenous |
| 713 | TNFRSF4 | NM_003327.2 | Endogenous |
| 714 | TNFRSF8 | NM_152942.2 | Endogenous |
| 715 | TNFRSF9 | NM_001561.4 | Endogenous |
| 716 | TNFSF10 | NM_003810.2 | Endogenous |
| 717 | TNFSF11 | NM_003701.2 | Endogenous |
| 718 | TNFSF12 | NM_003809.2 | Endogenous |
| 719 | TNFSF13 | NM_003808.3 | Endogenous |
| 720 | TNFSF13B | NM_006573.4 | Endogenous |
| 721 | TNFSF14 | NM_003807.3 | Endogenous |
| 722 | TNFSF15 | NM_001204344.1 | Endogenous |
| 723 | TNFSF18 | NM_005092.2 | Endogenous |
| 724 | TNFSF4 | NM_003326.2 | Endogenous |
| 725 | TNFSF8 | NM_001244.3 | Endogenous |
| 726 | TOLLIP | NM_019009.2 | Endogenous |
| 727 | TP53 | NM_000546.2 | Endogenous |
| 728 | TPSAB1 | NM_003294.3 | Endogenous |
| 729 | TPTE | NM_199259.2 | Endogenous |
| 730 | TRAF2 | NM_021138.3 | Endogenous |
| 731 | TRAF3 | NM_145725.1 | Endogenous |
| 732 | TRAF6 | NM_145803.1 | Endogenous |
| 733 | TREM1 | NM_018643.3 | Endogenous |
| 734 | TREM2 | NM_018965.3 | Endogenous |
| 735 | TTK | NM_003318.3 | Endogenous |
| 736 | TXK | NM_003328.1 | Endogenous |
| 737 | TXNIP | NM_006472.1 | Endogenous |
| 738 | TYK2 | NM_003331.3 | Endogenous |
| 739 | UBC | NM_021009.3 | Endogenous |
| 740 | ULBP2 | NM_025217.2 | Endogenous |
| 741 | USP9Y | NM_004654.3 | Endogenous |
| 742 | VCAM1 | NM_001078.3 | Endogenous |
| 743 | VEGFA | NM_001025366.1 | Endogenous |
| 744 | VEGFC | NM_005429.2 | Endogenous |
| 745 | XCL2 | NM_003175.3 | Endogenous |
| 746 | XCR1 | NM_005283.2 | Endogenous |
| 747 | YTHDF2 | NM_001172828.1 | Endogenous |
| 748 | ZAP70 | NM_001079.3 | Endogenous |
| 749 | ZNF205 | NM_001031686.1 | Endogenous |
| 750 | mTOR* | NM_004958.2 | Endogenous |
| 751 | ABCF1 | NM_001090.2 | Housekeeping |
| 752 | AGK | NM_018238.3 | Housekeeping |
| 753 | ALAS1 | NM_000688.4 | Housekeeping |
| 754 | AMMECR1L | NM_001199140.1 | Housekeeping |
| 755 | CC2D1B | NM_032449.2 | Housekeeping |
| 756 | CNOT10 | NM_001256741.1 | Housekeeping |
| 757 | CNOT4 | NM_001190848.1 | Housekeeping |
| 758 | COG7 | NM_153603.3 | Housekeeping |
| 759 | DDX50 | NM_024045.1 | Housekeeping |
| 760 | DHX16 | NM_001164239.1 | Housekeeping |
| 761 | DNAJC14 | NM_032364.5 | Housekeeping |
| 762 | EDC3 | NM_001142443.1 | Housekeeping |
| 763 | EIF2B4 | NM_172195.3 | Housekeeping |
| 764 | ERCC3 | NM_000122.1 | Housekeeping |
| 765 | FCF1 | NM_015962.4 | Housekeeping |
| 766 | G6PD | NM_000402.2 | Housekeeping |
| 767 | GPATCH3 | NM_022078.2 | Housekeeping |
| 768 | GUSB | NM_000181.1 | Housekeeping |
| 769 | HDAC3 | NM_003883.2 | Housekeeping |
| 770 | HPRT1 | NM_000194.1 | Housekeeping |
| 771 | MRPS5 | NM_031902.3 | Housekeeping |
| 772 | MTMR14 | NM_022485.3 | Housekeeping |
| 773 | NOL7 | NM_016167.3 | Housekeeping |
| 774 | NUBP1 | NM_001278506.1 | Housekeeping |
| 775 | POLR2A | NM_000937.2 | Housekeeping |
| 776 | PPIA | NM_021130.2 | Housekeeping |
| 777 | PRPF38A | NM_032864.3 | Housekeeping |
| 778 | SAP130 | NM_024545.3 | Housekeeping |
| 779 | SDHA | NM_004168.1 | Housekeeping |
| 780 | SF3A3 | NM_006802.2 | Housekeeping |
| 781 | TBP | NM_001172085.1 | Housekeeping |
| 782 | TLK2 | NM_006852.2 | Housekeeping |
| 783 | TMUB2 | NM_024107.2 | Housekeeping |
| 784 | TRIM39 | NM_021253.3 | Housekeeping |
| 785 | TUBB | NM_178014.2 | Housekeeping |
| 786 | USP39 | NM_001256725.1 | Housekeeping |
| 787 | ZC3H14 | NM_001160103.1 | Housekeeping |
| 788 | ZKSCAN5 | NM_014569.3 | Housekeeping |
| 789 | ZNF143 | NM_003442.5 | Housekeeping |
| 790 | ZNF346 | NM_012279.2 | Housekeeping |
| 791 | NEG_A | ERCC_00096.1 | Negative |
| 792 | NEG_B | ERCC_00041.1 | Negative |
| 793 | NEG_C | ERCC_00019.1 | Negative |
| 794 | NEG_D | ERCC_00076.1 | Negative |
| 795 | NEG_E | ERCC_00098.1 | Negative |
| 796 | NEG_F | ERCC_00126.1 | Negative |
| 797 | NEG_G | ERCC_00144.1 | Negative |
| 798 | NEG_H | ERCC_00154.1 | Negative |
| 799 | POS_A | ERCC_00117.1 | Positive |
| 800 | POS_B | ERCC_00112.1 | Positive |
| 801 | POS_C | ERCC_00002.1 | Positive |
| 802 | POS_D | ERCC_00092.1 | Positive |
| 803 | POS_E | ERCC_00035.1 | Positive |
| 804 | POS_F | ERCC_00034.1 | Positive |

Figure 9A:
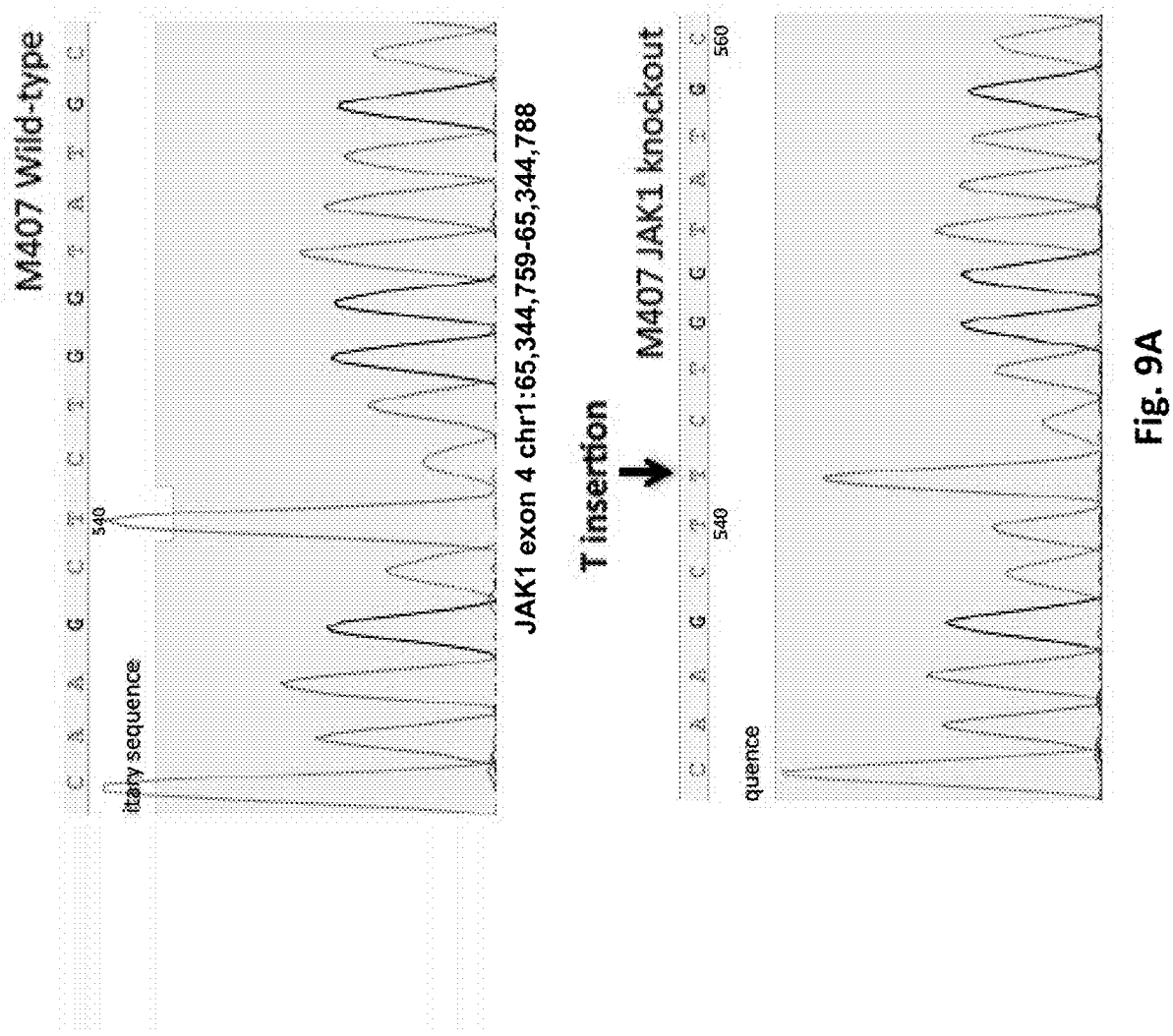
FIG. 9A. Shows Sanger sequence of JAK1 exon 4 in the M407 parental cell line (top) versus the CRISPR/Cas9 edited subline (bottom) showing insertion of a single thymine at the cutpoint.
Figure 9B:
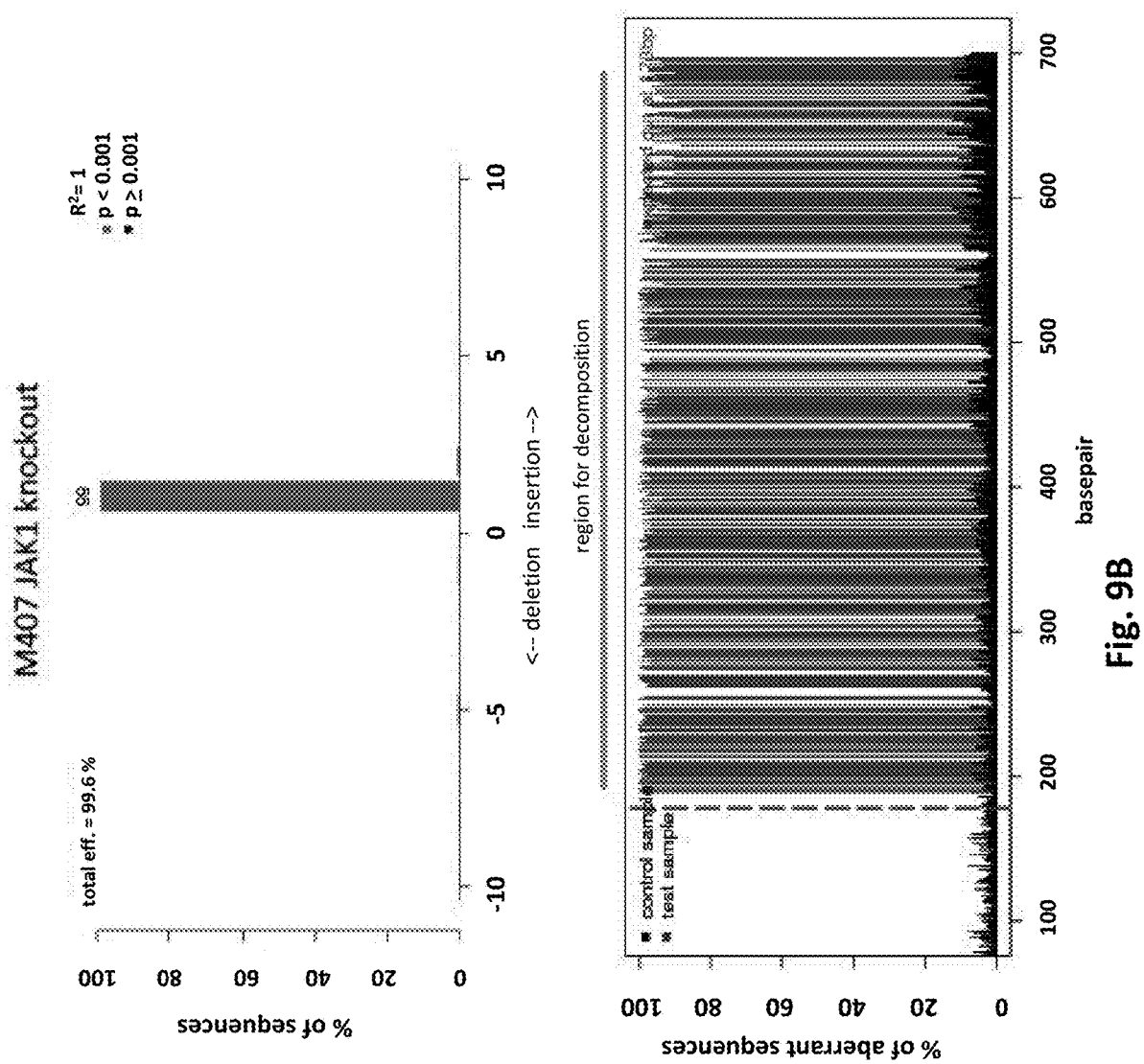
FIG. 9B. Shows trace decomposition analysis of the JAK1 mutation by TIDE[15], showing 99% of alleles of sequences contain the one base pair insertion.
Figure 9C:
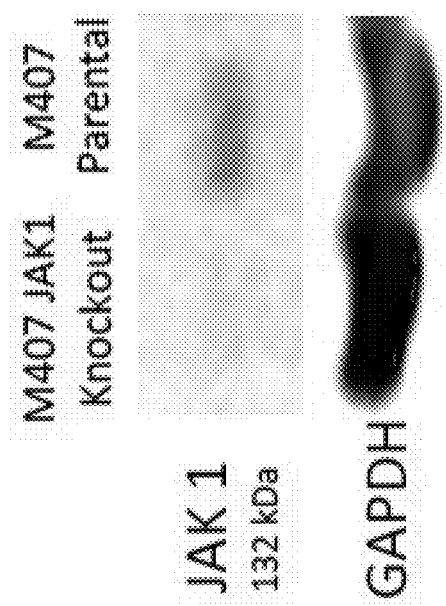
FIG. 9C. Shows total loss of JAK1 protein by Western blot in this cell line.
Figure 10A:
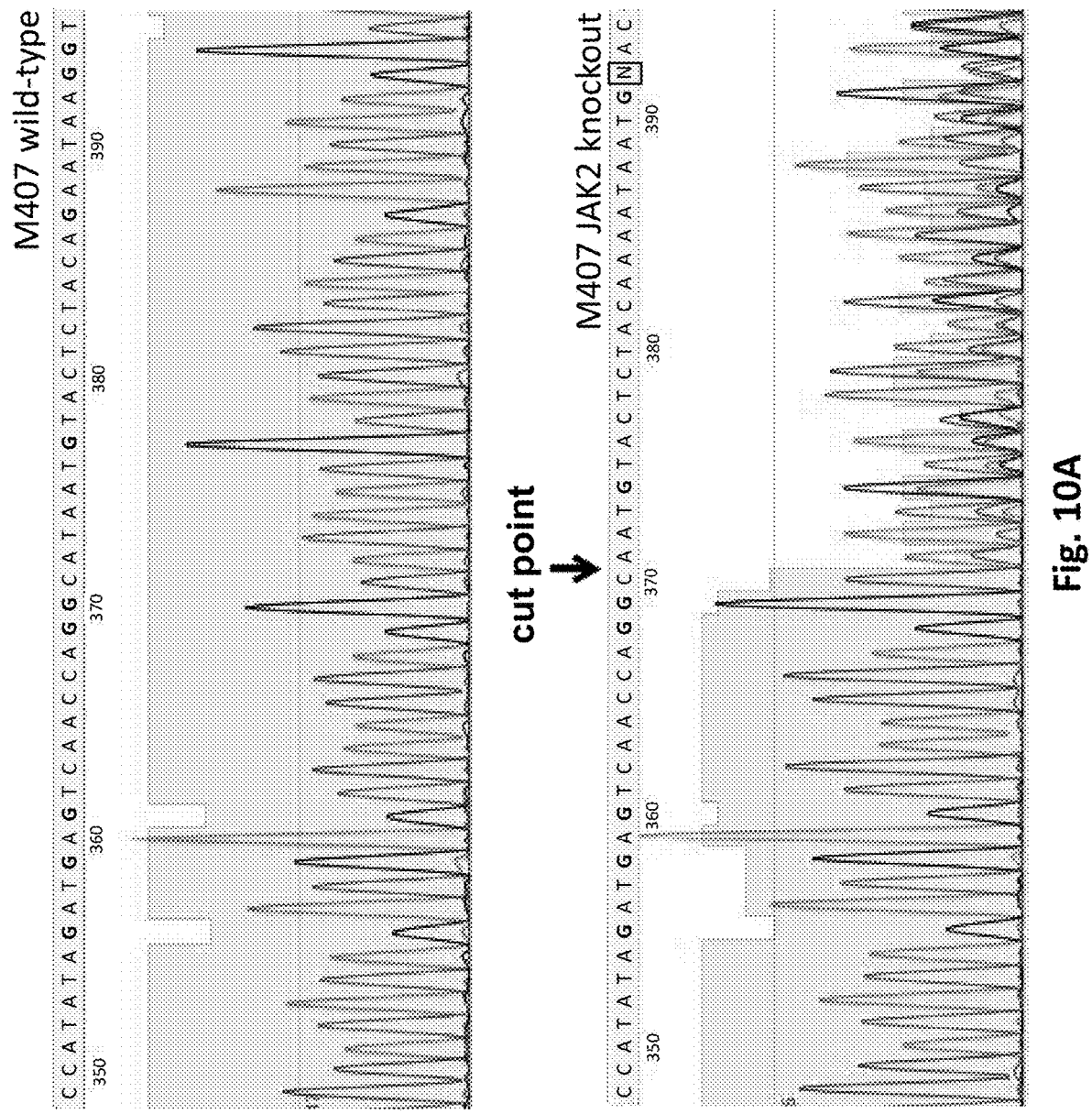
FIG. 10A. (SEQ ID NOs: 39-40) CRISPR/Cas-9 knockout of JAK2 in M407. Shows Sanger sequence of JAK2 exon 2 in the M407 parental cell line (top) versus the CRISPR/Cas9 edited subline (bottom). Arrow shows the main breakpoint.
Figure 10B:
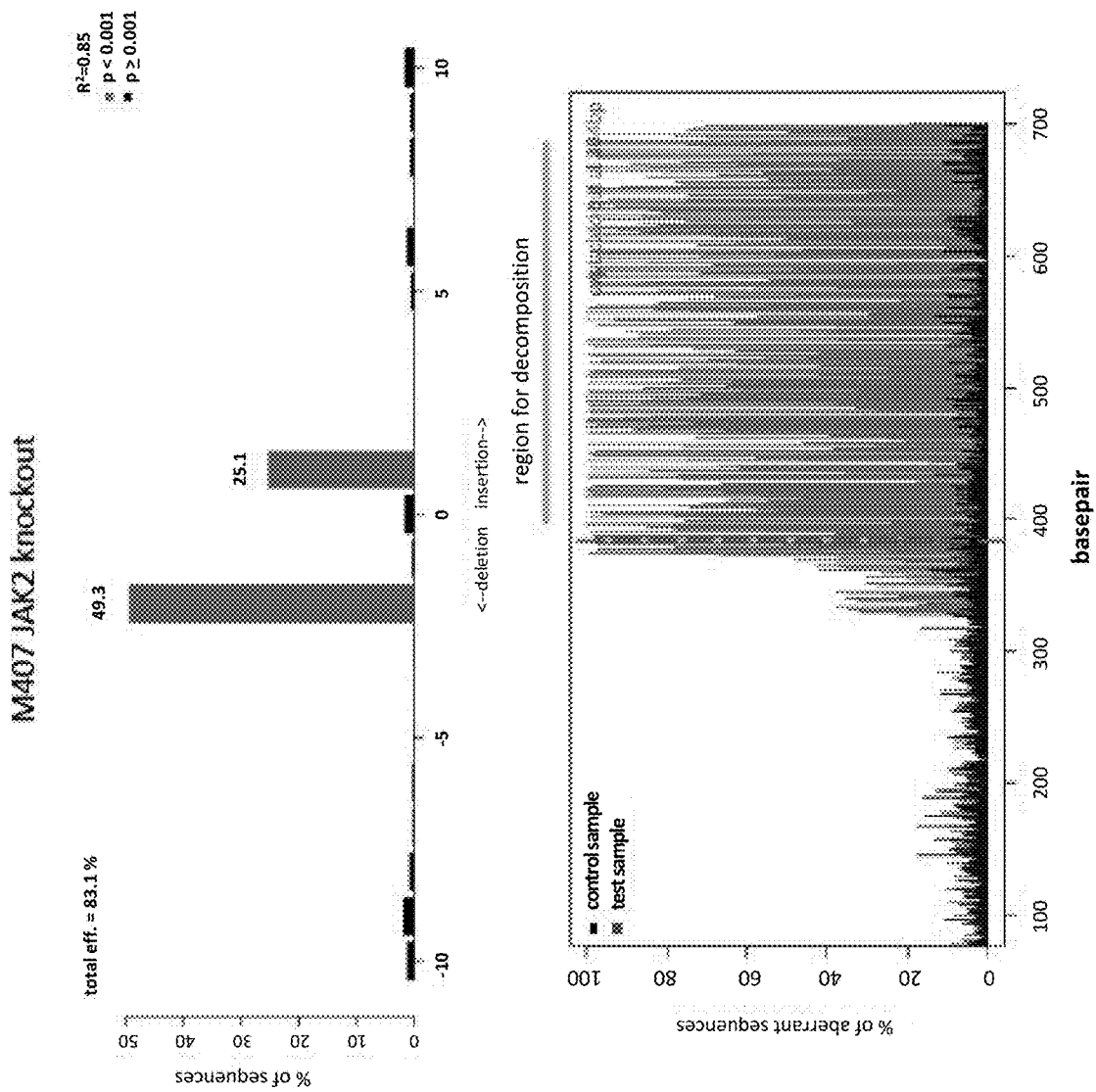
FIG. 10B. CRISPR/Cas-9 knockout of JAK2 in M407. Shows trace decomposition analysis of the JAK2 mutation by TIDE[15].
Figure 10C:
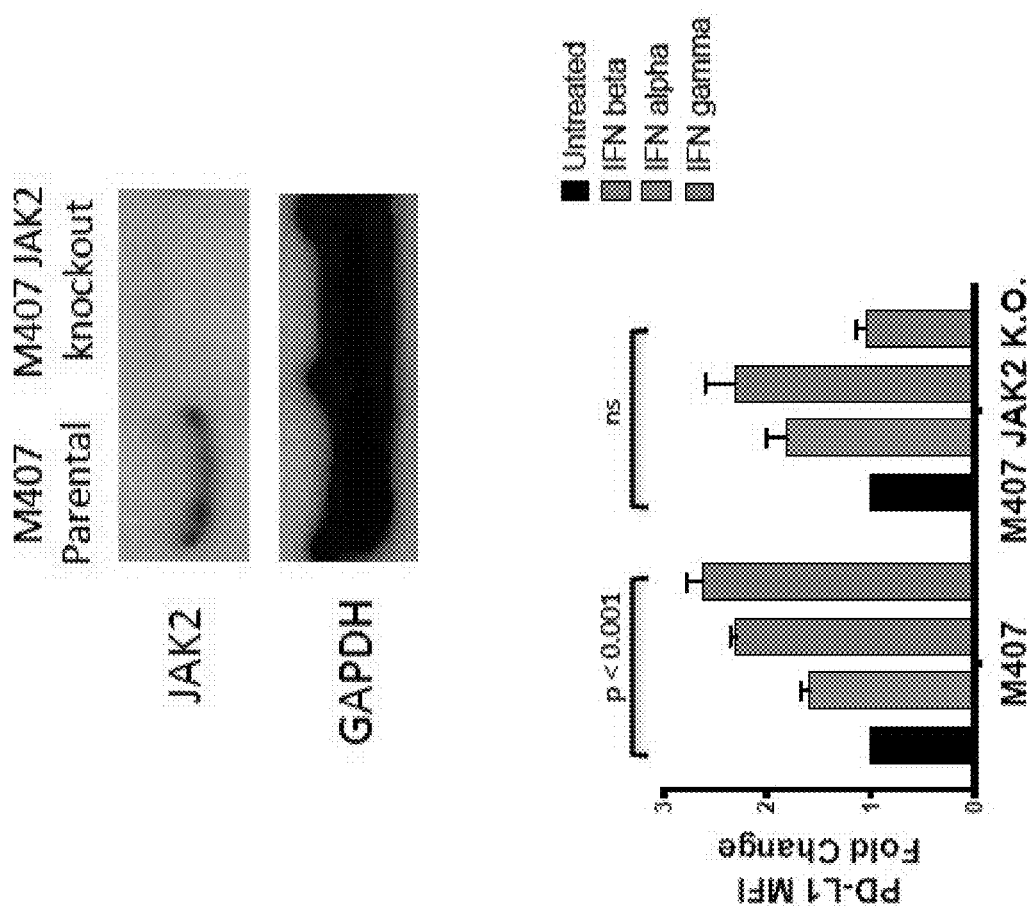
FIG. 10C. CRISPR/Cas-9 knockout of JAK2 in M407. Shows total loss of JAK2 protein by Western blot, and lack of PD-L1 upregulation in response interferon-gamma compared to parental cell line, with no change in response to interferon alpha or beta.
Figure 11:
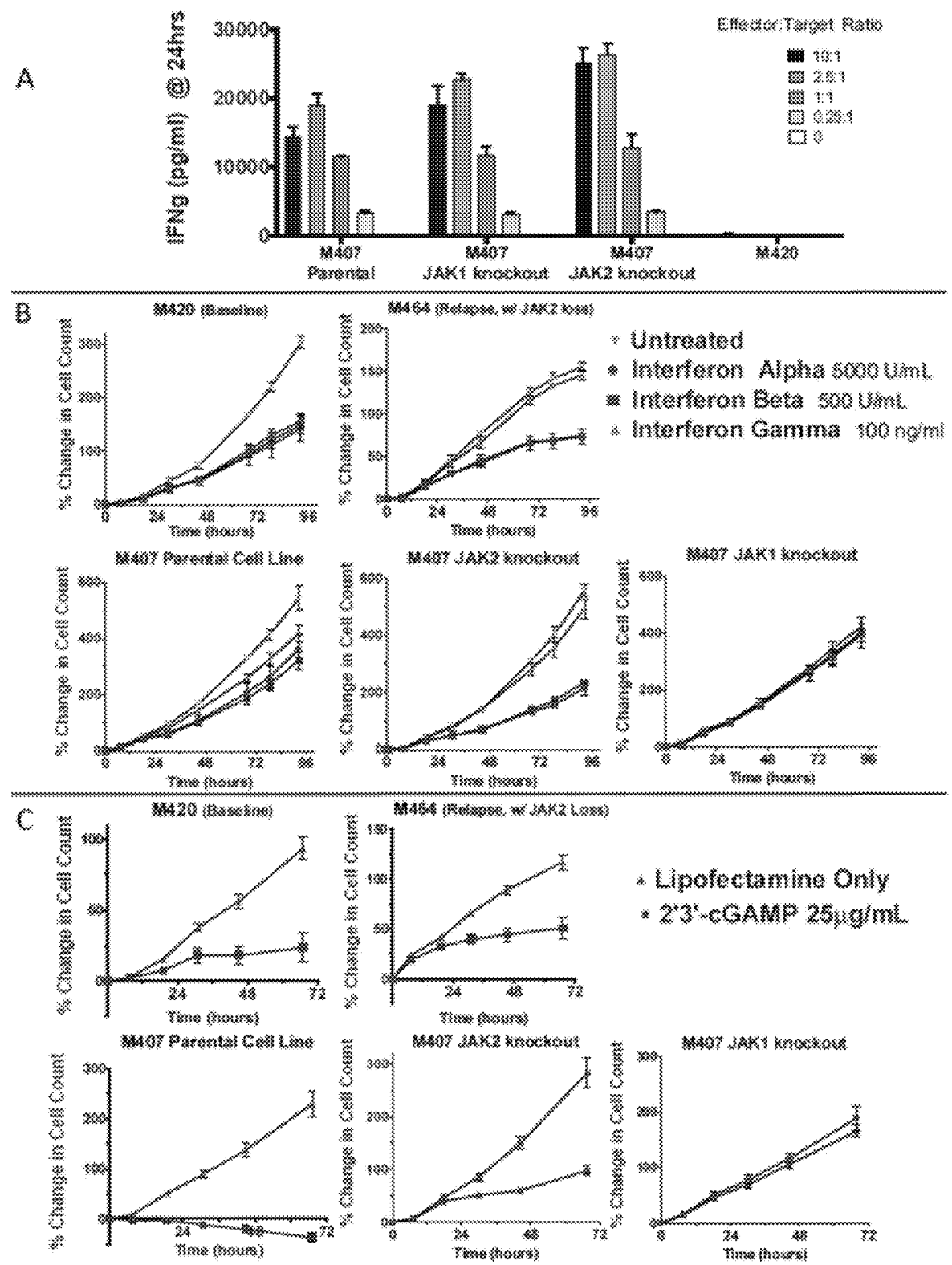
FIG. 11. Acquired JAK mutations abolished interferon-gamma-induced growth arrest. In Panel A, both the M407 parental cell line, as well as the M407 JAK1 or JAK2-knockout sublines were recognized by NY-ESO1 specific HLA-A*02:01 restricted T-cells, as assessed by interferon-gamma production following 24 hour in-vitro co-culture. M420 is HLA-A*02:01-negative and served as a negative control. In Panels B, cell lines M420 and M407 show growth-inhibition in response to direct in-vitro treatment with interferon alpha, beta, and gamma (left), while the JAK2 deficient counterpart M464 and the M407 JAK2 knockout were insensitive specifically to interferon gamma (middle). JAK1-deficient M407 was insensitive to all three interferons (right). In Panel C, treatment with 2'3'-cGAMP, a direct cytosolic agonist of the STimulator of INterferon Genes (STING), was able to produce growth arrest in all cell lines, regardless of JAK2 status, yet had no effect in M407 with JAK1 loss. Growth curves represent percent change in melanoma cell number over time measured by IncuCyte continuous live-cell imaging in one of three independent experiments. Error bars in Panels A, B, and C indicate standard deviation for three replicate wells. n.s.=not significant, ***=p<0.001 for percent of untreated growth at end-point, with Dunnet's multiple comparison correction applied in Panel B.

List of genes chosen for the nCounter analysis including housekeeping genes used for normalization, positive, and negative controls.
*indicates part of custom gene list Loss of Interferon Gamma-Induced Growth Inhibition with JAK2 Mutations Inactivating JAK mutations may result in a functional advantage for the progressive tumors because the lack of interferon signaling either decreased antigen presentation or allowed escape from interferon-induced growth inhibition. In addition to using M420 and M464, the human melanoma cell line M407 was engineered by a CRISPR/Cas9 approach to create sublines without expression of JAK1 or JAK2 (FIGS. 9-10). These create truncating mutations analogous to those from case #1 and #2, and M407 is HLA-A*0201 positive and expresses the cancer-testis antigen NY ESO-1, allowing modeling of T-cell recognition using T cells genetically modified to express an NY ESO-1-specific T-cell receptor[23]. M407 and both JAK-loss sublines were equally recognized by NY ESO-1-specific T cells, leading to high levels of interferon gamma production (FIG. 11A).

Figure 12:
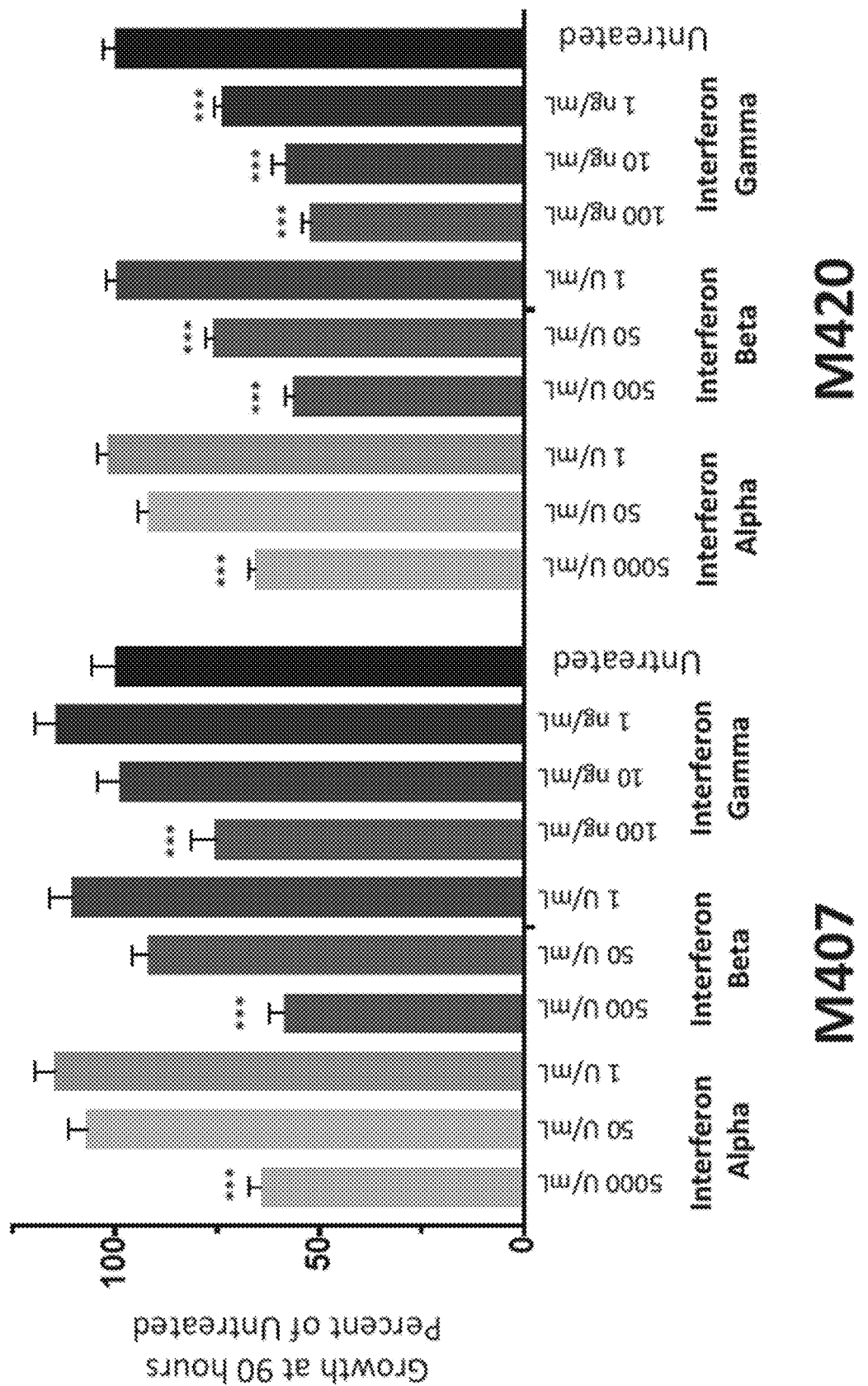
FIG. 12. Dose-dependent growth inhibition of M420 and M407 by interferon alpha, beta, and gamma. Cell lines M420 and M407 were cultured in-vitro with recombinant human interferon alpha, beta, or gamma. Both cell lines showed significant (~50%) decrease in growth at the 90-hour endpoint compared to untreated cells at the highest doses. M420 showed significant dose-sensitive inhibition at lower concentrations for beta and gamma, though there was a dose-sensitive trend for all interferons in both cell lines. Results are shown for a single representative experiment, three replicate wells per condition. Error bars show standard error of the mean. ***=p-value <0.001 with Dunnett's multiple comparison correction. All others not significant.

When cultured in recombinant interferon alpha, beta, or gamma, the M420 and the M407 parental cell lines exhibited interferon-induced growth inhibition in a dose-dependent manner (FIG. 12). However, both the JAK2-deficient case #2 relapse cell line M464 and the M407 JAK2 knockout subline were insensitive specifically to interferon gamma-induced growth arrest, yet remained sensitive to type I interferons alpha and beta, while the M407 JAK1 mutated subline was resistant to all three interferons (FIG. 11B). This is again consistent with the specific association of JAK2 with the interferon gamma receptor, and common use of JAK1 by all three interferon receptors[25-27]. As an orthogonal test of these effects, cell lines were treated with 2'-3'-cGAMP, a cyclic dinucleotide produced in response to cytosolic dsDNA, which directly activates STING (STimulator of INterferon Genes) and leads to interferon-beta production through activation of the interferon regulatory factor 3 (IRF3)[28]. Following 2'-3'-cGAMP treatment, growth arrest was observed in all cell lines independent of JAK2 status, but no effect in the JAK1 knockout subline (FIG. 11C). Therefore, the JAK1 and JAK2 loss of function mutations did not decrease in-vitro T-cell recognition, but selectively blocked the interferon gamma signaling that leads to cell growth inhibition, which for JAK2 loss could be corrected by Type I pathway activation or a STING agonist.

Functional Effects of B2M Mutation

Figure 13A:
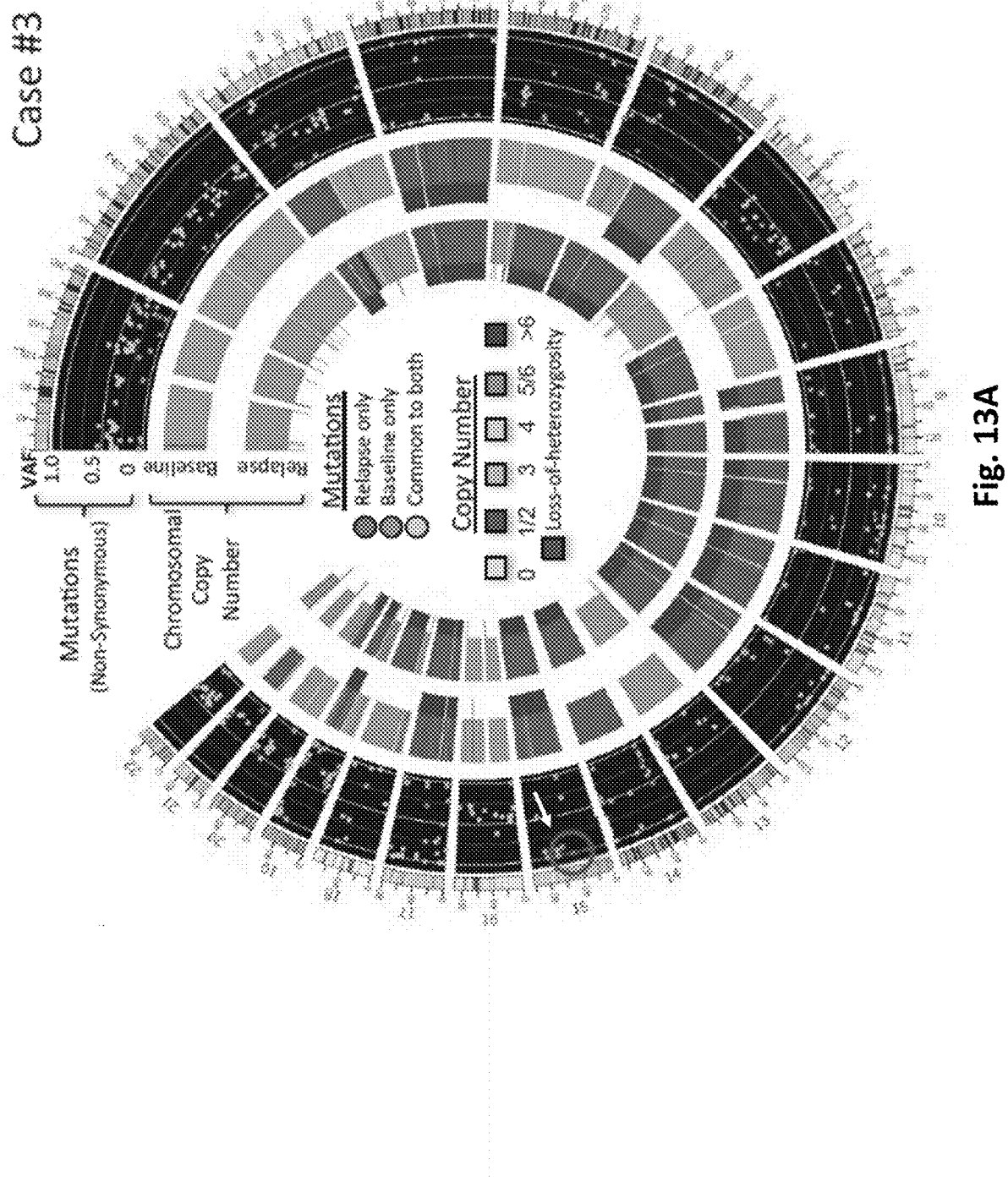
FIG. 13A. Genomic alterations in case #3 reveal Beta-2-microglobulin (B2M) mutation Panel A shows a Circos plot as in FIG. 2. A cell line (M437) derived from the baseline biopsy is compared to the progressing tumor. Both lesions shared a core of 304 non-synonymous mutations and a similar copy number profile with mostly shallow gains/losses. Most baseline-specific mutations were subclonal (62% of 149 mutations with allele frequency <0.35), while others were eliminated in loss-of-heterozygosity events on chromosomes 3p, 5q, 6p, 8, 14, and 20. Relapse was notable for a strong amplification of the microphthalmia-associated transcription factor (MITF) locus on chromosome 3 (asterisk), and a four base pair S14fs frameshift deletion in the MHC class I component B2M (arrow). Normal reads in the relapse come from stromal components.
Figure 13B:
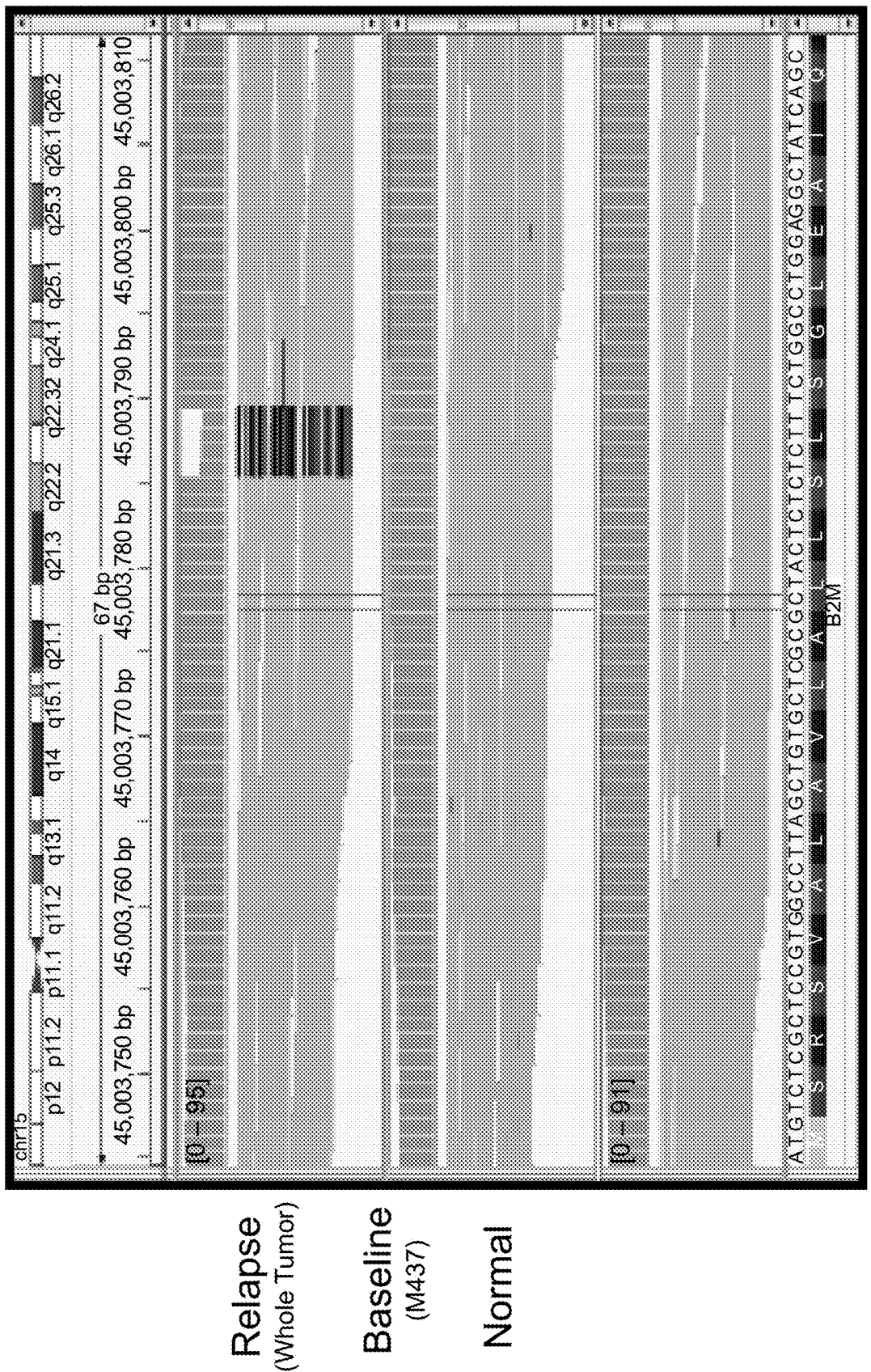
FIG. 13B. (SEQ ID NOs: 41-42) Genomic alterations in case #3 reveal Beta-2-microglobulin (B2M) mutation Panel B shows a four base pair S14fs frameshift deletion in the MHC class I component B2M shown in integrated genomics viewer (IGV) plot.

In case #3, whole exome sequencing of the baseline and progressive lesions showed a four base pair S14fs frameshift deletion in exon 1 of the B2M beta-2-microglobulin component of MHC class I as one of only 24 new relapse-specific mutations, and the only one that was homozygous (FIG. 13A,B).

Immunohistochemistry for MHC class I heavy chain revealed loss of outer-membrane localization compared to adjacent stroma or the baseline tumor, despite diffuse intracellular staining indicating continued production of MHC class I molecules (data not shown, see Zaretsky et al Supplementary Figure S14, herein incorporated by reference). This is in line with beta-2-microglobulin's role in proper MHC class I folding and transport to the cell surface[12-14]. Both the baseline and relapse biopsies were negative for MHC class II expression (data not shown, see Zaretsky et al Supplementary Figure S14, herein incorporated by reference), suggesting lack of compensatory MHC upregulation.

We could not find defined genetic alterations in case #4 with clear potential to result in acquired resistance to T cells, but cancer cells in the baseline and progressive biopsy did not express PD-L1 despite proximity to T-cells and PD-L1 expressing stroma, suggesting possible non-genetic mechanisms of altered expression of interferon-inducible genes[16] (data not shown, see Zaretsky et al Supplementary Figure S3D, herein incorporated by reference).

Example 1 Cited References

1. Atkins M B, Kunkel L, Sznol M, Rosenberg S A. High-dose recombinant interleukin-2 therapy in patients with metastatic melanoma: long-term survival update. Cancer Journal from Scientific American 2000; 6 Suppl 1:S11-4.
2. Rosenberg S A, Yang J C, Sherry R M, et al. Durable complete responses in heavily pretreated patients with metastatic melanoma using T-cell transfer immunotherapy. Clinical cancer research: an official journal of the American Association for Cancer Research 2011; 17:4550-7.
3. Prieto P A, Yang J C, Sherry R M, et al. CTLA-4 blockade with ipilimumab: long-term follow-up of 177 patients with metastatic melanoma. Clinical cancer research: an official journal of the American Association for Cancer Research 2012; 18:2039-47.
4. Eroglu Z, Kim D W, Wang X, et al. Long term survival with cytotoxic T lymphocyte-associated antigen 4 blockade using tremelimumab. Eur J Cancer 2015; 51:2689-97.
5. Schadendorf D, Hodi F S, Robert C, et al. Pooled Analysis of Long-Term Survival Data From Phase II and Phase III Trials of Ipilimumab in Unresectable or Metastatic Melanoma. J Clin Oncol 2015; 33:1889-94.
6. Hamid O, Robert C, Daud A, et al. Safety and tumor responses with lambrolizumab (anti-PD-1) in melanoma. N Engl J Med 2013; 369:134-44.
7. Robert C, Ribas A, Wolchok J D, et al. Anti-programmed-death-receptor-1 treatment with pembrolizumab in ipilimumab-refractory advanced melanoma: a randomised dose-comparison cohort of a phase 1 trial. Lancet 2014; 384:1109-17.
8. Ansell S M, Lesokhin A M, Borrello I, et al. PD-1 blockade with nivolumab in relapsed or refractory Hodgkin's lymphoma. N Engl J Med 2015; 372:311-9.
9. Robert C, Long G V, Brady B, et al. Nivolumab in previously untreated melanoma without BRAF mutation. N Engl J Med 2015; 372:320-30.
10. Robert C, Schachter J, Long G V, et al. Pembrolizumab versus Ipilimumab in Advanced Melanoma. N Engl J Med 2015; 372:2521-32.
11. Ribas A, Hamid O, Daud A, et al. Association of Pembrolizumab With Tumor Response and Survival Among Patients With Advanced Melanoma. JAMA 2016; 315:1600-9.
12. Restifo N P, Marincola F M, Kawakami Y, Taubenberger J, Yannelli J R, Rosenberg S A. Loss of functional beta 2-microglobulin in metastatic melanomas
13. D'Urso C M, Wang Z G, Cao Y, Tatake R, Zeff R A, Ferrone S. Lack of HLA class I antigen expression by cultured melanoma cells FO-1 due to a defect in B2m gene expression. J Clin Invest 1991; 87:284-92.
14. Sucker A, Zhao F, Real B, et al. Genetic evolution of T-cell resistance in the course of melanoma progression. Clin Cancer Res 2014; 20: 6593-604.
15. Kaplan D H, Shankaran V, Dighe A S, et al. Demonstration of an interferon gamma-dependent tumor surveillance system in immunocompetent mice. Proc Natl Acad Sci USA 1998; 95:7556-61.
16. Dunn G P, Sheehan K C, Old L J, Schreiber R D. IFN unresponsiveness in LNCaP cells due to the lack of JAK1 gene expression. Cancer Res 2005; 65:3447-53.
17. Eisenhauer E A, Therasse P, Bogaerts J, et al. New response evaluation criteria in solid tumours: revised RECIST guideline (version 1.1). Eur J Cancer 2009; 45:228-47.
18. Wolchok J D, Hoos A, O'Day S, et al. Guidelines for the evaluation of immune therapy activity in solid tumors: immune-related response criteria. Clin Cancer Res 2009; 15:7412-20.
19. Tumeh P C, Harview C L, Yearley J H, et al. PD-1 blockade induces responses by inhibiting adaptive immune resistance. Nature 2014; 515:568-71.
20. Nazarian R, Shi H, Wang O, et al. Melanomas acquire resistance to B-RAF(V600E) inhibition by RTK or N-RAS upregulation. Nature 2010; 468:973-7.
21. Atefi M, Avramis E, Lassen A, et al. Effects of MAPK and PI3K Pathways on PD-L1 Expression in Melanoma. Clin Cancer Res 2014; 20:3446-57.

22. Shi H, Hugo W, Kong X, et al. Acquired resistance and clonal evolution in melanoma during BRAF inhibitor therapy. Cancer Discov 2014; 4:80-93.
23. Robbins P F, Morgan R A, Feldman S A, et al. Tumor regression in patients with metastatic synovial cell sarcoma and melanoma using genetically engineered lymphocytes reactive with NY-ESO-1. Journal of clinical oncology: official journal of the American Society of Clinical Oncology 2011; 29:917-24.
24. Dunn G P, Bruce A T, Ikeda H, Old L J, Schreiber R D. Cancer immunoediting: from immunosurveillance to tumor escape. Nat Immunol 2002; 3:991-8.
25. Bach E A, Aguet M, Schreiber R D. The IFN gamma receptor: a paradigm for cytokine receptor signaling. Annu Rev Immunol 1997; 15:563-91. from five patients receiving immunotherapy. J Natl Cancer Inst 1996; 88:100-8.
26. Muller M, Briscoe J, Laxton C, et al. The protein tyrosine kinase JAK1 complements defects in interferon-alpha/beta and -gamma signal transduction. Nature 1993; 366:129-35.
27. Watling D, Guschin D, Muller M, et al. Complementation by the protein tyrosine kinase JAK2 of a mutant cell line defective in the interferon-gamma signal transduction pathway. Nature 1993; 366:166-70.
28. Corrales L, Gajewski T F. Endogenous and pharmacologic targeting of the STING pathway in cancer immunotherapy. Cytokine 2016; 77:245-7.
29. Pardoll D M. The blockade of immune checkpoints in cancer immunotherapy. Nature reviews Cancer 2012; 12:252-64.
30. Finke J H, Zea A H, Stanley J, et al. Loss of T-cell receptor zeta chain p56lck in t-cells infiltrating human renal cell carcinoma. Cancer Research 1993 53, 5613-5616
31. Marvel D, Gabrilovitch D I. Myeloid-derived suppressor cells in the tumor microenvironment: expect the unexpected. J Clin Invest. 2015; 125:335-6433.
32. Marincola F M, Jaffee E M, Hicklin D J, Ferrone S. Escape of human solid tumors from T-cell recognition: molecular mechanisms and functional significance. Adv Immunol 2000; 74:181-273.
33. Dunn G P, Old L J, Schreiber R D. The three Es of cancer immunoediting. Annual review of immunology 2004; 22:329-60.
34. Ribas A. Adaptive Immune Resistance: How Cancer Protects from Immune Attack. Cancer Discov 2015; 5:915-9.
35. Fish E N, Platanias L C. Interferon receptor signaling in malignancy: a network of cellular pathways defining biological outcomes. Mol Cancer Res 2014; 12:1691-703.
36. Krzywinski M, Schein J, Birol I, et al. Circos: an information aesthetic for comparative genomics. Genome research 2009; 19:1639-45.
37. Cerami E, Gao J, Dogrusoz U, et al. The cBio cancer genomics portal: an open platform for exploring multidimensional cancer genomics data. Cancer Discov 2012; 2:401-4.
38. Hamid O, Robert C, Daud A, et al. Safety and tumor responses with lambrolizumab (anti-PD-1) in melanoma. N Engl J Med 2013; 369:134-44.
39. Robert C, Ribas A, Wolchok J D, et al. Anti-programmed-death-receptor-1 treatment with pembrolizumab in ipilimumab-refractory advanced melanoma: a randomised dose-comparison cohort of a phase 1 trial. Lancet 2014; 384:1109-17.
40. Tumeh P C, Harview C L, Yearley J H, et al. PD-1 blockade induces responses by inhibiting adaptive immune resistance. Nature 2014; 515:568-71.
41. Nazarian R, Shi H, Wang Q, et al. Melanomas acquire resistance to B-RAF(V600E) inhibition by RTK or N-RAS upregulation. Nature 2010; 468:973-7.
42. Sondergaard J N, Nazarian R, Wang Q, et al. Differential sensitivity of melanoma cell lines with BRAFV600E mutation to the specific raf inhibitor PLX4032. J Transl Med 2010; 8:39.
43. Shi H, Hugo W, Kong X, et al. Acquired resistance and clonal evolution in melanoma during BRAF inhibitor therapy. Cancer Discov 2014; 4:80-93.
44. Cibulskis K, Lawrence M S, Carter S L, et al. Sensitive detection of somatic point mutations in impure and heterogeneous cancer samples. Nat Biotechnol 2013; 31:213-9.
45. Koboldt D C, Zhang Q, Larson D E, et al. VarScan 2: somatic mutation and copy number alteration discovery in cancer by exome sequencing. Genome research 2012; 22:568-76.
46. Ramos A H, Lichtenstein L, Gupta M, et al. Oncotator: cancer variant annotation tool. Human mutation 2015; 36:E2423-9.
47. Favero, F. et al. Sequenza: allele-specific copy number and mutation profiles from tumor sequencing data. Ann Oncol 26, 64-70, doi:10.1093/annonc/mdu479 (2015).
48. Wong D J, Robert L, Atefi M S, et al. Antitumor activity of the ERK inhibitor SCH722984 against BRAF mutant, NRAS mutant and wild-type melanoma. Mol Cancer 2014; 13:194.
49. Atefi M, Avramis E, Lassen A, et al. Effects of MAPK and PI3K Pathways on PD-L1 Expression in Melanoma. Clin Cancer Res 2014; 20:3446-57.
50. Kim D, Pertea G, Trapnell C, et al. TopHat2: accurate alignment of transcriptomes in the presence of insertions, deletions, and gene fusions. Genome Biology. 2013 14:R36
51. Robbins P F, Morgan R A, Feldman S A, et al. Tumor regression in patients with metastatic synovial cell sarcoma and melanoma using genetically engineered lymphocytes reactive with NY-ESO-1. Journal of clinical oncology: official journal of the American Society of Clinical Oncology 2011; 29:917-24.
52. Brinkman E K, Chen T, Amendola M, and van Steensel B Easy quantitative assessment of genome editing by sequence trace decomposition. Nucl. Acids Res. 2014 42(22)e168

Example 2: Mutations in the Interferon Gamma Signaling Lead to Primary Resistance to PD-1 Therapy Methods Tumor Samples Tumor biopsies were obtained from a subset of patients enrolled in a phase I expansion clinical trial with pembrolizumab after signing a written informed consent (32). Patients were selected for this analysis by having adequate tumor biopsy samples and clinical follow-up. Baseline biopsies of metastatic tumors were obtained within 30 days of starting on treatment, except for one in a patient with an eventual complete response (FIG. 14B, subject #4) collected after 84 days on treatment. Samples were immediately fixed in formalin followed by paraffin embedding, and when there was an additional sterile piece of the tumor, processed for snap-freezing in liquid nitrogen and to establish a cell line as previously described (33-35). Tumor biopsy and peripheral blood cell collection and analyses were approved by UCLA Institutional Review Boards 11-001918 and 11-003066.

Treatment and Response Assessment

Patients received single-agent pembrolizumab intravenously in one of three dosing regimens: 2 mg/kg every 3 weeks (2Q3W), 10 mg/kg every 3 weeks (10Q3W), or 10 mg/kg every 2 weeks (10Q2W; ref 32). Tumor responses to pembrolizumab were evaluated at 12 weeks after the first infusion (confirmed at 16 weeks), and every 12 weeks thereafter. The RECIST version 1.1 was used to define objective clinical responses. The protocol was allowed to proceed beyond initial progression at the restaging scans at 12 weeks and have repeated imaging scans 4 weeks later following the immune-related response criteria (irRC; ref 36).

IHC Staining

For CD8 T-cell density, 5 of the 11 cases were reanalyzed blindly from IHC samples already used in our prior work (11), and the other 6 cases were newly stained cases also analyzed blindly. Slides were stained with hematoxylin and eosin, S100, CD8, CD68, PD-1, and PD-L1 at the UCLA Anatomic Pathology IHC Laboratory. Immunostaining was performed on Leica Bond III autostainers using Leica Bond ancillary reagents and the REFINE polymer DAB detection system as previously described (11). Cell density (cells/mm 2) in the invasive margin or intratumoral area was calculated using the Indica Labs Halo platform as previously described (11).

Cell Lines, Cell Culture, and Conditions

Patient-derived melanoma cell lines were generated as reported previously and characterized for their oncogenic mutational status (33-35). Each melanoma cell line was thawed and maintained in RPMI-1640 medium supplemented with 10% FBS, 100 units/mL penicillin, and 100 µg/mL streptomycin at 37° C. in a humidified atmosphere of 5% CO 2. Cells were subject to experimental conditions after reaching two passages from thawing. Cell lines were periodically authenticated using GenePrint 10 System (Promega) and were matched with the earliest passage cell lines. Selected melanoma cell lines were subjected to Mycoplasma tests periodically (every 2-3 months) with the MycoAlert Mycoplasma Detection Kit (Lonza).

Surface Flow Cytometry Analysis for PD-L1 and MHC Class I

Figure 18:
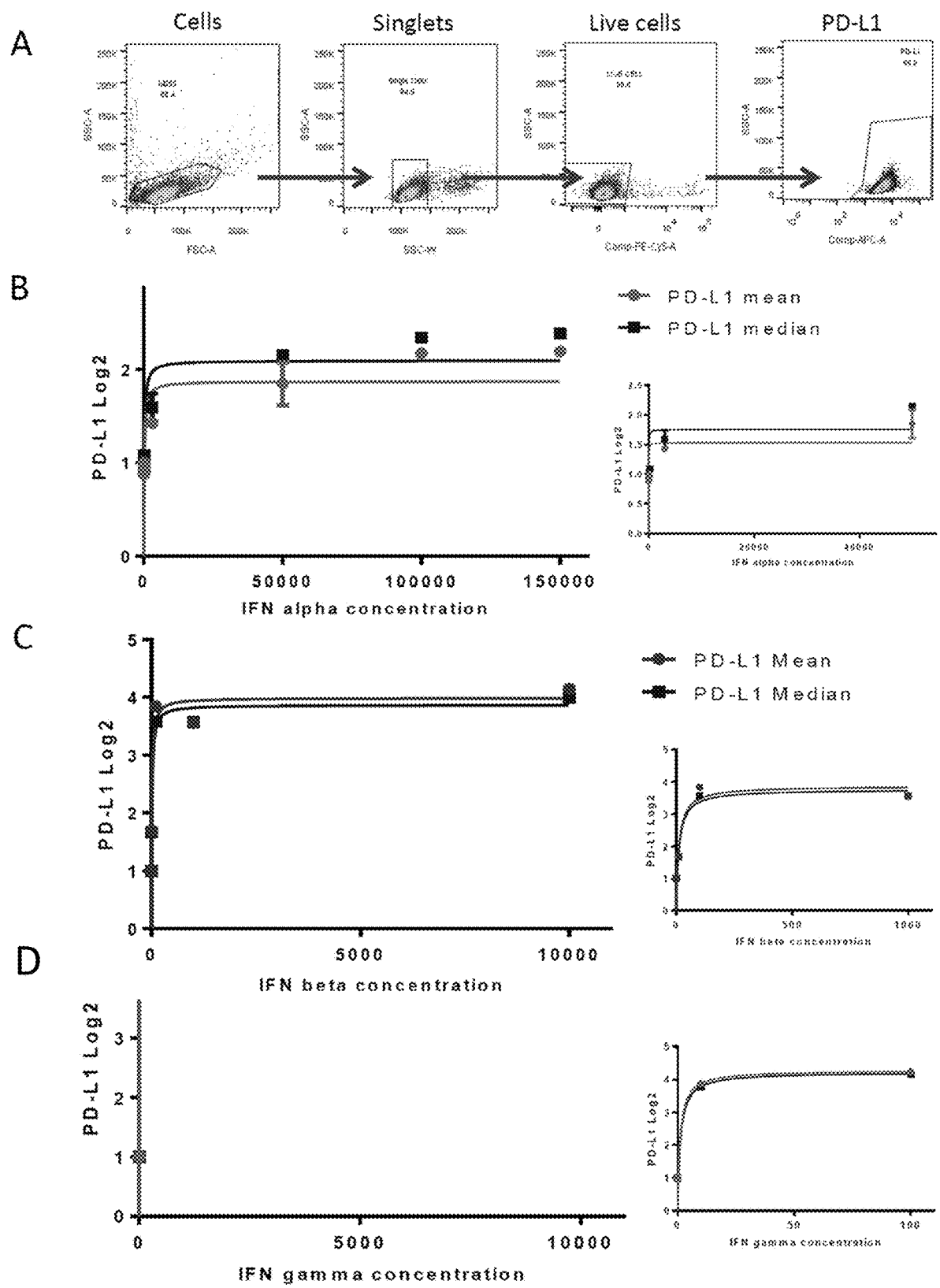
FIG. 18. Flow cytometry gating strategy and dose response curve of interferon alpha, beta and gamma to determine the optimal concentrations. A) Representative gating strategy for PD-L1 measurement by flow cytometry after 18 hours exposure to interferon alpha, beta or gamma. Cells were stained with anti-PD-L1 for flow cytometry and the mean fluorescence intensity (MFI) was determined. B) Dose response curve of interferon alpha. The representative melanoma cells were seeded into 6 well plates in different numbers to target 70-80% confluence at the time of completion of treatment for set amount of time. Inset on right side represent a smaller dose range of the same data to better illustrate the curve change at low concentration ranges. C) Dose response curve of interferon beta. D) Dose response of interferon gamma. We selected interferon alpha: 5000 IU/mL, interferon beta: 500 IU/mL and interferon gamma 100 IU/mL as the optimal conditions for further testing.
Figure 19:
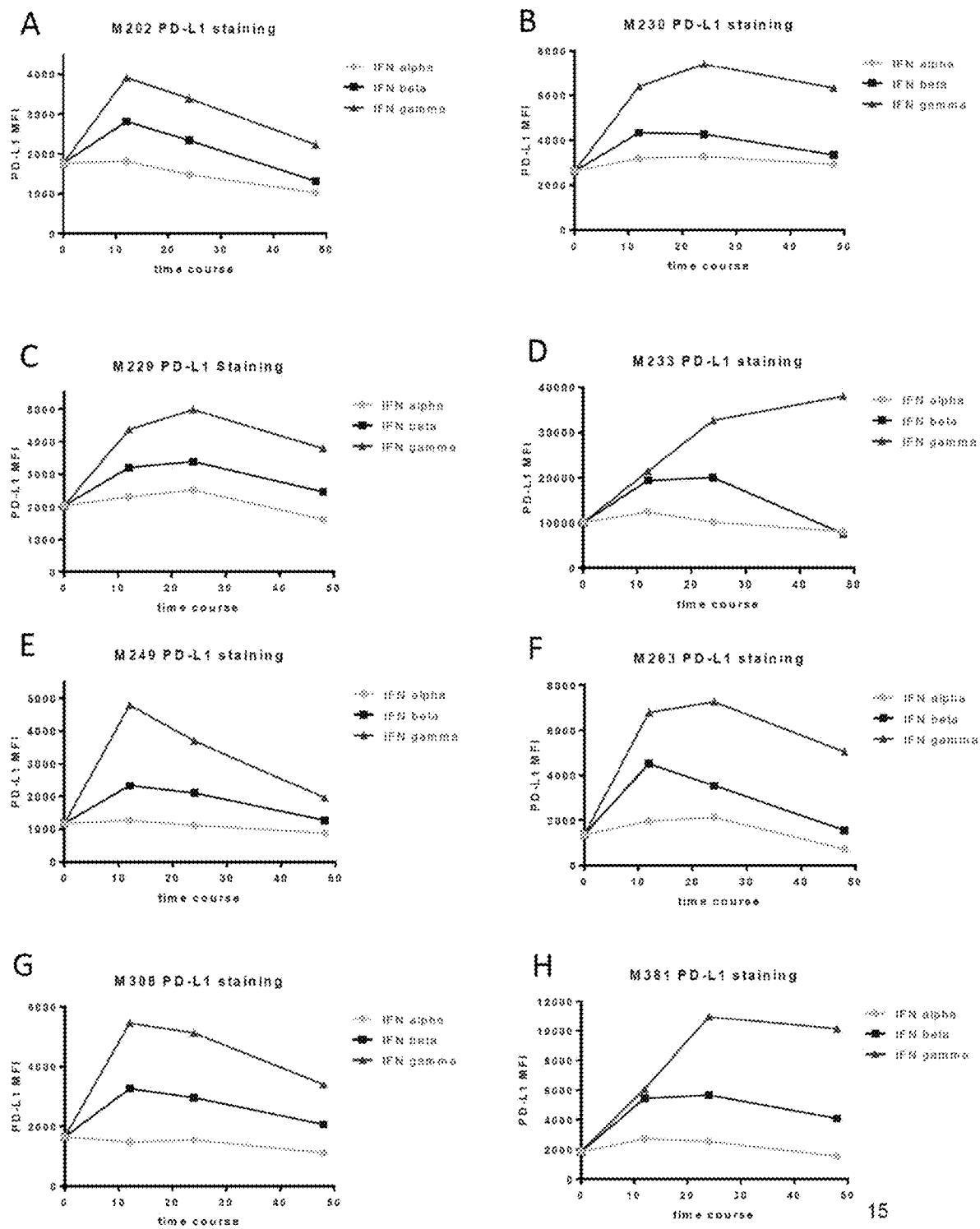
FIG. 19. Time course of PD-L1 surface expression upon interferon alpha, beta and gamma treatment for selected cell lines to determine the optimal time point for the screening. A to H) The selected melanoma cell lines (M202, M230, M229, M233, M249, M263, M308 and M381) were seeded into 6 well plates on day 1 with target confluence of 70-80% at the time of measuring PD-L1 expression by LSRII flow cytometry. Cells were treated on day 2 with pre-determined concentrations, interferon alpha, beta and gamma as described above. Based on these experiments, the optimal screening time point was chosen at 18-hours.
Figure 20:
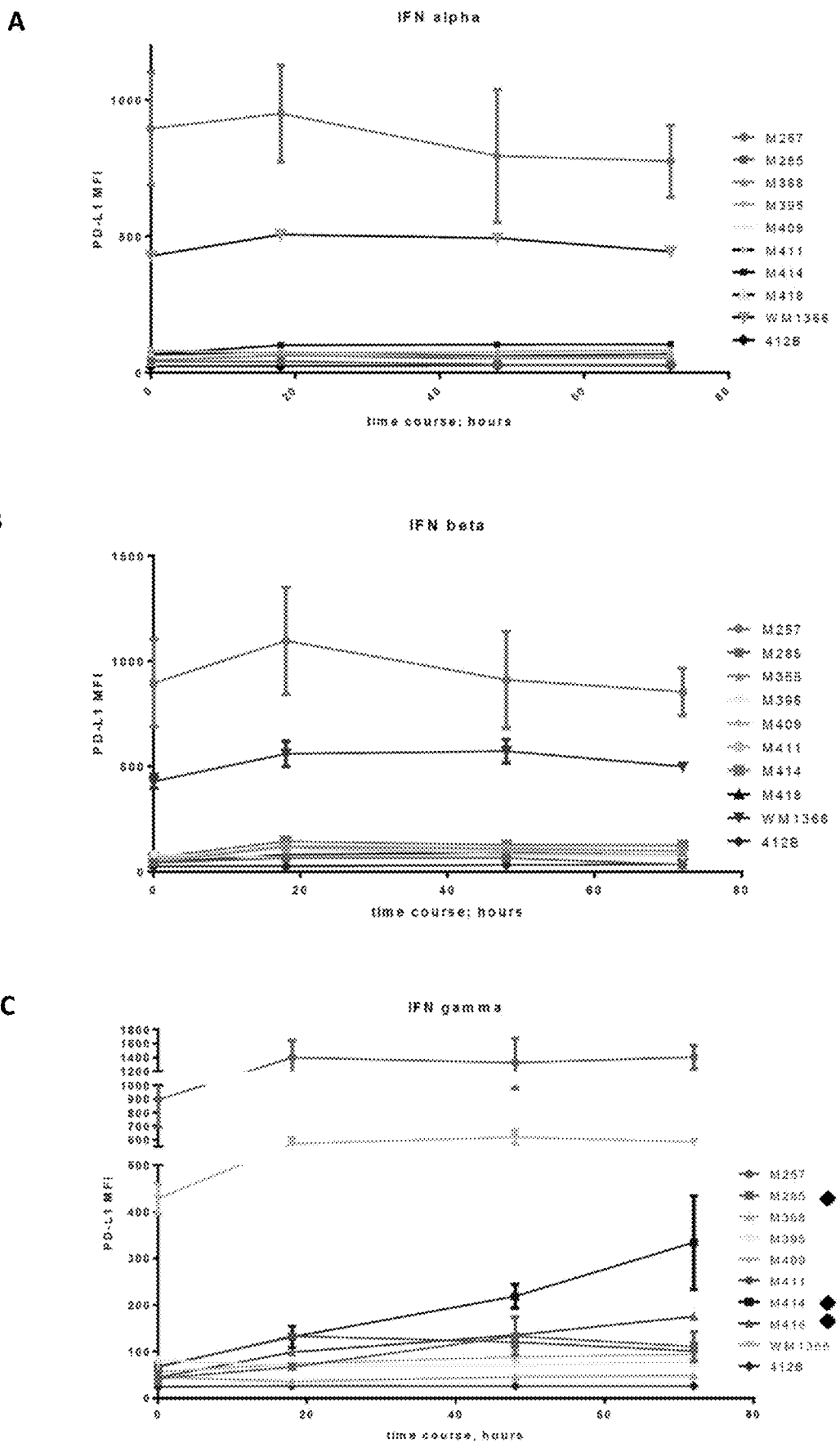
FIG. 20. Time course of PD-L1 expression upon interferon alpha, beta or gamma treatment for the cell lines with poor or no up-regulation upon 18 hours exposure. Time course PD-L1 expression upon interferon alpha (A), beta (B) or gamma (C) exposure for 10 selected melanoma cell lines with poor or no up-regulation of PD-L1 at 18 hours exposure. M285, M414 and M418 cell lines (marked as diamond) did show increased up-regulation of PD-L1 over 2-fold from baseline upon 48 to 72 hours of interferon gamma exposure ($P<0.05$), but not with interferon alpha or beta. This experiment confirms that the three non-responding cell lines, M368, M395 and M412b, still did not upregulate PD-L1 upon longer time exposure to interferon gamma.

Melanoma cells were seeded into 6-well plates on day 1, ranging from 420,000 to 485,000 depending on their doubling time, targeting 70% to 80% of confluence at the time of trypsinization after 18 hours of exposure to interferons. For 48-hour exposure, 225,000 to 280,000 cells were seeded, and 185,000 to 200,000 cells were seeded for 72-hour exposure. After trypsinization, cells were incubated at 37° C. for 2 hours with media containing different concentrations of interferons. Concentrations of each interferon were determined after optimization process (dose-response curves were generated with representative cell lines as shown in FIG. 18B-D). After 2 hours of incubation, the media were removed by centrifugation and cells were resuspended with 100% FBS and stained with APC anti-PD-L1 antibody on ice for 20 minutes. The staining was halted by washing with 3 mL of PBS, which was removed by centrifugation at 500×g for 4 minutes. The cells were resuspended with 300 µL of PBS, and 7-AAD for dead cell discrimination was added to samples prior to data acquisition by LSRII. The data were analyzed by FlowJo software (Version 10.0.8r1, Tree Star Inc.). Experiments were performed at least twice for each cell line; some cell lines with high assay variability were analyzed three times.

Phosphoflow Signaling Analyses

Cells were seeded into two 6-well plates for each cell line for single phospho-proteomics study. After 30-minute or 18-hour exposure to interferon alpha, beta, or gamma, cells were trypsinized and resuspended with 1 mL of PBS per 1 to 3 million cells and stained with live/dead agent at room temperature in the dark for 30 minutes.

Cells were then fixed with paraformaldehyde at room temperature for 10 minutes in the dark, permeabilized by methanol, and stained with pSTAT1. Cells were incubated at room temperature in the dark for 30 minutes, washed with phospho-flow cytometry buffer, and resuspended with 300 to 500 µL of the same buffer and analyzed with an LSRII. The flow cytometry standard (FCS) files obtained by LSRII were analyzed using the online flow cytometry program (Cytobank; ref 37). The raw FCS files were deconvoluted into four different conditions, three of which were exposed to interferon alpha, beta, and gamma and compared with an untreated condition at each time point. Data represented as Arcsinh ratio, which is one of transformed ratio of cytometry data (inverse hyperbolic sine) analyses; each data point was compared with its control [Value=arcsinh((x−control)/scale_argument)].

Western Blot Analyses

Selected melanoma cells were maintained in 10-cm cell culture dishes and exposed to interferon alpha, beta, or gamma (same concentrations as above) for 30 minutes or 18 hours. Western blotting was performed as described previously (38). Primary antibodies included pJAK1 (Tyr1022/1023), pJAK2 (Tyr221), pSTAT1 (Tyr701), pSTAT3 (Tyr705), pSTAT5 (Tyr695), and their total proteins; PIAS1, IRF1, SOCS1, and GAPDH (all from Cell Signaling Technology). Antibodies were diluted to 1:1,000 ratio for each blot. Immunoreactivity was revealed with an ECL-Plus Kit (Amersham Biosciences Co.), using the ChemiDoc MP system (Bio-rad Laboratories).

Lentiviral Vector Production and Gene Transfer

Lentivirus production was performed by transient cotransfection of 293T cells (ATCC). The lentiviral vectors pLenti-C-mGFP and pLenti-C-JAK1-mGFP were purchased from Origen (cat# RC213878L2). In brief, T175 tissue culture flasks coated with poly-L-lysine (Sigma Aldrich) containing $6 \times 10^6$ 293 T cells were used for each transfection. The constructs required for the packaging of third-generation self-inactivating lentiviral vectors pLenti-C-mGFP and pLenti-C-JAK1-mGFP (60 µg), pMDLGg/p (39 µg), pRSV-REV (15 µg), and pMD.G (21 µg) were dissolved in water in a total volume of 2.7 mL. A total of 300 µL of 2.5 mol/L CaCl 2 (Sigma Aldrich) was added to the DNA mixture. A total of 2.8 mL of the DNA/CaCl 2 mix was added dropwise to 2.8 mL of 2×HBS buffer, pH 7.12 (280 nmol/L NaCl, 1.5 mmol/L Na$_2$HPO$_4$, 100 mmol/L HEPES). The DNA/CaPO$_4$ suspension was added to each flask and incubated in a 5% CO$_2$ incubator at 37° C. overnight. The next morning, the medium was discarded, the cells were washed, and 15 mL DMEM with 10% FBS containing 20 mmol/L HEPES (Invitrogen) and 10 mmol/L sodium butyrate (Sigma Aldrich) was added, and the flask was incubated at 37° C. for 8 to 12 hours. After that, the cells were washed once, and 10 mL fresh DMEM medium with 20 mmol/L HEPES was added onto the 293T cells, which were further incubated in a 5% CO 2 incubator at 37° C. for 12 hours. The medium supernatants were then collected, filtered through 0.2 µmol/L filters, and cryopreserved at minus 80° C. Virus supernatant was added at different concentrations into 6-well plates containing 5×10⁵ cells per well. Protamine sulphate (Sigma Aldrich) was added at a final concentration of 5 μg/mL, and the transduction plates were incubated at 37° C. in 5% $CO_2$ overnight.

Whole-Exome Sequencing

Exon capture and library preparation were performed at the UCLA Clinical Microarray Core using the Roche Nimblegen SeqCap EZ Human Exome Library v3.0 targeting 65 Mb of genome. Paired-end sequencing (2×100 bp) was carried out on the HiSeq 2000 platform (Illumina) and sequences were aligned to the UCSC hg19 reference using BWA-mem (v0.7.9). Sequencing for tumors was performed to a target depth of 150× (actual min. 91×, max. 162×, mean 130×). Preprocessing followed the Genome Analysis Toolkit (GATK) Best Practices Workflow v3, including duplicate removal (PicardTools), indel realignment, and base quality score recalibration.

Somatic mutations were called by comparison to sequencing of matched normals for the PD1-treated whole-tumor patient samples. Methods were modified from ref 39; specifically, the substitution the GATK-HaplotypeCaller (HC, v3.3) for the UnifiedGenotyper. gVCF outputs from GATK-HC for all 23 tumor/normal exomes, and cell lines M395 and M431, were jointly genotyped and submitted for variant quality score recalibration. Somatic variants were determined using one-sided Fisher exact test (P value cutoff 0.01) between tumor/normal pairs with depth >10 reads. Only high-confidence mutations were retained for final consideration, defined as those identified by at least two out of three programs [MuTect (v1.1.7; ref 40), Varscan2 Somatic (v2.3.6; ref 41), and the GATK-HC] for single nucleotide variants, and those called by both Varscan2 and the GATK-HC for insertions/deletions. Variants were annotated by Oncotator (42), with nonsynonymous mutations for mutational load being those classified as nonsense, missense, splice site, or nonstop mutations, as well as frameshift, in frame, or start codon altering insertions/deletions. Adjusted variant allele frequency was calculated according to the following equation:

$$VAF_{adjusted}=n_{mut}/CN_t=VAF\times[1+(2\times Stromal\ Fraction)/(Tumor\ Fraction\times Local\ Copy\ Number)]$$

This is an algebraic rearrangement of the equation used in the clonal architecture analysis from McGranaham and colleagues (43) to calculate the fraction of mutated chromosomal copies while adjusting for the diluting contribution of stromal chromosomal copies. Local tumor copy number ($CN_p$) tumor fraction (purity, or p) and stromal fraction (1-p) were produced by Sequenza (44), which uses both depth ratio and SNP minor B-allele frequencies to estimate tumor ploidy and percent tumor content, and perform allele-specific copy-number variation analysis.

PDJ amplification was considered tumor/normal depth ratio 2 standard deviations above length-weighted genome average. BAM files for the 16 colorectal cases were previously mapped to hg18, and sequencing and analysis were performed at Personal Genome Diagnostics. After preprocessing and somatic variant calling, positions were remapped to hg19 using the Ensembl Assembly Converter before annotation.

M431 and M395 were compared with matched normal samples; the other 47 cell lines lacked a paired normal sample. For detection of potential JAK1 or JAK2 mutations, variants were detected using the Haplotype Caller, noted for membership in dbSNP 146 and allele frequency from the 1000 Genomes project, and confirmed by visual inspection with the Integrated Genomics Viewer.

RT-PCR

Forward 5'-AACCTTCTCACCAGGATGCG-3' (SEQ ID NO: 19) and reverse 5'-CTCAGCACGTACATCCCCTC-3' (SEQ ID NO: 20) primers were designed to perform RT-PCR (700 base pair of target PCR product to cover the P429 region of the JAK1 protein) on the M431 cell line. Total RNA was extracted by the mirVana miRNA Isolation Kit, with phenols as per the manufacturer's protocol (Thermo Fisher Scientific). RT-PCR was performed by utilizing ThermoScript RT-PCR Systems (Thermo Fisher Scientific, cat#11146-057). PCR product was subject to Sanger sequencing at the UCLA core facility.

TCGA Analysis

To determine the relevance of JAK1 and JAK2 alterations in a broader set of patients, the TCGA skin cutaneous melanoma provisional dataset was queried for the frequency of genetic and expression alterations in JAK1 and JAK2. The query was extended to the breast invasive carcinoma, prostate adenocarcinoma, lung adenocarcinoma, and colorectal adenocarcinoma provisional TCGA datasets. The association of various JAK1 and JAK2 alterations with overall survival for each dataset was examined. The results are based upon data generated by the TCGA Research Network and made available through the NCI Genomic Data Commons and cBioPortal (45, 46).

The mutation annotation format (MAF) files containing JAK1 and JAK2 mutations in the TCGA datasets were obtained from the Genomic Data Commons. In addition, mutations, putative copy-number alterations, mRNA expression, protein expression, and survival data were obtained using the cBioPortal resource. The putative copy-number alterations (homodeletion events, in particular) available in cBioPortal were obtained from the TCGA datasets using Genomic Identification of Significant Targets in Cancer (GISTIC; ref 47). The mRNA expression data available in cBioPortal were obtained from the TCGA datasets using RNA-seq (RNA Seq V2 RSEM). Upregulation and downregulation of JAK1 and JAK2 mRNA expression were determined using an mRNA z-score cutoff of 2.0. Protein expression data available in cBioPortal were obtained from the TCGA dataset using RPPA, with a z-score threshold of 2.0.

Mutation data between the MAF files and data from cBioPortal were combined. Genetic and expression alterations were characterized in one of six categories: amplifications, homodeletions, single-nucleotide polymorphisms, truncating mutations (stop codons and frameshift insertions and deletions), mRNA or protein downregulation, and mRNA or protein upregulation. The frequency of JAK1 and JAK2 alterations was determined using combined data from the *.MAF file and cBioPortal. Kaplan-Meier survival curves were generated in R, using the "survminer" package and the "ggsurvplot" function. Overall survival was determined using log-rank analysis.

Statistical Analysis

Statistical comparisons were performed by the unpaired two-tailed Student t test (GraphPad Prism, version 6.0 for Windows). Mutational load was compared by unpaired two-sided Mann-Whitney test. R programming was utilized to generate arrow graphs of PD-L1/MHC class I expression upon interferon exposures and the CCLE JAK1/2 mutation frequency graph.

Results

Figure 14A:
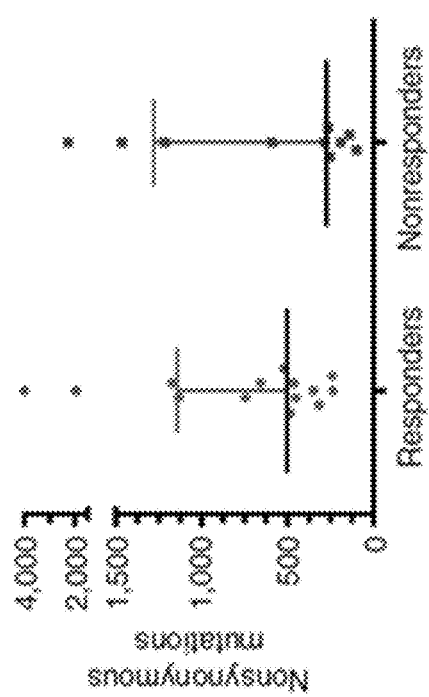
FIG. 14A. Mutational load and mutations in the interferon signaling pathway among patients with advanced melanoma with or without response to anti-PD-1 blockade therapy. A, Total nonsynonymous mutations per tumor from biopsies of patients with response (n=14) or without response (n=9) to anti-PD-1 per RECIST 1.1 criteria (median 503 vs. 274, P=0.27 by Mann-Whitney). Median and interquartile range are shown, with value for each individual tumor shown as dots.

JAK Loss-of-Function Mutations in Primary Resistance to PD-1 Blockade in Patients with Metastatic Melanoma Recent data indicate that tumors with a high mutational burden are more likely to have clinical responses to PD-1 blockade therapy (6, 19-21). However, in all of these series some patients failed to respond despite having a high mutational load. Whole-exome sequencing (WES) was performed on 23 pretreatment biopsies from patients with advanced melanoma treated with anti-PD-1 therapy, which included 14 patients with a tumor response by immune-related RECIST (irRECIST) criteria and 9 without a response (Table 5). Even though the mean mutational load was higher in responders than non-responders, as reported for lung, colon, and bladder cancers (6, 19, 21), some patients with a tumor response had a low mutational load and some patients without a tumor response had a high mutational load (FIG. 14A).

Figure 14B:
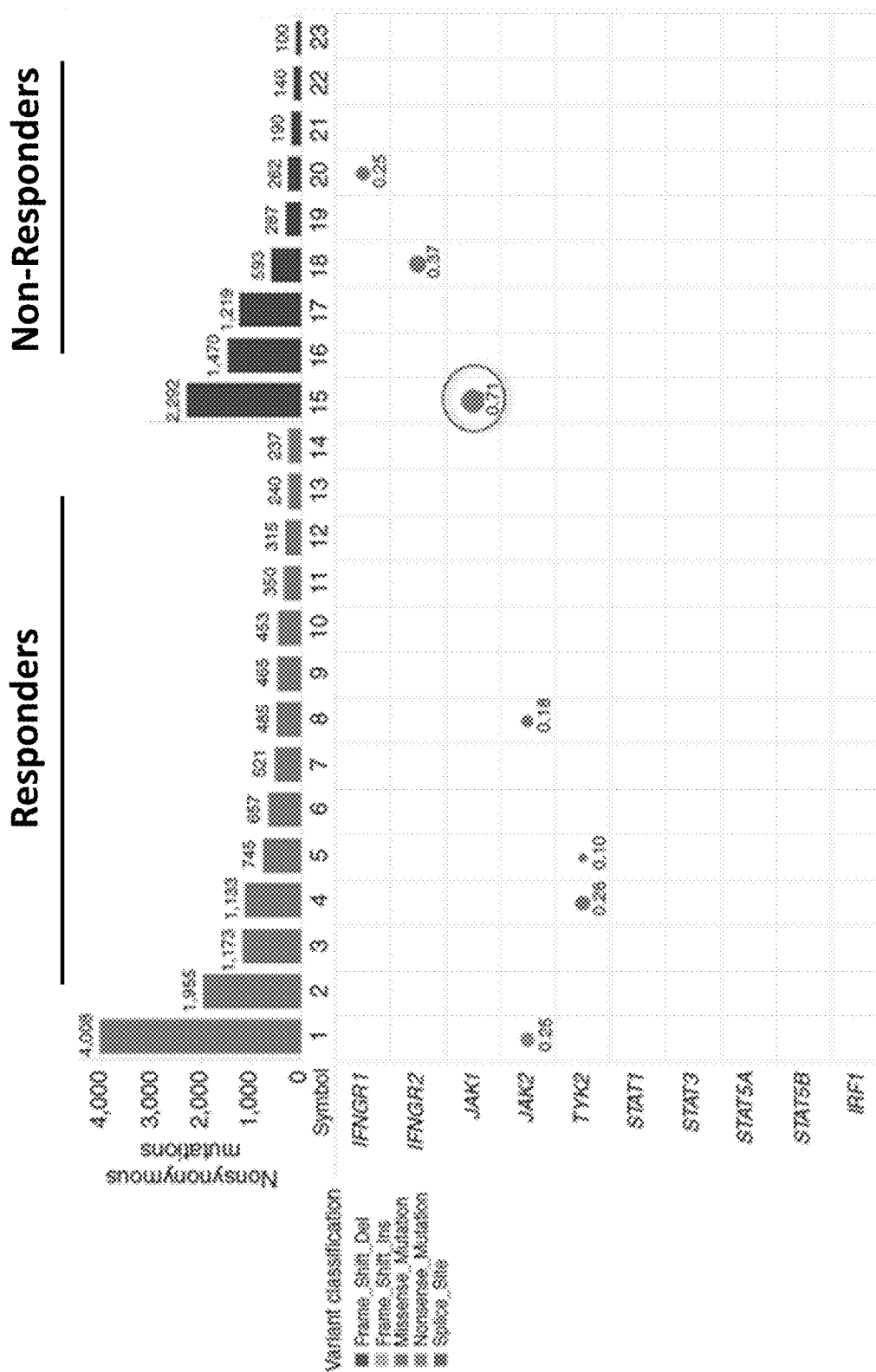
FIG. 14B. Mutational load and mutations in the interferon signaling pathway among patients with advanced melanoma with or without response to anti-PD-1 blockade therapy. In panel B, each column corresponds to an individual case from A. Depiction of mutational load (bar graph) and mutations in interferon receptor pathway genes. The size of circles and adjacent labels represents the tumor variant allele frequency (VAF) after adjustment for stromal content. Shading represents predicted functional effect. Circle highlights amplified JAK1 mutation in one patient who did not respond to anti-PD-1 therapy. All the tumor sequences were compared to normal germline sequences.
Figure 16:
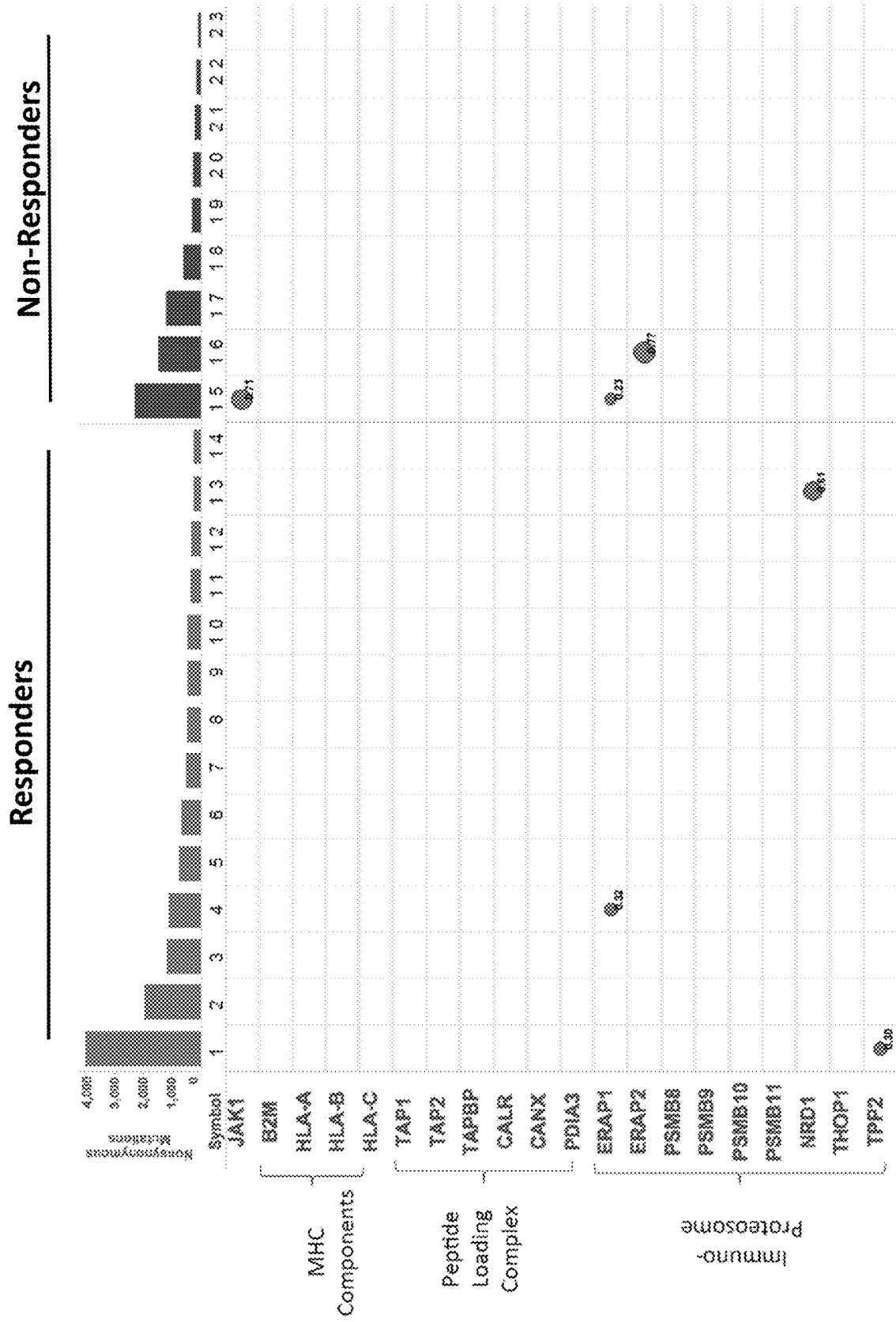
FIG. 16. Mutations in antigen presentation machinery from anti-PD1 treated melanoma cohort. Subjects were ordered as in FIG. 14B, and top bar graph re-depicts mutational load for reference. The size of circles and adjacent labels represent the tumor variant allele frequency (VAF) of the mutation after adjustment for stromal content. Shading represents predicted functional effect.
Figure 17A:
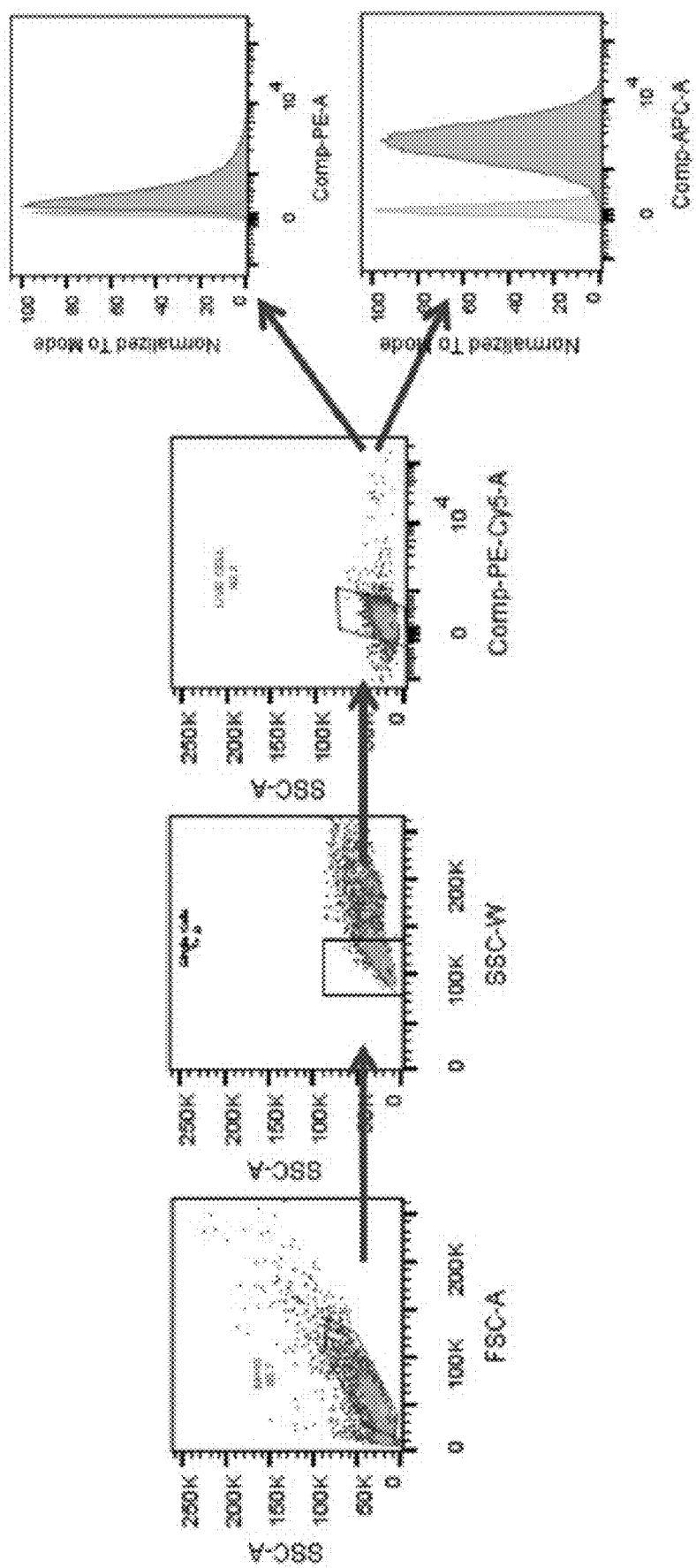
FIG. 17A. Selection of PD-L1 flow cytometry antibody and impact of phosphatase inhibitor as well as temperature on measuring surface PD-L1 expression and pAKT. PD-L1 surface staining with two different fluorochrome flow cytometry antibodies. The selected melanoma cells (M410) were harvested by trypsinization and stained with APC-PD-L1 and PE-PD-L1 flow cytometry antibodies. APC-PD-L1 antibody shows a clearer distinction of signal between control and stained sample.
Figure 17B:
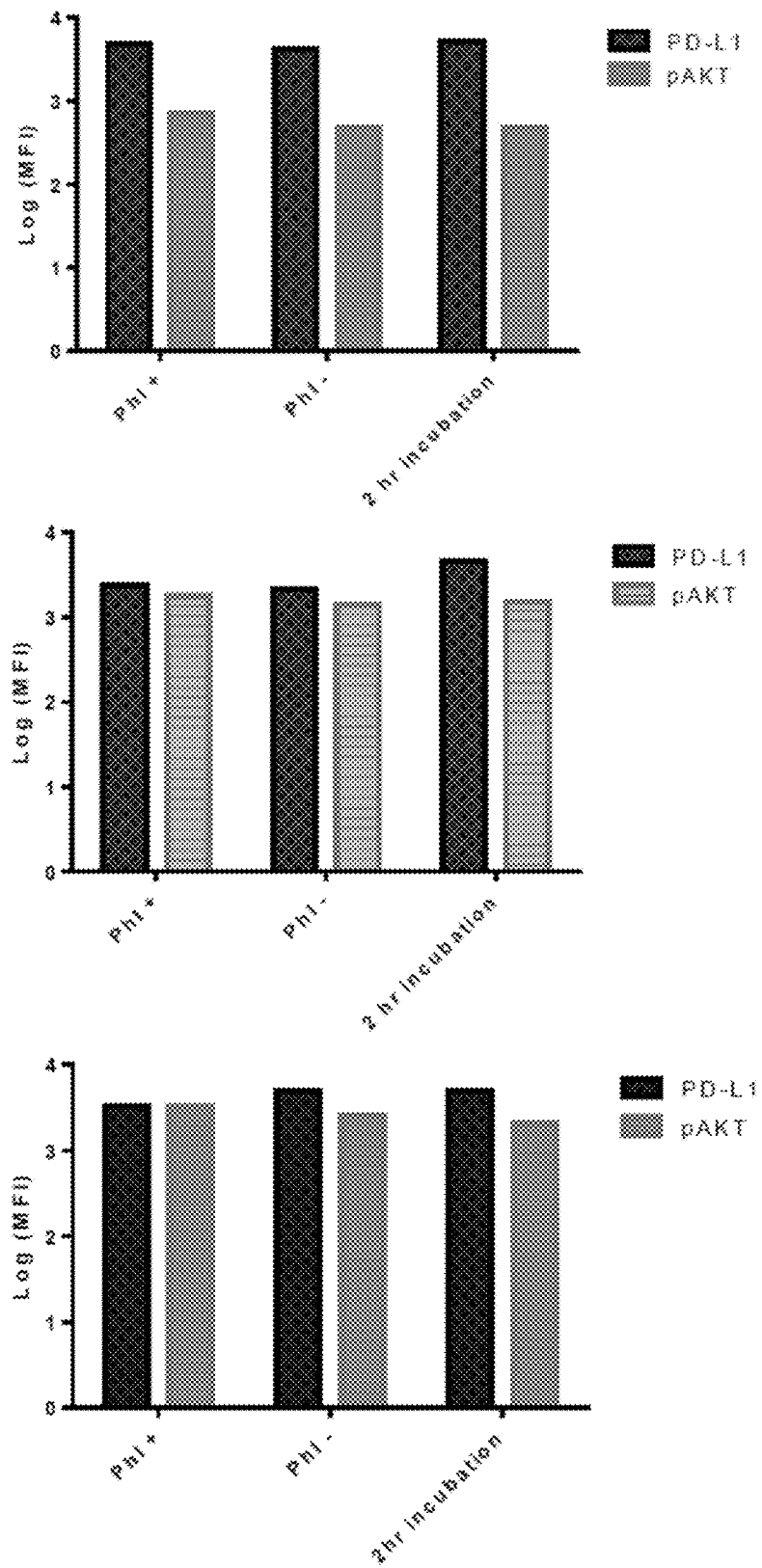
FIG. 17B. Selection of PD-L1 flow cytometry antibody and impact of phosphatase inhibitor as well as temperature on measuring surface PD-L1 expression and pAKT. Impact of phosphatase inhibitors and 2 hours of incubation at 37° C. after trypsinization on measuring surface PD-L1 expression and pAKT in melanoma cells. M233, M249 and M407 (top to bottom panels respectively) cells were trypsinized and re-suspended into three conditions. First two conditions were with and without phosphatase inhibitor then subjected to surface staining and intracellular staining with pAKT antibody. The third condition without phosphatase inhibitor, was incubated at 37° C., then subjected to surface PD-L1 staining and followed by pAKT staining.
Figure 17C:
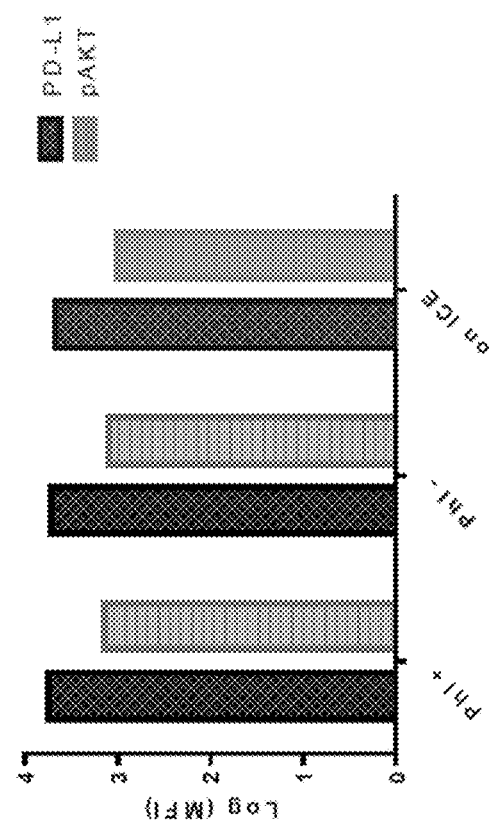
FIG. 17C. Selection of PD-L1 flow cytometry antibody and impact of phosphatase inhibitor as well as temperature on measuring surface PD-L1 expression and pAKT. Impact of temperature on measuring surface PD-L1 expression and pAKT in melanoma cells. M233 and M249 (left and right panels respectively) were trypsinized, re-suspended into three groups with and without phosphatase inhibitors, incubated at 37° C. for 2 hours, PD-L1 surface staining was performed at room temperature and on ice (without phosphatase inhibitor) anti-PD-L1 antibody. Based on these studies, the conditions chosen for further testing were without phosphatase inhibitor and on ice for 20 minutes.
Figure 17C:
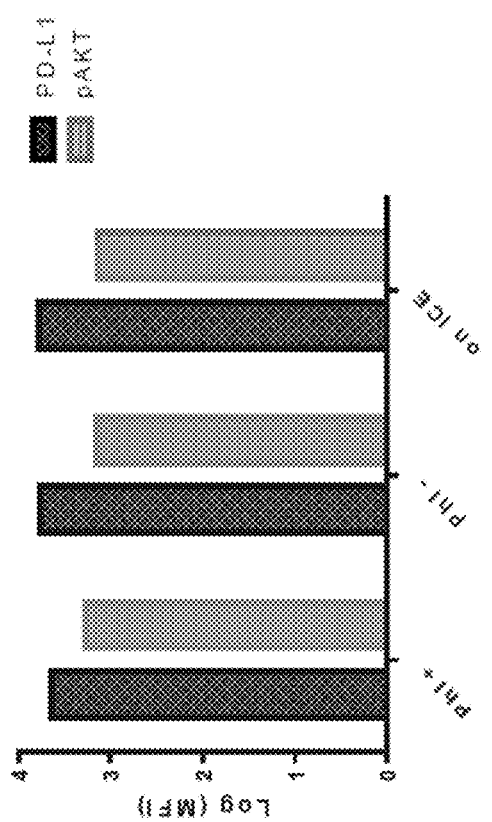

Whether loss-of-function mutations in interferon receptor signaling molecules, which would prevent adaptive expression of PD-L1, might be present in tumors with a relatively high mutational load that did not respond to therapy was assessed. A melanoma biopsy from the patient with the highest mutational load among the 9 nonresponders (patient #15) had a somatic P429S missense mutation in the src-homology (SH2) domain of JAK1 (FIG. 14B). WES of an early passage cell line derived from this tumor (M431) showed an amplification of chromosome 1p, including the JAK1 locus, and a 4:1 mutant:wild-type allele ratio was observed at both the DNA and RNA level (FIG. 15A-E and data not shown, see Shin et al. Supplementary Database S1, incorporated herein by reference in its entirety). None of the tumors from the other 22 patients had homozygous loss-of-function mutations or deletions in the interferon receptor pathway. Rather, the other JAK2 mutations found in biopsies of responders had low variant allele frequency (VAF) as shown in FIG. 14B and were likely heterozygous. These mutations would not carry the same functional significance, as signaling would still occur upon interferon exposure through the wild-type JAK protein from the non-mutated allele. Two non-responders had IFNGR mutations, also of low allele frequency and therefore uncertain significance. Potential mutations in genes involved in the antigen-presenting machinery were also analyzed and no loss-of-function mutations that were homozygous were found (FIG. 16).

Figure 14C:
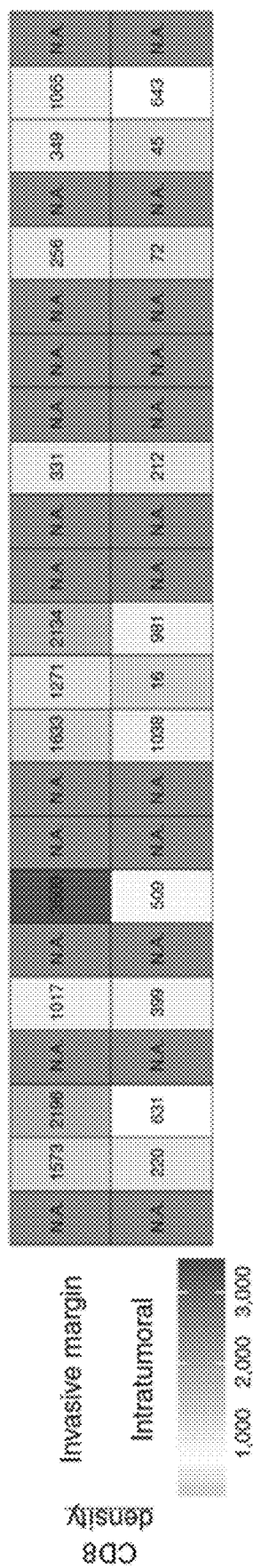
FIG. 14C. Mutational load and mutations in the interferon signaling pathway among patients with advanced melanoma with or without response to anti-PD-1 blockade therapy. In panel C, each column corresponds to an individual case from A. Heat map of the density of CD8 T cells in the invasive margin or intra-tumor compartment analyzed in baseline tumor biopsies by immunohistochemistry.
Figure 14D:
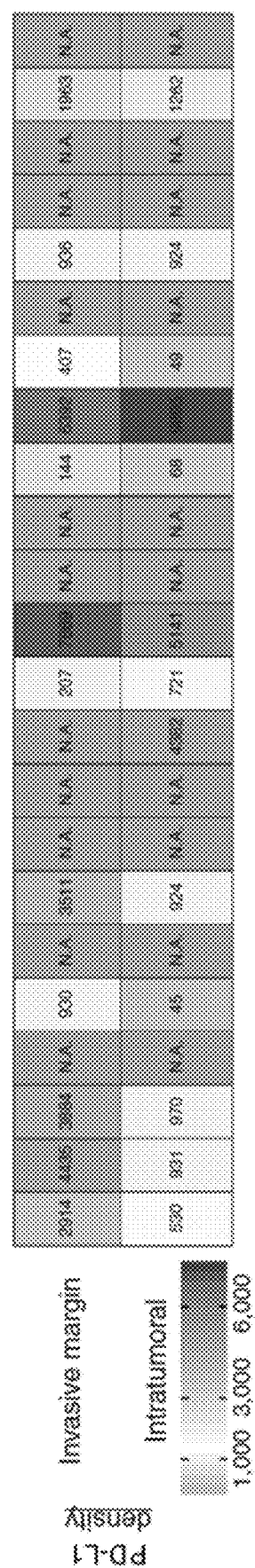
FIG. 14D. Mutational load and mutations in the interferon signaling pathway among patients with advanced melanoma with or without response to anti-PD-1 blockade therapy. In panel D, each column corresponds to an individual case from A. Heat map of density of PD-L1 expression in available tissue samples.
Figure 14E:
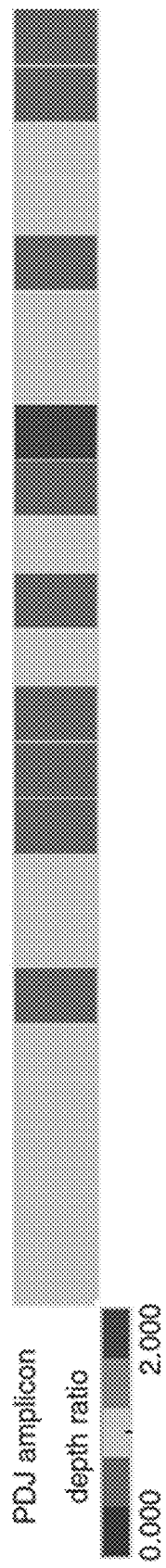
FIG. 14E. Mutational load and mutations in the interferon signaling pathway among patients with advanced melanoma with or without response to anti-PD-1 blockade therapy. In panel E, each column corresponds to an individual case from A. Genetic amplification of the chr9p24.1 (PD-L1, PD-L2, and JAK2 locus, termed the PDJ amplicon) was noted in one biopsy from a nonresponding patient. Heat map represents average read depth ratio versus paired germline normal.
Figure 15A:
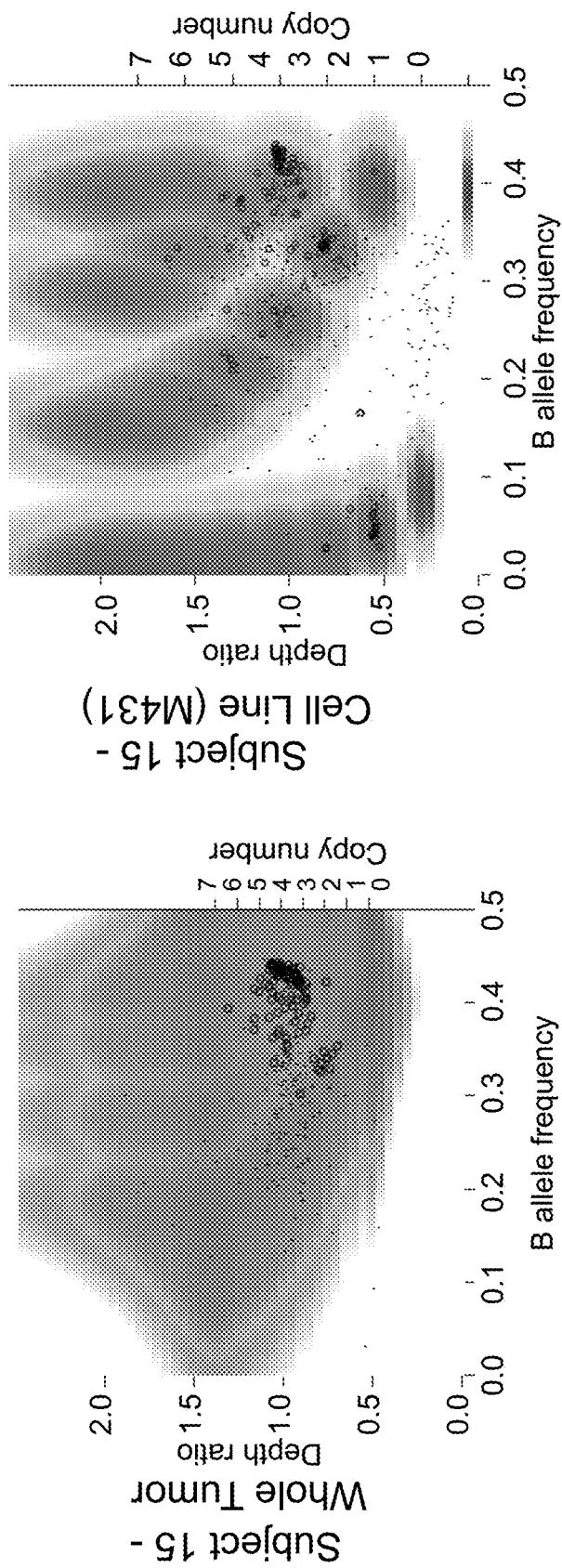
FIG. 15A. Exome sequencing and copy number changes in M431 and corresponding whole-tumor biopsy. A) Sequenza tumor purity (cellularity) inference in M431 and corresponding whole-tumor biopsy from FIG. 14B subject #15. Tumor purity was 0.32 for the whole-tumor extract (left) and 0.91 for the early-passage M431 cell line (right).
Figure 15B:
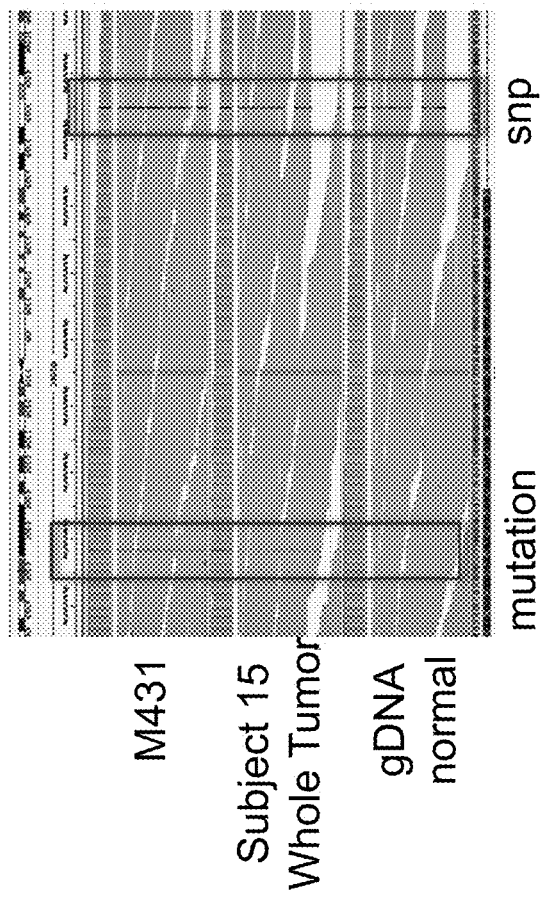
FIG. 15B. Exome sequencing and copy number changes in M431 and corresponding whole-tumor biopsy. B) IGV plot showing JAK1 chr1:65,325,837 G>A mutation (left box) and accompanying loss-of-heterozygosity (right box). Top panel M431 cell line (unadjusted VAF 0.68), middle whole tumor (unadjusted VAF 0.30), bottom normal genomic DNA.
Figure 15C:
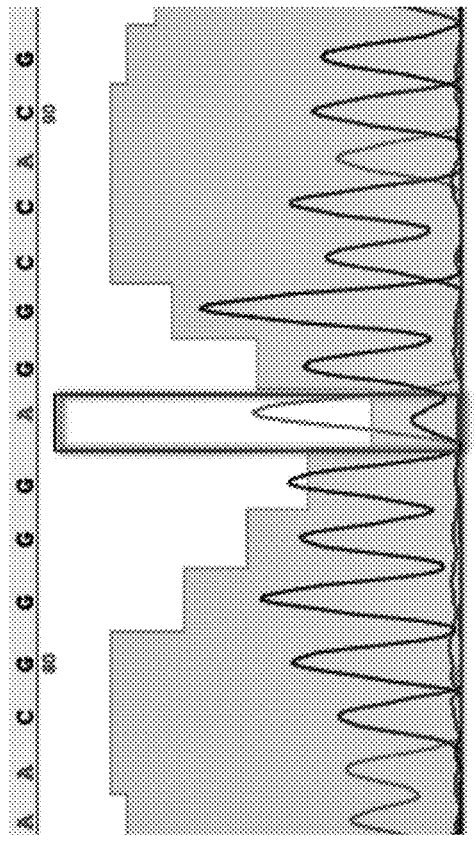
FIG. 15C. (SEQ ID NO: 43) Exome sequencing and copy number changes in M431 and corresponding whole-tumor biopsy. C) Sanger sequencing of cDNA from RT-PCR of RNA from M431. JAK1 mutation predominates over wild-type allele.
Figure 15D:
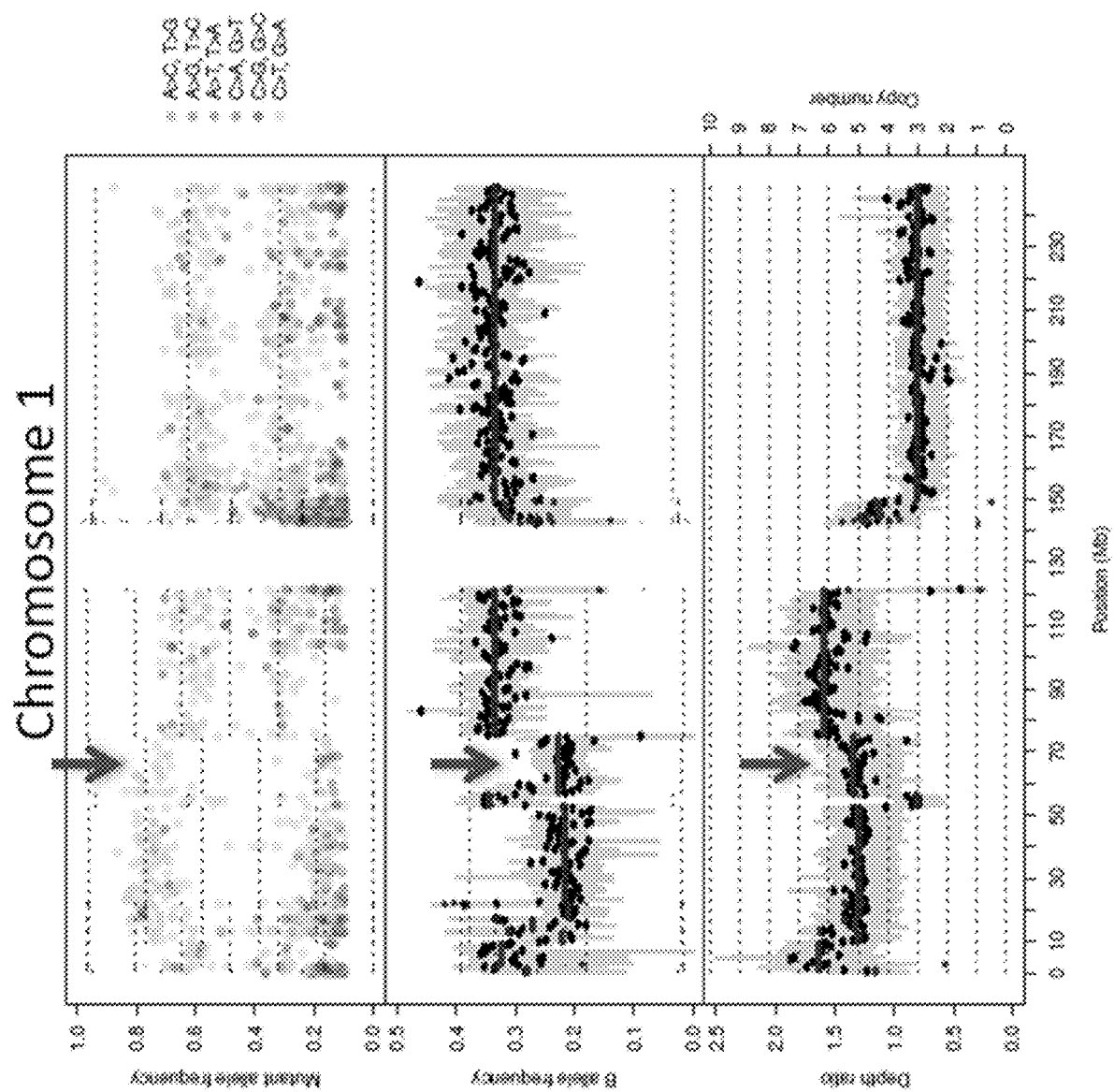
FIG. 15D. Exome sequencing and copy number changes in M431 and corresponding whole-tumor biopsy. D) View of chromosome 1 for cell line M431; arrows show JAK1 location (65 Mb), with inferred copy number 5 and 4:1 allele ratio. Top panel dots are individual mutations at their corresponding allele frequency. Middle and lower panel show SNP minor allele frequency and depth ratio respectively. Dotted lines show expected frequencies based on model-fit Copy Number assignment.
Figure 15E:
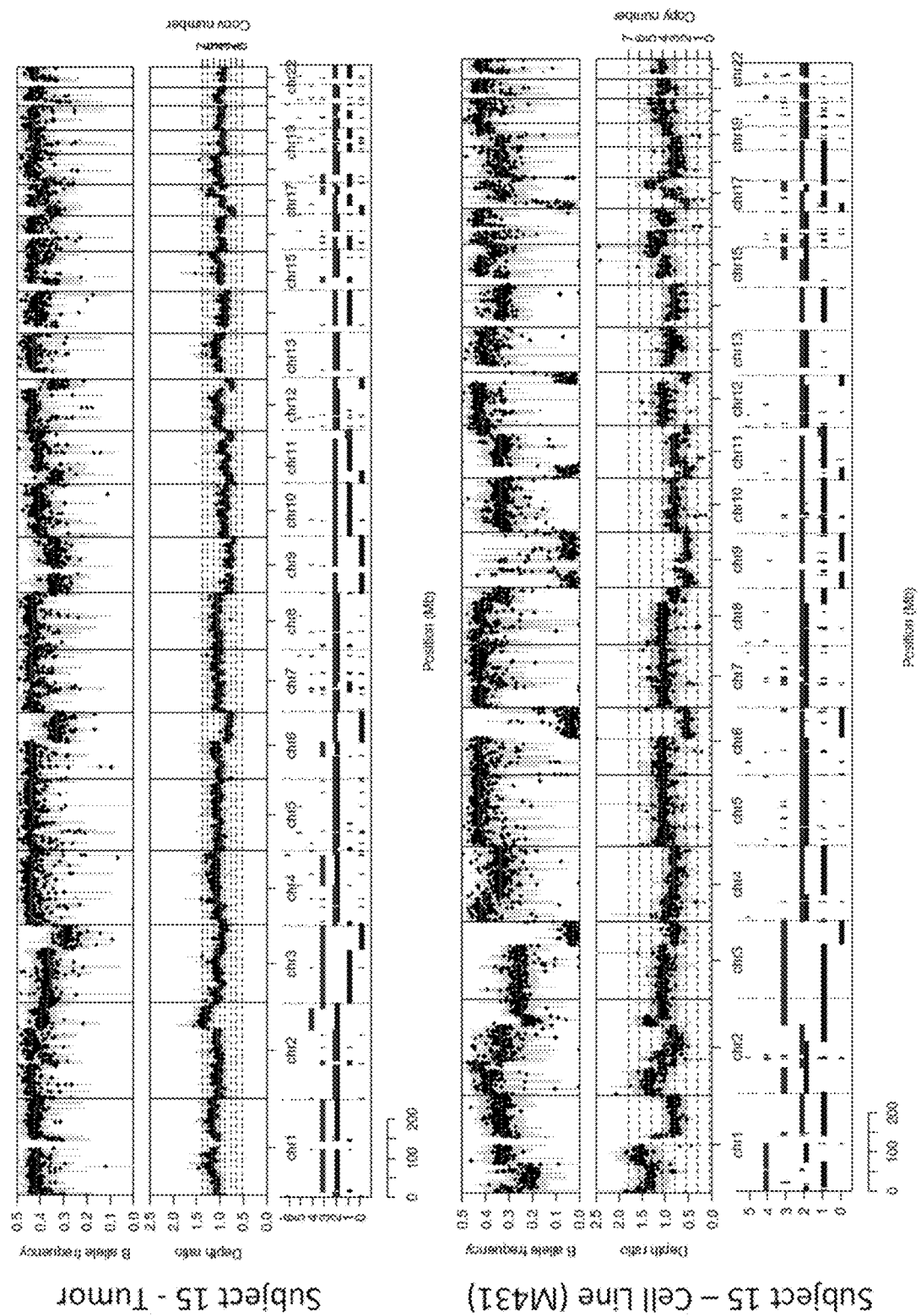
FIG. 15E. Exome sequencing and copy number changes in M431 and corresponding whole-tumor biopsy. E) Copy number profile is largely the same between whole tumor (upper series) and M431 (lower series). Figure reflects Sequenza output from tumor and cell line exome sequencing each compared to patient-matched blood-derived germline DNA. Top, middle, and lower panels display SNP minor-allele frequency, tumor:normal depth ratio, and inferred allele-specific copy number state respectively per chromosomal position. The whole tumor biopsy and M431 also displayed 2292 and 2202 non-synonymous mutations, respectively, with a 93.7% overlap between them (see Shin et al. [Cancer Discov. 2017 February; 7(2):188-201] Supplementary Database 1, incorporated herein by reference).

As expected, tumors from patients who responded had a higher density of CD8 cells and PD-L1 in the center and invasive tumor margin (FIGS. 14C and D). In contrast, the baseline biopsy from patient #15 with a high mutational load but with the JAK1$^{P429S}$ missense mutation had undetectable CD8 infiltrates, PD-1 and PD-L1 expression (data not shown, see Shin et al. Supplementary Fig. S3, herein incorporated by reference). The amplification of PD-L1, PD-L2, and JAK2 (PDJ amplicon), which has been associated with a high response rate in Hodgkin disease (4), was noted only in patient #16, who did not respond to PD-1 blockade therapy despite having the second highest mutational load and a high level of PD-L1 expression (FIGS. 14B, D and E).

TABLE 5

Demographic and baseline patient clinical characteristics

|  | Total patients 23 | |
| --- | --- | --- |
|  | Responders | Non-responders |
| Number of patients (M/F) | 14 (13/1) | 9 (5/4) |
| Mean age (M/F) | 62 (63/53) | 59 (67/54) |
| Stage |  |  |
| M0 | 1 | 0 |
| M1a | 0 | 0 |
| M1b | 2 | 1 |
| M1c | 11 | 8 |
| ECOG performance status |  |  |
| 0 | 11 | 8 |
| 1 | 3 | 1 |
| Brain metastasis |  |  |
| Yes | 1 | 0 |
| No | 13 | 9 |
| LDH |  |  |
| Normal | 10 | 5 |
| Elevated | 4 | 4 |
| BRAF and other mutational status |  |  |
| Wild type | 7 | 5 |
| BRAF V600E | 6 | 4 |
| BRAF 597 | 1 | 0 |
| NRAS mutated (from BRAF wild type) | 0 | 1 |
| RAF1 amplified (from BRAF wild type) | 0 | 1 |
| Prior treatment |  |  |
| None | 1 | 0 |
| Radiation only | 2 | 0 |
| Chemotherapy only | 0 | 0 |
| Immunotherapy | 8 | 10 |
| BCG | 1 | 0 |
| GM-CSF | 1 | 0 |
| Interferon | 1 | 2 |
| Ipilimumab | 6 | 9 |
| Ipilimumab + Interferon | 1 | 2 |
| Ipilimumab + IL-2 | 1 | 0 |
| Targeted therapy (vemurafenib or dabrafenib) | 5 | 4 |
| Adoptive cell therapy (TCR or TIL therapy) | 2 | 1 |
| Toxicities (Adverse effects) |  |  |
| Fatigue (grade 1-2) | 2 | 2 |
| Colitis (grade 1-3) | 2 | 1 |
| Pneumonitis (grade 1-2) | 1 | 1 |
| Myalgia (grade 1-2) | 0 | 1 |
| Vitiligo | 3 | 1 |
| Diverticulitis (grade 1-2) | 1 | 0 |
| Liver function test abnormality, grade 3 | 0 | 1 |
| Acute renal insufficiency, grade 4 | 1 | 0 |
| Response |  |  |
| Partial response (PR) | 11 | — |
| Complete response (CR) | 3 | — |
| Progression of disease (PD) | — | 9 |

Figure 21A:
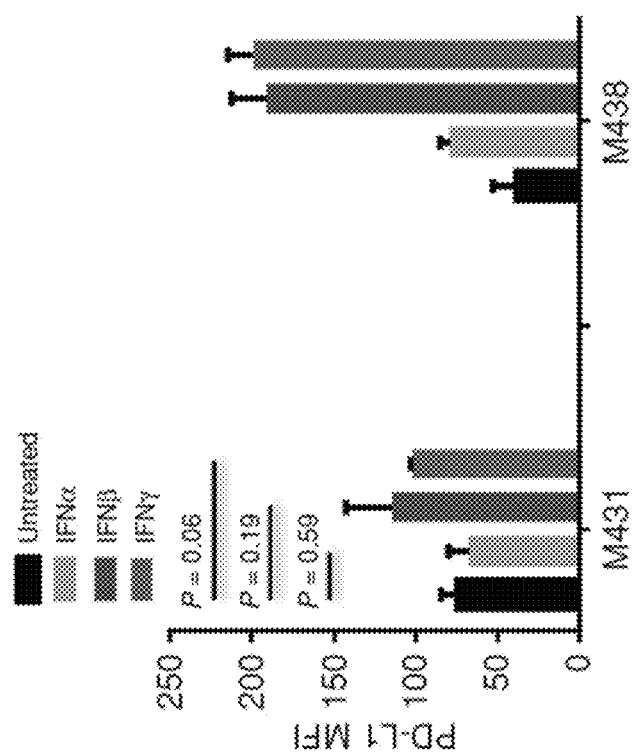
FIG. 21A. Altered interferon signaling with JAK1 loss-of-function mutation in M431 and interferon gamma-inducible PD-L1 expression by 48 melanoma cell lines. Mean fluorescent intensity (MFI) of PD-L1 expression by flow cytometry upon interferon alpha, beta, or gamma exposure over 18 hours in M431 (established from patient #15) compared with M438 (established from patient #8).
Figure 21B:
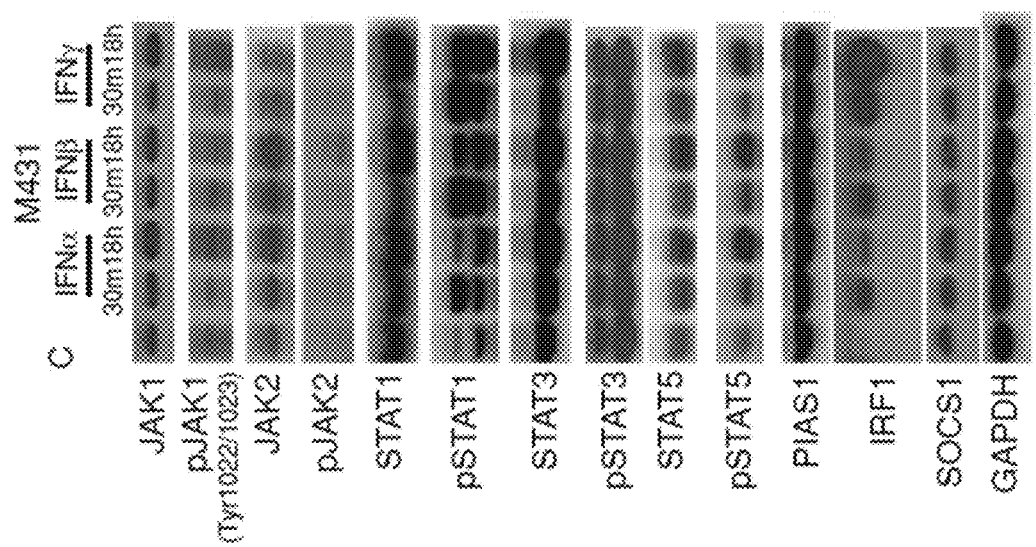
FIG. 21B. Altered interferon signaling with JAK1 loss-of-function mutation in M431 and interferon gamma-inducible PD-L1 expression by 48 melanoma cell lines. Corresponding Western blot analyses for M431 upon interferon exposure for 30 minutes or 18 hours.
Figure 21C:
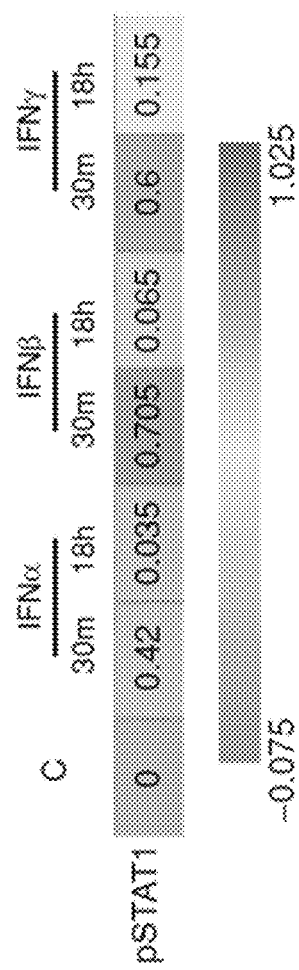
FIG. 21C. Altered interferon signaling with JAK1 loss-of-function mutation in M431 and interferon gamma-inducible PD-L1 expression by 48 melanoma cell lines. Phosphorylated STAT1 (pSTAT1) flow cytometry for M431 upon interferon exposure for 30 minutes or 18 hours (same scale as in FIG. 22A-C and FIG. 24C). The numbers in the heat map of pSTAT1 indicate the average Arcsinh ratio from two independent phosphor-flow cytometry experiments.

Functional Analyses of the Role of JAK Loss-of-Function Mutations in Regulating PD-L1 Expression The interferon response was characterized in M431, the melanoma cell line established from a biopsy of patient #15 with high mutational load and no response to therapy. First, flow cytometry conditions were optimized in selected human melanoma cell lines (FIGS. 17A-C, 18A-D, 19A-H, and 20A-C). PD-L1 expression increased less than 1.5-fold interferon gamma exposure in M431 (FIG. 21A), versus 5.1-fold in M438, a cell line established from patient #8 used as a positive control in this same series. Phosphorylated STAT1 (pSTAT1) was induced at 30 minutes in M431, but the signal dissipated at 18 hours, faster than in cell lines with more durable responses to interferon gamma leading to PD-L1 upregulation (FIG. 21B, C compared with FIG. 22A-C). These data are consistent with the 4:1 JAK1 mutant:wild-type allele frequency in the M431 cell line (FIG. 15A-E).

Figure 21D:
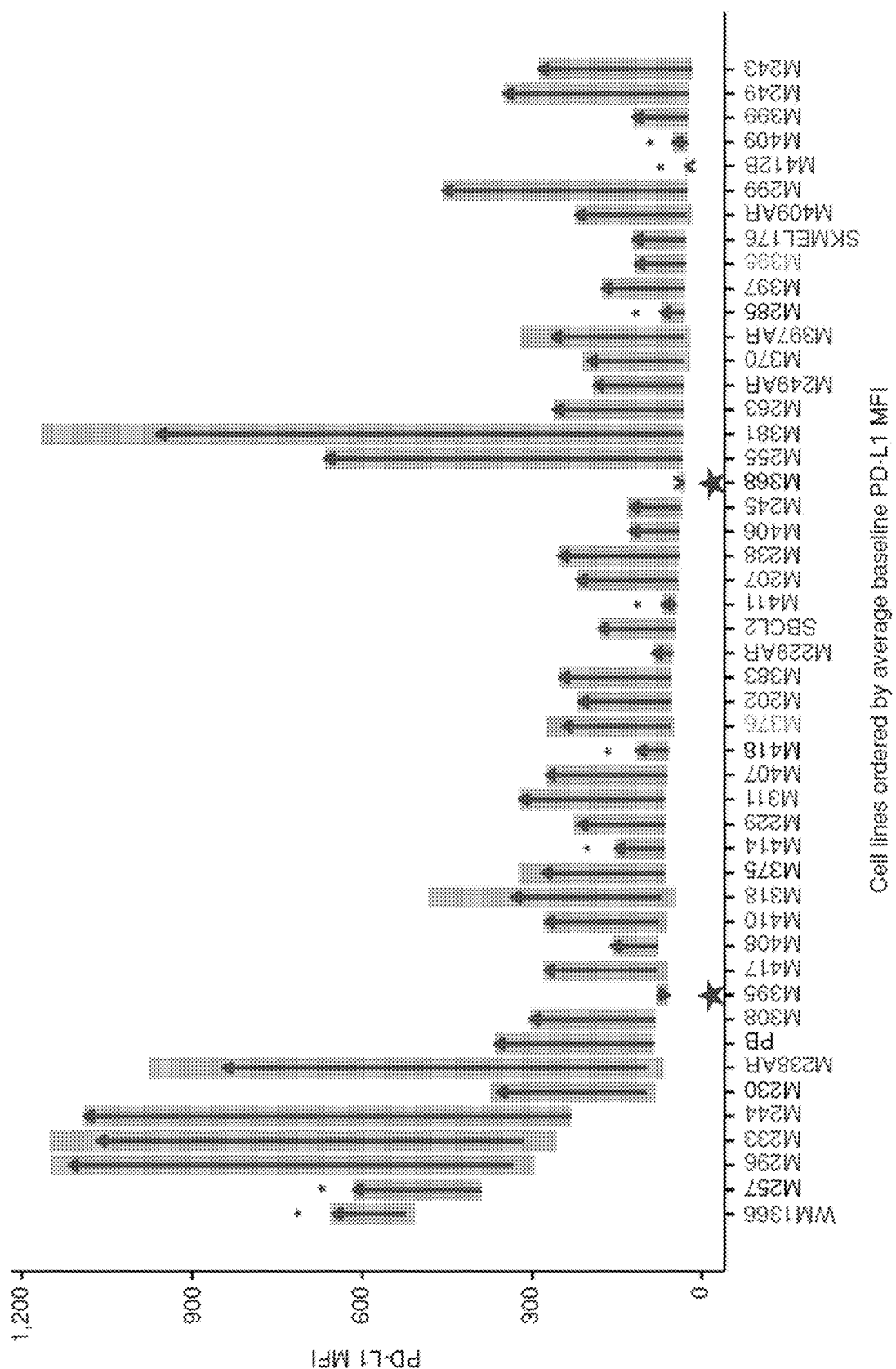
FIG. 21D. Altered interferon signaling with JAK1 loss-of-function mutation in M431 and interferon gamma-inducible PD-L1 expression by 48 melanoma cell lines. PD-L1 response to interferon gamma. Arrows represent average change from baseline upon interferon gamma exposure. Grey shades show the full range of measured values (n=2 or 3). Large stars indicate cell lines with no response due to having a JAK loss-of-function mutation, and asterisks indicate cell lines with poor response to interferons. Grey, BRAF and/or NRAS mutated; black, BRAF and NRAS wild-type.
Figure 22:
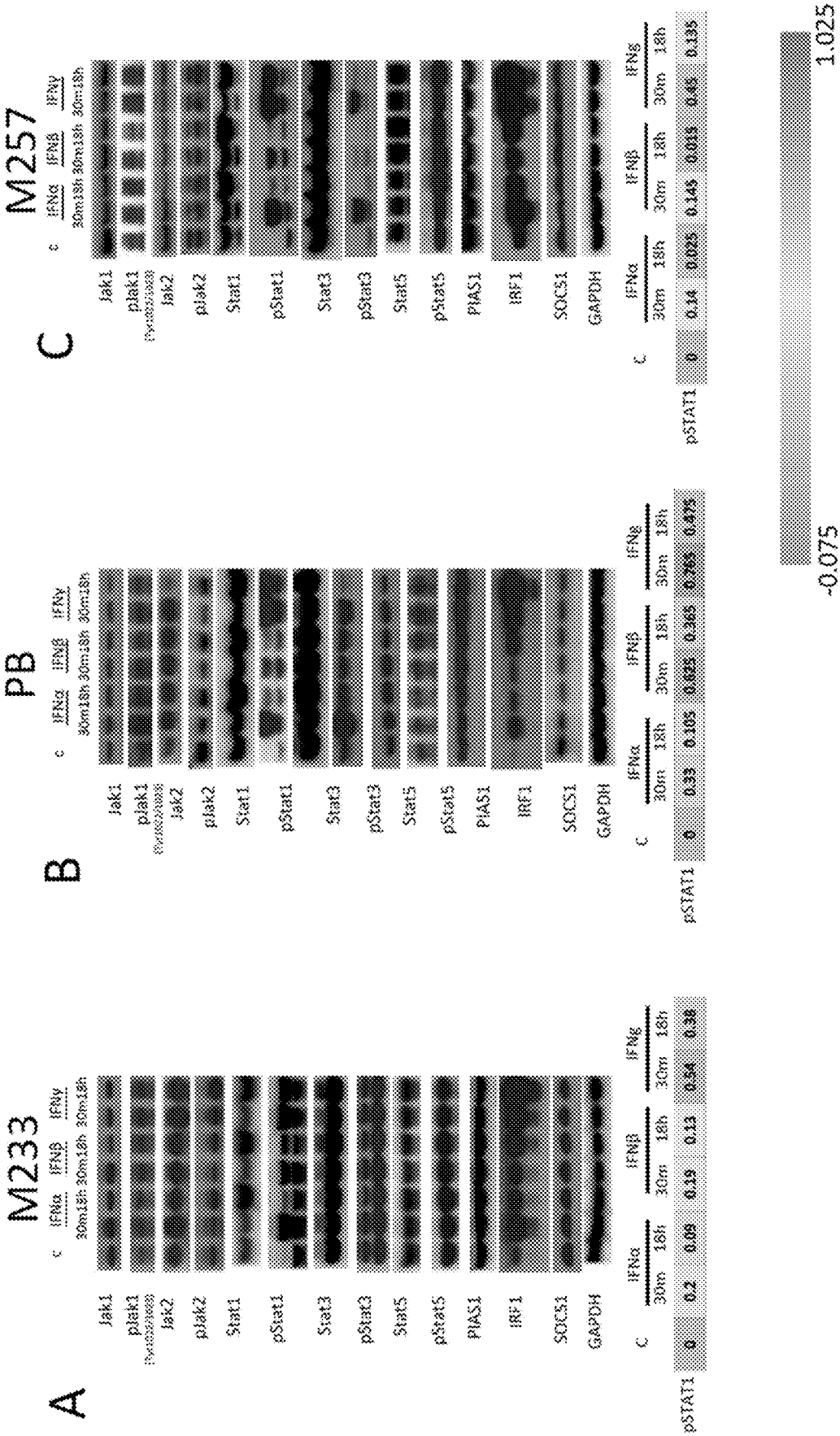
FIG. 22. Interferon signaling pathway in good and poorly responding cell lines. Two responding cell lines M233 (A), and PB (B); a poorly responding cell line M257 (C). For each cell line, cells were cultured with interferon alpha, interferon beta or interferon gamma for either 30 minutes or 18 hours, or with vehicle control (c, first column from the left in Western blots and phospho-flow data). Phosphorylated STAT1 (pSTAT1) detected by Western blotting (top panel) or phospho-flow cytometry data (bottom panel). The numbers in the heat map of pSTAT1 indicate the average Arcsinh ratio from two independent phospho-flow experiments.
Figure 23:
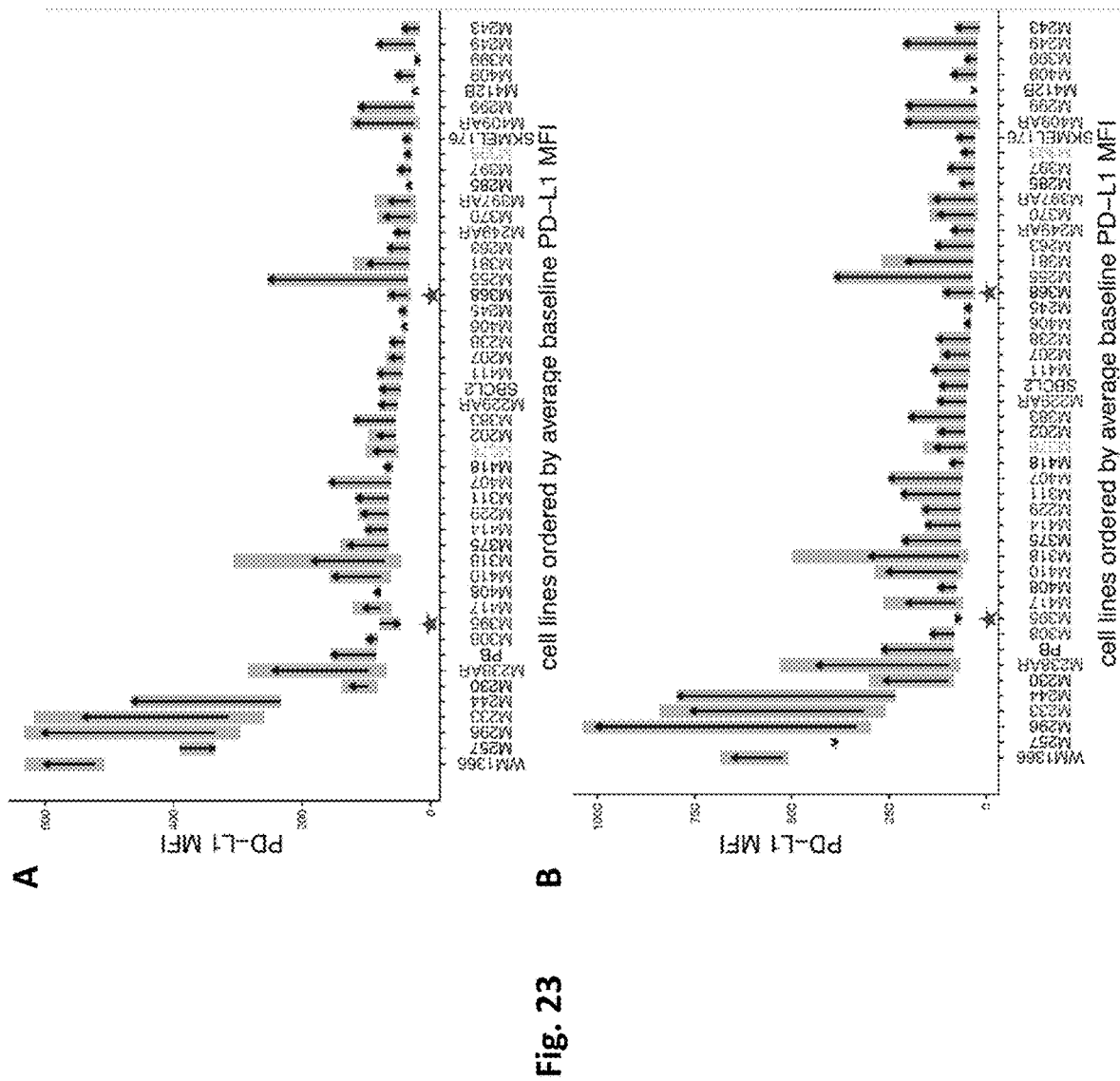
FIG. 23. PD-L1 expression upon interferon alpha and beta exposure. A and B) 48 melanoma cell lines were exposed with the pre-determined concentrations of interferon alpha (A) or beta (B) for 18 hours and PD-L1 expression was measured by flow cytometry. The cells are organized in order by average baseline expression; the arrow indicates the average changes upon interferon treatment, and the shaded grey area represents the full range of measurements from two independent experiments (three independent experiments were performed in some cell lines which showed large variation).
Figure 24A:
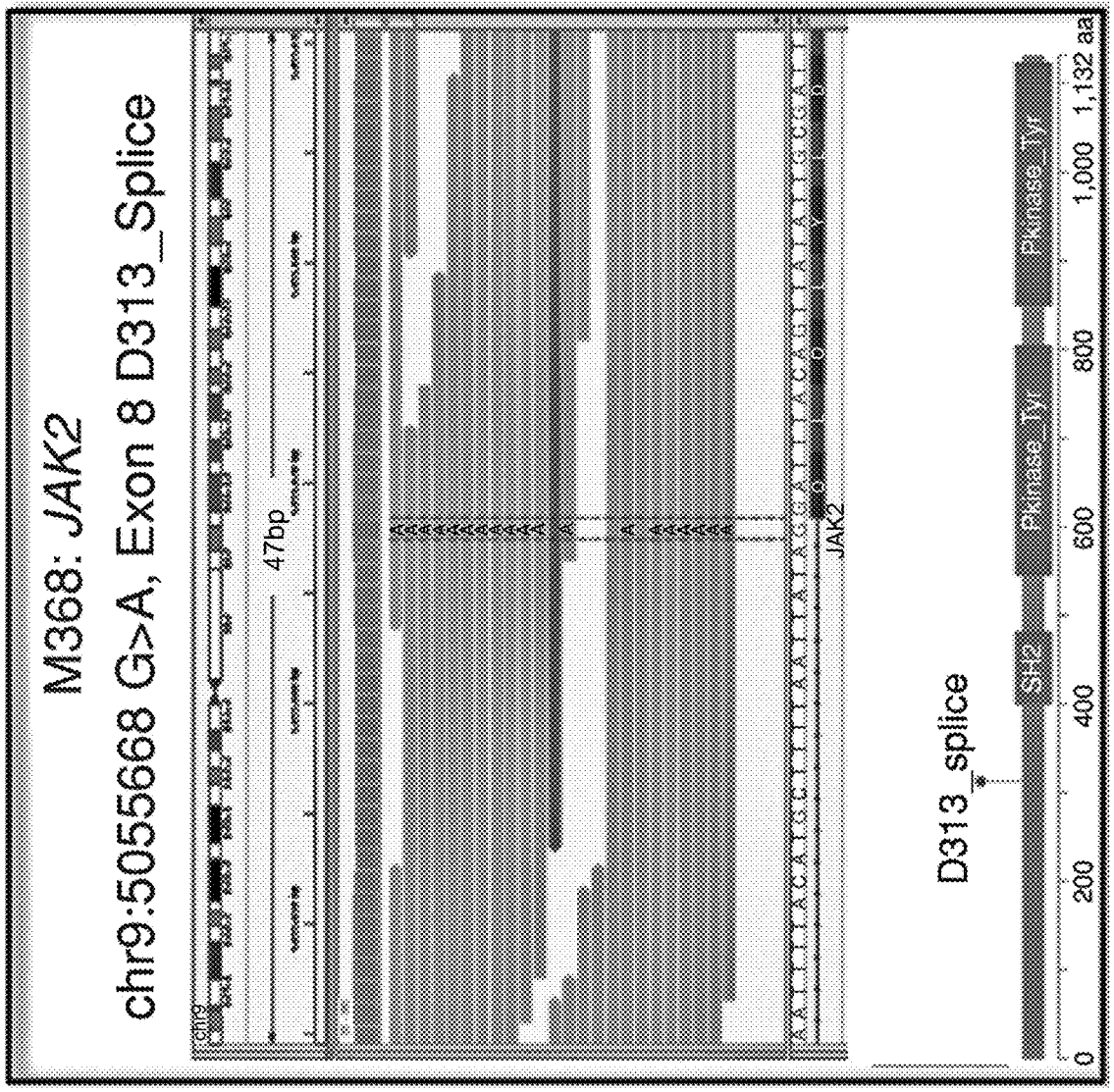
FIG. 24A. (SEQ ID NOs: 44-45) Defects in the interferon receptor signaling pathway with JAK homozygous loss-of-function mutations in M368 and M395. Exome sequencing data showing JAK2 D313 spice-site mutation in exon 8 in M368. Top, individual sequencing reads using the Integrated Genomics Viewer; bottom, position relative to kinase domains using the cBioPortal Mutation Mapper. C and D, for each cell line, cells were cultured with interferon alpha, interferon beta, or interferon gamma for either 30 minutes or 18 hours, or with vehicle control (c, first column from the left in Western blots and phospho-flow data). Phosphorylated STAT1 (pSTAT1) detected by Western blotting (top) or phospho-flow cytometry data (bottom). The numbers in the heat map of pSTAT1 indicate the average Arcsinh ratio from two independent phospho-flow experiments. Blots represent two independent replicate experiments. E and F, PD-L1 expression after interferon exposure on M395 and M431 after JAK1 wild-type (WT) lentiviral transduction respectively. G and H, Time course PD-L1 expression for M431 and JAK1 wild-type lentiviral vector trans-duced M431, respectively.
Figure 24B:
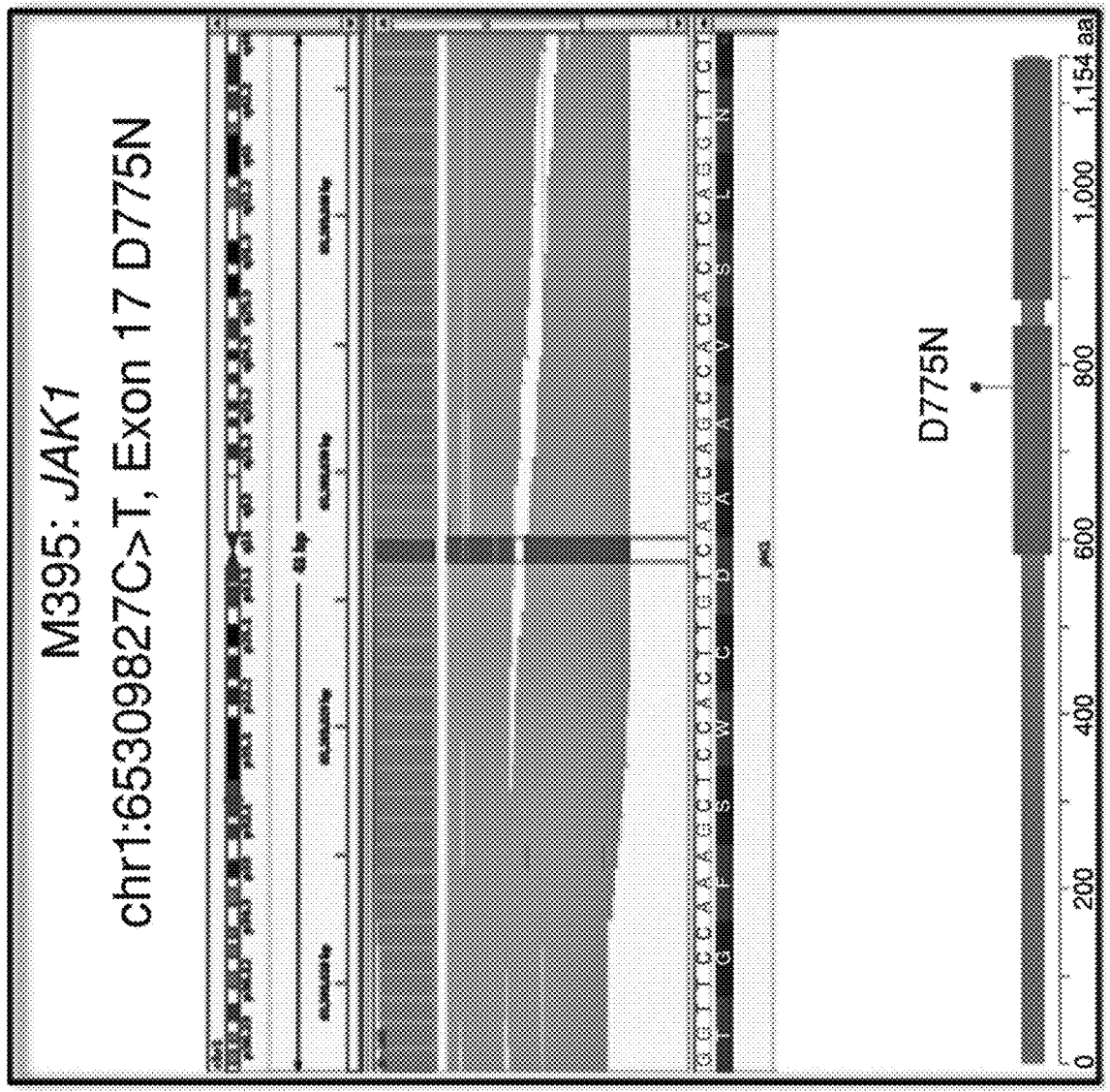
FIG. 24B. (SEQ ID NOs: 46-47) Defects in the interferon receptor signaling pathway with JAK homozygous loss-of-function mutations in M368 and M395. Exome sequencing data showing JAK1 D775N kinase domain mutation in exon 17 in M395. Top, individual sequencing reads using the Integrated Genomics Viewer; bottom, position relative to kinase domains using the cBioPortal Mutation Mapper.
Figure 25:
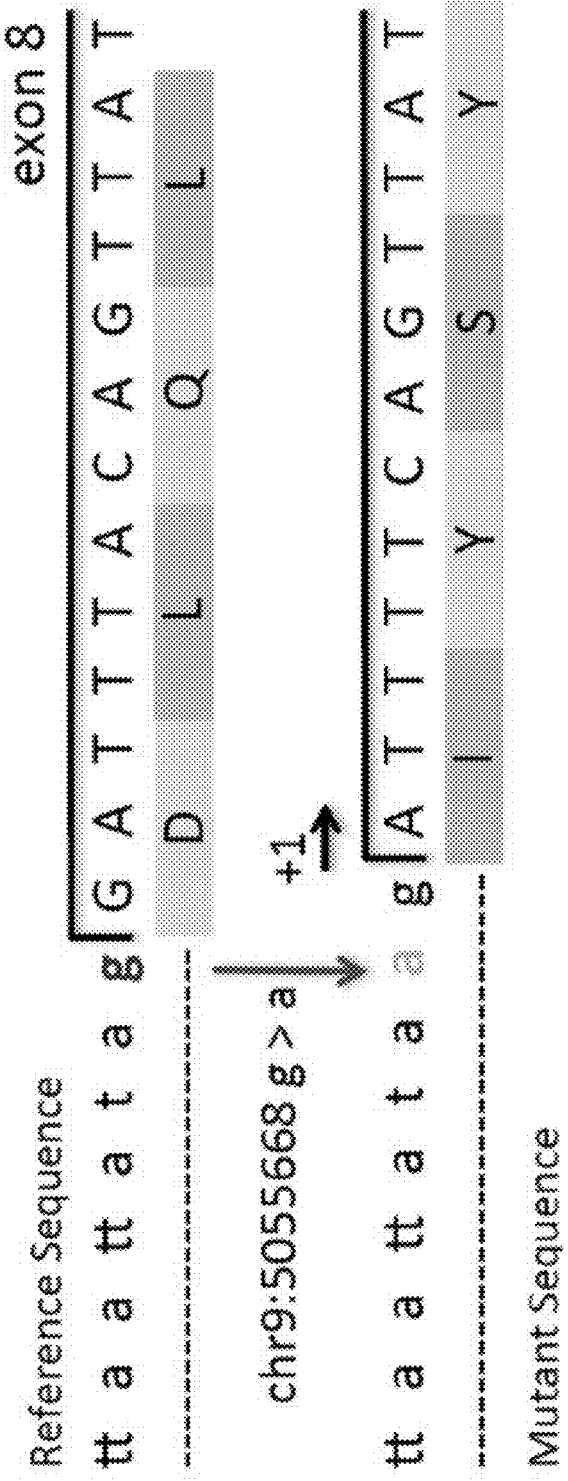
FIG. 25. (SEQ ID NOs: 48-55) Predicted functional consequences of M368 JAK2 D313 splice site mutation. A) Output from the Human Splice Finder 3.0 (http://www.um-d.be/HSF3/). Chromosome 9 5055668 G>A mutation is predicted to break the existing splice acceptor and create a new one shifted by a single nucleotide, producing a frameshift outcome. Transcripts from Ensembl Release 70. B) Schematic of genomic locus at JAK2 exon 8. Lower case=intronic nucleotides, upper case=exonic. Vertical arrow points to G to A mutation.

A panel of 48 human melanoma cell lines was screened for absolute absence of PD-L1 induction by either type I (alpha and beta) or type II (gamma) interferons. Among the three interferons, interferon gamma most potently induced PD-L1 expression (FIG. 21D and FIGS. 23A and 23B for type I interferons). Two cell lines had JAK1/2 homozygous loss-of-function mutations and did not respond to interferon gamma with upregulation of surface PD-L1 expression. M368 had a mutation in JAK2 (20 out of 22 reads, VAF=0.91) that is predicted to disrupt and shift the D313 splice-site acceptor in exon 8 by one nucleotide, changing the reading frame, and had loss of the wild-type allele (FIG. 24A and FIG. 25A-B). M395 had an inactivating JAK1$^{D775N}$ kinase domain mutation in exon 17 and loss of the other allele (140 out of 143 reads, variant allele frequency 0.98; FIG. 24B).

Figure 24C:
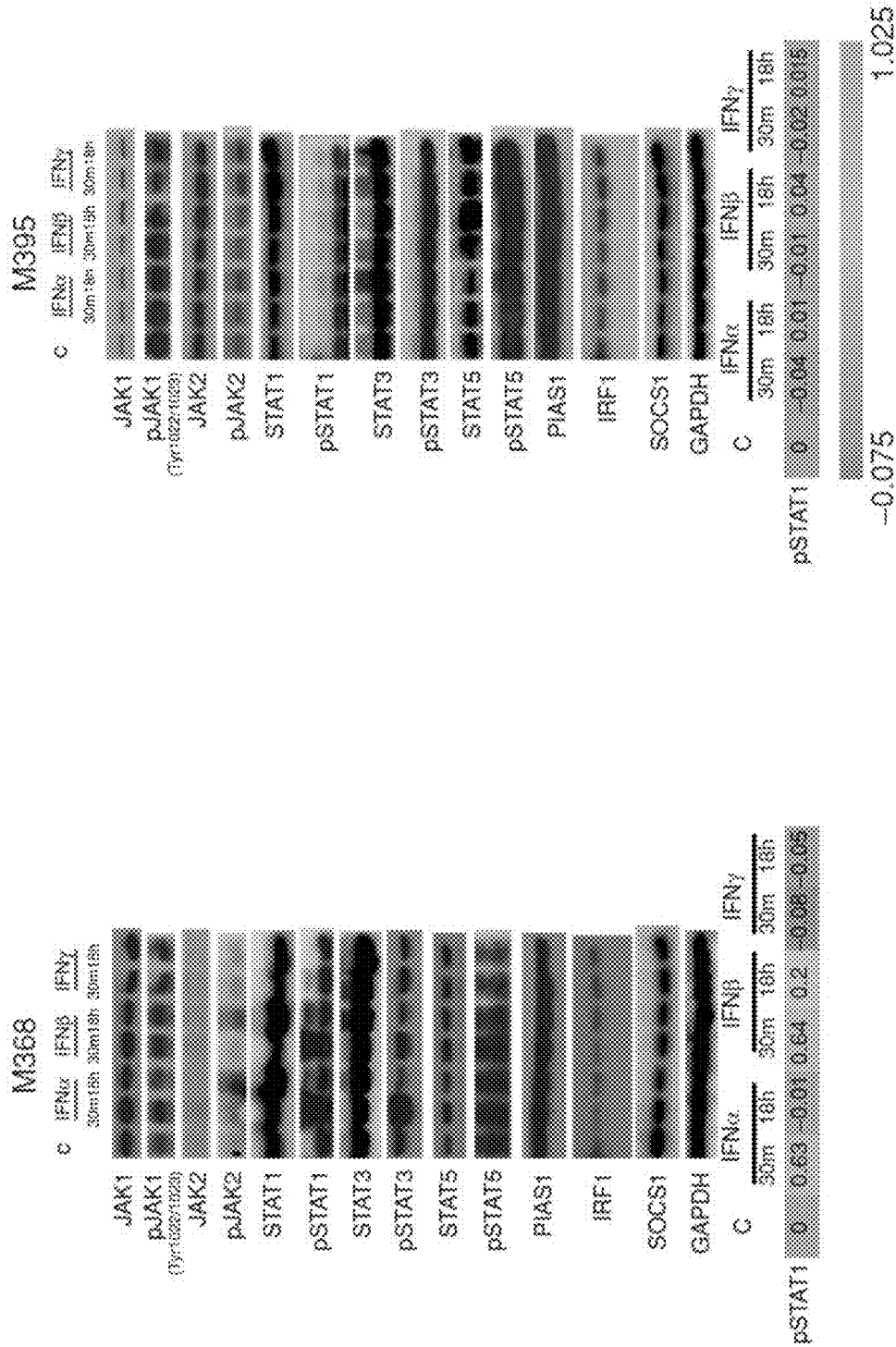
FIG. 24C. Defects in the interferon receptor signaling pathway with JAK homozygous loss-of-function mutations in M368 and M395. For each cell line, cells were cultured with interferon alpha, interferon beta, or interferon gamma for either 30 minutes or 18 hours, or with vehicle control (c, first column from the left in Western blots and phospho-flow data). Phosphorylated STAT1 (pSTAT1) detected by Western blotting (top) or phospho-flow cytometry data (bottom). The numbers in the heat map of pSTAT1 indicate the average Arcsinh ratio from two independent phospho-flow experiments. Blots represent two independent replicate experiments.

Signaling responses to interferon alpha, beta, and gamma were analyzed in these two cell lines. M368, which comprised the JAK2 loss-of-function mutation, maintained signaling in response to interferon alpha and beta, but did not respond to interferon gamma (FIG. 24C), which resulted in the ability of M368 to upregulate PD-L1 when exposed to interferon alpha and beta, but not to interferon gamma (FIG. 24C and FIG. 23A-B). M395, which comprised the JAK1 loss-of-function mutation, did not respond to downstream signaling to interferon alpha, beta, or gamma (FIG. 24C), and equally did not upregulate PD-L1 in response to any of these cytokines (FIG. 24C and FIGS. 23A and 23B). The tumor from which the cell line M395 had been established was retrieved, and this tumor exhibited an absence of CD8 infiltration similar to the finding in patient #15 with a JAK1 loss-of-function mutation who did not respond to anti-PD-1 therapy (data not shown, see Shin et al. Fig. S11, herein incorporated by reference). Taken together, these data are consistent with the knowledge that JAK1 (disabled in M395) is required to propagate signaling downstream of the interferon alpha/beta and gamma receptors, whereas JAK2 (disabled in M368) is required for signaling downstream only from the interferon gamma receptor (22-24).

Figure 24D:
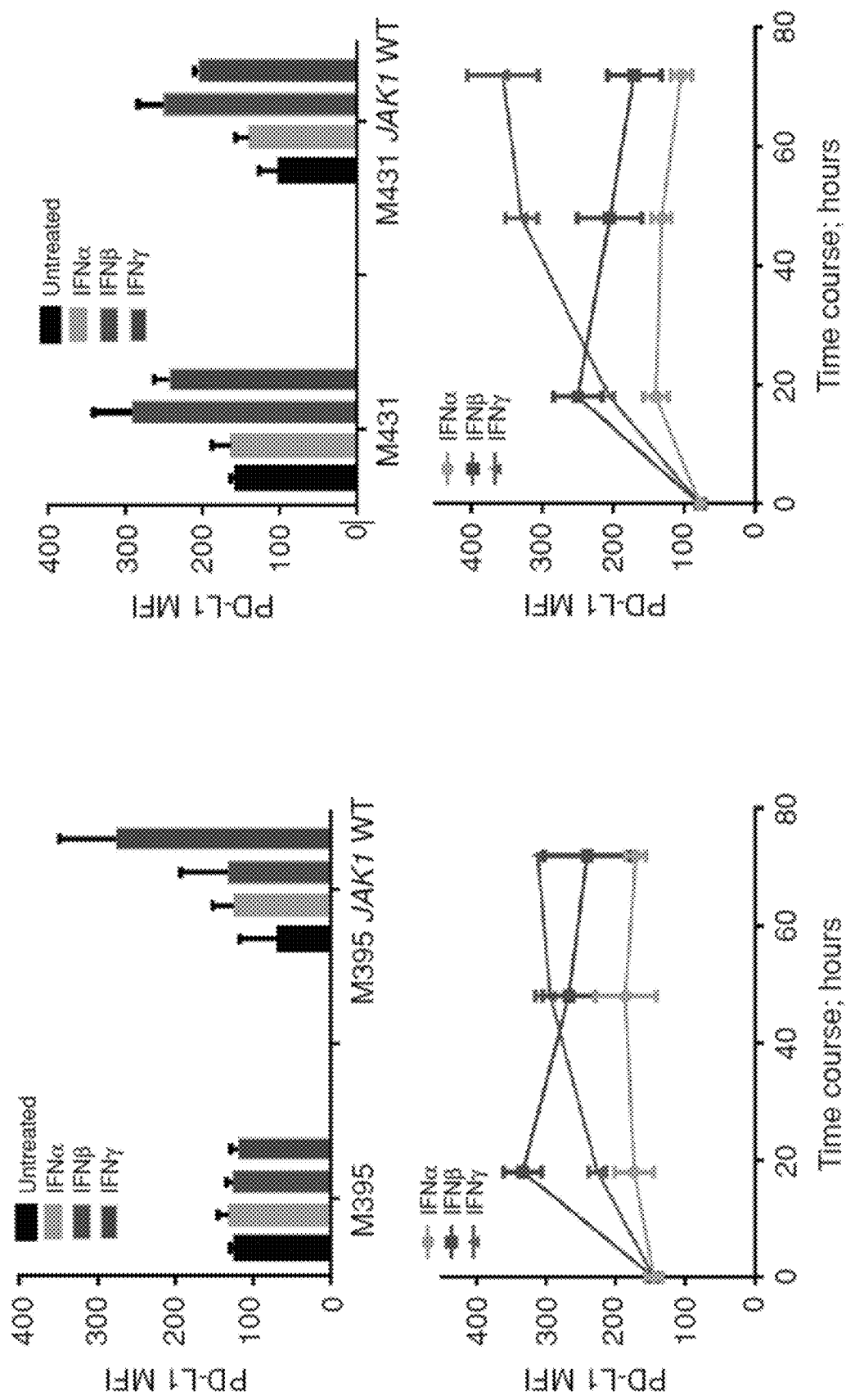
FIG. 24D. Defects in the interferon receptor signaling pathway with JAK homozygous loss-of-function mutations in M368 and M395. PD-L1 expression after interferon exposure on M395 and M431 after JAK1 wild-type (WT) lentiviral transduction respectively (top panels). Time course PD-L1 expression for M431 and JAK1 wild-type lentiviral vector transduced M431, respectively (bottom panels).
Figure 26:
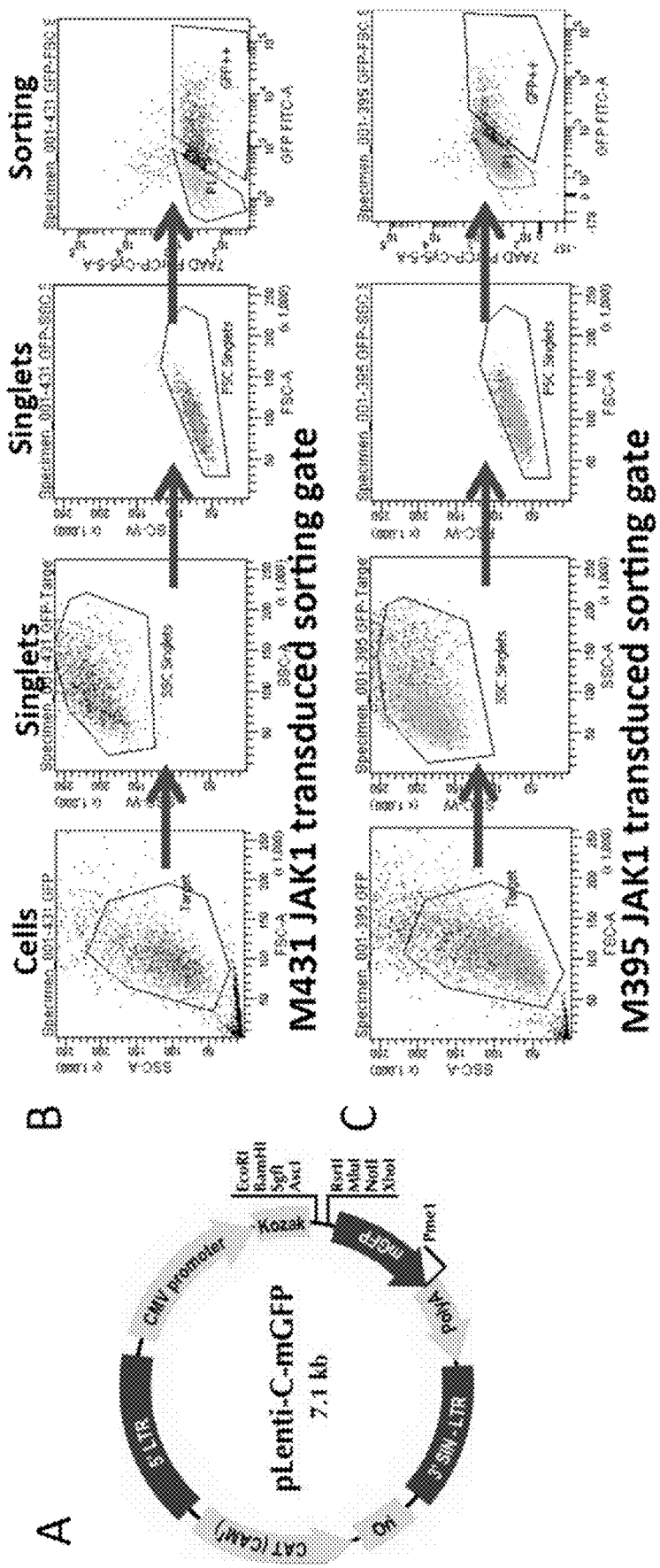
FIG. 26. JAK1 wild-type lentiviral vector transduction. A) Schematic of the JAK1 wild-type expressing lentiviral vector. B and C) Gating strategies for sorting based on GFP signal for M431 and M395 after JAK1 wild-type lentiviral vector transduction respectively.
Figure 27A:
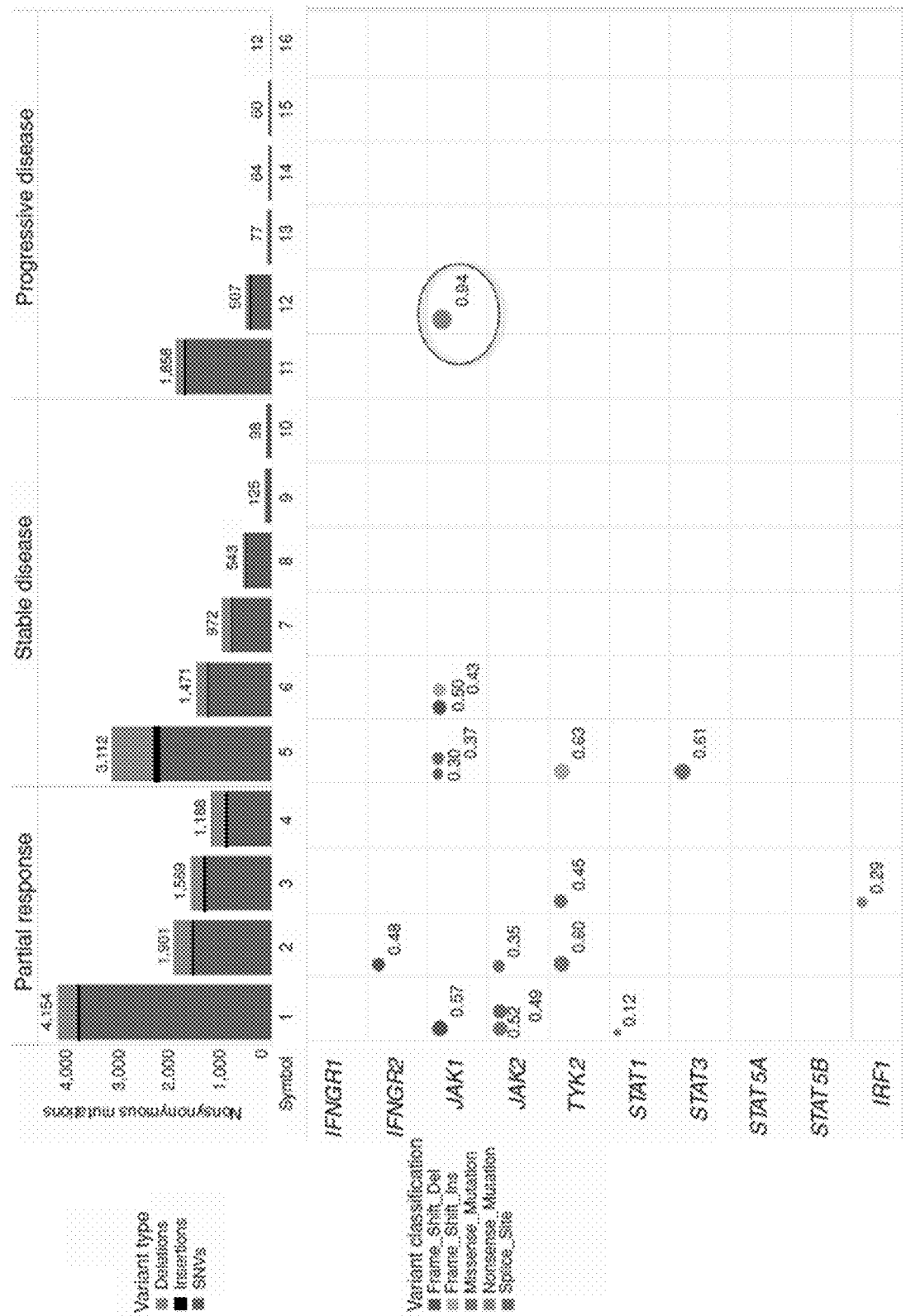
FIG. 27A. Mutational burden of somatic, protein-altering mutations per subject from WES for patients with advanced colon cancer who participated in PD-1 blockade clinical trial. Similar to FIG. 14B, bar graph shows mutational load in individual cases [fraction single nucleotide variants (SNV), dark grey; insertions, black; deletions light grey] divided by response to PD-1 blockade therapy. Bottom panel depicts mutations, insertions, or deletions in the interferon receptor pathway. Shading represents predicted functional effect. The size of circles and adjacent labels correspond to tumor VAF after adjusting for stromal content. Circle highlights homozygous nonsense mutation in JAK1 from one patient who did not respond to anti-PD-1 therapy.
Figure 27B:
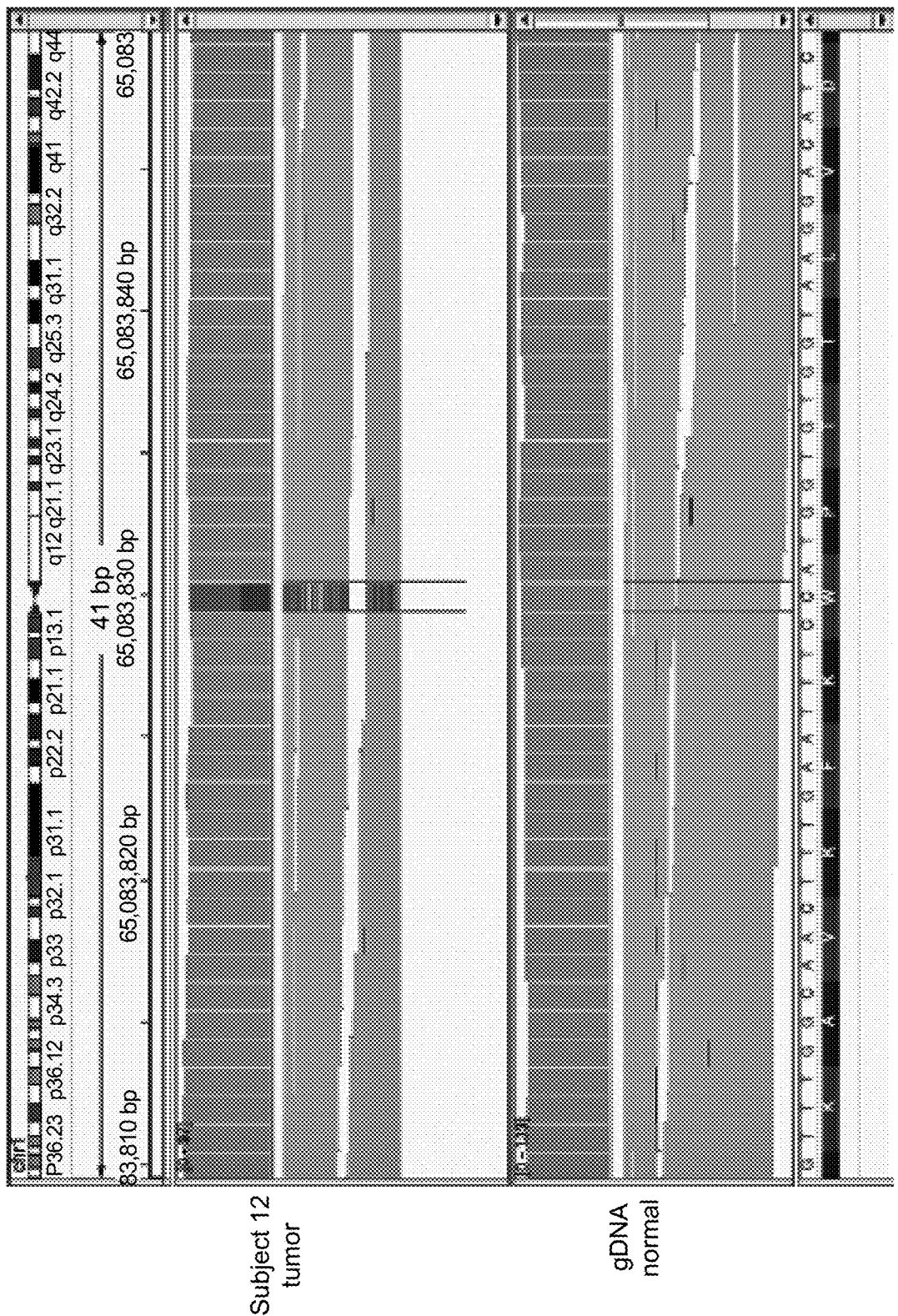
FIG. 27B. (SEQ ID NOs: 56-57) Mutational burden of somatic, protein-altering mutations per subject from WES for patients with advanced colon cancer who participated in PD-1 blockade clinical trial. Sequencing reads of JAK1 mutation in non-responder subject #12.
Figure 27C:
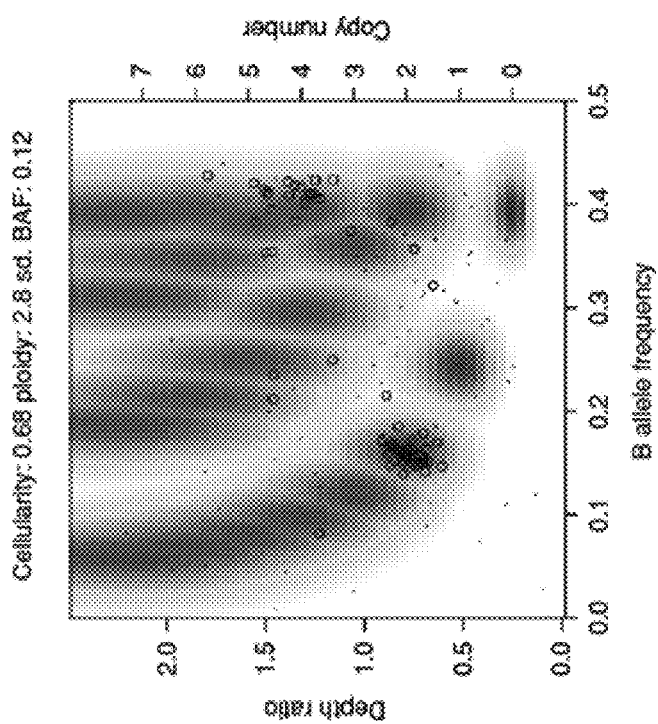
FIG. 27C. Mutational burden of somatic, protein-altering mutations per subject from WES for patients with advanced colon cancer who participated in PD-1 blockade clinical trial. Mutation observed in 51 reads out of 80 (VAF 0.64), which corresponds to a homozygous mutation (adjusted VAF 0.94) when adjusted for a tumor purity of 68%.
Figure 27D:
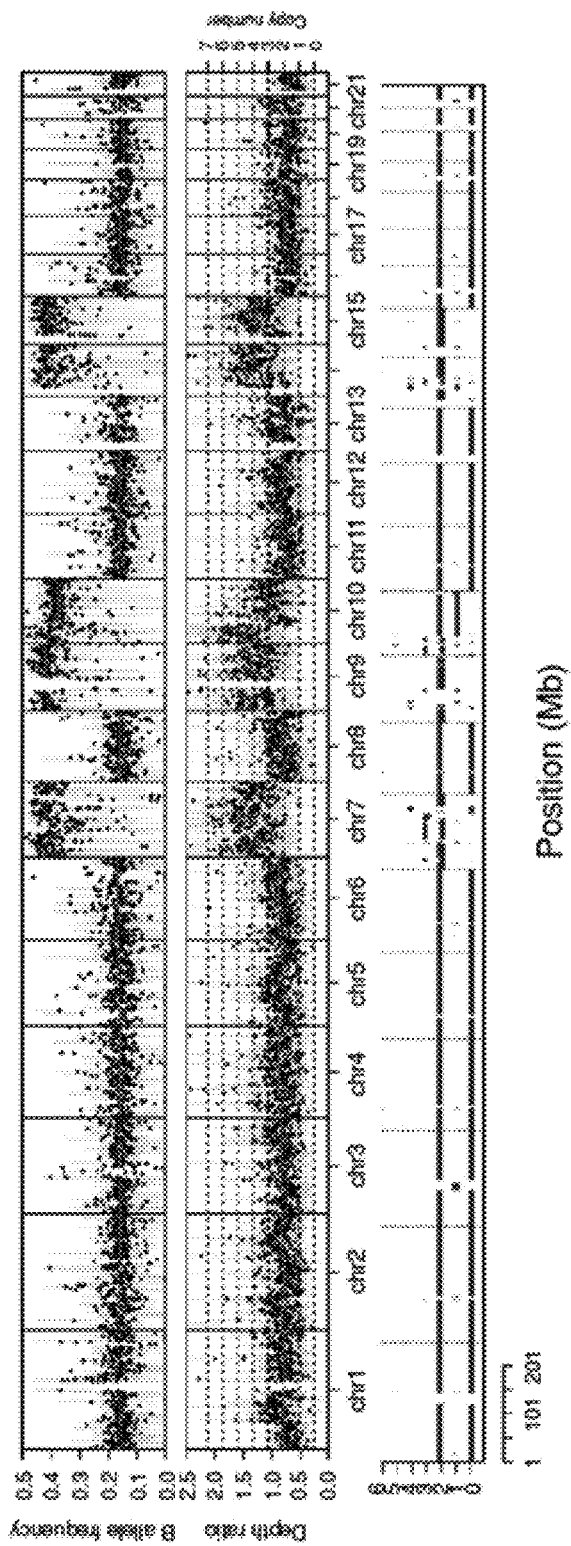
FIG. 27D. Mutational burden of somatic, protein-altering mutations per subject from WES for patients with advanced colon cancer who participated in PD-1 blockade clinical trial. Copy-number profile reveals loss of heterozygosity across most of the genome, including chromosome 1/JAK1.

To assess a causal relationship between loss of adaptive PD-L1 expression and loss-of-function JAK mutations, the M395 and M431 cell lines were transduced with a lentivirus vector expressing JAK1 wild-type (FIG. 26A-C). Reintroduction of wild-type JAK1 rescued PD-L1 expression in M395 cells, which exhibited a 4-fold increase in PD-L1 surface expression after interferon gamma exposure (FIG. 24D). For M431, the magnitude of change in PD-L1 expression after 18-hour interferon gamma exposure for M431 was modest after reintroducing the JAK1 wild-type protein (approximately 2-fold, compared with a 1.5-fold in the untransduced cell line; FIG. 24D). However, the difference between untransduced and JAK1 wild-type transduced M431 was more distinct when observed over a longer time course (FIG. 24D).

Figure 28:
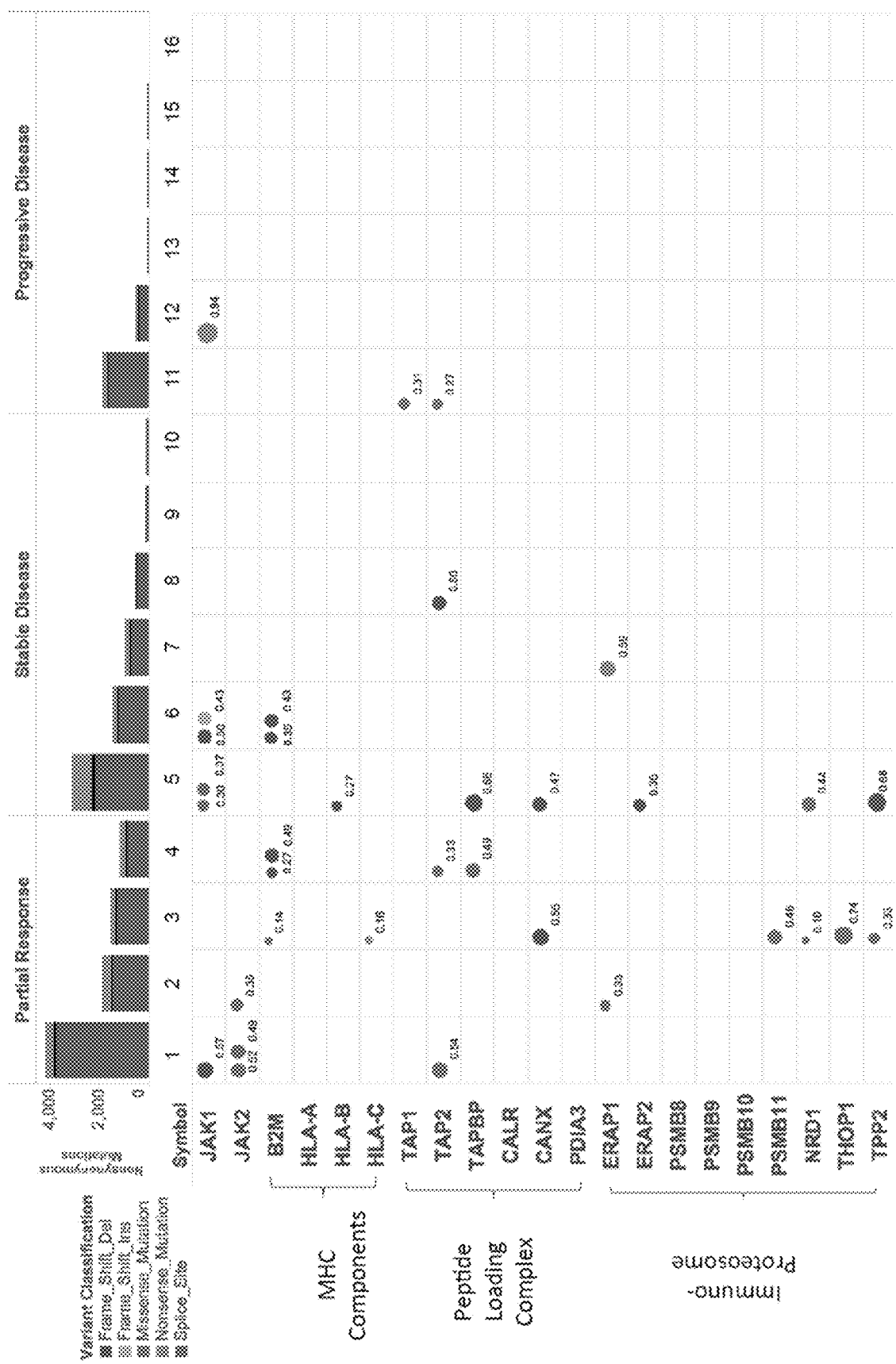
FIG. 28. Mutations in antigen presentation machinery from anti-PD1 treated colorectal cohort. Subjects were ordered as in FIG. 27A, and top bar graph re-depicts mutational load for reference. The size of circles and adjacent labels represent the tumor variant allele frequency (VAF) of the mutation after adjustment for stromal content. Shading represents predicted functional effect.

JAK Loss-of-Function Mutations in Primary Resistance to PD-1 Blockade in Patients with Metastatic Colon Carcinoma To determine whether JAK1/2 loss-of-function mutations are present and relate to response to PD-1 blockade therapy in another cancer histology, WES data from 16 biopsies of patients with colon cancer, many with a high mutational load resultant from mismatch-repair deficiency, was analyzed (6). One of the biopsies of a rare patient with high mutational load with neither an objective response nor disease control with anti-PD-1 had a homozygous JAK1W690* nonsense loss-of-function mutation, expected to truncate the protein within the first kinase domain, and an accompanying loss of heterozygosity at the JAK1 locus (FIG. 27A-D). No mutations in antigen presentation machinery were detected in this sample (FIG. 28). Although we observed other interferon pathway and antigen presentation mutations in the high mutational load patients with a response to therapy in this cohort, they appeared to be heterozygous by allele frequency (adjusted VAF<0.6) after adjustment for stromal content. Most were splice-site mutations or frameshift insertions/deletions unlikely to create a dominant-negative effect. Several samples bore two mutations in JAK1/2 or B2M, but either retained at least one wild-type copy (subjects #4 and #5), were too far apart to determine cis versus trans status (subject #6), or were of uncertain significance (subject #1, both near c-terminus).

Figure 29A:
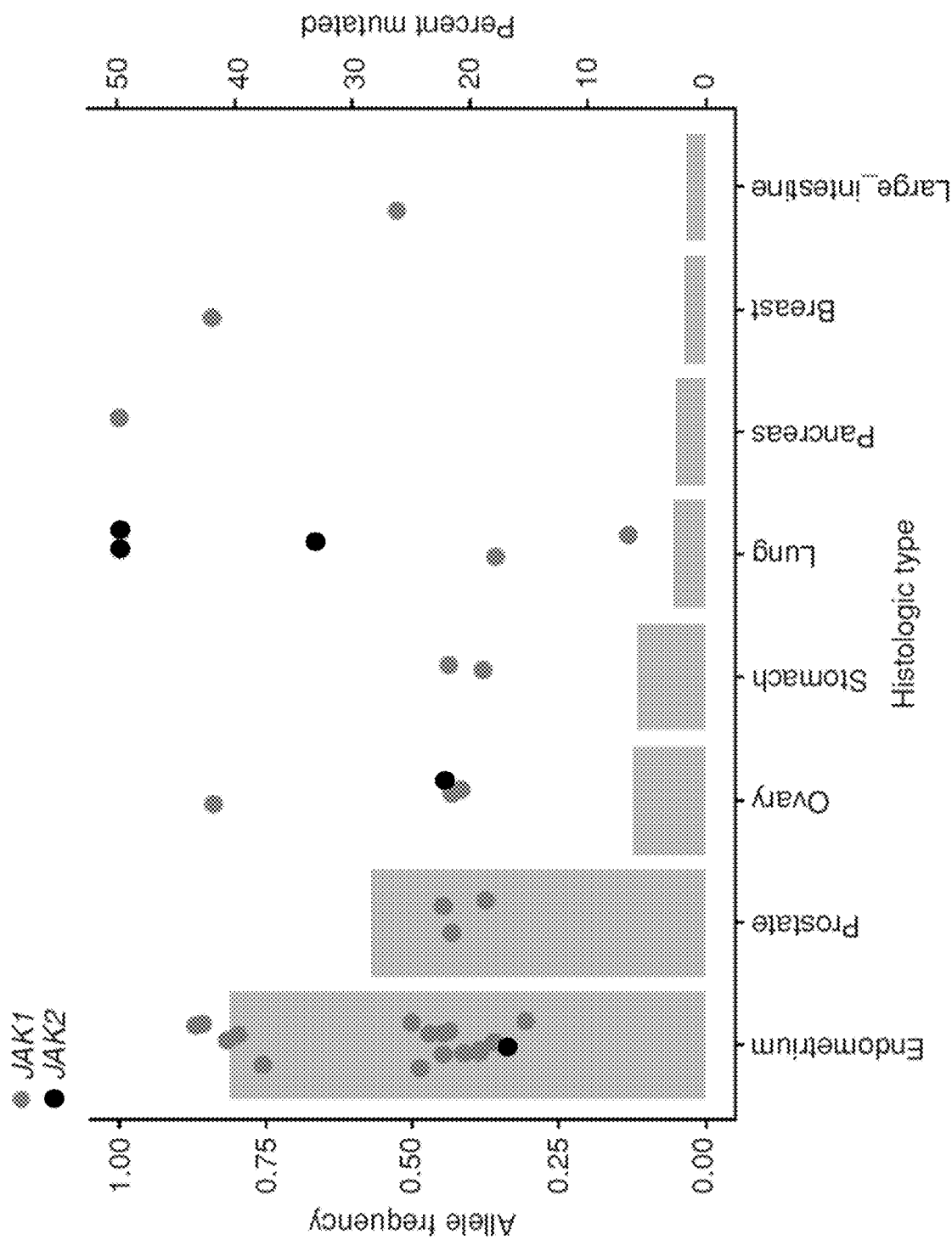
FIG. 29A. Analysis of JAK1 and JAK2 mutations in the CCLE database. Variant allele frequency (left axis, grey and black points) and percentage of tumors with mutations in JAK1 or JAK2 (right axis, gray bars) in the CCLE database from the cBioPortal.
Figure 29B:
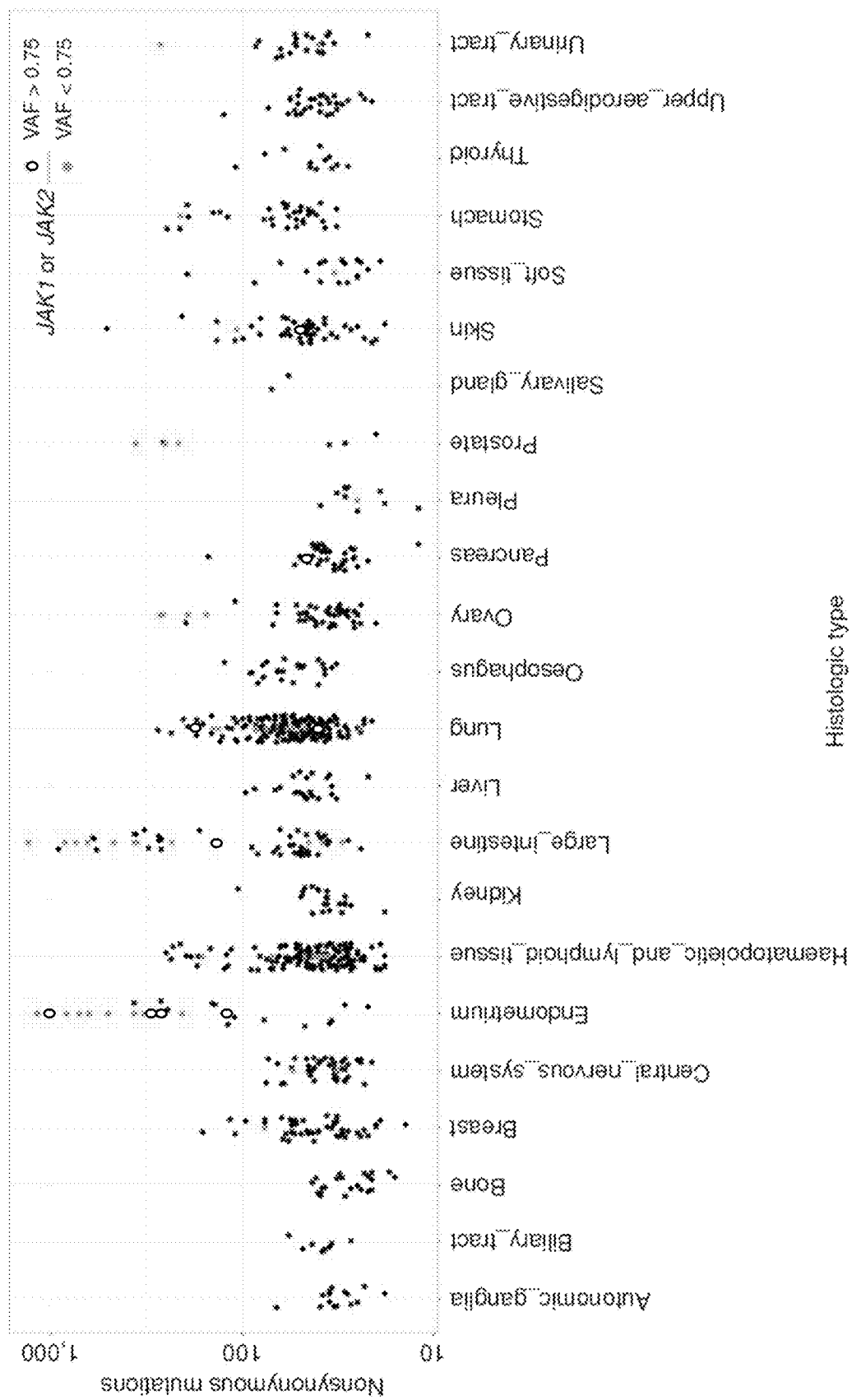
FIG. 29B. Analysis of JAK1 and JAK2 mutations in the CCLE database. Nonsynonymous mutational burden was analyzed for individual cell lines (each dot represents cell line) and plotted for each histologic type. JAK1 or JAK2 mutated cell lines were coded (open circles, VAF>0.75; grey circles VAF<0.75).
Figure 30:
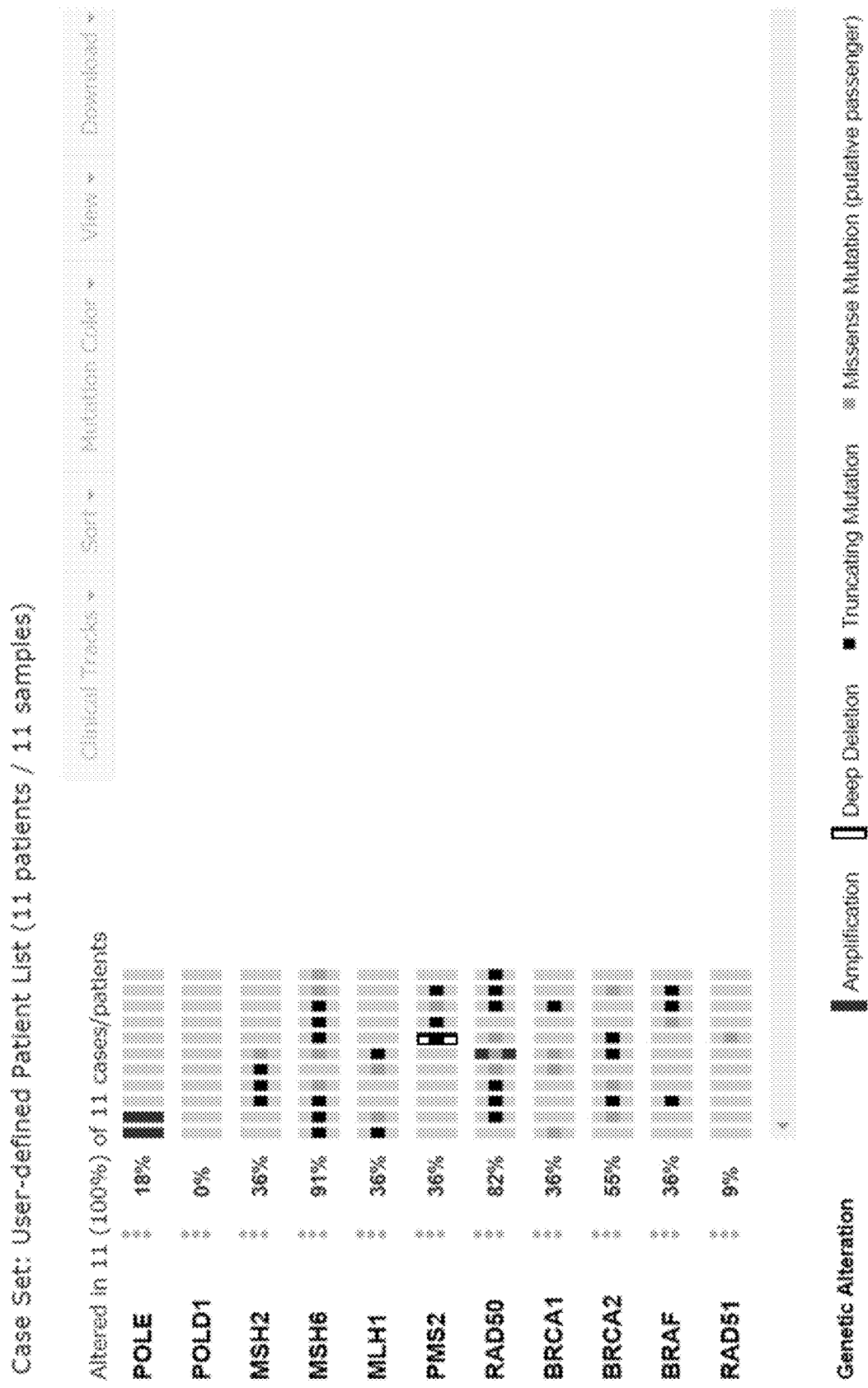
FIG. 30. DNA damage repair gene mutations in endometrial cancer cell lines with JAK1/2 mutations. Analysis of gene mutations involving DNA repair in the 11 endometrial carcinoma cell lines with JAK1/2 mutations, including POLE or POLD1 mutations, microsatellite instability and DNA damage gene mutations.

Frequency of JAK Loss-of-Function Mutations in Cell Lines of Multiple Histologies Data from the Cancer Cell Line Encyclopedia (CCLE) from cBioPortal was analyzed to determine the frequency of homozygous putative loss-of-function mutations in JAK1/2 in 905 cancer cell lines (25). For this analysis, a mutation was considered homozygous when the VAF was 0.8 or greater, as previously described (26). Approximately 0.7% of cell lines have loss-of-function mutations that may predict lack of response to interferons (FIG. 29A-B). The highest frequency of mutations was in endometrial cancers, as described previously (26). None of these cell lines had POLE or POLD1 mutations, but microsatellite instability and DNA-damage gene mutations were present in the JAK1/2 mutant cell lines (FIG. 30). The frequency of JAK1/2 mutations across all cancers suggests that there is a fitness gain with loss of interferon responsiveness.

JAK1/2 Loss-of-Function Alterations in The Cancer Genome Atlas

Analysis of WES, RNA sequencing (RNA-seq), and reverse-phase protein array (RPPA) data from tissue specimens from 472 patients in The Cancer Genome Atlas (TCGA) Skin Cutaneous Melanoma dataset revealed that 6% (28 of 472) and 11% (50 of 472) comprised alterations in JAK1 and JAK2, respectively. These include loss-of-function alterations in either JAK1 or JAK2 that would putatively diminish JAK1 or JAK2 signaling (homodeletions, truncating mutations, or gene or protein downregulation).

Figure 31A:
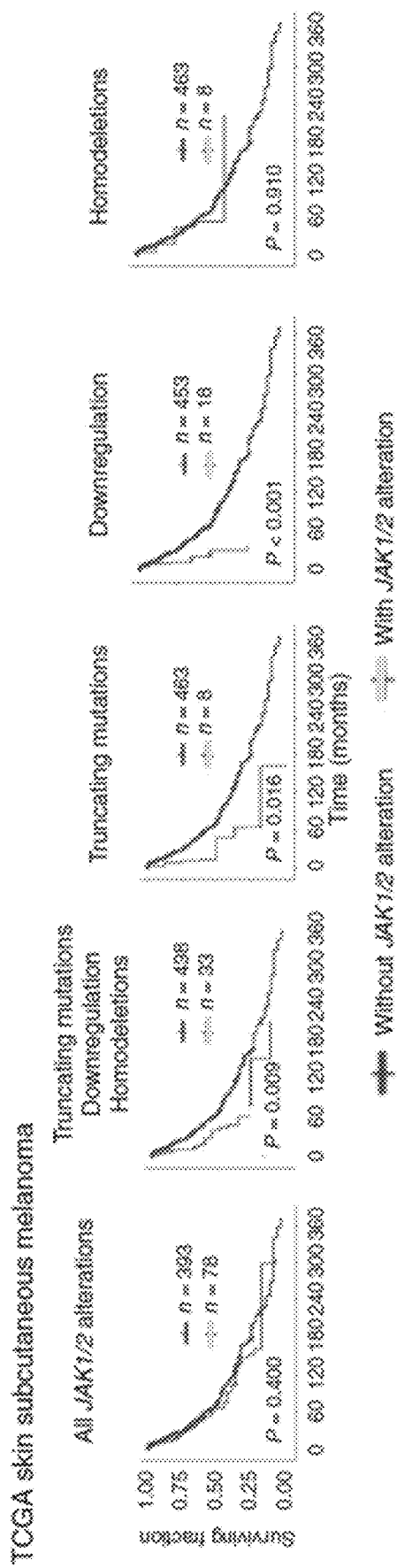
FIG. 31A. Frequency of JAK1 and JAK2 alterations and their association with overall survival in TCGA datasets. Kaplan-Meier survival analysis of TCGA skin cutaneous melanoma provisional datasets, comparing control patients (dark grey) and patients comprising specified alterations in JAK1 and JAK2 (light grey). Frequency and distribution of combined JAK1 and JAK2 alterations are shown within each set of Kaplan-Meier plots. Significance testing of overall survival was performed using log-rank analysis.

There was no survival difference in patients in the TCGA Skin Cutaneous Melanoma dataset comprising any JAK1 or JAK2 alteration (FIG. 31A). However, when considering only loss-of-function JAK1 or JAK2 alterations (homodeletions, truncating mutations, or gene or protein downregulation), patients with tumors that had JAK1 or JAK2 alterations had significantly decreased overall survival (P=0.009, log-rank test). When considered separately, the 8 patients with truncating mutations in JAK1 or JAK2 and the 18 patients with JAK1 or JAK2 gene or protein downregulation also had significantly decreased overall survival (P=0.016 and P<0.001, respectively).

To assess the relevance of these findings in a broader set of malignancies, the frequency of JAK1 and JAK2 alterations and their association with clinical outcome in TCGA datasets for four common malignancies (breast invasive carcinoma, prostate adenocarcinoma, lung adenocarcinoma, and colorectal adenocarcinoma) was analyzed. Similar to findings in melanoma, alterations in JAK1 were found in 6%, 8%, 10%, and 10% of patients with breast invasive carcinoma, prostate adeno-carcinoma, lung adenocarcinoma, and colorectal adenocarcinoma, respectively. Likewise, alterations in JAK2 were found in 12%, 7%, 12%, and 5% of these respective malignancies.

Figure 31B:
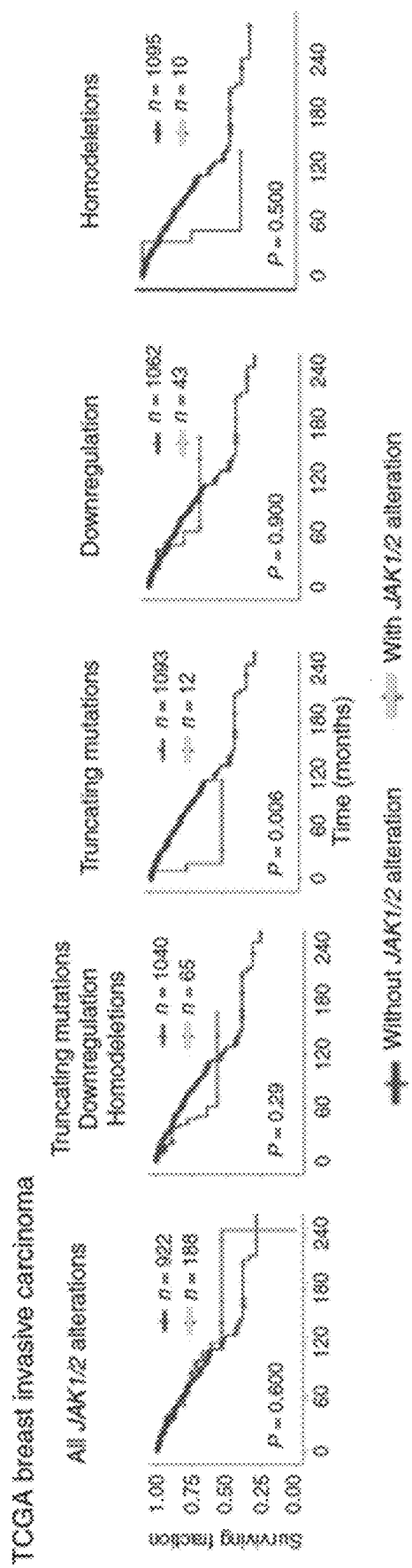
FIG. 31B. Frequency of JAK1 and JAK2 alterations and their association with overall survival in TCGA datasets. Kaplan-Meier survival analysis of TCGA skin cutaneous melanoma breast invasive carcinoma provisional datasets, comparing control patients (dark grey) and patients comprising specified alterations in JAK1 and JAK2 (light grey). Frequency and distribution of combined JAK1 and JAK2 alterations are shown within each set of Kaplan-Meier plots. Significance testing of overall survival was performed using log-rank analysis.
Figure 31C:
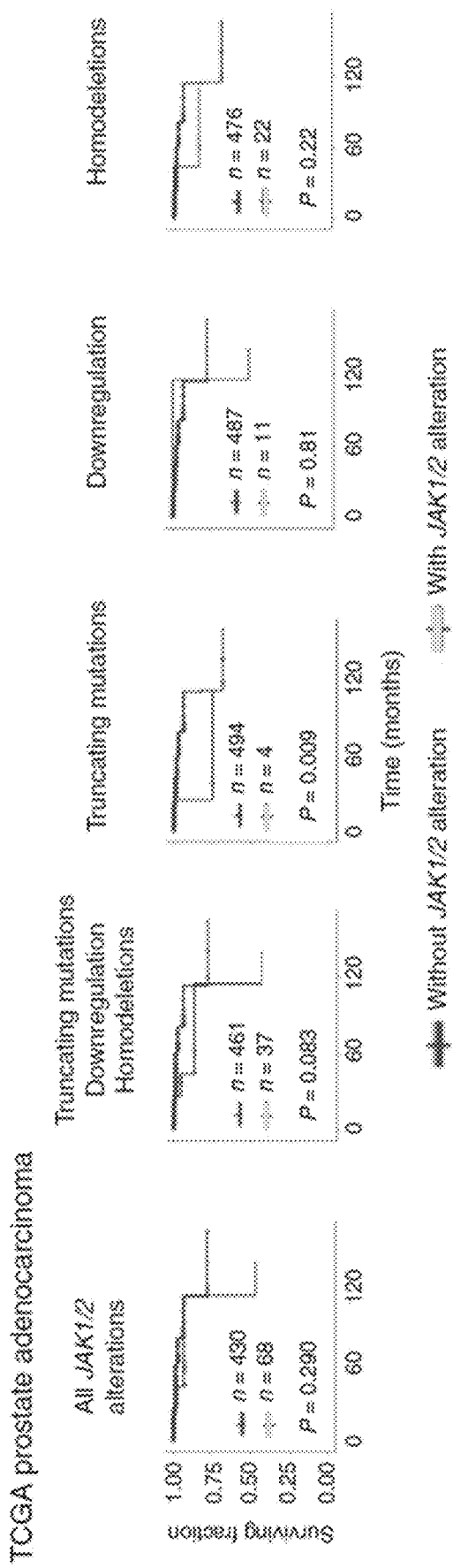
FIG. 31C. Frequency of JAK1 and JAK2 alterations and their association with overall survival in TCGA datasets. Kaplan-Meier survival analysis of TCGA skin cutaneous melanoma prostate adenocarcinoma provisional datasets, comparing control patients (dark grey) and patients comprising specified alterations in JAK1 and JAK2 (light grey). Frequency and distribution of combined JAK1 and JAK2 alterations are shown within each set of Kaplan-Meier plots. Significance testing of overall survival was performed using log-rank analysis.
Figure 32:
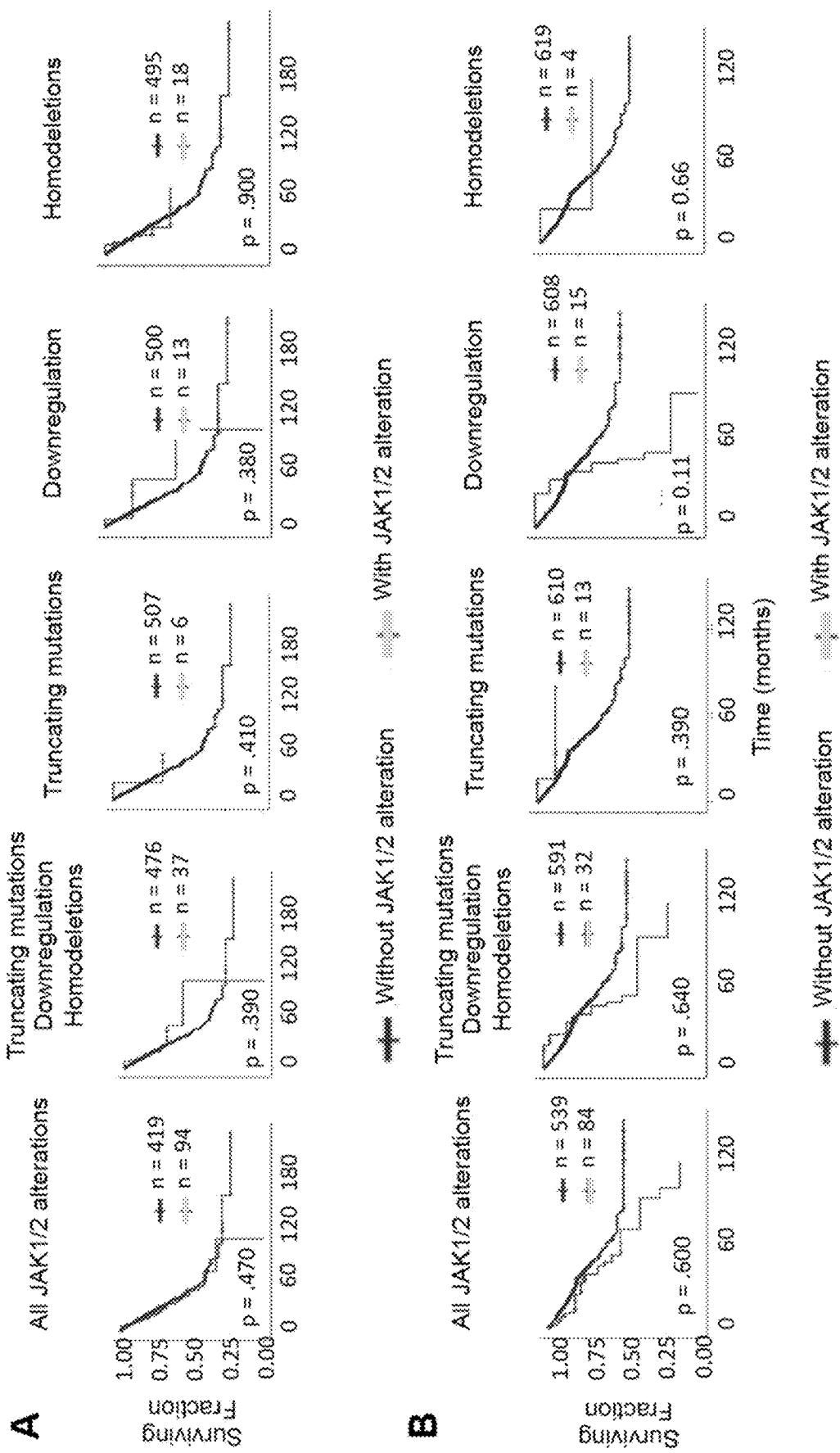
FIG. 32. Frequency of JAK1 and JAK2 alterations and their association with overall survival in additional TCGA datasets. Kaplan-Meier survival analysis of TCGA lung adenocarcinoma (A) and colorectal adenocarcinoma (B), comparing control patients (dark grey) and patients comprising specified alterations in JAK1 and JAK2 (light grey). Frequency and distribution of combined JAK1 and JAK2 alterations are shown within each set of Kaplan-Meier plots. Significance testing of overall survival was performed using log-rank analysis.

Consistent with the findings in melanoma, JAK1 or JAK2 alterations as a whole were not associated with a difference in survival in any of the four additional TCGA datasets. However, for patients with breast invasive carcinoma comprising truncating mutations, there was an association with decreased survival (P=0.006, log-rank test; FIG. 31B). Likewise, patients with prostate adenocarcinoma comprising truncating mutations had worse overall survival (P=0.009, log-rank test; FIG. 6C), with a similar trend noted in patients comprising any loss-of-function JAK1 or JAK2 alterations (P=0.083, FIG. 31C). We did not observe differences in survival in patients with lung adenocarcinoma or colorectal adenocarcinoma comprising JAK1 or JAK2 loss-of-function alterations, when considered either separately or as a whole (FIG. 32A-B).

Example 2 Cited References

1. Herbst R S, Soria J C, Kowanetz M, Fine G D, Hamid O, Gordon M S, et al. Predictive correlates of response to the anti-PD-L1 antibody MPDL3280A in cancer patients. Nature 2014; 515:563-7.
2. Powles T, Eder J P, Fine G D, Braiteh F S, Loriot Y, Cruz C, et al. MPDL3280A (anti-PD-L1) treatment leads to clinical activity in meta-static bladder cancer. Nature 2014; 515:558-62.
3. Robert C, Long G V, Brady B, Dutriaux C, Maio M, Mortier L, et al. Nivolumab in previously untreated melanoma without BRAF mutation. N Engl J Med 2015; 372:320-30.
4. Ansell S M, Lesokhin A M, Borrello I, Halwani A, Scott E C, Gutierrez M, et al. PD-1 blockade with nivolumab in relapsed or refractory Hodgkin's lymphoma. N Engl J Med 2015; 372:311-9.
5. Robert C, Schachter J, Long G V, Arance A, Grob J J, Mortier L, et al. Pembrolizumab versus ipilimumab in advanced melanoma. N Engl J Med 2015; 372:2521-32.
6. Le D T, Uram J N, Wang H, Bartlett B R, Kemberling H, Eyring A D, et al. PD-1 blockade in tumors with mismatch-repair deficiency. N Engl J Med 2015; 372:2509-20.
7. Garon E B, Rizvi N A, Hui R, Leighl N, Balmanoukian A S, Eder J P, et al. Pembrolizumab for the treatment of non-small-cell lung cancer. N Engl J Med 2015; 372:2018-28.
8. Nghiem P T, Bhatia S, Lipson E J, Kudchadkar R R, Miller N J, Anna-malai L, et al. PD-1 blockade with pembrolizumab in advanced merkel-cell carcinoma. N Engl J Med 2016; 374:2542-52.
9. Pardoll D M. The blockade of immune checkpoints in cancer immunotherapy. Nature reviews Cancer 2012; 12:252-64.
10. Taube J M, Anders R A, Young G D, Xu H, Sharma R, McMiller T L, et al. Colocalization of inflammatory response with B7-h1 expression in human melanocytic lesions supports an adaptive resistance mechanism of immune escape. Sci Transl Med 2012; 4:127ra37.
11. Tumeh P C, Harview C L, Yearley J H, Shintaku I P, Taylor E J, Robert L, et al. PD-1 blockade induces responses by inhibiting adaptive immune resistance. Nature 2014; 515:568-71.
12. Ribas A. Adaptive immune resistance: how cancer protects from immune attack. Cancer Discov 2015; 5:915-9.
13. Bach E A, Aguet M, Schreiber R D. The IFN gamma receptor: a para-digm for cytokine receptor signaling. Annu Rev Immunol 1997; 15: 563-91.
14. Zaretsky J M, Garcia-Diaz A, Shin D S, Escuin-Ordinas H, Hugo W, Hu-Lieskovan S, et al. Mutations associated with acquired resistance to PD-1 blockade in melanoma. N Engl J Med 2016; 375:819-29.
15. Dunn G P, Bruce A T, Ikeda H, Old L J, Schreiber RD. Cancer immu-noediting: from immunosurveillance to tumor escape. Nat Immunol 2002; 3:991-8.
16. Kaplan D H, Shankaran V, Dighe A S, Stockert E, Aguet M, Old L J, et al. Demonstration of an interferon gamma-dependent tumor sur¬veillance system in immunocompetent mice. Proc Natl Acad Sci USA 1998; 95:7556-61.
17. Mazzolini G, Narvaiza I, Martinez-Cruz L A, Anna A, Barajas M, Galofre J C, et al. Pancreatic cancer escape variants that evade immu-nogene therapy through loss of sensitivity to IFNgamma-induced apoptosis. Gene Ther 2003; 10:1067-78.
18. Gao J, Shi L Z, Zhao H, Chen J, Xiong L, He Q, et al. Loss of IFN-gamma pathway genes in tumor cells as a mechanism of resistance to Anti-CTLA-4 Therapy. Cell 2016; 167:397-404 e9.
19. Rizvi N A, Hellmann M D, Snyder A, Kvistborg P, Makarov V, Havel J J, et al. Cancer immunology. Mutational landscape determines sensitivity to PD-1 blockade in non-small cell lung cancer. Science 2015; 348:124-8.
20. Hugo W, Zaretsky J M, Sun L, Song C, Moreno B H, Hu-Lieskovan S, et al. Genomic and transcriptomic features of response to Anti-PD-1 therapy in metastatic melanoma. Cell 2016; 165:35-44.
21. Rosenberg J E, Hoffman-Censits J, Powles T, van der Heijden M S, Balar A V, Necchi A, et al. Atezolizumab in patients with locally advanced and metastatic urothelial carcinoma who have progressed following treatment with platinum-based chemotherapy: a single-arm, multicentre, phase 2 trial. Lancet 2016; 387:1909-20.
22. Rodig S J, Meraz M A, White J M, Lampe P A, Riley J K, Arthur C D, et al. Disruption of the Jak1 gene demonstrates obligatory and non-redundant roles of the Jaks in cytokine-induced biologic responses. Cell 1998; 93:373-83.
23. Muller M, Briscoe J, Laxton C, Guschin D, Ziemiecki A, Silvennoinen O, et al. The protein tyrosine kinase JAK1 complements defects in interferon-alpha/beta and -gamma signal transduction. Nature 1993; 366:129-35.
24. Watling D, Guschin D, Muller M, Silvennoinen O, Witthuhn B A, Quelle F W, et al. Complementation by the protein tyrosine kinase JAK2 of a mutant cell line defective in the interferon-gamma signal transduction pathway. Nature 1993; 366:166-70.
25. Barretina J, Caponigro G, Stransky N, Venkatesan K, Margolin A A, Kim S, et al. The cancer cell line encyclopedia enables predictive mod-elling of anticancer drug sensitivity. Nature 2012; 483:603-7.
26. Ren Y, Zhang Y, Liu R Z, Fenstermacher D A, Wright K L, Teer J K, et al. JAK1 truncating mutations in gynecologic cancer define new role of cancer-associated protein tyrosine kinase aberrations. Scientific reports 2013; 3:3042.
27. Platanias L C. Mechanisms of type-I- and type-II-interferon-mediated signalling. Nat Rev Immunol 2005; 5:375-86.
28. Fish E N, Platanias L C. Interferon receptor signaling in malignancy: a network of cellular pathways defining biological outcomes. Mol Cancer Res 2014; 12:1691-703.
29. Dunn G P, Sheehan K C, Old L J, Schreiber R D. IFN unresponsiveness in LNCaP cells due to the lack of JAK1 gene expression. Cancer Res 2005; 65:3447-53.

30. Spranger S, Bao R, Gajewski T F. Melanoma-intrinsic beta-catenin signalling prevents anti-tumour immunity. Nature 2015; 523:231-5.
31. Sharma P, Allison J P. The future of immune checkpoint therapy. Science 2015; 348:56-61.
32. Ribas A, Hamid O, Daud A, Hodi F S, Wolchok J D, Kefford R, et al. Association of pembrolizumab with tumor response and survival among patients with advanced melanoma. JAMA 2016; 315:1600-9.
33. Nazarian R, Shi H, Wang Q, Kong X, Koya R C, Lee H, et al. Melano-mas acquire resistance to B-RAF(V600E) inhibition by RTK or N-RAS upregulation. Nature 2010; 468:973-7.
34. Atefi M, Avramis E, Lassen A, Wong D J, Robert L, Foulad D, et al. Effects of MAPK and PI3K Pathways on PD-L1 expression in mela-noma. Clin Cancer Res 2014; 20:3446-57.
35. Wong D J, Robert L, Atefi M S, Lassen A, Avarappatt G, Cerniglia M, et al. Antitumor activity of the ERK inhibitor SCH722984 against BRAF mutant, NRAS mutant and wild-type melanoma. Mol Cancer 2014; 13:194.
36. Wolchok J D, Hoos A, O'Day S, Weber J S, Hamid O, Lebbe C, et al. Guidelines for the evaluation of immune therapy activity in solid tumors: immune-related response criteria. Clin Cancer Res 2009; 15:7412-20.
37. Kotecha N, Krutzik P O, Irish J M. Web-based analysis and publica-tion of flow cytometry experiments. Current protocols in cytometry/editorial board, J Paul Robinson managing editor [et al] 2010; Chapter 10:Unit10 7.
38. Escuin-Ordinas H, Atefi M, Fu Y, Cass A, Ng C, Huang R R, et al. COX-2 inhibition prevents the appearance of cutaneous squamous cell carci-nomas accelerated by BRAF inhibitors. Mol Oncol 2014; 8:250-60.
39. Shi H, Hugo W, Kong X, Hong A, Koya R C, Moriceau G, et al. Acquired resistance and clonal evolution in melanoma during BRAF inhibitor therapy. Cancer Discov 2014; 4:80-93.
40. Cibulskis K, Lawrence M S, Carter S L, Sivachenko A, Jaffe D, Sougnez C, et al. Sensitive detection of somatic point mutations in impure and heterogeneous cancer samples. Nat Biotechnol 2013; 31:213-9.
41. Koboldt D C, Zhang Q, Larson D E, Shen D, McLellan M D, Lin L, et al. VarScan 2: somatic mutation and copy number alteration discovery in cancer by exome sequencing. Genome research 2012; 22:568-76.
42. Ramos A H, Lichtenstein L, Gupta M, Lawrence M S, Pugh T J, Saksena G, et al. Oncotator: cancer variant annotation tool. Human mutation 2015; 36:E2423-9.
43. McGranahan N, Furness A J, Rosenthal R, Ramskov S, Lyngaa R, Saini S K, et al. Clonal neoantigens elicit T cell immunoreactivity and sensi-tivity to immune checkpoint blockade. Science 2016; 351:1463-9.
44. Favero F, Joshi T, Marquard A M, Birkbak N J, Krzystanek M, Li Q, et al. Sequenza: allele-specific copy number and mutation profiles from tumor sequencing data. Ann Oncol 2015; 26:64-70.
45. Cerami E, Gao J, Dogrusoz U, Gross B E, Sumer S O, Aksoy B A, et al. The cBio cancer genomics portal: an open platform for exploring multidimensional cancer genomics data. Cancer Discov 2012; 2:401-4.
46. Gao J, Aksoy B A, Dogrusoz U, Dresdner G, Gross B, Sumer S O, et al. Integrative analysis of complex cancer genomics and clinical profiles using the cBioPortal. Sci Signal 2013; 6:pl1.
47. Beroukhim R, Getz G, Nghiemphu L, Barretina J, Hsueh T, Linhart D, et al. Assessing the significance of chromosomal aberrations in cancer: methodology and application to glioma. Proc Natl Acad Sci USA 2007; 104:20007-12.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

The invention claimed is:

1. A method of treating a subject having cancer, comprising:
 a) administering to the subject an anti-PD-1 therapy, wherein the cancer has been determined to not comprise a loss of function mutation or disruption in Janus kinase 1 (JAK1) or Janus kinase 2 (JAK2); or
 b) administering to the subject a cancer therapy alternative to that in (a) wherein the cancer has been determined to comprise at least one loss of function mutation or disruption in Janus kinase 1 (JAK1) or Janus kinase 2 (JAK2).

2. A method of assessing and treating a subject having cancer, comprising:
 a) determining or having determined by sequencing whether the cancer comprises a loss of function mutation or disruption in Janus kinase 1 (JAK1) or Janus kinase 2 (JAK2); and
 b) determining or having determined from the results of (a) that the subject is a candidate for:
  1) an anti-PD-1 therapy when the cancer is negative for a loss of function mutation or disruption in Janus kinase 1 (JAK1) or Janus kinase 2 (JAK2); or
  2) a cancer therapy alternative to that in (1) when the cancer is positive for at least one loss of function mutation or disruption in Janus kinase 1 (JAK1) or Janus kinase 2 (JAK2); and
 (c) administering the therapy of (b) to the subject based on the results of step (b).

3. The method of claim 2, wherein the determining step comprises obtaining a dataset from a third party that has processed a sample from the cancer to experimentally determine mutation status, optionally wherein the third party is directed to process the sample from the cancer to produce the dataset.

4. The method of claim 2, wherein the loss of function mutation in Janus kinase 1 (JAK1) or Janus kinase 2 (JAK2) is a mutation or disruption that truncates a Janus kinase 1 (JAK1) or a Janus kinase 2 (JAK2) protein, inactivates a JAK1 or a JAK2 protein, deletes a JAK1 or a JAK2 gene, or alters normal mRNA processing of a JAK1 or a JAK2 gene.

5. The method of claim 4, wherein the mutation is JAK1 Q503*, JAK1 W690*, JAK1 D775N, JAK1 P429S, JAK1 F111L, JAK2 F547_splice, JAK2 D313_splice, JAK2 T555S, JAK2 N729I, JAK2 R761K, or JAK2 P1023S.

6. The method of claim 2, wherein the loss of function mutation or disruption in Janus kinase 1 (JAK1) or Janus kinase 2 (JAK2) has a mutation status selected from the group consisting of:
 a) the loss of function mutation is homozygous;
 b) the loss of function mutation is present at an allelic frequency different than that of a wild-type allele, optionally wherein no copies of the wild-type allele remain; and
 c) the disruption is epigenetic silencing.

7. The method of claim 2, wherein the method comprises determining or having determined from the results of (a) that the subject is a candidate for anti-PD-1 therapy, wherein the cancer has been determined to not comprise the loss of function mutation or disruption in Janus kinase 1 (JAK1) or Janus kinase 2 (JAK2).

8. The method of claim 2, wherein the method comprises determining or having determined from the results of (a) that the subject is a candidate for: the alternative cancer therapy of (2) wherein the cancer has been determined to comprise the at least one loss of function mutation or disruption in Janus kinase 1 (JAK1) or Janus kinase 2 (JAK2) or the at least one loss of function mutation.

9. The method of claim 2, wherein the cancer is a PD-L1 positive (+) cancer.

10. The method of claim 2, wherein the cancer is melanoma, skin cutaneous melanoma, non-small cell lung cancer, colon cancer, endometrial cancer, kidney cancer, bladder cancer, Merkel cell carcinoma, or Hodgkin lymphoma.

11. The method of claim 2, wherein the anti-PD-1 therapy comprises an anti-PD-1 antibody, optionally wherein the antibody comprises nivolumab/BMS-936558/MDX-1106, pembrolizumab/MK-3475, pidilizumab/CT-011, or PDR001.

12. The method of claim 2, wherein the alternative cancer therapy of (2)is selected from the group consisting of a mutant BRAF inhibitor, a MEK inhibitor, an ERK inhibitor, and any combination thereof.

13. The method of claim 2, wherein the sequencing further comprises prior target amplification by PCR.

14. A method of assessing and treating a subject having cancer, comprising:
 a) determining or having determined by sequencing whether the cancer comprises a loss of function mutation or disruption in Janus kinase 2 (JAK2);
 b) determining or having determined from the results of (a) that the subject is a candidate for
  an anti-PD-1 therapy when the cancer is negative for a loss of function mutation or disruption in Janus kinase 2 (JAK2);
 and
 (c) administering the therapy of (b) to the subject based on the results of step (b).

15. The method of claim 1, wherein the cancer has been determined to not comprise the loss of function mutation or disruption in Janus kinase 1 (JAK1) or Janus kinase 2 (JAK2) using a sequencing assay.

16. The method of claim 1, wherein the cancer has been determined to comprise the at least one loss of function mutation or disruption in Janus kinase 1 (JAK1) or Janus kinase 2 (JAK2) using a sequencing assay.

17. The method of claim 2, wherein the cancer is breast invasive carcinoma, prostate adenocarcinoma, lung adenocarcinoma, or colorectal adenocarcinoma.

* * * * *

SEQUENCE LISTING

```
<160> NUMBER OF SEQ ID NOS: 65

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide: JAK1

<400> SEQUENCE: 1
caatgccttc tcctggacct t                                               21

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide: JAK1

<400> SEQUENCE: 2
ccgaaccgtg cagactgtag                                                 20

<210> SEQ ID NO 3
<211> LENGTH: 22
```

<212> TYPE: DNA
<213> ORGANISM: Artificial Sequence
<220> FEATURE:
<223> OTHER INFORMATION: Synthetic oligonucleotide: JAk2

<400> SEQUENCE: 3
acctcaccaa cattacagag gc                                    22

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide: JAk2

<400> SEQUENCE: 4
acatctaaca caaggttggc a                                     21

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide: B2M

<400> SEQUENCE: 5
cttgtcctga ttggctgggc                                       20

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide: B2M

<400> SEQUENCE: 6
acttggagaa gggaagtcac g                                     21

<210> SEQ ID NO 7
<211> LENGTH: 22
<212> TYPE: DNA
<213> ORGANISM: Artificial Sequence
<220> FEATURE:
<223> OTHER INFORMATION: Synthetic oligonucleotide: guide sequence for
      exon 4

<400> SEQUENCE: 7
ccaagctctg gtatgctcca aa                                    22

<210> SEQ ID NO 8
<211> LENGTH: 22
<212> TYPE: DNA
<213> ORGANISM: Artificial Sequence
<220> FEATURE:
<223> OTHER INFORMATION: Synthetic oligonucleotide: guide sequence for
      exon 5

<400> SEQUENCE: 8
ccaattggca tggaaccaac ga                                    22

<210> SEQ ID NO 9
<211> LENGTH: 22
<212> TYPE: DNA
<213> ORGANISM: Artificial Sequence
<220> FEATURE:
<223> OTHER INFORMATION: Synthetic oligonucleotide: guide sequence for
      exon 1

```
<400> SEQUENCE: 9
cctgccttac gatgacagaa at                                              22

<210> SEQ ID NO 10
<211> LENGTH: 22
<212> TYPE: DNA
<213> ORGANISM: Artificial Sequence
<220> FEATURE:
<223> OTHER INFORMATION: Synthetic oligonucleotide: guide sequence for
      exon 2

<400> SEQUENCE: 10
ccaggcataa tgtactctac ag                                              22

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide: JAK1 Exon4

<400> SEQUENCE: 11
agtcctttct cacatcaagc a                                               21

<210> SEQ ID NO 12
<211> LENGTH: 21
<212> TYPE: DNA
<213> ORGANISM: Artificial Sequence
<220> FEATURE:
<223> OTHER INFORMATION: Synthetic oligonucleotide: JAK1 Exon4

<400> SEQUENCE: 12
gccaggaatt tgtttgcatg t                                               21

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide: JAK1 Exon 5

<400> SEQUENCE: 13
cagggttgtc tgcctgcttc                                                 20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide: JAK1 Exon 5

<400> SEQUENCE: 14
gaagctggag tttgtgggat                                                 20

<210> SEQ ID NO 15
<211> LENGTH: 22
<212> TYPE: DNA
<213> ORGANISM: Artificial Sequence
<220> FEATURE:
<223> OTHER INFORMATION: Synthetic oligonucleotide: JAK2 Exon 1

<400> SEQUENCE: 15
acttctgggc tcaagctatc tg                                              22
```

```
<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide: JAK2 Exon 1

<400> SEQUENCE: 16
cttgggaaat ctgaggcaga                                               20

<210> SEQ ID NO 17
<211> LENGTH: 24
<212> TYPE: DNA
<213> ORGANISM: Artificial Sequence
<220> FEATURE:
<223> OTHER INFORMATION: Synthetic oligonucleotide: JAK2 Exon2

<400> SEQUENCE: 17
ggtgctgaca gacttactag attc                                          24

<210> SEQ ID NO 18
<211> LENGTH: 22
<212> TYPE: DNA
<213> ORGANISM: Artificial Sequence
<220> FEATURE:
<223> OTHER INFORMATION: Synthetic oligonucleotide: JAK2 Exon2

<400> SEQUENCE: 18
gatattgctg gtttgtgcag cg                                            22

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide: forward primer

<400> SEQUENCE: 19
aaccttctca ccaggatgcg                                               20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide: reverse primer

<400> SEQUENCE: 20
ctcagcacgt acatcccctc                                               20

<210> SEQ ID NO 21
<211> LENGTH: 29
<212> TYPE: DNA
<213> ORGANISM: Artificial Sequence
<220> FEATURE:
<223> OTHER INFORMATION: Synthetic

<400> SEQUENCE: 21
gtagcggccc ttctgcacct cgatctgaa                                     29

<210> SEQ ID NO 22
<211> LENGTH: 10
<212> TYPE: PRT
<213> ORGANISM: Artificial Sequence
<220> FEATURE:
<223> OTHER INFORMATION: Synthetic
```

<400> SEQUENCE: 22

Tyr Arg Gly Lys Gln Val Glu Ile Gln Phe
1               5                   10

<210> SEQ ID NO 23
<211> LENGTH: 26
<212> TYPE: DNA
<213> ORGANISM: Artificial Sequence
<220> FEATURE:
<223> OTHER INFORMATION: Synthetic

<400> SEQUENCE: 23
agatttgata tttgtaagtc attaga                                        26

<210> SEQ ID NO 24
<211> LENGTH: 4
<212> TYPE: PRT
<213> ORGANISM: Artificial Sequence
<220> FEATURE:
<223> OTHER INFORMATION: Synthetic

<400> SEQUENCE: 24

Asp Leu Ile Phe
1

<210> SEQ ID NO 25
<211> LENGTH: 71
<212> TYPE: DNA
<213> ORGANISM: Artificial Sequence
<220> FEATURE:
<223> OTHER INFORMATION: Synthetic

<400> SEQUENCE: 25
tgtttcacaa aatcagaaat gaagatttga tatttgtaag tcattagata ctcattactg   60
tcttttttgt c                                                        71

<210> SEQ ID NO 26
<211> LENGTH: 6
<212> TYPE: PRT
<213> ORGANISM: Artificial Sequence
<220> FEATURE:
<223> OTHER INFORMATION: Synthetic

<400> SEQUENCE: 26

Val Ser Gln Asn Gln Lys
1               5

<210> SEQ ID NO 27
<211> LENGTH: 16
<212> TYPE: PRT
<213> ORGANISM: Artificial Sequence
<220> FEATURE:
<223> OTHER INFORMATION: Synthetic

<400> SEQUENCE: 27

Arg Phe Asp Ile Cys Lys Ser Leu Asp Thr His Tyr Cys Leu Phe Cys
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Synthetic

<400> SEQUENCE: 28

Val Phe His Lys Ile Arg Asn Glu Asp Leu Ile Phe Val Ser His
1               5                   10                  15

<210> SEQ ID NO 29
<211> LENGTH: 8
<212> TYPE: PRT
<213> ORGANISM: Artificial Sequence
<220> FEATURE:
<223> OTHER INFORMATION: Synthetic

<400> SEQUENCE: 29

Ile Leu Ile Thr Val Phe Phe Val
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic

<400> SEQUENCE: 30

Cys Phe Thr Lys Ser Glu Met Lys Ile
1               5

<210> SEQ ID NO 31
<211> LENGTH: 11
<212> TYPE: PRT
<213> ORGANISM: Artificial Sequence
<220> FEATURE:
<223> OTHER INFORMATION: Synthetic

<400> SEQUENCE: 31

Val Ile Arg Tyr Ser Leu Leu Ser Phe Leu Ser
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Synthetic

<400> SEQUENCE: 32

Val Phe His Lys Ile Arg Asn Glu Asp Leu Ile Phe
1               5                   10

<210> SEQ ID NO 33
<211> LENGTH: 17
<212> TYPE: DNA
<213> ORGANISM: Artificial Sequence
<220> FEATURE:
<223> OTHER INFORMATION: Synthetic

<400> SEQUENCE: 33
gcccttctgc acctcga                                                      17

<210> SEQ ID NO 34
<211> LENGTH: 14
<212> TYPE: DNA
<213> ORGANISM: Artificial Sequence
<220> FEATURE:
<223> OTHER INFORMATION: Synthetic

<400> SEQUENCE: 34
atatttgtaa gtca                                                         14

<210> SEQ ID NO 35
<211> LENGTH: 5
<212> TYPE: PRT
<213> ORGANISM: Artificial Sequence
<220> FEATURE:
<223> OTHER INFORMATION: Synthetic

<400> SEQUENCE: 35

Ile Phe Val Ser His
1               5

<210> SEQ ID NO 36
<211> LENGTH: 16
<212> TYPE: DNA
<213> ORGANISM: Artificial Sequence
<220> FEATURE:
<223> OTHER INFORMATION: Synthetic

<400> SEQUENCE: 36
ctctctttct ggcctg                                                    16

<210> SEQ ID NO 37
<211> LENGTH: 15
<212> TYPE: DNA
<213> ORGANISM: Artificial Sequence
<220> FEATURE:
<223> OTHER INFORMATION: Synthetic

<400> SEQUENCE: 37
caagctctgg tatgc                                                     15

<210> SEQ ID NO 38
<211> LENGTH: 16
<212> TYPE: DNA
<213> ORGANISM: Artificial Sequence
<220> FEATURE:
<223> OTHER INFORMATION: Synthetic

<400> SEQUENCE: 38
caagcttctg gtatgc                                                    16

<210> SEQ ID NO 39
<211> LENGTH: 47
<212> TYPE: DNA
<213> ORGANISM: Artificial Sequence
<220> FEATURE:
<223> OTHER INFORMATION: Synthetic

<400> SEQUENCE: 39
ccatatagat gagtcaacca ggcataatgt actctacaga ataaggt                  47

<210> SEQ ID NO 40
<211> LENGTH: 47
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (45)..(45)
<223> OTHER INFORMATION: n is a, c, g, or t

<400> SEQUENCE: 40
ccatatagat gagtcaacca ggcaatgtac tctacaaaat aatgnac                  47

```
<210> SEQ ID NO 41
<211> LENGTH: 66
<212> TYPE: DNA
<213> ORGANISM: Artificial Sequence
<220> FEATURE:
<223> OTHER INFORMATION: Synthetic

<400> SEQUENCE: 41
atgtctcgct ccgtggcctt agctgtcgtc gcgctactct ctctttctgg cctggaggct      60
atcagc                                                                66

<210> SEQ ID NO 42
<211> LENGTH: 22
<212> TYPE: PRT
<213> ORGANISM: Artificial Sequence
<220> FEATURE:
<223> OTHER INFORMATION: Synthetic

<400> SEQUENCE: 42

Met Ser Arg Ser Val Ala Leu Ala Val Leu Ala Leu Leu Ser Leu Ser
1               5                   10                  15

Gly Leu Glu Ala Ile Gln
            20

<210> SEQ ID NO 43
<211> LENGTH: 15
<212> TYPE: DNA
<213> ORGANISM: Artificial Sequence
<220> FEATURE:
<223> OTHER INFORMATION: Synthetic

<400> SEQUENCE: 43
aacggggagg ccacg                                                      15

<210> SEQ ID NO 44
<211> LENGTH: 46
<212> TYPE: DNA
<213> ORGANISM: Artificial Sequence
<220> FEATURE:
<223> OTHER INFORMATION: Synthetic

<400> SEQUENCE: 44
aattttacat gcttttaatt ataggattta cagttatatt gcgatt                    46

<210> SEQ ID NO 45
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid

<400> SEQUENCE: 45

Xaa Leu Xaa Leu Tyr Leu Asp
1               5

<210> SEQ ID NO 46
<211> LENGTH: 41
<212> TYPE: DNA
<213> ORGANISM: Artificial Sequence
```

```
<220> FEATURE:
<223> OTHER INFORMATION: Synthetic

<400> SEQUENCE: 46
ggttccaaag ctccacttgt cagcagccac actcaggttc t                    41

<210> SEQ ID NO 47
<211> LENGTH: 13
<212> TYPE: PRT
<213> ORGANISM: Artificial Sequence
<220> FEATURE:
<223> OTHER INFORMATION: Synthetic

<400> SEQUENCE: 47

Thr Gly Phe Ser Trp Cys Asp Ala Ala Val Ser Leu Asn
1               5                   10

<210> SEQ ID NO 48
<211> LENGTH: 14
<212> TYPE: DNA
<213> ORGANISM: Artificial Sequence
<220> FEATURE:
<223> OTHER INFORMATION: Synthetic

<400> SEQUENCE: 48
ttttaattat agga                                                  14

<210> SEQ ID NO 49
<211> LENGTH: 14
<212> TYPE: DNA
<213> ORGANISM: Artificial Sequence
<220> FEATURE:
<223> OTHER INFORMATION: Synthetic

<400> SEQUENCE: 49
ttttaattat aaga                                                  14

<210> SEQ ID NO 50
<211> LENGTH: 14
<212> TYPE: DNA
<213> ORGANISM: Artificial Sequence
<220> FEATURE:
<223> OTHER INFORMATION: Synthetic

<400> SEQUENCE: 50
tttaattata ggat                                                  14

<210> SEQ ID NO 51
<211> LENGTH: 14
<212> TYPE: DNA
<213> ORGANISM: Artificial Sequence
<220> FEATURE:
<223> OTHER INFORMATION: Synthetic

<400> SEQUENCE: 51
tttaattata agat                                                  14

<210> SEQ ID NO 52
<211> LENGTH: 23
<212> TYPE: DNA
<213> ORGANISM: Artificial Sequence
<220> FEATURE:
<223> OTHER INFORMATION: Synthetic

<400> SEQUENCE: 52
ttaattatag gatttacagt tat                                        23
```

<210> SEQ ID NO 53
<211> LENGTH: 4
<212> TYPE: PRT
<213> ORGANISM: Artificial Sequence
<220> FEATURE:
<223> OTHER INFORMATION: Synthetic

<400> SEQUENCE: 53

Asp Leu Gln Leu
1

<210> SEQ ID NO 54
<211> LENGTH: 23
<212> TYPE: DNA
<213> ORGANISM: Artificial Sequence
<220> FEATURE:
<223> OTHER INFORMATION: Synthetic

<400> SEQUENCE: 54
ttaattataa gattttcagt tat                                          23

<210> SEQ ID NO 55
<211> LENGTH: 4
<212> TYPE: PRT
<213> ORGANISM: Artificial Sequence
<220> FEATURE:
<223> OTHER INFORMATION: Synthetic

<400> SEQUENCE: 55

Ile Tyr Ser Tyr
1

<210> SEQ ID NO 56
<211> LENGTH: 40
<212> TYPE: DNA
<213> ORGANISM: Artificial Sequence
<220> FEATURE:
<223> OTHER INFORMATION: Synthetic

<400> SEQUENCE: 56
gtttggcaac tttgaatttc catggtgtgg taaggacatc                        40

<210> SEQ ID NO 57
<211> LENGTH: 13
<212> TYPE: PRT
<213> ORGANISM: Artificial Sequence
<220> FEATURE:
<223> OTHER INFORMATION: Synthetic

<400> SEQUENCE: 57

Lys Ala Val Lys Phe Lys Trp Pro Thr Thr Leu Val Asp
1               5                   10

<210> SEQ ID NO 58
<211> LENGTH: 18
<212> TYPE: DNA
<213> ORGANISM: Artificial Sequence
<220> FEATURE:
<223> OTHER INFORMATION: Synthetic

<400> SEQUENCE: 58
gcccttctgc acctcgat                                                18

<210> SEQ ID NO 59
<211> LENGTH: 19

```
<212> TYPE: DNA
<213> ORGANISM: Artificial Sequence
<220> FEATURE:
<223> OTHER INFORMATION: Synthetic

<400> SEQUENCE: 59
tgatatttgt aagtcatta                                                  19

<210> SEQ ID NO 60
<211> LENGTH: 14
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: n is a, c, g, or t

<400> SEQUENCE: 60
tcgaggtgna gaag                                                       14

<210> SEQ ID NO 61
<211> LENGTH: 4
<212> TYPE: PRT
<213> ORGANISM: Artificial Sequence
<220> FEATURE:
<223> OTHER INFORMATION: Synthetic

<400> SEQUENCE: 61

Ile Glu Val Lys
1

<210> SEQ ID NO 62
<211> LENGTH: 15
<212> TYPE: DNA
<213> ORGANISM: Artificial Sequence
<220> FEATURE:
<223> OTHER INFORMATION: Synthetic

<400> SEQUENCE: 62
atatttgtga agtca                                                      15

<210> SEQ ID NO 63
<211> LENGTH: 5
<212> TYPE: PRT
<213> ORGANISM: Artificial Sequence
<220> FEATURE:
<223> OTHER INFORMATION: Synthetic

<400> SEQUENCE: 63

Ile Phe Val Lys Ser
1               5

<210> SEQ ID NO 64
<211> LENGTH: 16
<212> TYPE: DNA
<213> ORGANISM: Artificial Sequence
<220> FEATURE:
<223> OTHER INFORMATION: Synthetic

<400> SEQUENCE: 64
ctctctgtct gggctg                                                     16

<210> SEQ ID NO 65
<211> LENGTH: 5
<212> TYPE: PRT
```

```
<213> ORGANISM: Artificial Sequence
<220> FEATURE:
<223> OTHER INFORMATION: Synthetic

<400> SEQUENCE: 65

Ser Leu Ser Gly Leu
1               5
```